US012624074B2

(12) United States Patent
Nanchahal et al.

(10) Patent No.: US 12,624,074 B2
(45) Date of Patent: May 12, 2026

(54) POLYPEPTIDES RELATED TO HMGB1 USEFUL FOR PROMOTING TISSUE REGENERATION, COMPOSITIONS COMPRISING SAME, AND USES THEREOF

(71) Applicant: Oxford University Innovation Limited, Oxford (GB)

(72) Inventors: Jagdeep Nanchahal, Oxford (GB); Alvaro Vinals Guitart, Oxford (GB); Wyatt Yue, Oxford (GB); Nicola Burgess-Brown, Oxford (GB); Tzung Yuan Lee, Oxford (GB); Ana Isabel Espirito Santo, Oxford (GB)

(73) Assignee: OXFORD UNIVERSITY INNOVATION LIMITED, Oxford (GB)

( * ) Notice: Subject to any disclaimer, the term of this patent is extended or adjusted under 35 U.S.C. 154(b) by 948 days.

(21) Appl. No.: 17/743,321

(22) Filed: May 12, 2022

(65) Prior Publication Data

US 2023/0046828 A1    Feb. 16, 2023

Related U.S. Application Data

(63) Continuation-in-part of application No. PCT/IB2020/060674, filed on Nov. 12, 2020.

(60) Provisional application No. 63/190,429, filed on May 19, 2021, provisional application No. 62/934,299, filed on Nov. 12, 2019.

(51) Int. Cl.
| | |
|---|---|
| *C07K 14/47* | (2006.01) |
| *A61P 9/00* | (2006.01) |
| *A61P 21/00* | (2006.01) |

(52) U.S. Cl.
CPC ............ *C07K 14/4702* (2013.01); *A61P 9/00* (2018.01); *A61P 21/00* (2018.01)

(58) Field of Classification Search
None
See application file for complete search history.

(56) References Cited

FOREIGN PATENT DOCUMENTS

| | | |
|---|---|---|
| EP | 2 494 977 A1 | 9/2012 |
| EP | 2 703 487 A1 | 3/2014 |
| EP | 3 358 011 A1 | 8/2016 |
| JP | 2017-078067 | 4/2017 |
| WO | WO 2006/083301 A2 | 8/2006 |
| WO | WO 2021/094983 A1 | 5/2021 |

OTHER PUBLICATIONS

Huan Yang et al., "High Mobility Group Box Protein 1 (HMGB1): The Prototypical Endogenous Danger Molecule.", Molecular Medicine, vol. 21, Oct. 27, 2015.
Huttunen H. J. et al., "Receptor For Advanced Glycation End Products-Binding COOH-Terminal Motif of Amphoterin Inhibits Invasive Migration and Metastasis", Cancer Research, American Association for Cancer Research, vol. 62, No. 16, Aug. 15, 2002.
International Search Report issued Sep. 13, 2022 in connection with PCT International Application No. PCT/IB2022/054688.
Written Opinion issued Sep. 13, 2022 in connection with PCT International Application No. PCT/IB2022/054688.
International Preliminary Report on Patentability issued Nov. 21, 2023 in connection with PCT International Application No. PCT/IB2022/054688.
Japanese Office Action issued Oct. 29, 2024 in connection with Japanese Application No. 2022-528186, including an English language summary.
Communication pursuant to Article 94(3) EPC issued Jan. 10, 2024 in connection with European Patent Application No. 20824631.4.
Huttunen, H. J. et al., "Receptor for Advanced Glycation End Products-binding COOH-terminal Motif of Amphoterin Inhibits Invasive Migration and Metastasis". Cancer Research, 2002, vol. 62, pp. 4805-4811.
International Search Report issued Mar. 15, 2021 in connection with PCT International Application No. PCT/IB2020/060674.
Mccauley, M. J. et al., "HMGB Binding to DNA: Single and Double Box Motifs". J. Mol. Biol., 2007, vol. 374, pp. 993-1004.
Notification of Transmittal of The International Search Report and the Written Opinion of the International Searching Authority, or the Declaration, issued Mar. 15, 2021 in connection with PCT International Application No. PCT/IB2020/060674.
Sánchez-Giraldo, R et al., "Two high-mobility group box domains act together to unwind and kink DNA". Biological Crystallography, 2015, vol. 71(7), pp. 1423-1432.
Written Opinion of the International Searching Authority issued Mar. 15, 2021 in connection with PCT International Application No. PCT/IB2020/060674.
International Preliminary Report on Patentability issued May 17, 2022, including Written Opinion of the International Searching Authority issued Mar. 15, 2021, in connection with PCT International Application No. PCT/IB2020/060674.

*Primary Examiner* — Sergio Coffa
(74) *Attorney, Agent, or Firm* — John P. White

(57) ABSTRACT

This invention provides polypeptides represented by the following formula:

$$H_2N\text{-}A\text{-}X\text{-}B\text{-}A\text{-}X\text{-}B\text{-}HOOC$$

which are based on HMGB1 as well as compositions comprising, and treatment methods using, such polypeptide.

20 Claims, 37 Drawing Sheets
(37 of 37 Drawing Sheet(s) Filed in Color)
Specification includes a Sequence Listing.

| | Kinetics rates derived from interferogram | | | Michaelis-Menten (saturation) R$_{eq}$ fit |
|---|---|---|---|---|
| | $K_{Off}$ (s$^{-1}$) | $k_{On}$ (s$^{-1}$µM$^{-1}$) | $K_d$ (µM) | $K_d$ (µM) |
| FR 1-214 | 0.181±0.014 | 0.009±0.002 | 20.9±3.99 | 15.26±2.25 |
| 3S 1-214 | 0.145±0.013 | 0.012±0.001 | 11.7±1.49 | 8.79±0.75 |
| FR 8-78 | 0.312±0.034 | 0.017±0.004 | 18.7±4.6 | 17.53±1.74 |
| FR 94-162 | 0.64±0.069 | 0.016±0.004 | 39±10.7 | 65.02±8.79 |
| FR 1-88 | 0.079±0.015 | 0.013±0.001 | 6.1±1.36 | 12.55±1.6 |
| FR 89-174 | 0.159±0.026 | 0.022±0.003 | 7.1±1.45 | 8.19±1.16 |
| AICc for different values model? | >99.99% (19.07 difference) | 93.44% (14.06 difference) | N/A | >99.99% (19.06 difference) |

```
BoxA  0    MGKGDP KP GKM  Y FFVQTCREE K  PDASVNFSEFSKKCSERWK  49
           ---.||..|:...|::..|....|.:.|.:||..|:--.:.:||..|.|.
BoxB  89   ---K PNAP  PP A FL C EY PK GEHPGLSI--GDVAKKLGEMWN  133
BoxA  50   TMSAKE GKFEDMA A KARYER M TY- PPKGETKKKF-              88
           ..:|.:|..:|..|...|.:||:::..|-...|.:..||.-
BoxB  134  NT AADDKQPYEKKAAKL  KYEKD AA RAKG P AAKKGV            174
```

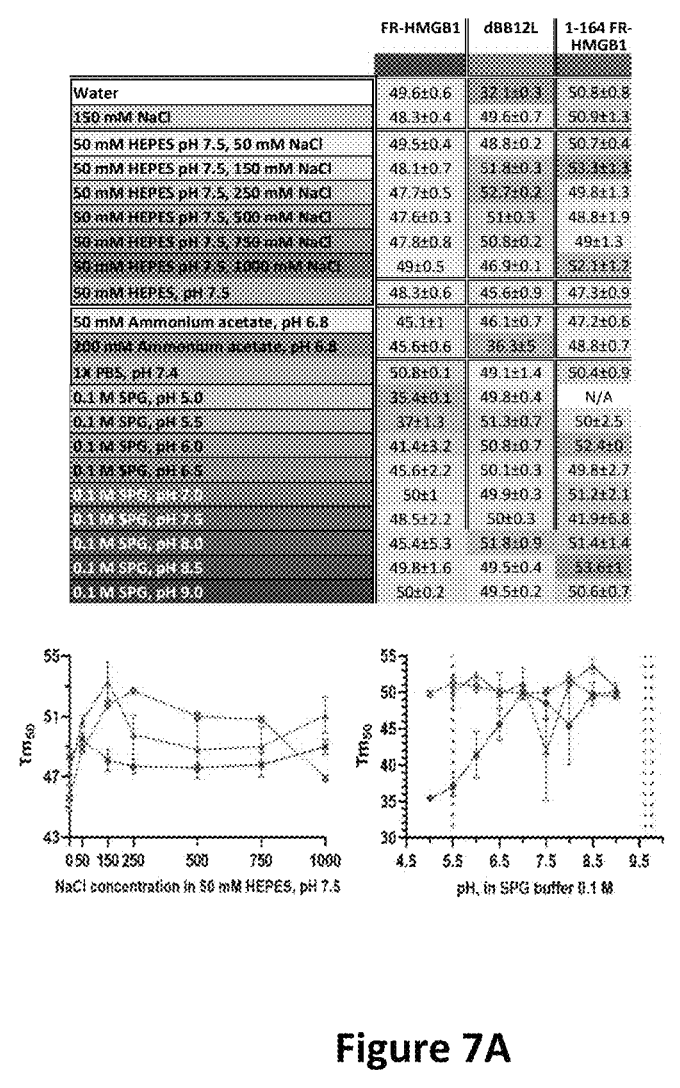

| | FR-HMGB1 | d8B12L | 1-164 FR-HMGB1 |
|---|---|---|---|
| Water | 49.6±0.6 | 32.1±0.3 | 50.8±0.8 |
| 150 mM NaCl | 48.3±0.4 | 49.6±0.7 | 50.9±1.3 |
| 50 mM HEPES pH 7.5, 50 mM NaCl | 49.5±0.4 | 48.8±0.2 | 50.7±0.4 |
| 50 mM HEPES pH 7.5, 150 mM NaCl | 48.1±0.7 | 51.8±0.3 | 50.4±0.3 |
| 50 mM HEPES pH 7.5, 250 mM NaCl | 47.7±0.5 | 53.7±0.2 | 49.8±1.3 |
| 50 mM HEPES pH 7.5, 500 mM NaCl | 47.6±0.3 | 51±0.3 | 48.8±1.9 |
| 50 mM HEPES pH 7.5, 750 mM NaCl | 47.8±0.8 | 50.8±0.2 | 49±1.3 |
| 50 mM HEPES pH 7.5, 1000 mM NaCl | 49±0.5 | 46.9±0.1 | 52.1±1.2 |
| 50 mM HEPES, pH 7.5 | 48.3±0.6 | 45.6±0.9 | 47.3±0.9 |
| 50 mM Ammonium acetate, pH 6.8 | 45.1±1 | 46.1±0.7 | 47.2±0.6 |
| 300 mM Ammonium acetate, pH 6.8 | 45.6±0.6 | 36.3±5 | 48.8±0.7 |
| 1X PBS, pH 7.4 | 50.8±0.1 | 49.1±1.4 | 50.4±0.9 |
| 0.1 M SPG, pH 5.0 | 35.4±0.1 | 49.8±0.4 | N/A |
| 0.1 M SPG, pH 5.5 | 37±1.3 | 51.3±0.7 | 50±2.5 |
| 0.1 M SPG, pH 6.0 | 41.4±1.2 | 50.8±0.7 | 52.4±0 |
| 0.1 M SPG, pH 6.5 | 45.6±2.2 | 50.1±0.3 | 49.8±2.7 |
| 0.1 M SPG, pH 7.0 | 50±1 | 49.9±0.3 | 51.2±2.1 |
| 0.1 M SPG, pH 7.5 | 48.5±2.2 | 50±0.3 | 41.9±6.8 |
| 0.1 M SPG, pH 8.0 | 45.4±5.3 | 51.8±0.9 | 51.4±1.4 |
| 0.1 M SPG, pH 8.5 | 49.8±1.6 | 49.5±0.4 | 53.6±1 |
| 0.1 M SPG, pH 9.0 | 50±0.2 | 49.5±0.2 | 50.6±0.7 |

Figure 7A

| Surface area w/ SEM (Å²) | FR-HMGB1 | FR-HMGB1A 1-164 | dBB12L |
|---|---|---|---|
| Unfolded (ProtSA) | 26337 | 20691 | 21075 |
| Unfolded (0.2 % FA) | 22555±65 | 22555±65 | 22555±65 |
| 2YRQ (1-164) folded/unfolded | N/A | 14251/19299 | N/A |
| Average monomer | 17953±13 | 15191±318 | 15428±51 |
| Compact monomer | 11531±48 | 9091±199 | 9809±34 |
| Extended monomer | 21754±56 | 19310±280 | 19193±49 |
| SASA from SEC | 18006±180 | 19804±396 | 15905±318 |
| % IDR | 35% | 18% | 19% |

| Calculation method | ELISA | | $K_d$ (µM) | | BLI | |
| | $B_{max}$ (nM) | $K_d$ (nM) | Saturation fit | Kinetics plot | $K_{on}$ (µM⁻¹s⁻¹) Kinetics plot | $k_{off}$ (s⁻¹) Kinetics plot |
|---|---|---|---|---|---|---|
| DS-HMGB1 | 1±0.02 | 4.35±0.35 | 1.3±0.2 | 0.2±0.04 | 0.215±0.038 | 0.043±0.003 |
| FR-HMGB1 | 1±0.02 | 86.11±7.06 | 3.3±0.4 | 0.8±0.27 | 0.051±0.011 | 0.041±0.01 |
| dBB12L | 0.06±0.01 | Invalid fit | 5.5±0.7 | 1.3±0.33 | 0.164±0.034 | 0.206±0.033 |
| DS Box A 1-88 | 0.04±0.02 | Invalid fit | 13.3±6.3 | 15.6±15.87 | 0.028±0.029 | 0.419±0.093 |
| 3S-HMGB1 | 1.03±0.03 | 7.22±0.97 | 3±0.5 | 0.9±0.11 | 0.017±0.002 | 0.015±0.001 |
| DS-HMGB1 1-184 | 0.59±0.02 | 33.87±3.54 | 0.5±0.1 | 0.2±0.04 | 0.349±0.059 | 0.067±0.01 |
| DS-HMGB1 1-164 | 0.2±0.01 | Invalid fit | 3.1±0.3 | 0.9±0.26 | 0.178±0.037 | 0.152±0.035 |

HMGB1A-c001    HMGB1A-c006    HMGB1A-c027    HMGB1A-c028
1-214, FR      1-214, 3S      8-78, Box A, FR  94-162, Box B

HMGB1A-c007, 0.3 mM (before the experiment)
HMGB1A-c007, 0.3 mM (end of the experiment)
HMGB1A-c007, 0.3 mM + 0.6 mM CXCL12A-c021 (1:1 ratio)
15N HSQC-HQMC, 500 MHz + 15N TOCSY-HSQC + 15N NOESY-HSQC
10 mM HEPES pH 7.5, 150 mM NaCl. TEV-cleaved HMGB1.

SEQUENCE LISTING

```
<160> NUMBER OF SEQ ID NOS: 178

<210> SEQ ID NO 1
<211> LENGTH: 214
<212> TYPE: PRT
<213> ORGANISM: Artificial Sequence
<220> FEATURE:
<223> OTHER INFORMATION: WT HMGB1

<400> SEQUENCE: 1

Gly Lys Gly Asp Pro Lys Lys Pro Arg Gly Lys Met Ser Ser Tyr Ala
1               5                   10                  15

Phe Phe Val Gln Thr Cys Arg Glu Glu His Lys Lys Lys His Pro Asp
            20                  25                  30

Ala Ser Val Asn Phe Ser Glu Phe Ser Lys Lys Cys Ser Glu Arg Trp
        35                  40                  45

Lys Thr Met Ser Ala Lys Glu Lys Gly Lys Phe Glu Asp Met Ala Lys
    50                  55                  60

Ala Asp Lys Ala Arg Tyr Glu Arg Glu Met Lys Thr Tyr Ile Pro Pro
65                  70                  75                  80

Lys Gly Glu Thr Lys Lys Lys Phe Lys Asp Pro Asn Ala Pro Lys Arg
                85                  90                  95

Pro Pro Ser Ala Phe Phe Leu Phe Cys Ser Glu Tyr Arg Pro Lys Ile
            100                 105                 110

Lys Gly Glu His Pro Gly Leu Ser Ile Gly Asp Val Ala Lys Lys Leu
        115                 120                 125

Gly Glu Met Trp Asn Asn Thr Ala Ala Asp Asp Lys Gln Pro Tyr Glu
    130                 135                 140

Lys Lys Ala Ala Lys Leu Lys Glu Lys Tyr Glu Lys Asp Ile Ala Ala
145                 150                 155                 160

Tyr Arg Ala Lys Gly Lys Pro Asp Ala Ala Lys Lys Gly Val Val Lys
                165                 170                 175

Ala Glu Lys Ser Lys Lys Lys Lys Glu Glu Glu Glu Asp Glu Glu Asp
            180                 185                 190

Glu Glu Asp Glu Glu Glu Glu Glu Asp Glu Glu Asp Glu Asp Glu Glu
        195                 200                 205

Glu Asp Asp Asp Asp Glu
    210
```

-continued

```
<210> SEQ ID NO 2
<211> LENGTH: 172
<212> TYPE: PRT
<213> ORGANISM: Artificial Sequence
<220> FEATURE:
<223> OTHER INFORMATION: Dbb12L

<400> SEQUENCE: 2

Lys Asp Pro Asn Ala Pro Lys Arg Pro Pro Ser Ala Phe Phe Leu Phe
1               5                   10                  15

Cys Ser Glu Tyr Arg Pro Lys Ile Lys Gly Glu His Pro Gly Leu Ser
            20                  25                  30

Ile Gly Asp Val Ala Lys Lys Leu Gly Glu Met Trp Asn Asn Thr Ala
            35                  40                  45

Ala Asp Asp Lys Gln Pro Tyr Glu Lys Lys Ala Ala Lys Leu Lys Glu
            50                  55                  60

Lys Tyr Glu Lys Asp Ile Ala Ala Tyr Arg Ala Lys Gly Lys Pro Asp
65                  70                  75                  80

Ala Ala Lys Lys Gly Val Lys Asp Pro Asn Ala Pro Lys Arg Pro Pro
                85                  90                  95

Ser Ala Phe Phe Leu Phe Cys Ser Glu Tyr Arg Pro Lys Ile Lys Gly
                100                 105                 110

Glu His Pro Gly Leu Ser Ile Gly Asp Val Ala Lys Lys Leu Gly Glu
            115                 120                 125

Met Trp Asn Asn Thr Ala Ala Asp Asp Lys Gln Pro Tyr Glu Lys Lys
            130                 135                 140

Ala Ala Lys Leu Lys Glu Lys Tyr Glu Lys Asp Ile Ala Ala Tyr Arg
145                 150                 155                 160

Ala Lys Gly Lys Pro Asp Ala Ala Lys Lys Gly Val
                165                 170

<210> SEQ ID NO 3
<211> LENGTH: 89
<212> TYPE: PRT
<213> ORGANISM: Artificial Sequence
<220> FEATURE:
<223> OTHER INFORMATION: HMGB1 portion containing Box A shown in
      alignment

<400> SEQUENCE: 3

Met Gly Lys Gly Asp Pro Lys Lys Pro Arg Gly Lys Met Ser Ser Tyr
1               5                   10                  15

Ala Phe Phe Val Gln Thr Cys Arg Glu Glu His Lys Lys Lys His Pro
            20                  25                  30

Asp Ala Ser Val Asn Phe Ser Glu Phe Ser Lys Lys Cys Ser Glu Arg
            35                  40                  45

Trp Lys Thr Met Ser Ala Lys Glu Lys Gly Lys Phe Glu Asp Met Ala
            50                  55                  60

Lys Ala Asp Lys Ala Arg Tyr Glu Arg Glu Met Lys Thr Tyr Ile Pro
65                  70                  75                  80

Pro Lys Gly Glu Thr Lys Lys Lys Phe
                85

<210> SEQ ID NO 4
<211> LENGTH: 86
<212> TYPE: PRT
<213> ORGANISM: Artificial Sequence
<220> FEATURE:
<223> OTHER INFORMATION: HMGB1 portion containing Box B shown in
```

-continued

```
        alignment

<400> SEQUENCE: 4

Lys Asp Pro Asn Ala Pro Lys Arg Pro Pro Ser Ala Phe Phe Leu Phe
1               5                   10                  15

Cys Ser Glu Tyr Arg Pro Lys Ile Lys Gly Glu His Pro Gly Leu Ser
                20                  25                  30

Ile Gly Asp Val Ala Lys Lys Leu Gly Glu Met Trp Asn Asn Thr Ala
            35                  40                  45

Ala Asp Asp Lys Gln Pro Tyr Glu Lys Lys Ala Ala Lys Leu Lys Glu
        50                  55                  60

Lys Tyr Glu Lys Asp Ile Ala Ala Tyr Arg Ala Lys Gly Lys Pro Asp
65                  70                  75                  80

Ala Ala Lys Lys Gly Val
                85

<210> SEQ ID NO 5
<211> LENGTH: 85
<212> TYPE: PRT
<213> ORGANISM: Artificial Sequence
<220> FEATURE:
<223> OTHER INFORMATION: HMGB1 Box B

<400> SEQUENCE: 5

Asp Pro Asn Ala Pro Lys Arg Pro Pro Ser Ala Phe Phe Leu Phe Cys
1               5                   10                  15

Ser Glu Tyr Arg Pro Lys Ile Lys Gly Glu His Pro Gly Leu Ser Ile
            20                  25                  30

Gly Asp Val Ala Lys Lys Leu Gly Glu Met Trp Asn Asn Thr Ala Ala
            35                  40                  45

Asp Asp Lys Gln Pro Tyr Glu Lys Lys Ala Ala Lys Leu Lys Glu Lys
        50                  55                  60

Tyr Glu Lys Asp Ile Ala Ala Tyr Arg Ala Lys Gly Lys Pro Asp Ala
65                  70                  75                  80

Ala Lys Lys Gly Val
                85

<210> SEQ ID NO 6
<211> LENGTH: 84
<212> TYPE: PRT
<213> ORGANISM: Artificial Sequence
<220> FEATURE:
<223> OTHER INFORMATION: HMGB1 3S Box B

<400> SEQUENCE: 6

Asp Pro Asn Ala Pro Lys Arg Pro Pro Ser Ala Phe Phe Leu Phe Ser
1               5                   10                  15

Ser Glu Tyr Arg Pro Lys Ile Lys Gly Glu His Pro Gly Leu Ser Ile
            20                  25                  30

Gly Asp Val Ala Lys Lys Leu Gly Glu Met Trp Asn Asn Thr Ala Ala
            35                  40                  45

Asp Asp Lys Gln Pro Tyr Glu Lys Lys Ala Ala Lys Leu Lys Glu Lys
        50                  55                  60

Tyr Glu Lys Asp Ile Ala Ala Tyr Arg Ala Lys Gly Lys Pro Asp Ala
65                  70                  75                  80

Lys Lys Gly Val

<210> SEQ ID NO 7
```

```
<211> LENGTH: 85
<212> TYPE: PRT
<213> ORGANISM: Artificial Sequence
<220> FEATURE:
<223> OTHER INFORMATION: HMGB1 3S Box A

<400> SEQUENCE: 7

Asp Pro Lys Lys Pro Arg Gly Lys Met Ser Ser Tyr Ala Phe Phe Val
1               5                   10                  15

Gln Thr Ser Arg Glu Glu His Lys Lys Lys His Pro Asp Ala Ser Val
            20                  25                  30

Asn Phe Ser Glu Phe Ser Lys Lys Ser Ser Glu Arg Trp Lys Thr Met
        35                  40                  45

Ser Ala Lys Glu Lys Gly Lys Phe Glu Asp Met Ala Lys Ala Asp Lys
    50                  55                  60

Ala Arg Tyr Glu Arg Glu Met Lys Thr Tyr Ile Pro Pro Lys Gly Glu
65                  70                  75                  80

Thr Lys Lys Lys Phe
                85

<210> SEQ ID NO 8
<211> LENGTH: 15
<212> TYPE: PRT
<213> ORGANISM: Artificial Sequence
<220> FEATURE:
<223> OTHER INFORMATION: HMGB1 peptide

<400> SEQUENCE: 8

Met Gly Lys Gly Asp Pro Lys Lys Pro Arg Gly Lys Met Ser Ser
1               5                   10                  15

<210> SEQ ID NO 9
<211> LENGTH: 15
<212> TYPE: PRT
<213> ORGANISM: Artificial Sequence
<220> FEATURE:
<223> OTHER INFORMATION: HMGB1 peptide

<400> SEQUENCE: 9

Lys Gly Asp Pro Lys Lys Pro Arg Gly Lys Met Ser Ser Tyr Ala
1               5                   10                  15

<210> SEQ ID NO 10
<211> LENGTH: 15
<212> TYPE: PRT
<213> ORGANISM: Artificial Sequence
<220> FEATURE:
<223> OTHER INFORMATION: HMGB1 peptide

<400> SEQUENCE: 10

Asp Pro Lys Lys Pro Arg Gly Lys Met Ser Ser Tyr Ala Phe Phe
1               5                   10                  15

<210> SEQ ID NO 11
<211> LENGTH: 15
<212> TYPE: PRT
<213> ORGANISM: Artificial Sequence
<220> FEATURE:
<223> OTHER INFORMATION: HMGB1 peptide

<400> SEQUENCE: 11

Lys Lys Pro Arg Gly Lys Met Ser Ser Tyr Ala Phe Phe Val Gln
1               5                   10                  15
```

<210> SEQ ID NO 12
<211> LENGTH: 15
<212> TYPE: PRT
<213> ORGANISM: Artificial Sequence
<220> FEATURE:
<223> OTHER INFORMATION: HMGB1 peptide

<400> SEQUENCE: 12

Pro Arg Gly Lys Met Ser Ser Tyr Ala Phe Phe Val Gln Thr Cys
1               5                   10                  15

<210> SEQ ID NO 13
<211> LENGTH: 15
<212> TYPE: PRT
<213> ORGANISM: Artificial Sequence
<220> FEATURE:
<223> OTHER INFORMATION: HMGB1 peptide

<400> SEQUENCE: 13

Gly Lys Met Ser Ser Tyr Ala Phe Phe Val Gln Thr Cys Arg Glu
1               5                   10                  15

<210> SEQ ID NO 14
<211> LENGTH: 15
<212> TYPE: PRT
<213> ORGANISM: Artificial Sequence
<220> FEATURE:
<223> OTHER INFORMATION: HMGB1 peptide

<400> SEQUENCE: 14

Met Ser Ser Tyr Ala Phe Phe Val Gln Thr Cys Arg Glu Glu His
1               5                   10                  15

<210> SEQ ID NO 15
<211> LENGTH: 15
<212> TYPE: PRT
<213> ORGANISM: Artificial Sequence
<220> FEATURE:
<223> OTHER INFORMATION: HMGB1 peptide

<400> SEQUENCE: 15

Ser Tyr Ala Phe Phe Val Gln Thr Cys Arg Glu Glu His Lys Lys
1               5                   10                  15

<210> SEQ ID NO 16
<211> LENGTH: 15
<212> TYPE: PRT
<213> ORGANISM: Artificial Sequence
<220> FEATURE:
<223> OTHER INFORMATION: HMGB1 peptide

<400> SEQUENCE: 16

Ala Phe Phe Val Gln Thr Cys Arg Glu Glu His Lys Lys Lys His
1               5                   10                  15

<210> SEQ ID NO 17
<211> LENGTH: 15
<212> TYPE: PRT
<213> ORGANISM: Artificial Sequence
<220> FEATURE:
<223> OTHER INFORMATION: HMGB1 peptide

<400> SEQUENCE: 17

Phe Val Gln Thr Cys Arg Glu Glu His Lys Lys Lys His Pro Asp
1               5                   10                  15

<210> SEQ ID NO 18

```
<211> LENGTH: 15
<212> TYPE: PRT
<213> ORGANISM: Artificial Sequence
<220> FEATURE:
<223> OTHER INFORMATION: HMGB1 peptide

<400> SEQUENCE: 18

Gln Thr Cys Arg Glu Glu His Lys Lys Lys His Pro Asp Ala Ser
1               5                   10                  15

<210> SEQ ID NO 19
<211> LENGTH: 15
<212> TYPE: PRT
<213> ORGANISM: Artificial Sequence
<220> FEATURE:
<223> OTHER INFORMATION: HMGB1 peptide

<400> SEQUENCE: 19

Cys Arg Glu Glu His Lys Lys Lys His Pro Asp Ala Ser Val Asn
1               5                   10                  15

<210> SEQ ID NO 20
<211> LENGTH: 15
<212> TYPE: PRT
<213> ORGANISM: Artificial Sequence
<220> FEATURE:
<223> OTHER INFORMATION: HMGB1 peptide

<400> SEQUENCE: 20

Glu Glu His Lys Lys Lys His Pro Asp Ala Ser Val Asn Phe Ser
1               5                   10                  15

<210> SEQ ID NO 21
<211> LENGTH: 15
<212> TYPE: PRT
<213> ORGANISM: Artificial Sequence
<220> FEATURE:
<223> OTHER INFORMATION: HMGB1 peptide

<400> SEQUENCE: 21

His Lys Lys Lys His Pro Asp Ala Ser Val Asn Phe Ser Glu Phe
1               5                   10                  15

<210> SEQ ID NO 22
<211> LENGTH: 15
<212> TYPE: PRT
<213> ORGANISM: Artificial Sequence
<220> FEATURE:
<223> OTHER INFORMATION: HMGB1 peptide

<400> SEQUENCE: 22

Lys Lys His Pro Asp Ala Ser Val Asn Phe Ser Glu Phe Ser Lys
1               5                   10                  15

<210> SEQ ID NO 23
<211> LENGTH: 15
<212> TYPE: PRT
<213> ORGANISM: Artificial Sequence
<220> FEATURE:
<223> OTHER INFORMATION: HMGB1 peptide

<400> SEQUENCE: 23

His Pro Asp Ala Ser Val Asn Phe Ser Glu Phe Ser Lys Lys Cys
1               5                   10                  15

<210> SEQ ID NO 24
<211> LENGTH: 15
```

```
<212> TYPE: PRT
<213> ORGANISM: Artificial Sequence
<220> FEATURE:
<223> OTHER INFORMATION: HMGB1 peptide

<400> SEQUENCE: 24

Asp Ala Ser Val Asn Phe Ser Glu Phe Ser Lys Lys Cys Ser Glu
1               5                   10                  15

<210> SEQ ID NO 25
<211> LENGTH: 15
<212> TYPE: PRT
<213> ORGANISM: Artificial Sequence
<220> FEATURE:
<223> OTHER INFORMATION: HMGB1 peptide

<400> SEQUENCE: 25

Ser Val Asn Phe Ser Glu Phe Ser Lys Lys Cys Ser Glu Arg Trp
1               5                   10                  15

<210> SEQ ID NO 26
<211> LENGTH: 15
<212> TYPE: PRT
<213> ORGANISM: Artificial Sequence
<220> FEATURE:
<223> OTHER INFORMATION: HMGB1 peptide

<400> SEQUENCE: 26

Asn Phe Ser Glu Phe Ser Lys Lys Cys Ser Glu Arg Trp Lys Thr
1               5                   10                  15

<210> SEQ ID NO 27
<211> LENGTH: 15
<212> TYPE: PRT
<213> ORGANISM: Artificial Sequence
<220> FEATURE:
<223> OTHER INFORMATION: HMGB1 peptide

<400> SEQUENCE: 27

Ser Glu Phe Ser Lys Lys Cys Ser Glu Arg Trp Lys Thr Met Ser
1               5                   10                  15

<210> SEQ ID NO 28
<211> LENGTH: 15
<212> TYPE: PRT
<213> ORGANISM: Artificial Sequence
<220> FEATURE:
<223> OTHER INFORMATION: HMGB1 peptide

<400> SEQUENCE: 28

Phe Ser Lys Lys Cys Ser Glu Arg Trp Lys Thr Met Ser Ala Lys
1               5                   10                  15

<210> SEQ ID NO 29
<211> LENGTH: 15
<212> TYPE: PRT
<213> ORGANISM: Artificial Sequence
<220> FEATURE:
<223> OTHER INFORMATION: HMGB1 peptide

<400> SEQUENCE: 29

Lys Lys Cys Ser Glu Arg Trp Lys Thr Met Ser Ala Lys Glu Lys
1               5                   10                  15

<210> SEQ ID NO 30
<211> LENGTH: 15
<212> TYPE: PRT
```

<213> ORGANISM: Artificial Sequence
<220> FEATURE:
<223> OTHER INFORMATION: HMGB1 peptide

<400> SEQUENCE: 30

Cys Ser Glu Arg Trp Lys Thr Met Ser Ala Lys Glu Lys Gly Lys
1               5                   10                  15

<210> SEQ ID NO 31
<211> LENGTH: 15
<212> TYPE: PRT
<213> ORGANISM: Artificial Sequence
<220> FEATURE:
<223> OTHER INFORMATION: HMGB1 peptide

<400> SEQUENCE: 31

Glu Arg Trp Lys Thr Met Ser Ala Lys Glu Lys Gly Lys Phe Glu
1               5                   10                  15

<210> SEQ ID NO 32
<211> LENGTH: 15
<212> TYPE: PRT
<213> ORGANISM: Artificial Sequence
<220> FEATURE:
<223> OTHER INFORMATION: HMGB1 peptide

<400> SEQUENCE: 32

Trp Lys Thr Met Ser Ala Lys Glu Lys Gly Lys Phe Glu Asp Met
1               5                   10                  15

<210> SEQ ID NO 33
<211> LENGTH: 15
<212> TYPE: PRT
<213> ORGANISM: Artificial Sequence
<220> FEATURE:
<223> OTHER INFORMATION: HMGB1 peptide

<400> SEQUENCE: 33

Thr Met Ser Ala Lys Glu Lys Gly Lys Phe Glu Asp Met Ala Lys
1               5                   10                  15

<210> SEQ ID NO 34
<211> LENGTH: 15
<212> TYPE: PRT
<213> ORGANISM: Artificial Sequence
<220> FEATURE:
<223> OTHER INFORMATION: HMGB1 peptide

<400> SEQUENCE: 34

Ser Ala Lys Glu Lys Gly Lys Phe Glu Asp Met Ala Lys Ala Asp
1               5                   10                  15

<210> SEQ ID NO 35
<211> LENGTH: 15
<212> TYPE: PRT
<213> ORGANISM: Artificial Sequence
<220> FEATURE:
<223> OTHER INFORMATION: HMGB1 peptide

<400> SEQUENCE: 35

Lys Glu Lys Gly Lys Phe Glu Asp Met Ala Lys Ala Asp Lys Ala
1               5                   10                  15

<210> SEQ ID NO 36
<211> LENGTH: 15
<212> TYPE: PRT
<213> ORGANISM: Artificial Sequence -continued

```
<220> FEATURE:
<223> OTHER INFORMATION: HMGB1 peptide

<400> SEQUENCE: 36

Lys Gly Lys Phe Glu Asp Met Ala Lys Ala Asp Lys Ala Arg Tyr
1               5                   10                  15

<210> SEQ ID NO 37
<211> LENGTH: 15
<212> TYPE: PRT
<213> ORGANISM: Artificial Sequence
<220> FEATURE:
<223> OTHER INFORMATION: HMGB1 peptide

<400> SEQUENCE: 37

Lys Phe Glu Asp Met Ala Lys Ala Asp Lys Ala Arg Tyr Glu Arg
1               5                   10                  15

<210> SEQ ID NO 38
<211> LENGTH: 15
<212> TYPE: PRT
<213> ORGANISM: Artificial Sequence
<220> FEATURE:
<223> OTHER INFORMATION: HMGB1 peptide

<400> SEQUENCE: 38

Glu Asp Met Ala Lys Ala Asp Lys Ala Arg Tyr Glu Arg Glu Met
1               5                   10                  15

<210> SEQ ID NO 39
<211> LENGTH: 15
<212> TYPE: PRT
<213> ORGANISM: Artificial Sequence
<220> FEATURE:
<223> OTHER INFORMATION: HMGB1 peptide

<400> SEQUENCE: 39

Met Ala Lys Ala Asp Lys Ala Arg Tyr Glu Arg Glu Met Lys Thr
1               5                   10                  15

<210> SEQ ID NO 40
<211> LENGTH: 15
<212> TYPE: PRT
<213> ORGANISM: Artificial Sequence
<220> FEATURE:
<223> OTHER INFORMATION: HMGB1 peptide

<400> SEQUENCE: 40

Lys Ala Asp Lys Ala Arg Tyr Glu Arg Glu Met Lys Thr Tyr Ile
1               5                   10                  15

<210> SEQ ID NO 41
<211> LENGTH: 15
<212> TYPE: PRT
<213> ORGANISM: Artificial Sequence
<220> FEATURE:
<223> OTHER INFORMATION: HMGB1 peptide

<400> SEQUENCE: 41

Asp Lys Ala Arg Tyr Glu Arg Glu Met Lys Thr Tyr Ile Pro Pro
1               5                   10                  15

<210> SEQ ID NO 42
<211> LENGTH: 15
<212> TYPE: PRT
<213> ORGANISM: Artificial Sequence
<220> FEATURE:
```

-continued

```
<223> OTHER INFORMATION: HMGB1 peptide

<400> SEQUENCE: 42

Ala Arg Tyr Glu Arg Glu Met Lys Thr Tyr Ile Pro Pro Lys Gly
1               5                   10                  15

<210> SEQ ID NO 43
<211> LENGTH: 15
<212> TYPE: PRT
<213> ORGANISM: Artificial Sequence
<220> FEATURE:
<223> OTHER INFORMATION: HMGB1 peptide

<400> SEQUENCE: 43

Tyr Glu Arg Glu Met Lys Thr Tyr Ile Pro Pro Lys Gly Glu Thr
1               5                   10                  15

<210> SEQ ID NO 44
<211> LENGTH: 15
<212> TYPE: PRT
<213> ORGANISM: Artificial Sequence
<220> FEATURE:
<223> OTHER INFORMATION: HMGB1 peptide

<400> SEQUENCE: 44

Arg Glu Met Lys Thr Tyr Ile Pro Pro Lys Gly Glu Thr Lys Lys
1               5                   10                  15

<210> SEQ ID NO 45
<211> LENGTH: 15
<212> TYPE: PRT
<213> ORGANISM: Artificial Sequence
<220> FEATURE:
<223> OTHER INFORMATION: HMGB1 peptide

<400> SEQUENCE: 45

Met Lys Thr Tyr Ile Pro Pro Lys Gly Glu Thr Lys Lys Lys Phe
1               5                   10                  15

<210> SEQ ID NO 46
<211> LENGTH: 15
<212> TYPE: PRT
<213> ORGANISM: Artificial Sequence
<220> FEATURE:
<223> OTHER INFORMATION: HMGB1 peptide

<400> SEQUENCE: 46

Thr Tyr Ile Pro Pro Lys Gly Glu Thr Lys Lys Lys Phe Lys Asp
1               5                   10                  15

<210> SEQ ID NO 47
<211> LENGTH: 15
<212> TYPE: PRT
<213> ORGANISM: Artificial Sequence
<220> FEATURE:
<223> OTHER INFORMATION: HMGB1 peptide

<400> SEQUENCE: 47

Ile Pro Pro Lys Gly Glu Thr Lys Lys Lys Phe Lys Asp Pro Asn
1               5                   10                  15

<210> SEQ ID NO 48
<211> LENGTH: 15
<212> TYPE: PRT
<213> ORGANISM: Artificial Sequence
<220> FEATURE:
<223> OTHER INFORMATION: HMGB1 peptide
```

<400> SEQUENCE: 48

Pro Lys Gly Glu Thr Lys Lys Lys Phe Lys Asp Pro Asn Ala Pro
1               5                   10                  15

<210> SEQ ID NO 49
<211> LENGTH: 15
<212> TYPE: PRT
<213> ORGANISM: Artificial Sequence
<220> FEATURE:
<223> OTHER INFORMATION: HMGB1 peptide

<400> SEQUENCE: 49

Gly Glu Thr Lys Lys Lys Phe Lys Asp Pro Asn Ala Pro Lys Arg
1               5                   10                  15

<210> SEQ ID NO 50
<211> LENGTH: 15
<212> TYPE: PRT
<213> ORGANISM: Artificial Sequence
<220> FEATURE:
<223> OTHER INFORMATION: HMGB1 peptide

<400> SEQUENCE: 50

Thr Lys Lys Lys Phe Lys Asp Pro Asn Ala Pro Lys Arg Pro Pro
1               5                   10                  15

<210> SEQ ID NO 51
<211> LENGTH: 15
<212> TYPE: PRT
<213> ORGANISM: Artificial Sequence
<220> FEATURE:
<223> OTHER INFORMATION: HMGB1 peptide

<400> SEQUENCE: 51

Lys Lys Phe Lys Asp Pro Asn Ala Pro Lys Arg Pro Pro Ser Ala
1               5                   10                  15

<210> SEQ ID NO 52
<211> LENGTH: 15
<212> TYPE: PRT
<213> ORGANISM: Artificial Sequence
<220> FEATURE:
<223> OTHER INFORMATION: HMGB1 peptide

<400> SEQUENCE: 52

Phe Lys Asp Pro Asn Ala Pro Lys Arg Pro Pro Ser Ala Phe Phe
1               5                   10                  15

<210> SEQ ID NO 53
<211> LENGTH: 15
<212> TYPE: PRT
<213> ORGANISM: Artificial Sequence
<220> FEATURE:
<223> OTHER INFORMATION: HMGB1 peptide

<400> SEQUENCE: 53

Asp Pro Asn Ala Pro Lys Arg Pro Pro Ser Ala Phe Phe Leu Phe
1               5                   10                  15

<210> SEQ ID NO 54
<211> LENGTH: 15
<212> TYPE: PRT
<213> ORGANISM: Artificial Sequence
<220> FEATURE:
<223> OTHER INFORMATION: HMGB1 peptide

<400> SEQUENCE: 54

Asn Ala Pro Lys Arg Pro Pro Ser Ala Phe Phe Leu Phe Cys Ser
1               5                   10                  15

<210> SEQ ID NO 55
<211> LENGTH: 15
<212> TYPE: PRT
<213> ORGANISM: Artificial Sequence
<220> FEATURE:
<223> OTHER INFORMATION: HMGB1 peptide

<400> SEQUENCE: 55

Pro Lys Arg Pro Pro Ser Ala Phe Phe Leu Phe Cys Ser Glu Tyr
1               5                   10                  15

<210> SEQ ID NO 56
<211> LENGTH: 15
<212> TYPE: PRT
<213> ORGANISM: Artificial Sequence
<220> FEATURE:
<223> OTHER INFORMATION: HMGB1 peptide

<400> SEQUENCE: 56

Arg Pro Pro Ser Ala Phe Phe Leu Phe Cys Ser Glu Tyr Arg Pro
1               5                   10                  15

<210> SEQ ID NO 57
<211> LENGTH: 15
<212> TYPE: PRT
<213> ORGANISM: Artificial Sequence
<220> FEATURE:
<223> OTHER INFORMATION: HMGB1 peptide

<400> SEQUENCE: 57

Pro Ser Ala Phe Phe Leu Phe Cys Ser Glu Tyr Arg Pro Lys Ile
1               5                   10                  15

<210> SEQ ID NO 58
<211> LENGTH: 15
<212> TYPE: PRT
<213> ORGANISM: Artificial Sequence
<220> FEATURE:
<223> OTHER INFORMATION: HMGB1 peptide

<400> SEQUENCE: 58

Ala Phe Phe Leu Phe Cys Ser Glu Tyr Arg Pro Lys Ile Lys Gly
1               5                   10                  15

<210> SEQ ID NO 59
<211> LENGTH: 15
<212> TYPE: PRT
<213> ORGANISM: Artificial Sequence
<220> FEATURE:
<223> OTHER INFORMATION: HMGB1 peptide

<400> SEQUENCE: 59

Phe Leu Phe Cys Ser Glu Tyr Arg Pro Lys Ile Lys Gly Glu His
1               5                   10                  15

<210> SEQ ID NO 60
<211> LENGTH: 15
<212> TYPE: PRT
<213> ORGANISM: Artificial Sequence
<220> FEATURE:
<223> OTHER INFORMATION: HMGB1 peptide

<400> SEQUENCE: 60

```
Phe Cys Ser Glu Tyr Arg Pro Lys Ile Lys Gly Glu His Pro Gly
1               5                   10                  15

<210> SEQ ID NO 61
<211> LENGTH: 15
<212> TYPE: PRT
<213> ORGANISM: Artificial Sequence
<220> FEATURE:
<223> OTHER INFORMATION: HMGB1 peptide

<400> SEQUENCE: 61

Ser Glu Tyr Arg Pro Lys Ile Lys Gly Glu His Pro Gly Leu Ser
1               5                   10                  15

<210> SEQ ID NO 62
<211> LENGTH: 15
<212> TYPE: PRT
<213> ORGANISM: Artificial Sequence
<220> FEATURE:
<223> OTHER INFORMATION: HMGB1 peptide

<400> SEQUENCE: 62

Tyr Arg Pro Lys Ile Lys Gly Glu His Pro Gly Leu Ser Ile Gly
1               5                   10                  15

<210> SEQ ID NO 63
<211> LENGTH: 15
<212> TYPE: PRT
<213> ORGANISM: Artificial Sequence
<220> FEATURE:
<223> OTHER INFORMATION: HMGB1 peptide

<400> SEQUENCE: 63

Pro Lys Ile Lys Gly Glu His Pro Gly Leu Ser Ile Gly Asp Val
1               5                   10                  15

<210> SEQ ID NO 64
<211> LENGTH: 15
<212> TYPE: PRT
<213> ORGANISM: Artificial Sequence
<220> FEATURE:
<223> OTHER INFORMATION: HMGB1 peptide

<400> SEQUENCE: 64

Ile Lys Gly Glu His Pro Gly Leu Ser Ile Gly Asp Val Ala Lys
1               5                   10                  15

<210> SEQ ID NO 65
<211> LENGTH: 15
<212> TYPE: PRT
<213> ORGANISM: Artificial Sequence
<220> FEATURE:
<223> OTHER INFORMATION: HMGB1 peptide

<400> SEQUENCE: 65

Gly Glu His Pro Gly Leu Ser Ile Gly Asp Val Ala Lys Lys Leu
1               5                   10                  15

<210> SEQ ID NO 66
<211> LENGTH: 15
<212> TYPE: PRT
<213> ORGANISM: Artificial Sequence
<220> FEATURE:
<223> OTHER INFORMATION: HMGB1 peptide

<400> SEQUENCE: 66
```

```
His Pro Gly Leu Ser Ile Gly Asp Val Ala Lys Lys Leu Gly Glu
1               5                   10                  15

<210> SEQ ID NO 67
<211> LENGTH: 15
<212> TYPE: PRT
<213> ORGANISM: Artificial Sequence
<220> FEATURE:
<223> OTHER INFORMATION: HMGB1 peptide

<400> SEQUENCE: 67

Gly Leu Ser Ile Gly Asp Val Ala Lys Lys Leu Gly Glu Met Trp
1               5                   10                  15

<210> SEQ ID NO 68
<211> LENGTH: 15
<212> TYPE: PRT
<213> ORGANISM: Artificial Sequence
<220> FEATURE:
<223> OTHER INFORMATION: HMGB1 peptide

<400> SEQUENCE: 68

Ser Ile Gly Asp Val Ala Lys Lys Leu Gly Glu Met Trp Asn Asn
1               5                   10                  15

<210> SEQ ID NO 69
<211> LENGTH: 15
<212> TYPE: PRT
<213> ORGANISM: Artificial Sequence
<220> FEATURE:
<223> OTHER INFORMATION: HMGB1 peptide

<400> SEQUENCE: 69

Gly Asp Val Ala Lys Lys Leu Gly Glu Met Trp Asn Asn Thr Ala
1               5                   10                  15

<210> SEQ ID NO 70
<211> LENGTH: 15
<212> TYPE: PRT
<213> ORGANISM: Artificial Sequence
<220> FEATURE:
<223> OTHER INFORMATION: HMGB1 peptide

<400> SEQUENCE: 70

Val Ala Lys Lys Leu Gly Glu Met Trp Asn Asn Thr Ala Ala Asp
1               5                   10                  15

<210> SEQ ID NO 71
<211> LENGTH: 15
<212> TYPE: PRT
<213> ORGANISM: Artificial Sequence
<220> FEATURE:
<223> OTHER INFORMATION: HMGB1 peptide

<400> SEQUENCE: 71

Lys Lys Leu Gly Glu Met Trp Asn Asn Thr Ala Ala Asp Asp Lys
1               5                   10                  15

<210> SEQ ID NO 72
<211> LENGTH: 15
<212> TYPE: PRT
<213> ORGANISM: Artificial Sequence
<220> FEATURE:
<223> OTHER INFORMATION: HMGB1 peptide

<400> SEQUENCE: 72

Leu Gly Glu Met Trp Asn Asn Thr Ala Ala Asp Asp Lys Gln Pro
```

-continued

```
1               5               10              15
```

```
<210> SEQ ID NO 73
<211> LENGTH: 15
<212> TYPE: PRT
<213> ORGANISM: Artificial Sequence
<220> FEATURE:
<223> OTHER INFORMATION: HMGB1 peptide

<400> SEQUENCE: 73

Glu Met Trp Asn Asn Thr Ala Ala Asp Asp Lys Gln Pro Tyr Glu
1               5               10              15

<210> SEQ ID NO 74
<211> LENGTH: 15
<212> TYPE: PRT
<213> ORGANISM: Artificial Sequence
<220> FEATURE:
<223> OTHER INFORMATION: HMGB1 peptide

<400> SEQUENCE: 74

Trp Asn Asn Thr Ala Ala Asp Asp Lys Gln Pro Tyr Glu Lys Lys
1               5               10              15

<210> SEQ ID NO 75
<211> LENGTH: 15
<212> TYPE: PRT
<213> ORGANISM: Artificial Sequence
<220> FEATURE:
<223> OTHER INFORMATION: HMGB1 peptide

<400> SEQUENCE: 75

Asn Thr Ala Ala Asp Asp Lys Gln Pro Tyr Glu Lys Lys Ala Ala
1               5               10              15

<210> SEQ ID NO 76
<211> LENGTH: 15
<212> TYPE: PRT
<213> ORGANISM: Artificial Sequence
<220> FEATURE:
<223> OTHER INFORMATION: HMGB1 peptide

<400> SEQUENCE: 76

Ala Ala Asp Asp Lys Gln Pro Tyr Glu Lys Lys Ala Ala Lys Leu
1               5               10              15

<210> SEQ ID NO 77
<211> LENGTH: 15
<212> TYPE: PRT
<213> ORGANISM: Artificial Sequence
<220> FEATURE:
<223> OTHER INFORMATION: HMGB1 peptide

<400> SEQUENCE: 77

Asp Asp Lys Gln Pro Tyr Glu Lys Lys Ala Ala Lys Leu Lys Glu
1               5               10              15

<210> SEQ ID NO 78
<211> LENGTH: 15
<212> TYPE: PRT
<213> ORGANISM: Artificial Sequence
<220> FEATURE:
<223> OTHER INFORMATION: HMGB1 peptide

<400> SEQUENCE: 78

Lys Gln Pro Tyr Glu Lys Lys Ala Ala Lys Leu Lys Glu Lys Tyr
1               5               10              15
```

-continued

<210> SEQ ID NO 79
<211> LENGTH: 15
<212> TYPE: PRT
<213> ORGANISM: Artificial Sequence
<220> FEATURE:
<223> OTHER INFORMATION: HMGB1 peptide

<400> SEQUENCE: 79

Pro Tyr Glu Lys Lys Ala Ala Lys Leu Lys Glu Lys Tyr Glu Lys
1               5                   10                  15

<210> SEQ ID NO 80
<211> LENGTH: 15
<212> TYPE: PRT
<213> ORGANISM: Artificial Sequence
<220> FEATURE:
<223> OTHER INFORMATION: HMGB1 peptide

<400> SEQUENCE: 80

Glu Lys Lys Ala Ala Lys Leu Lys Glu Lys Tyr Glu Lys Asp Ile
1               5                   10                  15

<210> SEQ ID NO 81
<211> LENGTH: 15
<212> TYPE: PRT
<213> ORGANISM: Artificial Sequence
<220> FEATURE:
<223> OTHER INFORMATION: HMGB1 peptide

<400> SEQUENCE: 81

Lys Ala Ala Lys Leu Lys Glu Lys Tyr Glu Lys Asp Ile Ala Ala
1               5                   10                  15

<210> SEQ ID NO 82
<211> LENGTH: 15
<212> TYPE: PRT
<213> ORGANISM: Artificial Sequence
<220> FEATURE:
<223> OTHER INFORMATION: HMGB1 peptide

<400> SEQUENCE: 82

Ala Lys Leu Lys Glu Lys Tyr Glu Lys Asp Ile Ala Ala Tyr Arg
1               5                   10                  15

<210> SEQ ID NO 83
<211> LENGTH: 15
<212> TYPE: PRT
<213> ORGANISM: Artificial Sequence
<220> FEATURE:
<223> OTHER INFORMATION: HMGB1 peptide

<400> SEQUENCE: 83

Leu Lys Glu Lys Tyr Glu Lys Asp Ile Ala Ala Tyr Arg Ala Lys
1               5                   10                  15

<210> SEQ ID NO 84
<211> LENGTH: 15
<212> TYPE: PRT
<213> ORGANISM: Artificial Sequence
<220> FEATURE:
<223> OTHER INFORMATION: HMGB1 peptide

<400> SEQUENCE: 84

Glu Lys Tyr Glu Lys Asp Ile Ala Ala Tyr Arg Ala Lys Gly Lys
1               5                   10                  15

```
<210> SEQ ID NO 85
<211> LENGTH: 15
<212> TYPE: PRT
<213> ORGANISM: Artificial Sequence
<220> FEATURE:
<223> OTHER INFORMATION: HMGB1 peptide

<400> SEQUENCE: 85

Tyr Glu Lys Asp Ile Ala Ala Tyr Arg Ala Lys Gly Lys Pro Asp
1               5                   10                  15

<210> SEQ ID NO 86
<211> LENGTH: 15
<212> TYPE: PRT
<213> ORGANISM: Artificial Sequence
<220> FEATURE:
<223> OTHER INFORMATION: HMGB1 peptide

<400> SEQUENCE: 86

Lys Asp Ile Ala Ala Tyr Arg Ala Lys Gly Lys Pro Asp Ala Ala
1               5                   10                  15

<210> SEQ ID NO 87
<211> LENGTH: 15
<212> TYPE: PRT
<213> ORGANISM: Artificial Sequence
<220> FEATURE:
<223> OTHER INFORMATION: HMGB1 peptide

<400> SEQUENCE: 87

Ile Ala Ala Tyr Arg Ala Lys Gly Lys Pro Asp Ala Ala Lys Lys
1               5                   10                  15

<210> SEQ ID NO 88
<211> LENGTH: 15
<212> TYPE: PRT
<213> ORGANISM: Artificial Sequence
<220> FEATURE:
<223> OTHER INFORMATION: HMGB1 peptide

<400> SEQUENCE: 88

Asp Ala Ala Lys Lys Gly Val Val Lys Ala Glu Lys Ser Lys Lys
1               5                   10                  15

<210> SEQ ID NO 89
<211> LENGTH: 15
<212> TYPE: PRT
<213> ORGANISM: Artificial Sequence
<220> FEATURE:
<223> OTHER INFORMATION: HMGB1 peptide

<400> SEQUENCE: 89

Ala Lys Lys Gly Val Val Lys Ala Glu Lys Ser Lys Lys Lys Lys
1               5                   10                  15

<210> SEQ ID NO 90
<211> LENGTH: 15
<212> TYPE: PRT
<213> ORGANISM: Artificial Sequence
<220> FEATURE:
<223> OTHER INFORMATION: HMGB1 peptide

<400> SEQUENCE: 90

Lys Gly Val Val Lys Ala Glu Lys Ser Lys Lys Lys Lys Glu Glu
1               5                   10                  15
```

```
<210> SEQ ID NO 91
<211> LENGTH: 15
<212> TYPE: PRT
<213> ORGANISM: Artificial Sequence
<220> FEATURE:
<223> OTHER INFORMATION: HMGB1 peptide

<400> SEQUENCE: 91

Val Val Lys Ala Glu Lys Ser Lys Lys Lys Glu Glu Glu Glu
1               5                   10                  15

<210> SEQ ID NO 92
<211> LENGTH: 15
<212> TYPE: PRT
<213> ORGANISM: Artificial Sequence
<220> FEATURE:
<223> OTHER INFORMATION: HMGB1 peptide

<400> SEQUENCE: 92

Lys Ala Glu Lys Ser Lys Lys Lys Lys Glu Glu Glu Glu Asp Glu
1               5                   10                  15

<210> SEQ ID NO 93
<211> LENGTH: 15
<212> TYPE: PRT
<213> ORGANISM: Artificial Sequence
<220> FEATURE:
<223> OTHER INFORMATION: HMGB1 peptide

<400> SEQUENCE: 93

Glu Lys Ser Lys Lys Lys Lys Glu Glu Glu Glu Asp Glu Glu Asp
1               5                   10                  15

<210> SEQ ID NO 94
<211> LENGTH: 15
<212> TYPE: PRT
<213> ORGANISM: Artificial Sequence
<220> FEATURE:
<223> OTHER INFORMATION: HMGB1 peptide

<400> SEQUENCE: 94

Ser Lys Lys Lys Lys Glu Glu Glu Glu Asp Glu Glu Asp Glu Glu
1               5                   10                  15

<210> SEQ ID NO 95
<211> LENGTH: 15
<212> TYPE: PRT
<213> ORGANISM: Artificial Sequence
<220> FEATURE:
<223> OTHER INFORMATION: HMGB1 peptide

<400> SEQUENCE: 95

Lys Lys Lys Glu Glu Glu Glu Asp Glu Glu Asp Glu Glu Asp Glu
1               5                   10                  15

<210> SEQ ID NO 96
<211> LENGTH: 15
<212> TYPE: PRT
<213> ORGANISM: Artificial Sequence
<220> FEATURE:
<223> OTHER INFORMATION: HMGB1 peptide

<400> SEQUENCE: 96

Lys Glu Glu Glu Glu Asp Glu Glu Asp Glu Glu Asp Glu Glu Glu
1               5                   10                  15

<210> SEQ ID NO 97
```

```
<211> LENGTH: 15
<212> TYPE: PRT
<213> ORGANISM: Artificial Sequence
<220> FEATURE:
<223> OTHER INFORMATION: HMGB1 peptide

<400> SEQUENCE: 97

Glu Glu Glu Asp Glu Glu Asp Glu Glu Asp Glu Glu Glu Glu Glu
1               5                   10                  15

<210> SEQ ID NO 98
<211> LENGTH: 15
<212> TYPE: PRT
<213> ORGANISM: Artificial Sequence
<220> FEATURE:
<223> OTHER INFORMATION: HMGB1 peptide

<400> SEQUENCE: 98

Glu Asp Glu Glu Asp Glu Glu Asp Glu Glu Glu Glu Glu Asp Glu
1               5                   10                  15

<210> SEQ ID NO 99
<211> LENGTH: 15
<212> TYPE: PRT
<213> ORGANISM: Artificial Sequence
<220> FEATURE:
<223> OTHER INFORMATION: HMGB1 peptide

<400> SEQUENCE: 99

Glu Glu Asp Glu Glu Asp Glu Glu Glu Glu Glu Asp Glu Glu Asp
1               5                   10                  15

<210> SEQ ID NO 100
<211> LENGTH: 15
<212> TYPE: PRT
<213> ORGANISM: Artificial Sequence
<220> FEATURE:
<223> OTHER INFORMATION: HMGB1 peptide

<400> SEQUENCE: 100

Asp Glu Glu Asp Glu Glu Glu Glu Glu Asp Glu Glu Asp Glu Asp
1               5                   10                  15

<210> SEQ ID NO 101
<211> LENGTH: 15
<212> TYPE: PRT
<213> ORGANISM: Artificial Sequence
<220> FEATURE:
<223> OTHER INFORMATION: HMGB1 peptide

<400> SEQUENCE: 101

Glu Asp Glu Glu Glu Glu Glu Asp Glu Glu Asp Glu Asp Glu Glu
1               5                   10                  15

<210> SEQ ID NO 102
<211> LENGTH: 15
<212> TYPE: PRT
<213> ORGANISM: Artificial Sequence
<220> FEATURE:
<223> OTHER INFORMATION: HMGB1 peptide

<400> SEQUENCE: 102

Glu Glu Glu Glu Glu Asp Glu Glu Asp Glu Asp Glu Glu Glu Asp
1               5                   10                  15

<210> SEQ ID NO 103
<211> LENGTH: 15
```

```
<212> TYPE: PRT
<213> ORGANISM: Artificial Sequence
<220> FEATURE:
<223> OTHER INFORMATION: HMGB1 peptide

<400> SEQUENCE: 103

Glu Glu Glu Asp Glu Glu Asp Glu Asp Glu Glu Glu Asp Asp Asp
1               5                   10                  15

<210> SEQ ID NO 104
<211> LENGTH: 15
<212> TYPE: PRT
<213> ORGANISM: Artificial Sequence
<220> FEATURE:
<223> OTHER INFORMATION: HMGB1 peptide

<400> SEQUENCE: 104

Glu Asp Glu Glu Asp Glu Asp Glu Glu Glu Asp Asp Asp Asp Glu
1               5                   10                  15

<210> SEQ ID NO 105
<211> LENGTH: 17
<212> TYPE: PRT
<213> ORGANISM: Artificial Sequence
<220> FEATURE:
<223> OTHER INFORMATION: HMGB1 peptide

<400> SEQUENCE: 105

Asp Pro Lys Lys Pro Arg Gly Lys Met Ser Ser Tyr Ala Phe Phe Val
1               5                   10                  15

Gln

<210> SEQ ID NO 106
<211> LENGTH: 15
<212> TYPE: PRT
<213> ORGANISM: Artificial Sequence
<220> FEATURE:
<223> OTHER INFORMATION: HMGB1 peptide

<400> SEQUENCE: 106

Met Ser Ser Tyr Ala Phe Phe Val Gln Thr Cys Arg Glu Glu His
1               5                   10                  15

<210> SEQ ID NO 107
<211> LENGTH: 15
<212> TYPE: PRT
<213> ORGANISM: Artificial Sequence
<220> FEATURE:
<223> OTHER INFORMATION: HMGB1 peptide

<400> SEQUENCE: 107

His Lys Lys Lys His Pro Asp Ala Ser Val Asn Phe Ser Glu Phe
1               5                   10                  15

<210> SEQ ID NO 108
<211> LENGTH: 19
<212> TYPE: PRT
<213> ORGANISM: Artificial Sequence
<220> FEATURE:
<223> OTHER INFORMATION: HMGB1 peptide

<400> SEQUENCE: 108

Lys Ala Asp Lys Ala Arg Tyr Glu Arg Glu Met Lys Thr Tyr Ile Pro
1               5                   10                  15

Pro Lys Gly
```

-continued

```
<210> SEQ ID NO 109
<211> LENGTH: 19
<212> TYPE: PRT
<213> ORGANISM: Artificial Sequence
<220> FEATURE:
<223> OTHER INFORMATION: HMGB1 peptide

<400> SEQUENCE: 109

Asp Pro Asn Ala Pro Lys Arg Pro Pro Ser Ala Phe Phe Leu Phe Cys
1               5                   10                  15

Ser Glu Tyr

<210> SEQ ID NO 110
<211> LENGTH: 15
<212> TYPE: PRT
<213> ORGANISM: Artificial Sequence
<220> FEATURE:
<223> OTHER INFORMATION: HMGB1 peptide

<400> SEQUENCE: 110

Tyr Arg Pro Lys Ile Lys Gly Glu His Pro Gly Leu Ser Ile Gly
1               5                   10                  15

<210> SEQ ID NO 111
<211> LENGTH: 19
<212> TYPE: PRT
<213> ORGANISM: Artificial Sequence
<220> FEATURE:
<223> OTHER INFORMATION: HMGB1 peptide

<400> SEQUENCE: 111

Leu Lys Glu Lys Tyr Glu Lys Asp Ile Ala Ala Tyr Arg Ala Lys Gly
1               5                   10                  15

Lys Pro Asp

<210> SEQ ID NO 112
<211> LENGTH: 45
<212> TYPE: DNA
<213> ORGANISM: Artificial Sequence
<220> FEATURE:
<223> OTHER INFORMATION: Wt HMGB1 1-214 (HMGB1A-s001) pNIC-CTHF Forward
     LIC cloning primer

<400> SEQUENCE: 112
ttaagaagga gatatactat gggcaaagga gatcctaaga agccg                     45

<210> SEQ ID NO 113
<211> LENGTH: 45
<212> TYPE: DNA
<213> ORGANISM: Artificial Sequence
<220> FEATURE:
<223> OTHER INFORMATION: Wt HMGB1 1-214 (HMGB1A-s001) pNIC-CTHF Reverse
     LIC cloning primer

<400> SEQUENCE: 113
ttaagaagga gatatactat gggcaaagga gatcctaaga agccg                     45

<210> SEQ ID NO 114
<211> LENGTH: 645
<212> TYPE: DNA
<213> ORGANISM: Artificial Sequence
<220> FEATURE:
<223> OTHER INFORMATION: Wt HMGB1 1-214 (HMGB1A-s001) pNIC-CTHF DNA
     sequence cloned into the vector

<400> SEQUENCE: 114
```
atgggcaaag gagatcctaa gaagccgaga ggcaaaatgt catcatatgc attttttgtg          60
caaacttgtc gggaggagca taagaagaag cacccagatg cttcagtcaa cttctcagag         120
ttttctaaga agtgctcaga gaggtggaag accatgtctg ctaaagagaa aggaaaattt         180
gaagatatgg caaaagcgga caaggcccgt tatgaaagaa aaatgaaaac ctatatccct         240
cccaaagggg agacaaaaaa gaagttcaag gatcccaatg cacccaagag gcctccttcg         300
gccttcttcc tcttctgctc tgagtatcgc ccaaaaatca aaggagaaca tcctggcctg         360
tccattggtg atgttgcgaa gaaactggga gagatgtgga ataacactgc tgcagatgac         420
aagcagcctt atgaaaagaa ggctgcgaag ctgaaggaa aatacgaaaa ggatattgct         480
gcatatcgag ctaaaggaaa gcctgatgca gcaaaaaagg gagttgtcaa ggctgaaaaa         540
agcaagaaaa agaaggaaga ggaggaagat gaggaagatg aagaggatga ggaggaggag         600
gaagatgaag aagatgaaga tgaagaagaa gatgatgatg atgaa                         645

<210> SEQ ID NO 115
<211> LENGTH: 522
<212> TYPE: DNA
<213> ORGANISM: Artificial Sequence
<220> FEATURE:
<223> OTHER INFORMATION: dBB12L pNIC-CTHF DNA sequence cloned into the
      vector

<400> SEQUENCE: 115
atgaaggacc cgaacgcgcc gaagcgccca ccgtccgctt tttttctgtt ctgtagcgaa          60
taccgtccaa aaattaaagg tgaacaccca ggcctttcta tcggcgatgt tgcgaaaaaa         120
ctgggtgaga tgtggaacaa tactgcagca gatgataaac aaccgtatga aaagaaagcg         180
gcgaagctga agaaaaata cgaaaaagat atcgctgcgt atcgggccaa ggggaaaccg         240
gatgcggcga aaaaggcgt caaggatccc aacgcgccga aacgtccacc gagcgcgttc         300
tttctgtttt gttcagaata ccgcccgaaa attaaaggcg aacacccggg cctttcgatt         360
ggtgacgttg cgaaaaaact ggcgaaatg tggaataaca cggcagcgga cgataagcag         420
ccttatgaaa aaaagccgc caaacttaaa gaaaaatacg agaaagacat tgcagcttac         480
cgcgcgaagg gtaaacctga cgctgcaaaa aaaggtgttt aa                           522

<210> SEQ ID NO 116
<211> LENGTH: 45
<212> TYPE: DNA
<213> ORGANISM: Artificial Sequence
<220> FEATURE:
<223> OTHER INFORMATION: 3S-HMGB1 1-214 (HMGB1A-s002) pNIC-CTHF Forward
      LIC cloning primer

<400> SEQUENCE: 116
ttaagaagga gatatactat gggcaaagga gatcctaaga agccg                          45

<210> SEQ ID NO 117
<211> LENGTH: 45
<212> TYPE: DNA
<213> ORGANISM: Artificial Sequence
<220> FEATURE:
<223> OTHER INFORMATION: 3S-HMGB1 1-214 (HMGB1A-s002) pNIC-CTHF Reverse
      LIC cloning primer

<400> SEQUENCE: 117
ttaagaagga gatatactat gggcaaagga gatcctaaga agccg                          45

-continued

```
<210> SEQ ID NO 118
<211> LENGTH: 645
<212> TYPE: DNA
<213> ORGANISM: Artificial Sequence
<220> FEATURE:
<223> OTHER INFORMATION: 3S-HMGB1 1-214 (HMGB1A-s002) pNIC-CTHF DNA
      sequence cloned into the vector

<400> SEQUENCE: 118
atgggcaaag gagatcctaa gaagccgaga ggcaaaatgt catcatatgc attttttgtg      60
caaactagtc gggaggagca taagaagaag cacccagatg cttcagtcaa cttctcagag     120
ttttctaaga agagctcaga gaggtggaag accatgtctg ctaaagagaa aggaaaattt     180
gaagatatgg caaaagcgga caaggcccgt tatgaaagag aaatgaaaac ctatatccct     240
cccaaagggg agacaaaaaa gaagttcaag gatcccaatg cacccaagag gcctccttcg     300
gccttcttcc tcttcagctc tgagtatcgc ccaaaaatca aggagaaca tcctggcctg     360 tccattggtg atgttgcgaa gaaactggga gagatgtgga ataacactgc tgcagatgac     420
aagcagcctt atgaaaagaa ggctgcgaag ctgaaggaaa aatacgaaaa ggatattgct     480
gcatatcgag ctaaaggaaa gcctgatgca gcaaaaaagg gagttgtcaa ggctgaaaaa     540
agcaagaaaa agaaggaaga ggaggaagat gaggaagatg aagaggatga ggaggaggag     600
gaagatgaag aagatgaaga tgaagaagaa gatgatgatg atgaa                     645

<210> SEQ ID NO 119
<211> LENGTH: 45
<212> TYPE: DNA
<213> ORGANISM: Artificial Sequence
<220> FEATURE:
<223> OTHER INFORMATION: Wt HMGB1 1-184 pNIC-CTHF Forward LIC cloning
      primer

<400> SEQUENCE: 119
ttaagaagga gatatactat gggcaaagga gatcctaaga agccg                      45

<210> SEQ ID NO 120
<211> LENGTH: 50
<212> TYPE: DNA
<213> ORGANISM: Artificial Sequence
<220> FEATURE:
<223> OTHER INFORMATION: Wt HMGB1 1-184 pNIC-CTHF Reverse LIC cloning
      primer

<400> SEQUENCE: 120
tatccacctt tactgctttc atcatcatca tcttcttctt catcttcatc                 50

<210> SEQ ID NO 121
<211> LENGTH: 555
<212> TYPE: DNA
<213> ORGANISM: Artificial Sequence
<220> FEATURE:
<223> OTHER INFORMATION: Wt HMGB1 1-184 pNIC-CTHF DNA sequence cloned
      into the vector

<400> SEQUENCE: 121
atgggcaaag gagatcctaa gaagccgaga ggcaaaatgt catcatatgc attttttgtg      60
caaacttgtc gggaggagca taagaagaag cacccagatg cttcagtcaa cttctcagag     120
ttttctaaga agtgctcaga gaggtggaag accatgtctg ctaaagagaa aggaaaattt     180
gaagatatgg caaaagcgga caaggcccgt tatgaaagag aaatgaaaac ctatatccct     240
cccaaagggg agacaaaaaa gaagttcaag gatcccaatg cacccaagag gcctccttcg     300
```

-continued

```
gccttcttcc tcttctgctc tgagtatcgc ccaaaaatca aaggagaaca tcctggcctg    360
tccattggtg atgttgcgaa gaaactggga gagatgtgga ataacactgc tgcagatgac    420
aagcagcctt atgaaagaa ggctgcgaag ctgaaggaaa aatacgaaaa ggatattgct     480
gcatatcgag ctaaaggaaa gcctgatgca gcaaaaaagg gagttgtcaa ggctgaaaaa    540
agcaagaaaa agaag                                                      555
```

<210> SEQ ID NO 122
<211> LENGTH: 45
<212> TYPE: DNA
<213> ORGANISM: Artificial Sequence
<220> FEATURE:
<223> OTHER INFORMATION: Wt HMGB1 1-164 pNIC-CTHF Forward LIC cloning
      primer

<400> SEQUENCE: 122

```
ttaagaagga gatatactat gggcaaagga gatcctaaga agccg                      45
```

<210> SEQ ID NO 123
<211> LENGTH: 33
<212> TYPE: DNA
<213> ORGANISM: Artificial Sequence
<220> FEATURE:
<223> OTHER INFORMATION: Wt HMGB1 1-164 pNIC-CTHF Reverse LIC cloning
      primer

<400> SEQUENCE: 123

```
tacttccaat ccatgccgag aggcaaaatg tca                                   33
```

<210> SEQ ID NO 124
<211> LENGTH: 495
<212> TYPE: DNA
<213> ORGANISM: Artificial Sequence
<220> FEATURE:
<223> OTHER INFORMATION: Wt HMGB1 1-164 pNIC-CTHF DNA sequence cloned
      into the vector

<400> SEQUENCE: 124

```
atgggcaaag gagatcctaa gaagccgaga ggcaaaatgt catcatatgc attttttgtg      60
caaacttgtc gggaggagca taagaagaag cacccagatg cttcagtcaa cttctcagag    120
ttttctaaga agtgctcaga gaggtggaag accatgtctg ctaaagagaa aggaaaattt    180
gaagatatgg caaaagcgga caaggcccgt tatgaaagag aaatgaaaac ctatatccct    240
cccaaagggg agacaaaaaa gaagttcaag gatcccaatg cacccaagag gcctccttcg    300
gccttcttcc tcttctgctc tgagtatcgc ccaaaaatca aaggagaaca tcctggcctg    360
tccattggtg atgttgcgaa gaaactggga gagatgtgga ataacactgc tgcagatgac    420
aagcagcctt atgaaagaa ggctgcgaag ctgaaggaaa aatacgaaaa ggatattgct     480
gcatatcgag ctaaa                                                      495
```

<210> SEQ ID NO 125
<211> LENGTH: 37
<212> TYPE: DNA
<213> ORGANISM: Artificial Sequence
<220> FEATURE:
<223> OTHER INFORMATION: HMGB1 1-88, biotinylated pNIC-Bio3 Forward LIC
      cloning primer

<400> SEQUENCE: 125

```
tacttccaat ccatgggcaa aggagatcct aagaagc                               37
```

```
<210> SEQ ID NO 126
<211> LENGTH: 39
<212> TYPE: DNA
<213> ORGANISM: Artificial Sequence
<220> FEATURE:
<223> OTHER INFORMATION: HMGB1 1-88, biotinylated pNIC-Bio3 Reverse LIC
      cloning primer

<400> SEQUENCE: 126
tatccacctt tactgctgaa cttctttttt gtctcccct                              39

<210> SEQ ID NO 127
<211> LENGTH: 333
<212> TYPE: DNA
<213> ORGANISM: Artificial Sequence
<220> FEATURE:
<223> OTHER INFORMATION: HMGB1 1-88, biotinylated pNIC-Bio3 DNA sequence
      cloned into the vector

<400> SEQUENCE: 127
atgcaccatc atcatcatca ttcttctggt gtagatctgg gtaccgagaa cctgtacttc      60
caatccatgg gcaaaggaga tcctaagaag ccgagaggca aaatgtcatc atatgcattt     120
tttgtgcaaa cttgtcggga ggagcataag aagaagcacc cagatgcttc agtcaacttc     180
tcagagtttt ctaagaagtg ctcagagagg tggaagacca tgtctgctaa agagaaagga     240
aaatttgaag atatggcaaa agcggacaag gcccgttatg aaagagaaat gaaaacctat     300
atccctccca aaggggagac aaaaaagaag ttc                                   333

<210> SEQ ID NO 128
<211> LENGTH: 33
<212> TYPE: DNA
<213> ORGANISM: Artificial Sequence
<220> FEATURE:
<223> OTHER INFORMATION: HMGB1 89-174, biotinylated pNIC-Bio3 Forward
      LIC cloning primer

<400> SEQUENCE: 128
tacttccaat ccatgaagga tcccaatgca ccc                                   33

<210> SEQ ID NO 129
<211> LENGTH: 39
<212> TYPE: DNA
<213> ORGANISM: Artificial Sequence
<220> FEATURE:
<223> OTHER INFORMATION: HMGB1 89-174, biotinylated pNIC-Bio3 Reverse
      LIC cloning primer

<400> SEQUENCE: 129
tatccacctt tactgctaac tccctttttt gctgcatca                              39

<210> SEQ ID NO 130
<211> LENGTH: 327
<212> TYPE: DNA
<213> ORGANISM: Artificial Sequence
<220> FEATURE:
<223> OTHER INFORMATION: HMGB1 89-174, biotinylated pNIC-Bio3 DNA
      sequence cloned into the vector

<400> SEQUENCE: 130
atgcaccatc atcatcatca ttcttctggt gtagatctgg gtaccgagaa cctgtacttc      60
caatccatga aggatcccaa tgcacccaag aggcctcctt cggccttctt cctcttctgc     120
tctgagtatc gcccaaaaat caaaggagaa catcctggcc tgtccattgg tgatgttgcg     180
aagaaactgg gagagatgtg gaataacact gctgcagatg acaagcagcc ttatgaaaag     240
```

-continued

```
aaggctgcga agctgaagga aaaatacgaa aaggatattg ctgcatatcg agctaaagga      300
aagcctgatg cagcaaaaaa gggagtt                                         327

<210> SEQ ID NO 131
<211> LENGTH: 45
<212> TYPE: DNA
<213> ORGANISM: Artificial Sequence
<220> FEATURE:
<223> OTHER INFORMATION: HMGB1 1-88 pNIC-CTHF Forward LIC cloning primer

<400> SEQUENCE: 131
ttaagaagga gatatactat gggcaaagga gatcctaaga agccg                      45

<210> SEQ ID NO 132
<211> LENGTH: 44
<212> TYPE: DNA
<213> ORGANISM: Artificial Sequence
<220> FEATURE:
<223> OTHER INFORMATION: HMGB1 1-88 pNIC-CTHF Reverse LIC cloning primer

<400> SEQUENCE: 132
gattggaagt agaggttctc tgcgaacttc ttttttgtct cccc                       44

<210> SEQ ID NO 133
<211> LENGTH: 267
<212> TYPE: DNA
<213> ORGANISM: Artificial Sequence
<220> FEATURE:
<223> OTHER INFORMATION: HMGB1 1-88 pNIC-CTHF DNA sequence cloned into
      the vector

<400> SEQUENCE: 133
atgggcaaag gagatcctaa gaagccgaga ggcaaaatgt catcatatgc attttttgtg       60
caaacttgtc gggaggagca taagaagaag cacccagatg cttcagtcaa cttctcagag      120
ttttctaaga agtgctcaga gaggtggaag accatgtctg ctaaagagaa aggaaaattt      180
gaagatatgg caaaagcgga caaggcccgt tatgaaagag aaatgaaaac ctatatccct      240
cccaaagggg agacaaaaaa gaagttc                                         267

<210> SEQ ID NO 134
<211> LENGTH: 44
<212> TYPE: DNA
<213> ORGANISM: Artificial Sequence
<220> FEATURE:
<223> OTHER INFORMATION: HMGB1 89-174 pNIC-CTHF Forward LIC cloning
      primer

<400> SEQUENCE: 134
ttaagaagga gatatactat gaaggatccc aatgcaccca agag                       44

<210> SEQ ID NO 135
<211> LENGTH: 42
<212> TYPE: DNA
<213> ORGANISM: Artificial Sequence
<220> FEATURE:
<223> OTHER INFORMATION: HMGB1 89-174 pNIC-CTHF Reverse LIC cloning
      primer

<400> SEQUENCE: 135
gattggaagt agaggttctc tgcaactccc ttttttgctg ca                         42

<210> SEQ ID NO 136
<211> LENGTH: 261
```

-continued

```
<212> TYPE: DNA
<213> ORGANISM: Artificial Sequence
<220> FEATURE:
<223> OTHER INFORMATION: HMGB1 89-174 pNIC-CTHF DNA sequence cloned into
      the vector

<400> SEQUENCE: 136
atgaaggatc ccaatgcacc caagaggcct ccttcggcct tcttcctctt ctgctctgag        60
tatcgcccaa aaatcaaagg agaacatcct ggcctgtcca ttggtgatgt tgcgaagaaa       120
ctgggagaga tgtggaataa cactgctgca gatgacaagc agccttatga aaagaaggct       180
gcgaagctga aggaaaaata cgaaaaggat attgctgcat atcgagctaa aggaaagcct       240
gatgcagcaa aaaagggagt t                                                 261

<210> SEQ ID NO 137
<211> LENGTH: 33
<212> TYPE: DNA
<213> ORGANISM: Artificial Sequence
<220> FEATURE:
<223> OTHER INFORMATION: HMGB1 8-78, biotinylated pNIC-Bio3 Forward LIC
      cloning primer

<400> SEQUENCE: 137
tacttccaat ccatgccgag aggcaaaatg tca                                     33

<210> SEQ ID NO 138
<211> LENGTH: 49
<212> TYPE: DNA
<213> ORGANISM: Artificial Sequence
<220> FEATURE:
<223> OTHER INFORMATION: HMGB1 8-78, biotinylated pNIC-Bio3 Reverse LIC
      cloning primer

<400> SEQUENCE: 138
tatccacctt tactgctgat ataggttttc atttctcttt cataacggg                    49

<210> SEQ ID NO 139
<211> LENGTH: 282
<212> TYPE: DNA
<213> ORGANISM: Artificial Sequence
<220> FEATURE:
<223> OTHER INFORMATION: HMGB1 8-78, biotinylated pNIC-Bio3 DNA sequence
      cloned into the vector

<400> SEQUENCE: 139
atgcaccatc atcatcatca ttcttctggt gtagatctgg gtaccgagaa cctgtacttc        60
caatccatgc cgagaggcaa aatgtcatca tatgcatttt ttgtgcaaac ttgtcgggag       120
gagcataaga agaagcaccc agatgcttca gtcaacttct cagagttttc taagaagtgc       180
tcagagaggt ggaagaccat gtctgctaaa gagaaaggaa aatttgaaga tatggcaaaa       240
gcggacaagg cccgttatga aagagaaatg aaaacctata tc                          282

<210> SEQ ID NO 140
<211> LENGTH: 33
<212> TYPE: DNA
<213> ORGANISM: Artificial Sequence
<220> FEATURE:
<223> OTHER INFORMATION: HMGB1 94-162, biotinylated pNIC-Bio3 Forward
      LIC cloning primer

<400> SEQUENCE: 140
tacttccaat ccatgcccaa gaggcctcct tcg                                     33
```

```
<210> SEQ ID NO 141
<211> LENGTH: 42
<212> TYPE: DNA
<213> ORGANISM: Artificial Sequence
<220> FEATURE:
<223> OTHER INFORMATION: HMGB1 94-162, biotinylated pNIC-Bio3 Reverse
      LIC cloning primer

<400> SEQUENCE: 141
tatccacctt tactgcttcg atatgcagca atatcctttt cg                           42

<210> SEQ ID NO 142
<211> LENGTH: 276
<212> TYPE: DNA
<213> ORGANISM: Artificial Sequence
<220> FEATURE:
<223> OTHER INFORMATION: HMGB1 94-162, biotinylated pNIC-Bio3 DNA
      sequence cloned into the vector

<400> SEQUENCE: 142
atgcaccatc atcatcatca ttcttctggt gtagatctgg gtaccgagaa cctgtacttc         60
caatccatgc ccaagaggcc tccttcggcc ttcttcctct tctgctctga gtatcgccca        120
aaaatcaaag gagaacatcc tggcctgtcc attggtgatg ttgcgaagaa actgggagag        180
atgtggaata acactgctgc agatgacaag cagccttatg aaaagaaggc tgcgaagctg        240
aaggaaaaat acgaaaagga tattgctgca tatcga                                  276

<210> SEQ ID NO 143
<211> LENGTH: 43
<212> TYPE: DNA
<213> ORGANISM: Artificial Sequence
<220> FEATURE:
<223> OTHER INFORMATION: Wt CXCL12 with SUMO pDsbC-HT-CBio Forward LIC
      cloning primer

<400> SEQUENCE: 143
tacttccaat ccatgtctga ccaggaggca aaaccttcaa ctg                          43

<210> SEQ ID NO 144
<211> LENGTH: 45
<212> TYPE: DNA
<213> ORGANISM: Artificial Sequence
<220> FEATURE:
<223> OTHER INFORMATION: Wt CXCL12 with SUMO pDsbC-HT-CBio Reverse LIC
      cloning primer

<400> SEQUENCE: 144
tatccacctt tactgtcatt acttgtttaa agctttctcc aggta                        45

<210> SEQ ID NO 145
<211> LENGTH: 495
<212> TYPE: DNA
<213> ORGANISM: Artificial Sequence
<220> FEATURE:
<223> OTHER INFORMATION: Wt CXCL12 with SUMO pDsbC-HT-CBio DNA sequence
      cloned into the vector

<400> SEQUENCE: 145
atgtctgacc aggaggcaaa accttcaact gaggacttgg gggataagaa ggaaggtgaa         60
tatattaaac tcaaagtcat tggacaggat agcagtgaga ttcacttcaa agtgaaaatg        120
acaacacatc tcaagaaact caaagaatca tactgtcaaa gacagggtgt tccaatgaat        180
tcactcaggt ttctctttga gggtcagaga attgctgata tcatactcc aaaagaactg         240 ggaatggagg aagaagatgt gattgaagtt taccaggagc aaacgggagg taagcccgtc        300
```

-continued

```
agcctgagct acagatgccc atgccgattc ttcgaaagcc atgttgccag agccaacgtc      360
aagcatctca aaattctcaa cactccaaac tgtgcccttc agattgtagc ccggctgaag      420
aacaacaaca gacaagtgtg cattgacccg aagctaaagt ggattcagga gtacctggag      480
aaagctttaa acaag                                                       495
```

```
<210> SEQ ID NO 146
<211> LENGTH: 28
<212> TYPE: DNA
<213> ORGANISM: Artificial Sequence
<220> FEATURE:
<223> OTHER INFORMATION: HMGB1WTLICF

<400> SEQUENCE: 146
atgggcaaag gcgatccgaa aaaaccgc                                          28
```

```
<210> SEQ ID NO 147
<211> LENGTH: 30
<212> TYPE: DNA
<213> ORGANISM: Artificial Sequence
<220> FEATURE:
<223> OTHER INFORMATION: HMGB1C106S

<400> SEQUENCE: 147
gcgatactca gagctgaaga ggaagaaggc                                        30
```

```
<210> SEQ ID NO 148
<211> LENGTH: 29
<212> TYPE: DNA
<213> ORGANISM: Artificial Sequence
<220> FEATURE:
<223> OTHER INFORMATION: HMGB1C45S

<400> SEQUENCE: 148
ttttctaaga agagctcaga gaggtggaa                                         29
```

```
<210> SEQ ID NO 149
<211> LENGTH: 28
<212> TYPE: DNA
<213> ORGANISM: Artificial Sequence
<220> FEATURE:
<223> OTHER INFORMATION: HMGB1WTLICR

<400> SEQUENCE: 149
ttattcatca tcatcatctt cttcttca                                          28
```

```
<210> SEQ ID NO 150
<211> LENGTH: 28
<212> TYPE: DNA
<213> ORGANISM: Artificial Sequence
<220> FEATURE:
<223> OTHER INFORMATION: HMGB1C23S

<400> SEQUENCE: 150
tttttgtgca gaccagccgc gaagaaca                                          28
```

```
<210> SEQ ID NO 151
<211> LENGTH: 215
<212> TYPE: PRT
<213> ORGANISM: Artificial Sequence
<220> FEATURE:
<223> OTHER INFORMATION: Wt HMGB1 1-214 (HMGB1A-s001) pNIC-CTHF

<400> SEQUENCE: 151
```

-continued

```
Met Gly Lys Gly Asp Pro Lys Lys Pro Arg Gly Lys Met Ser Ser Tyr
1               5                   10                  15

Ala Phe Phe Val Gln Thr Cys Arg Glu Glu His Lys Lys Lys His Pro
            20                  25                  30

Asp Ala Ser Val Asn Phe Ser Glu Phe Ser Lys Lys Cys Ser Glu Arg
            35                  40                  45

Trp Lys Thr Met Ser Ala Lys Glu Lys Gly Lys Phe Glu Asp Met Ala
    50                  55                  60

Lys Ala Asp Lys Ala Arg Tyr Glu Arg Glu Met Lys Thr Tyr Ile Pro
65                  70                  75                  80

Pro Lys Gly Glu Thr Lys Lys Lys Phe Lys Asp Pro Asn Ala Pro Lys
                85                  90                  95

Arg Pro Pro Ser Ala Phe Phe Leu Phe Cys Ser Glu Tyr Arg Pro Lys
            100                 105                 110

Ile Lys Gly Glu His Pro Gly Leu Ser Ile Gly Asp Val Ala Lys Lys
            115                 120                 125

Leu Gly Glu Met Trp Asn Asn Thr Ala Ala Asp Asp Lys Gln Pro Tyr
    130                 135                 140

Glu Lys Lys Ala Ala Lys Leu Lys Glu Lys Tyr Glu Lys Asp Ile Ala
145                 150                 155                 160

Ala Tyr Arg Ala Lys Gly Lys Pro Asp Ala Ala Lys Lys Gly Val Val
            165                 170                 175

Lys Ala Glu Lys Ser Lys Lys Lys Glu Glu Glu Glu Asp Glu Glu
            180                 185                 190

Asp Glu Glu Asp Glu Glu Glu Glu Asp Glu Glu Asp Glu Asp Glu
            195                 200                 205

Glu Glu Asp Asp Asp Asp Glu
    210                 215
```

```
<210> SEQ ID NO 152
<211> LENGTH: 222
<212> TYPE: PRT
<213> ORGANISM: Artificial Sequence
<220> FEATURE:
<223> OTHER INFORMATION: Wt HMGB1 1-214 (HMGB1A-s001) pNIC-CTHF purified
      protein sequence

<400> SEQUENCE: 152
```

```
Met Gly Lys Gly Asp Pro Lys Lys Pro Arg Gly Lys Met Ser Ser Tyr
1               5                   10                  15

Ala Phe Phe Val Gln Thr Cys Arg Glu Glu His Lys Lys Lys His Pro
            20                  25                  30

Asp Ala Ser Val Asn Phe Ser Glu Phe Ser Lys Lys Cys Ser Glu Arg
            35                  40                  45

Trp Lys Thr Met Ser Ala Lys Glu Lys Gly Lys Phe Glu Asp Met Ala
    50                  55                  60

Lys Ala Asp Lys Ala Arg Tyr Glu Arg Glu Met Lys Thr Tyr Ile Pro
65                  70                  75                  80

Pro Lys Gly Glu Thr Lys Lys Lys Phe Lys Asp Pro Asn Ala Pro Lys
                85                  90                  95

Arg Pro Pro Ser Ala Phe Phe Leu Phe Cys Ser Glu Tyr Arg Pro Lys
            100                 105                 110

Ile Lys Gly Glu His Pro Gly Leu Ser Ile Gly Asp Val Ala Lys Lys
            115                 120                 125

Leu Gly Glu Met Trp Asn Asn Thr Ala Ala Asp Asp Lys Gln Pro Tyr
    130                 135                 140
```

-continued

```
Glu Lys Lys Ala Ala Lys Leu Lys Glu Lys Tyr Glu Lys Asp Ile Ala
145             150                 155                 160

Ala Tyr Arg Ala Lys Gly Lys Pro Asp Ala Ala Lys Lys Gly Val Val
                165                 170                 175

Lys Ala Glu Lys Ser Lys Lys Lys Glu Glu Glu Glu Asp Glu Glu
            180                 185                 190

Asp Glu Glu Asp Glu Glu Glu Glu Glu Asp Glu Glu Asp Glu Asp Glu
        195                 200                 205

Glu Glu Asp Asp Asp Asp Glu Ala Glu Asn Leu Tyr Phe Gln
    210                 215                 220

<210> SEQ ID NO 153
<211> LENGTH: 173
<212> TYPE: PRT
<213> ORGANISM: Artificial Sequence
<220> FEATURE:
<223> OTHER INFORMATION: dBB12L pNIC-CTHF

<400> SEQUENCE: 153

Met Lys Asp Pro Asn Ala Pro Lys Arg Pro Pro Ser Ala Phe Phe Leu
1               5                   10                  15

Phe Cys Ser Glu Tyr Arg Pro Lys Ile Lys Gly Glu His Pro Gly Leu
                20                  25                  30

Ser Ile Gly Asp Val Ala Lys Lys Leu Gly Glu Met Trp Asn Asn Thr
            35                  40                  45

Ala Ala Asp Asp Lys Gln Pro Tyr Glu Lys Lys Ala Ala Lys Leu Lys
        50                  55                  60

Glu Lys Tyr Glu Lys Asp Ile Ala Ala Tyr Arg Ala Lys Gly Lys Pro
65                  70                  75                  80

Asp Ala Ala Lys Lys Gly Val Lys Asp Pro Asn Ala Pro Lys Arg Pro
                85                  90                  95

Pro Ser Ala Phe Phe Leu Phe Cys Ser Glu Tyr Arg Pro Lys Ile Lys
                100                 105                 110

Gly Glu His Pro Gly Leu Ser Ile Gly Asp Val Ala Lys Lys Leu Gly
            115                 120                 125

Glu Met Trp Asn Asn Thr Ala Ala Asp Asp Lys Gln Pro Tyr Glu Lys
        130                 135                 140

Lys Ala Ala Lys Leu Lys Glu Lys Tyr Glu Lys Asp Ile Ala Ala Tyr
145             150                 155                 160

Arg Ala Lys Gly Lys Pro Asp Ala Ala Lys Lys Gly Val
                165                 170

<210> SEQ ID NO 154
<211> LENGTH: 180
<212> TYPE: PRT
<213> ORGANISM: Artificial Sequence
<220> FEATURE:
<223> OTHER INFORMATION: dBB12L pNIC-CTHF purified protein sequence

<400> SEQUENCE: 154

Met Lys Asp Pro Asn Ala Pro Lys Arg Pro Pro Ser Ala Phe Phe Leu
1               5                   10                  15

Phe Cys Ser Glu Tyr Arg Pro Lys Ile Lys Gly Glu His Pro Gly Leu
                20                  25                  30

Ser Ile Gly Asp Val Ala Lys Lys Leu Gly Glu Met Trp Asn Asn Thr
            35                  40                  45

Ala Ala Asp Asp Lys Gln Pro Tyr Glu Lys Lys Ala Ala Lys Leu Lys
```

-continued

```
        50                  55                  60

Glu Lys Tyr Glu Lys Asp Ile Ala Ala Tyr Arg Ala Lys Gly Lys Pro
65                  70                  75                  80

Asp Ala Ala Lys Lys Gly Val Lys Asp Pro Asn Ala Pro Lys Arg Pro
                85                  90                  95

Pro Ser Ala Phe Phe Leu Phe Cys Ser Glu Tyr Arg Pro Lys Ile Lys
                100                 105                 110

Gly Glu His Pro Gly Leu Ser Ile Gly Asp Val Ala Lys Lys Leu Gly
                115                 120                 125

Glu Met Trp Asn Asn Thr Ala Ala Asp Asp Lys Gln Pro Tyr Glu Lys
                130                 135                 140

Lys Ala Ala Lys Leu Lys Glu Lys Tyr Glu Lys Asp Ile Ala Ala Tyr
145                 150                 155                 160

Arg Ala Lys Gly Lys Pro Asp Ala Ala Lys Lys Gly Val Ala Glu Asn
                165                 170                 175

Leu Tyr Phe Gln
                180

<210> SEQ ID NO 155
<211> LENGTH: 215
<212> TYPE: PRT
<213> ORGANISM: Artificial Sequence
<220> FEATURE:
<223> OTHER INFORMATION: 3S-HMGB1 1-214 (HMGB1A-s002) pNIC-CTHF

<400> SEQUENCE: 155

Met Gly Lys Gly Asp Pro Lys Lys Pro Arg Gly Lys Met Ser Ser Tyr
1                   5                   10                  15

Ala Phe Phe Val Gln Thr Ser Arg Glu Glu His Lys Lys Lys His Pro
                20                  25                  30

Asp Ala Ser Val Asn Phe Ser Glu Phe Ser Lys Lys Ser Ser Glu Arg
                35                  40                  45

Trp Lys Thr Met Ser Ala Lys Glu Lys Gly Lys Phe Glu Asp Met Ala
        50                  55                  60

Lys Ala Asp Lys Ala Arg Tyr Glu Arg Glu Met Lys Thr Tyr Ile Pro
65                  70                  75                  80

Pro Lys Gly Glu Thr Lys Lys Lys Phe Lys Asp Pro Asn Ala Pro Lys
                85                  90                  95

Arg Pro Pro Ser Ala Phe Phe Leu Phe Ser Ser Glu Tyr Arg Pro Lys
                100                 105                 110

Ile Lys Gly Glu His Pro Gly Leu Ser Ile Gly Asp Val Ala Lys Lys
                115                 120                 125

Leu Gly Glu Met Trp Asn Asn Thr Ala Ala Asp Asp Lys Gln Pro Tyr
                130                 135                 140

Glu Lys Lys Ala Ala Lys Leu Lys Glu Lys Tyr Glu Lys Asp Ile Ala
145                 150                 155                 160

Ala Tyr Arg Ala Lys Gly Lys Pro Asp Ala Ala Lys Lys Gly Val Val
                165                 170                 175

Lys Ala Glu Lys Ser Lys Lys Lys Lys Glu Glu Glu Glu Asp Glu Glu
                180                 185                 190

Asp Glu Glu Asp Glu Glu Glu Glu Glu Asp Glu Glu Asp Glu Asp Glu
                195                 200                 205

Glu Glu Asp Asp Asp Asp Glu
        210                 215
```

-continued

<210> SEQ ID NO 156
<211> LENGTH: 222
<212> TYPE: PRT
<213> ORGANISM: Artificial Sequence
<220> FEATURE:
<223> OTHER INFORMATION: 3S-HMGB1 1-214 (HMGB1A-s002) pNIC-CTHF purified
      protein sequence

<400> SEQUENCE: 156

Met Gly Lys Gly Asp Pro Lys Lys Pro Arg Gly Lys Met Ser Ser Tyr
1               5                   10                  15

Ala Phe Phe Val Gln Thr Ser Arg Glu Glu His Lys Lys Lys His Pro
                20                  25                  30

Asp Ala Ser Val Asn Phe Ser Glu Phe Ser Lys Lys Ser Ser Glu Arg
            35                  40                  45

Trp Lys Thr Met Ser Ala Lys Glu Lys Gly Lys Phe Glu Asp Met Ala
        50                  55                  60

Lys Ala Asp Lys Ala Arg Tyr Glu Arg Glu Met Lys Thr Tyr Ile Pro
65                  70                  75                  80

Pro Lys Gly Glu Thr Lys Lys Lys Phe Lys Asp Pro Asn Ala Pro Lys
                85                  90                  95

Arg Pro Pro Ser Ala Phe Phe Leu Phe Ser Ser Glu Tyr Arg Pro Lys
                100                 105                 110

Ile Lys Gly Glu His Pro Gly Leu Ser Ile Gly Asp Val Ala Lys Lys
            115                 120                 125

Leu Gly Glu Met Trp Asn Asn Thr Ala Ala Asp Asp Lys Gln Pro Tyr
        130                 135                 140

Glu Lys Lys Ala Ala Lys Leu Lys Glu Lys Tyr Glu Lys Asp Ile Ala
145                 150                 155                 160

Ala Tyr Arg Ala Lys Gly Lys Pro Asp Ala Ala Lys Lys Gly Val Val
                165                 170                 175

Lys Ala Glu Lys Ser Lys Lys Lys Glu Glu Glu Glu Asp Glu Glu
                180                 185                 190

Asp Glu Glu Asp Glu Glu Glu Glu Asp Glu Glu Asp Glu Asp Glu
            195                 200                 205

Glu Glu Asp Asp Asp Asp Glu Ala Glu Asn Leu Tyr Phe Gln
        210                 215                 220

<210> SEQ ID NO 157
<211> LENGTH: 185
<212> TYPE: PRT
<213> ORGANISM: Artificial Sequence
<220> FEATURE:
<223> OTHER INFORMATION: Wt HMGB1 1-184 pNIC-CTHF

<400> SEQUENCE: 157

Met Gly Lys Gly Asp Pro Lys Lys Pro Arg Gly Lys Met Ser Ser Tyr
1               5                   10                  15

Ala Phe Phe Val Gln Thr Cys Arg Glu Glu His Lys Lys Lys His Pro
                20                  25                  30

Asp Ala Ser Val Asn Phe Ser Glu Phe Ser Lys Lys Cys Ser Glu Arg
            35                  40                  45

Trp Lys Thr Met Ser Ala Lys Glu Lys Gly Lys Phe Glu Asp Met Ala
        50                  55                  60

Lys Ala Asp Lys Ala Arg Tyr Glu Arg Glu Met Lys Thr Tyr Ile Pro
65                  70                  75                  80

Pro Lys Gly Glu Thr Lys Lys Lys Phe Lys Asp Pro Asn Ala Pro Lys
                85                  90                  95

```
Arg Pro Pro Ser Ala Phe Phe Leu Phe Cys Ser Glu Tyr Arg Pro Lys
            100                 105                 110

Ile Lys Gly Glu His Pro Gly Leu Ser Ile Gly Asp Val Ala Lys Lys
            115                 120                 125

Leu Gly Glu Met Trp Asn Asn Thr Ala Ala Asp Asp Lys Gln Pro Tyr
            130                 135                 140

Glu Lys Lys Ala Ala Lys Leu Lys Glu Lys Tyr Glu Lys Asp Ile Ala
145                 150                 155                 160

Ala Tyr Arg Ala Lys Gly Lys Pro Asp Ala Ala Lys Lys Gly Val Val
                165                 170                 175

Lys Ala Glu Lys Ser Lys Lys Lys
            180                 185
```

<210> SEQ ID NO 158
<211> LENGTH: 192
<212> TYPE: PRT
<213> ORGANISM: Artificial Sequence
<220> FEATURE:
<223> OTHER INFORMATION: Wt HMGB1 1-184 pNIC-CTHF purified protein
      sequence

<400> SEQUENCE: 158

```
Met Gly Lys Gly Asp Pro Lys Lys Pro Arg Gly Lys Met Ser Ser Tyr
1               5                   10                  15

Ala Phe Phe Val Gln Thr Cys Arg Glu Glu His Lys Lys Lys His Pro
                20                  25                  30

Asp Ala Ser Val Asn Phe Ser Glu Phe Ser Lys Lys Cys Ser Glu Arg
            35                  40                  45

Trp Lys Thr Met Ser Ala Lys Glu Lys Gly Lys Phe Glu Asp Met Ala
            50                  55                  60

Lys Ala Asp Lys Ala Arg Tyr Glu Arg Glu Met Lys Thr Tyr Ile Pro
65                  70                  75                  80

Pro Lys Gly Glu Thr Lys Lys Lys Phe Lys Asp Pro Asn Ala Pro Lys
                85                  90                  95

Arg Pro Pro Ser Ala Phe Phe Leu Phe Cys Ser Glu Tyr Arg Pro Lys
            100                 105                 110

Ile Lys Gly Glu His Pro Gly Leu Ser Ile Gly Asp Val Ala Lys Lys
            115                 120                 125

Leu Gly Glu Met Trp Asn Asn Thr Ala Ala Asp Asp Lys Gln Pro Tyr
            130                 135                 140

Glu Lys Lys Ala Ala Lys Leu Lys Glu Lys Tyr Glu Lys Asp Ile Ala
145                 150                 155                 160

Ala Tyr Arg Ala Lys Gly Lys Pro Asp Ala Ala Lys Lys Gly Val Val
                165                 170                 175

Lys Ala Glu Lys Ser Lys Lys Lys Ala Glu Asn Leu Tyr Phe Gln
            180                 185                 190
```

<210> SEQ ID NO 159
<211> LENGTH: 165
<212> TYPE: PRT
<213> ORGANISM: Artificial Sequence
<220> FEATURE:
<223> OTHER INFORMATION: Wt HMGB1 1-164 pNIC-CTHF

<400> SEQUENCE: 159

```
Met Gly Lys Gly Asp Pro Lys Lys Pro Arg Gly Lys Met Ser Ser Tyr
1               5                   10                  15
```

```
Ala Phe Phe Val Gln Thr Cys Arg Glu Glu His Lys Lys Lys His Pro
            20              25              30

Asp Ala Ser Val Asn Phe Ser Glu Phe Ser Lys Lys Cys Ser Glu Arg
        35              40              45

Trp Lys Thr Met Ser Ala Lys Glu Lys Gly Lys Phe Glu Asp Met Ala
    50              55              60

Lys Ala Asp Lys Ala Arg Tyr Glu Arg Glu Met Lys Thr Tyr Ile Pro
65              70              75              80

Pro Lys Gly Glu Thr Lys Lys Lys Phe Lys Asp Pro Asn Ala Pro Lys
                85              90              95

Arg Pro Pro Ser Ala Phe Phe Leu Phe Cys Ser Glu Tyr Arg Pro Lys
            100             105             110

Ile Lys Gly Glu His Pro Gly Leu Ser Ile Gly Asp Val Ala Lys Lys
            115             120             125

Leu Gly Glu Met Trp Asn Asn Thr Ala Ala Asp Asp Lys Gln Pro Tyr
    130             135             140

Glu Lys Lys Ala Ala Lys Leu Lys Glu Lys Tyr Glu Lys Asp Ile Ala
145             150             155             160

Ala Tyr Arg Ala Lys
                165
```

```
<210> SEQ ID NO 160
<211> LENGTH: 172
<212> TYPE: PRT
<213> ORGANISM: Artificial Sequence
<220> FEATURE:
<223> OTHER INFORMATION: Wt HMGB1 1-164 pNIC-CTHF purified protein
      sequence

<400> SEQUENCE: 160
```

```
Met Gly Lys Gly Asp Pro Lys Lys Pro Arg Gly Lys Met Ser Ser Tyr
1               5               10              15

Ala Phe Phe Val Gln Thr Cys Arg Glu Glu His Lys Lys Lys His Pro
            20              25              30

Asp Ala Ser Val Asn Phe Ser Glu Phe Ser Lys Lys Cys Ser Glu Arg
        35              40              45

Trp Lys Thr Met Ser Ala Lys Glu Lys Gly Lys Phe Glu Asp Met Ala
    50              55              60

Lys Ala Asp Lys Ala Arg Tyr Glu Arg Glu Met Lys Thr Tyr Ile Pro
65              70              75              80

Pro Lys Gly Glu Thr Lys Lys Lys Phe Lys Asp Pro Asn Ala Pro Lys
                85              90              95

Arg Pro Pro Ser Ala Phe Phe Leu Phe Cys Ser Glu Tyr Arg Pro Lys
            100             105             110

Ile Lys Gly Glu His Pro Gly Leu Ser Ile Gly Asp Val Ala Lys Lys
            115             120             125

Leu Gly Glu Met Trp Asn Asn Thr Ala Ala Asp Asp Lys Gln Pro Tyr
    130             135             140

Glu Lys Lys Ala Ala Lys Leu Lys Glu Lys Tyr Glu Lys Asp Ile Ala
145             150             155             160

Ala Tyr Arg Ala Lys Ala Glu Asn Leu Tyr Phe Gln
                165             170
```

```
<210> SEQ ID NO 161
<211> LENGTH: 88
<212> TYPE: PRT
<213> ORGANISM: Artificial Sequence
```

```
<220> FEATURE:
<223> OTHER INFORMATION: HMGB1 1-88, biotinylated pNIC-Bio3

<400> SEQUENCE: 161

Gly Lys Gly Asp Pro Lys Lys Pro Arg Gly Lys Met Ser Ser Tyr Ala
1               5                   10                  15

Phe Phe Val Gln Thr Cys Arg Glu Glu His Lys Lys Lys His Pro Asp
            20                  25                  30

Ala Ser Val Asn Phe Ser Glu Phe Ser Lys Lys Cys Ser Glu Arg Trp
        35                  40                  45

Lys Thr Met Ser Ala Lys Glu Lys Gly Lys Phe Glu Asp Met Ala Lys
    50                  55                  60

Ala Asp Lys Ala Arg Tyr Glu Arg Glu Met Lys Thr Tyr Ile Pro Pro
65                  70                  75                  80

Lys Gly Glu Thr Lys Lys Lys Phe
                85

<210> SEQ ID NO 162
<211> LENGTH: 111
<212> TYPE: PRT
<213> ORGANISM: Artificial Sequence
<220> FEATURE:
<223> OTHER INFORMATION: HMGB1 1-88, biotinylated pNIC-Bio3 purified
      protein sequence

<400> SEQUENCE: 162

Ser Met Gly Lys Gly Asp Pro Lys Lys Pro Arg Gly Lys Met Ser Ser
1               5                   10                  15

Tyr Ala Phe Phe Val Gln Thr Cys Arg Glu Glu His Lys Lys Lys His
            20                  25                  30

Pro Asp Ala Ser Val Asn Phe Ser Glu Phe Ser Lys Lys Cys Ser Glu
        35                  40                  45

Arg Trp Lys Thr Met Ser Ala Lys Glu Lys Gly Lys Phe Glu Asp Met
    50                  55                  60

Ala Lys Ala Asp Lys Ala Arg Tyr Glu Arg Glu Met Lys Thr Tyr Ile
65                  70                  75                  80

Pro Pro Lys Gly Glu Thr Lys Lys Lys Phe Ser Ser Lys Gly Gly Tyr
                85                  90                  95

Gly Leu Asn Asp Ile Phe Glu Ala Gln Lys Ile Glu Trp His Glu
            100                 105                 110

<210> SEQ ID NO 163
<211> LENGTH: 86
<212> TYPE: PRT
<213> ORGANISM: Artificial Sequence
<220> FEATURE:
<223> OTHER INFORMATION: HMGB1 89-174, biotinylated pNIC-Bio3

<400> SEQUENCE: 163

Lys Asp Pro Asn Ala Pro Lys Arg Pro Pro Ser Ala Phe Phe Leu Phe
1               5                   10                  15

Cys Ser Glu Tyr Arg Pro Lys Ile Lys Gly Glu His Pro Gly Leu Ser
            20                  25                  30

Ile Gly Asp Val Ala Lys Lys Leu Gly Glu Met Trp Asn Asn Thr Ala
        35                  40                  45

Ala Asp Asp Lys Gln Pro Tyr Glu Lys Lys Ala Ala Lys Leu Lys Glu
    50                  55                  60

Lys Tyr Glu Lys Asp Ile Ala Ala Tyr Arg Ala Lys Gly Lys Pro Asp
65                  70                  75                  80
```

Ala Ala Lys Lys Gly Val
                85

<210> SEQ ID NO 164
<211> LENGTH: 107
<212> TYPE: PRT
<213> ORGANISM: Artificial Sequence
<220> FEATURE:
<223> OTHER INFORMATION: HMGB1 89-174, biotinylated pNIC-Bio3 purified
      protein sequence

<400> SEQUENCE: 164

Lys Asp Pro Asn Ala Pro Lys Arg Pro Pro Ser Ala Phe Phe Leu Phe
1               5                   10                  15

Cys Ser Glu Tyr Arg Pro Lys Ile Lys Gly Glu His Pro Gly Leu Ser
                20                  25                  30

Ile Gly Asp Val Ala Lys Lys Leu Gly Glu Met Trp Asn Asn Thr Ala
            35                  40                  45

Ala Asp Asp Lys Gln Pro Tyr Glu Lys Lys Ala Ala Lys Leu Lys Glu
        50                  55                  60

Lys Tyr Glu Lys Asp Ile Ala Ala Tyr Arg Ala Lys Gly Lys Pro Asp
65                  70                  75                  80

Ala Ala Lys Lys Gly Val Ser Ser Lys Gly Gly Tyr Gly Leu Asn Asp
                85                  90                  95

Ile Phe Glu Ala Gln Lys Ile Glu Trp His Glu
            100                 105

<210> SEQ ID NO 165
<211> LENGTH: 89
<212> TYPE: PRT
<213> ORGANISM: Artificial Sequence
<220> FEATURE:
<223> OTHER INFORMATION: HMGB1 1-88 pNIC-CTHF

<400> SEQUENCE: 165

Met Gly Lys Gly Asp Pro Lys Lys Pro Arg Gly Lys Met Ser Ser Tyr
1               5                   10                  15

Ala Phe Phe Val Gln Thr Cys Arg Glu Glu His Lys Lys Lys His Pro
                20                  25                  30

Asp Ala Ser Val Asn Phe Ser Glu Phe Ser Lys Lys Cys Ser Glu Arg
            35                  40                  45

Trp Lys Thr Met Ser Ala Lys Glu Lys Gly Lys Phe Glu Asp Met Ala
        50                  55                  60

Lys Ala Asp Lys Ala Arg Tyr Glu Arg Glu Met Lys Thr Tyr Ile Pro
65                  70                  75                  80

Pro Lys Gly Glu Thr Lys Lys Lys Phe
                85

<210> SEQ ID NO 166
<211> LENGTH: 96
<212> TYPE: PRT
<213> ORGANISM: Artificial Sequence
<220> FEATURE:
<223> OTHER INFORMATION: HMGB1 1-88 pNIC-CTHF purified protein sequence

<400> SEQUENCE: 166

Met Gly Lys Gly Asp Pro Lys Lys Pro Arg Gly Lys Met Ser Ser Tyr
1               5                   10                  15

Ala Phe Phe Val Gln Thr Cys Arg Glu Glu His Lys Lys Lys His Pro
                20                  25                  30

-continued

```
Asp Ala Ser Val Asn Phe Ser Glu Phe Ser Lys Lys Cys Ser Glu Arg
        35                  40                  45

Trp Lys Thr Met Ser Ala Lys Glu Lys Gly Lys Phe Glu Asp Met Ala
        50                  55                  60

Lys Ala Asp Lys Ala Arg Tyr Glu Arg Glu Met Lys Thr Tyr Ile Pro
65                  70                  75                  80

Pro Lys Gly Glu Thr Lys Lys Lys Phe Ala Glu Asn Leu Tyr Phe Gln
                85                  90                  95

<210> SEQ ID NO 167
<211> LENGTH: 87
<212> TYPE: PRT
<213> ORGANISM: Artificial Sequence
<220> FEATURE:
<223> OTHER INFORMATION: HMGB1 89-174 pNIC-CTHF

<400> SEQUENCE: 167

Met Lys Asp Pro Asn Ala Pro Lys Arg Pro Pro Ser Ala Phe Phe Leu
1               5                  10                  15

Phe Cys Ser Glu Tyr Arg Pro Lys Ile Lys Gly Glu His Pro Gly Leu
                20                  25                  30

Ser Ile Gly Asp Val Ala Lys Lys Leu Gly Glu Met Trp Asn Asn Thr
        35                  40                  45

Ala Ala Asp Asp Lys Gln Pro Tyr Glu Lys Lys Ala Ala Lys Leu Lys
        50                  55                  60

Glu Lys Tyr Glu Lys Asp Ile Ala Ala Tyr Arg Ala Lys Gly Lys Pro
65                  70                  75                  80

Asp Ala Ala Lys Lys Gly Val
                85

<210> SEQ ID NO 168
<211> LENGTH: 94
<212> TYPE: PRT
<213> ORGANISM: Artificial Sequence
<220> FEATURE:
<223> OTHER INFORMATION: HMGB1 89-174 pNIC-CTHF purified protein
      sequence

<400> SEQUENCE: 168

Met Lys Asp Pro Asn Ala Pro Lys Arg Pro Pro Ser Ala Phe Phe Leu
1               5                  10                  15

Phe Cys Ser Glu Tyr Arg Pro Lys Ile Lys Gly Glu His Pro Gly Leu
                20                  25                  30

Ser Ile Gly Asp Val Ala Lys Lys Leu Gly Glu Met Trp Asn Asn Thr
        35                  40                  45

Ala Ala Asp Asp Lys Gln Pro Tyr Glu Lys Lys Ala Ala Lys Leu Lys
        50                  55                  60

Glu Lys Tyr Glu Lys Asp Ile Ala Ala Tyr Arg Ala Lys Gly Lys Pro
65                  70                  75                  80

Asp Ala Ala Lys Lys Gly Val Ala Glu Asn Leu Tyr Phe Gln
                85                  90

<210> SEQ ID NO 169
<211> LENGTH: 71
<212> TYPE: PRT
<213> ORGANISM: Artificial Sequence
<220> FEATURE:
<223> OTHER INFORMATION: HMGB1 8-78, biotinylated pNIC-Bio3

<400> SEQUENCE: 169
```

```
Pro Arg Gly Lys Met Ser Ser Tyr Ala Phe Phe Val Gln Thr Cys Arg
1               5                   10                  15

Glu Glu His Lys Lys Lys His Pro Asp Ala Ser Val Asn Phe Ser Glu
                20              25                  30

Phe Ser Lys Lys Cys Ser Glu Arg Trp Lys Thr Met Ser Ala Lys Glu
            35              40                  45

Lys Gly Lys Phe Glu Asp Met Ala Lys Ala Asp Lys Ala Arg Tyr Glu
        50              55                  60

Arg Glu Met Lys Thr Tyr Ile
65                  70
```

```
<210> SEQ ID NO 170
<211> LENGTH: 94
<212> TYPE: PRT
<213> ORGANISM: Artificial Sequence
<220> FEATURE:
<223> OTHER INFORMATION: HMGB1 8-78, biotinylated pNIC-Bio3 purified
      protein sequence

<400> SEQUENCE: 170
```

```
Ser Met Pro Arg Gly Lys Met Ser Ser Tyr Ala Phe Phe Val Gln Thr
1               5                   10                  15

Cys Arg Glu Glu His Lys Lys Lys His Pro Asp Ala Ser Val Asn Phe
                20              25                  30

Ser Glu Phe Ser Lys Lys Cys Ser Glu Arg Trp Lys Thr Met Ser Ala
            35              40                  45

Lys Glu Lys Gly Lys Phe Glu Asp Met Ala Lys Ala Asp Lys Ala Arg
        50              55                  60

Tyr Glu Arg Glu Met Lys Thr Tyr Ile Ser Ser Lys Gly Gly Tyr Gly
65                  70                  75                  80

Leu Asn Asp Ile Phe Glu Ala Gln Lys Ile Glu Trp His Glu
                85                  90
```

```
<210> SEQ ID NO 171
<211> LENGTH: 69
<212> TYPE: PRT
<213> ORGANISM: Artificial Sequence
<220> FEATURE:
<223> OTHER INFORMATION: HMGB1 94-162, biotinylated pNIC-Bio3

<400> SEQUENCE: 171
```

```
Pro Lys Arg Pro Pro Ser Ala Phe Phe Leu Phe Cys Ser Glu Tyr Arg
1               5                   10                  15

Pro Lys Ile Lys Gly Glu His Pro Gly Leu Ser Ile Gly Asp Val Ala
                20              25                  30

Lys Lys Leu Gly Glu Met Trp Asn Asn Thr Ala Ala Asp Asp Lys Gln
            35              40                  45

Pro Tyr Glu Lys Lys Ala Ala Lys Leu Lys Glu Lys Tyr Glu Lys Asp
        50              55                  60

Ile Ala Ala Tyr Arg
65
```

```
<210> SEQ ID NO 172
<211> LENGTH: 90
<212> TYPE: PRT
<213> ORGANISM: Artificial Sequence
<220> FEATURE:
<223> OTHER INFORMATION: HMGB1 94-162, biotinylated pNIC-Bio3 purified
      protein sequence
```

```
<400> SEQUENCE: 172

Pro Lys Arg Pro Pro Ser Ala Phe Phe Leu Phe Cys Ser Glu Tyr Arg
1               5                   10                  15

Pro Lys Ile Lys Gly Glu His Pro Gly Leu Ser Ile Gly Asp Val Ala
            20                  25                  30

Lys Lys Leu Gly Glu Met Trp Asn Asn Thr Ala Ala Asp Asp Lys Gln
        35                  40                  45

Pro Tyr Glu Lys Lys Ala Ala Lys Leu Lys Glu Lys Tyr Glu Lys Asp
    50                  55                  60

Ile Ala Ala Tyr Arg Ser Ser Lys Gly Gly Tyr Gly Leu Asn Asp Ile
65                  70                  75                  80

Phe Glu Ala Gln Lys Ile Glu Trp His Glu
                85                  90

<210> SEQ ID NO 173
<211> LENGTH: 165
<212> TYPE: PRT
<213> ORGANISM: Artificial Sequence
<220> FEATURE:
<223> OTHER INFORMATION: Wt CXCL12 with SUMO pDsbC-HT-Cbio

<400> SEQUENCE: 173

Met Ser Asp Gln Glu Ala Lys Pro Ser Thr Glu Asp Leu Gly Asp Lys
1               5                   10                  15

Lys Glu Gly Glu Tyr Ile Lys Leu Lys Val Ile Gly Gln Asp Ser Ser
            20                  25                  30

Glu Ile His Phe Lys Val Lys Met Thr Thr His Leu Lys Lys Leu Lys
        35                  40                  45

Glu Ser Tyr Cys Gln Arg Gln Gly Val Pro Met Asn Ser Leu Arg Phe
    50                  55                  60

Leu Phe Glu Gly Gln Arg Ile Ala Asp Asn His Thr Pro Lys Glu Leu
65                  70                  75                  80

Gly Met Glu Glu Glu Asp Val Ile Glu Val Tyr Gln Glu Gln Thr Gly
                85                  90                  95

Gly Lys Pro Val Ser Leu Ser Tyr Arg Cys Pro Cys Arg Phe Phe Glu
            100                 105                 110

Ser His Val Ala Arg Ala Asn Val Lys His Leu Lys Ile Leu Asn Thr
        115                 120                 125

Pro Asn Cys Ala Leu Gln Ile Val Ala Arg Leu Lys Asn Asn Asn Arg
    130                 135                 140

Gln Val Cys Ile Asp Pro Lys Leu Lys Trp Ile Gln Glu Tyr Leu Glu
145                 150                 155                 160

Lys Ala Leu Asn Lys
                165

<210> SEQ ID NO 174
<211> LENGTH: 68
<212> TYPE: PRT
<213> ORGANISM: Artificial Sequence
<220> FEATURE:
<223> OTHER INFORMATION: Wt CXCL12 with SUMO pDsbC-HT-CBio purified
      protein sequence

<400> SEQUENCE: 174

Lys Pro Val Ser Leu Ser Tyr Arg Cys Pro Cys Arg Phe Phe Glu Ser
1               5                   10                  15

His Val Ala Arg Ala Asn Val Lys His Leu Lys Ile Leu Asn Thr Pro
            20                  25                  30
```

-continued

```
Asn Cys Ala Leu Gln Ile Val Ala Arg Leu Lys Asn Asn Asn Arg Gln
        35              40              45

Val Cys Ile Asp Pro Lys Leu Lys Trp Ile Gln Glu Tyr Leu Glu Lys
    50              55              60

Ala Leu Asn Lys
65

<210> SEQ ID NO 175
<211> LENGTH: 5
<212> TYPE: PRT
<213> ORGANISM: Artificial Sequence
<220> FEATURE:
<223> OTHER INFORMATION: Glycine-Serine Linker

<400> SEQUENCE: 175

Gly Ser Gly Ser Gly
1               5

<210> SEQ ID NO 176
<211> LENGTH: 5
<212> TYPE: PRT
<213> ORGANISM: Artificial Sequence
<220> FEATURE:
<223> OTHER INFORMATION: Glycine-Serine Linker

<400> SEQUENCE: 176

Gly Ser Ser Ser Gly
1               5

<210> SEQ ID NO 177
<211> LENGTH: 5
<212> TYPE: PRT
<213> ORGANISM: Artificial Sequence
<220> FEATURE:
<223> OTHER INFORMATION: Glycine-Serine Linker

<400> SEQUENCE: 177

Gly Ser Ser Gly Ser
1               5

<210> SEQ ID NO 178
<211> LENGTH: 5
<212> TYPE: PRT
<213> ORGANISM: Artificial Sequence
<220> FEATURE:
<223> OTHER INFORMATION: Glycine-Serine Linker

<400> SEQUENCE: 178

Gly Gly Ser Gly Gly
1               5
```

1

POLYPEPTIDES RELATED TO HMGB1 USEFUL FOR PROMOTING TISSUE REGENERATION, COMPOSITIONS COMPRISING SAME, AND USES THEREOF

This application is (a) a continuation-in-part of PCT International Application No. PCT/IB2020/060674, filed Nov. 12, 2020, which claims the benefit of U.S. Provisional Application No. 62/934,299, filed Nov. 12, 2019; and (b) claims the benefit of U.S. Provisional Application No. 63/190,429, filed May 19, 2021, the entire contents of each of which are hereby incorporated by reference into the subject application.

Throughout this application, various publications are referenced, each such reference in its entirety is hereby incorporated by reference into this application.

REFERENCE TO SEQUENCE LISTING

This application also incorporates-by-reference each of the nucleotide sequences which are present in the text file named "220512_91203-B_Sequence_Listing_AWG.txt", which is 78 kilobytes in size, and which was created on May 11, 2022 in the IBM-PC machine format, having an operating system compatibility with MS-Windows, which is being filed as part of this application.

TECHNICAL FIELD

This invention concerns polypeptides related to HMGB1 that promote tissue regeneration without inducing deleterious inflammation and methods of treating acute and chronic conditions involving tissue injury by administering such a polypeptide to a subject in need of treatment for such a condition.

BACKGROUND OF THE INVENTION

Resident stem and progenitor cells play a key role in maintaining homeostasis and effecting repair of many tissues following injury [1]. However, most tissues in adults heal by scarring. Following the success of bone marrow transplantation [2] there has been considerable interest in exogenous stem cell therapies to promote regeneration of solid organs. However, this has met with limited success, except in a few organs such as the eye [3] and skin [4]. The inflammatory environment following tissue injury is not conducive to stem cell engraftment and the subsequent scarring disrupts the stem cell niche [5]. Therefore, focus has shifted to promoting tissue regeneration by stimulating endogenous repair mechanisms [6]. Development of a successful therapeutic would depend on identification of soluble mediators to promote these pathways [7]. We previously identified High Mobility Group Box 1 (HMGB1) as a key mediator of repair in multiple tissues, including bone, blood and skeletal muscle [8].

HMGB1 is a prototypical alarmin [9,10] and under physiological conditions has an essential role in transcription [11,12]. On cell injury it is passively released from the damaged and necrotic cells into the extracellular space and the circulation to act on endogenous stem and progenitor cells to transition them to Gaien [8], a state intermediate between $G_0$ and $G_1$ [13]. On exposure to the appropriate activating factors, cells in $G_{Alert}$ can rapidly enter $G_1$ and effect tissue repair. If not required, stem cells in $G_{Alert}$ revert back to $G_0$ after approximately 3 weeks [13], thereby ensuring that they are not exhausted and the niche is not depleted.

HMBG1 comprises two L-shaped Box domains, A and B, each containing three α-helices (I-III) connected by flexible regions (FIG. 1A). The C-terminus of the protein is intrinsically disordered and contains a high proportion of carboxylic acid residues (Glu/Asp) comprising the acidic tail. The oxidation status of HMGB1 cysteine residues (Cys 22, Cys 44 in Box A and Cys 105 in Box B) is a key determinant of the extracellular activities of HMGB1 and in turn is dependent on the mechanism of release. Three different redox forms have been described in vivo [14]. HMGB1 passively released from the nuclei following injury or cell necrosis is the fully-reduced form (FR-HMGB1). It binds to CXCL12 and the heterocomplex signals via the cell surface receptor CXCR4 to transition stem and progenitor cells to Gaien [8]. Partial oxidation in the local inflammatory environment results in the formation of the disulfide HMGB1 (DS-HMGB1) [15,16], which has a disulfide bond between Cys 22 and Cys 44. This is also the form that is actively secreted by immune cells following acetylation [17] and N-glycosylation [18]. TLR-4 signaling by DS-HMGB1 results in production of several proinflammatory cytokines, including TNF [19], whilst TLR-2 signaling has been shown to be detrimental in multiple processes, including thrombosis and reperfusion injury [20], and autoimmune disorders [21]. DS-HMGB1 signaling via RAGE plays a key role in platelet activation and NET formation by neutrophils to promote thrombus formation [20,22-24]. Intracellular signaling via all three receptors converges to induce NF-κβ activity [25] in a MyD88-dependent manner [26,27]. Oxidation of all three cysteine residues through the action of extracellular reactive oxygen species results in sulfonyl-HMGB1 ($SO_3$), which is biologically inactive [14,19].

The disulfide bridge in Box A of DS-HMGB1 (Cys22-Cys44) is essential for TLR-4 signaling (FIG. 1B and FIG. 1C), initiating binding to TLR-4 but also has a relatively high dissociation rate. MD-2 then binds to Box B with low affinity but very low dissociation rates, stabilizing the interaction [28]; the Phe-Cys-Ser-Glu (FCSE, 104-107) peptide in Box B is essential for this interaction [29]. The capacity of DS-HMGB1 to signal via TLR-4 has been overcome by substituting cysteines at positions 22, 44 and 105 with serine, resulting in an engineered form described as 3S-HMGB1 [14]. Whilst the authors claimed that 3S-HMGB1 has enhanced regenerative properties compared to FR-HMGB1 [30], we found that in bone, blood and skeletal muscle injuries it was equivalent to FR-HMGB1. Interestingly, 3S-HMGB1 has been reported to be deleterious when administered locally following myocardial infraction whereas FR-HMGB1 resulted in a smaller infarct and enhanced cardiac function assessed over 4 weeks [31]. There are no published data on the effect of the 3S substitutions on TLR-2 or RAGE signaling.

The sites for TLR-2 interaction are not clearly defined but glycyrrhizin is known to inhibit this interaction [21]. This suggests that at least one, and potentially both HMG Box domains and the acidic tail [11], are involved. The acidic tail negatively modulates the binding and it has been reported that co-ligands [32] are necessary to displace the acidic tail of HMGB1 from the Box domains to permit signaling via TLR-2 [33]. However, several publications have reported TLR-2 dependent proinflammatory signaling with HMGB1 alone [34,35]. The role of the redox state of HMGB1 with regards to TLR-2 signaling remains unclear as both the disulfide form [36] and the fully-reduced form [32] have been proposed to signal through TLR-2. RAGE interaction has been primarily mapped to a peptide in HMG Box B (residues 149-182) [37](FIG. 1B and FIG. 1C), and peptides derived from this sequence can effectively inhibit HMGB1-RAGE signaling [38]. More recently a second RAGE binding site has identified on HMG Box A [39], although it is only been shown to be active after proteolysis by Caspase 11 [39]. However, the relative contribution of each site to RAGE signaling remains unknown. It is also recognized that prothrombotic signaling mediated by RAGE requires the disulfide form of HMGB1, implying that Box A may be involved [36], although the site of binding is currently not known. The acidic tail of HMGB1 may negatively regulate RAGE signaling in a manner analogous to TLR-2 as it binds residues within the RAGE binding peptide [11,40,41].

Successful translation of the regenerative activities of FR-HMGB1 to the clinic is dependent on the elimination of all potential deleterious proinflammatory signaling whilst maintaining CXCL12-binding and signaling via CXCR4. Here we identify the residues in HMGB1 that are critical for binding to CXCL12, TLR-4, TLR-2 and RAGE, and describe an HMGB1 variant that retains regenerative activity whilst eliminating RAGE binding and TLR-2 and TLR-4 signaling. Based on our data, other potential HMGB1 constructs that possess these properties are described.

SUMMARY OF THE INVENTION

This invention provides a polypeptide represented by the following formula:

H2N-A-X-B-A-X-B-HOOC wherein A represents consecutive amino acids, the sequence of which (1) includes a sequence identical to the sequence of amino acids 90-93 of wild type HMGB1, (2) has at its amino terminal end, between one and six consecutive amino acids, the sequence of which is identical to the sequence of the corresponding one to six amino acids preceding amino acid 90 in wild type HMGB1, and optionally (3) has a methionine at the amino terminus;

wherein X represents consecutive amino acids, the sequence of which is identical to the sequence of amino acids 94-162 of wild type HMGB1; and wherein B represents consecutive amino acids, the sequence of which (1) includes a sequence identical to the sequence of amino acids 163-168 of wild type HMGB1 and (2) has at its carboxy terminal end, between one and six consecutive amino acids, the sequence of which is identical to the sequence of the corresponding one to six amino acids following amino acid 168 in wild type HMGB1; and wherein each - represents a peptide bond between each of A and X, X and B, B and A, A and X, and X and B.

This invention also provides a polypeptide represented by the following formula:

H$_2$N-A-X-B-A-X-B-HOOC wherein each A represents consecutive amino acids, the sequence of which (1) is a sequence of four amino acids
   (a) identical to the sequence of amino acids 90-93 of wild type human HMGB1 (SEQ ID NO: 1), or
   (b) which differs from the sequence of (a) in respect to one or more amino acids; and
(2) has at its amino terminal end, between one and six consecutive amino acids,
the sequence of which
   (a) is identical to the sequence of the corresponding one to six amino acids preceding amino acid 90 in wild type human HMGB1, or (b) differs from the sequence of (a) in respect to one or more amino acids;
   and
(3) optionally has a methionine at the amino terminus,
wherein each A may be the same or different;
wherein each X represents consecutive amino acids, the sequence of which is
identical to the sequence of amino acids 94-162 of Wild type human HMGB1;
wherein each B represents consecutive amino acids, the sequence of which
   (1) is a sequence of five or six amino acids
      (a) identical to the sequence of amino acids 163-168 of wild type human HMGB1,
      (b) identical to the sequence of amino acids 163-167 of wild type human HMGB1,
      (c) the sequence of (a) in which any one of amino acids 163, 167, or 168 is changed to any other amino acid;
      (d) the sequence of (b) in which any one of amino acids 163 or 167 is changed to any other amino acid;
      (e) the sequence of (a) or (b) in which amino acid 164 is changed from lysine to arginine; or
      (f) the sequence of (a) or (b) in which amino acid 165 is changed from glycine to alanine, serine or threonine;
      (g) the sequence of (a) or (b) in which amino acid 166 is changed from lysine to arginine; or
      (h) the sequence of (a) or (b) in combination with the changes in (e) and (f), (e) and (g), (f) and (g), or (e), (f) and (g);
      (i) the sequence of (a), (b), or (c) in combination with the changes in one or more of (e), (f), and (g); or
      (j) the sequence of (d) in combination with the changes in one or more of (e), (f), and (g); and
   (2) has at its carboxy terminal end, between one and six consecutive amino acids, the sequence of which
      (a) is identical to the sequence of the corresponding one to six amino acids following amino acid 168 in wild type human HMGB1,
      (b) is identical to the sequence of the corresponding one to six amino acids following amino acid 167 in wild type human HMGB1,
      (c) differs at one or more positions from the sequence of the corresponding one to six amino acids following amino acid 168 in wild type human HMGB1, or
      (d) differs at one or more positions from the sequence of the corresponding one to six amino acids following amino acid 167 in wild type human HMGB1, and
wherein each B may be the same or different; and
wherein each - represents a peptide bond between each of A and X, X and B, B and A, A and X, and X and B;
with the proviso that in the B-A between the two Xs, the number of amino acids must be at least 12; and
with the additional proviso that in the B at the carboxy terminal end of the polypeptide, the one to six consecutive amino acids of (2) may be absent.

This invention also provides a composition comprising a polypeptide in accordance with the invention and a carrier, and methods of treating a subject suffering from, or at risk for developing, a condition which would be alleviated by promoting regeneration of a tissue or cells that rely upon CXCR4$^+$ cells for repair which comprise administering to the subject a polypeptide or a composition of the invention in an amount effective to promote regeneration of the tissue or cells and to have a therapeutic or prophylactic effect.

BRIEF DESCRIPTION OF THE DRAWINGS

This patent or application file contains at least one drawing executed in color. Copies of this patent or patent application publication with color drawing(s) will be provided by the Office upon request and payment of the neccessary fee.

FIG. 1A: Structure of HMGB1 (PDB 2YRQ, conformer 1) showing the alpha helices of each Box domain. FIG. 1B: Structure from (FIG. 1A) coloured in PyMol according to known interactions with LPS, TLR-4 or RAGE. The regions involved in TLR-2 binding are currently unknown. The acidic tail, which is involved in transcriptional modulation and bactericidal activities is not shown in the structure. Pink: residues involved in glycyrrhizin binding. Red: flexible N-terminal regions adjacent to Box A or Box B. Orange: cysteine residues. White: linker region between HMG Boxes. Bright green and yellow: RAGE binding region (incomplete in FIG. 1A, where it extends into the acidic tail, yellow. Structure of HMGB1 showing the alpha helices of each Box domain. FIG. 1C: Schematic representation of regions known to modulate DAMP signaling of HMGB1, as described in the literature. Box A—blue. Box B—green. The disulfide bond has also been listed.

FIG. 2A: Peptide array (11×10) of HMGB1 15-mers incubated with 1 μM CXCL12-His6 and detected with anti-His5-HRP antibody. Intensity of spots corresponds to amount of CXCL12 bound to the peptides; first two and last two spots in the array comprised 10-His positive controls. FIG. 2B: Intensity quantification of spot intensity in (FIG. 2A) (duplicate runs) normalised to 10-his control. Peptides used for alanine scanning experiments in (FIG. 2C) are marked in the graph. Peptides in the acidic tail were not included, as it would non-specifically bind cationic molecules such as CXCL12 due to the high negative charge. Peptides in graphs are represented in SEQ ID NOs: 8-104, left to right. FIG. 2C: Peptide arrays of alanine point mutagenesis of domains identified in FIG. 2A and FIG. 2B. First spot in each row corresponds to the positive control; second spot to the unmodified peptide. Peptides shown are represented in SEQ ID NOs: 105-111, top to bottom. FIG. 2D: Intensity quantification of the array in (FIG. 2C, SEQ ID NOs: 105-111), normalized to the unmodified peptide. Residues which showed increase in CXCL12 binding compared to alanine residues (Ala→Ala; synonymous mutation, in grey) are show in red. FIG. 2E: Michaelis-Menten saturation fits of biotinylated HMGB1 constructs [full-length FR red/3S black; minimal Box A 8-78 (violet) and Box B 94-162 (brown), extended box A 1-88 (pink) and box B 89-174 (gray)]binding to CXCL12. FIG. 2F: Summary of kinetic parameters derived from (FIG. 2E). Affinity (Kd) constants from both fits follow the same relationship and are greatly decreased for HMGB1 94-162; analyzed by 1-way Brown-Forsythe ANOVA from the fitted data. Kd values were compared via a post-hoc 2-way ANOVA if AICc supported a model with multiple constants, averaging both values as no significant differences were found in the paired comparison (column factor). Raw interferograms can be found in FIG. 12. Req: response at equilibrium, $k_{Off}$: dissociation constant $(s^{-1})$, $k_{On}$: association constant $((\mu M^*s)^{-1})$, AICc: Statistical comparison by Aikaike's Information Criterion (corrected).

FIG. 5A: Cumulative CSP of helical-only biotinylated Box B (94-162, HMGB1A-c028) or complete Box B (89-174, HMGB1A-c038) after titration with CXCL12 (0.42, 0.84 and 1.42 molar equivalents), calculated over several HSQC spectra including a parallel control with no CXCL12 measured after the last concentration point (CSP drift control). Intensity of the green color in the graph indicates relative CSP. The sequence of each HMGB1 construct has been overlaid with the residue number; an empty column (no number) represents residues which could not be mapped in the parallel 3D $^1$H-$^{15}$N HSQC/NOE/TOCSY experiments. The sequence of the residues corresponding to each HMG Box is shown as: Light blue, residues previously reported in the literature as involved in CXCL12 binding; red, residues weakly involved in the peptide array; purple, residues involved according to both published literature and peptide array. Grey, alanine residues within CXCL12 binding peptides (underlined) that could not be assessed in the peptide arrays. Sequence shown is represented in SEQ ID NO: 5. FIG. 5B: Cumulative peak height change of FIG. 5A; Heatmap of NMR changes. Red indicates I/I0 change over 1 SEM of all residues, blue decrease over −1 SEM. Sequence shown is represented in SEQ ID NO: 5.

FIG. 6A: Sequence alignment of Box A+linkers (1-88) (SEQ ID NO: 3) with Box B+linkers (89-174) (SEQ ID NO: 4); numbers correspond to residue numbering from the NMR structure (excluding N-terminal methionine). Vertical lines designate strictly conserved positions, and double dots similar amino acid types. Underlined: peptide regions binding CXCL12 from the first peptide array. Red: residues flagged in the alanine scan as involved in CXCL12 binding which could not be verified by NMR. Orange: residues flagged in the alanine scan and also showing either CSP or peak volume change by NMR. Cyan: residues not flagged in our NMR or peptide array experiments but described in the NMR literature as contributing to CXCL12 binding [46]. Purple: residues flagged peptide array experiments and confirmed by the published or our NMR data. In green: residues flagged only on NMR experiments, which can either directly bind CXCL12 or be affected by binding to nearby residues. Pink: residues flagged by both our NMR experiments and the published data. FIG. 6B: Structure of FR-HMGB1 1-166 (2YRQ), with residues coloured as in FIG. 6A. Side chains of all coloured residues shown. Dashed circles indicate the glycyrrhizin binding region in each HMG Box. On the right, Pymol surface representation of the CXCL12 binding residues; those residues flagged in NMR and peptide arrays form a similar binding pocket on the concave surface of each HMGB Box if Box A is reduced. FIG. 6C: Schematic of dBB12L construct design. The initiation codon Met 1 is numbered as Met 0 herein, as it is partially lost in the cleaved peptide. Therefore, HMGB1 Met 1-Gly 2 . . . Glu 215 becomes Met 0-Gly 1 . . . Glu 214. Comparison of the domain organization and sequences of FR-HMGB1 (top—SEQ ID NO: 1) and dBB12L construct (bottom—SEQ ID NO: 2) are shown. The dBB12L construct is designed such that: 1. The acidic tail and part of the RAGE binding domain (175-214) deleted; 2. Residues 1-88 (Box A) substituted by residues 90-175, resulting in two HMG Box B domains; and 3. Residues 163-174 C-terminal to Box B replace the native flexible linker (79-88) C-terminal to Box A in native HMGB1. CXCL12 binding peptides shown as red letters. The repeat Box B units are separated in the diagram by a vertical dashed black line. DAMP receptor binding peptides in Box A shown as dashed lines, those in Box B by solid lines. The TLR-2 and RAGE peptides are truncated in DBB12L, and all Box A peptides are no longer present in the construct due to the substitution.

FIGS. 7A-7D show dBB12L has similar stability and surface charge conformation to FR-HMGB1 1-214/1-164. FIG. 7A: Calculated $Tm_{50}$ values (in ° C.) for full-length and 1-164 FR-HMGB1, and dBB12L under various buffer conditions, shown as a heat map of highest (green) and lowest (red) values within the global dataset for all constructs. N/A: curve not fittable. Effects of pH and NaCl concentration have been summarized below the table. FIG. 7B: Native ESI/MS of HMGB1 constructs in either 50 mM or 0.2 M ammonium acetate, pH 6.5. All three HMGB1 constructs have similar native M/Z profiles, with dBB12L closely resembling a reduced HMGB1 construct with two HMG Boxes apart from each other. Continuous line; compact monomer. Dashed line; extended monomer (HMG Boxes distal to each other). Removal of the acidic tail (FR HMGB1 1-164, blue curves compared to FR-HMGB1, red curves) and higher ionic strength (Comparison of the spectra for the same construct in either 50 mM or 200 mM ammonium acetate) increases the prevalence of higher M/Z states (partial unfolding). FIG. 7C: Solvent accessible surface area (SASA) calculations for the average folded HMGB1 monomer, the extended and compact monomer states, and the unfolded monomer from FIG. 7D. FIG. 7D: Denaturing ESI/MS deconvolution, SDS-PAGE and SEC profiles of HMGB1 constructs after storage at room temperature for 180 days (D0-D180), in 0.2 M ammonium acetate, pH 6.5.

FIG. 8A: Michaelis-Menten saturation fits from hybrid ELISA (n=4 per concentration, global fit) showing absence of RAGE binding by dBB12L construct, regardless of oxidation status. DS-HMGB1 binds RAGE more avidly compared to FR-HMGB1. Data normalized with respect to DS-HMGB1 control. FIG. 8B: Michaelis-Menten saturation fits from biolayer interferometry (0-25 μM HMGB1; n=6 sensor runs, shown in FIG. 14). Association and dissociation rates were calculated from the raw interferogram data only. Kinetics parameters and color legends (disulfide forms are indicated by dashed lines) are summarized in FIG. 8C: Invalid fits represent $R^2 < 0.6$ (poor binding). ELISA data represent steady state conditions. For each kinetic parameter, green indicates the construct with the highest affinity, fastest association ($k_{on}$) or slowest dissociation ($k_{Off}$); midpoint in yellow, lowest in red. FIGS. 8D-8E show DS-HMGB1 promoted NF-κβ activity in reporter HEK-Dual cells expressing human TLR-2 and CD14 (FIG. 8D) or murine TLR-4, MD-2 and CD14. (FIG. 8E). dBB12L and FR-HMGB1 did not promote NF-κβ signaling in either cell line. Data shown as mean±SEM fold change compared to control (media alone). FIG. 8F: Disulfide HMGB1 (DS-HMGB1) increased TNF production in monocytes, which was further enhanced by the presence of suboptimal amounts of LTA, but not of LPS. FR-HMGB1 and dBB12L did not promote TNF expression, even when pre-incubated for 24 h with LPS or LTA. Response to LPS pre-incubated with these constructs was also significantly reduced. n=3 donors, each with three technical replicates.

FIG. 10A: Volcano plot showing differentially expressed genes in muscle stem cells by fold change following injury or HMGB1 induced $G_{Alert}$. Integration demonstrates conserved up—(brown dots in figures with color) and down—(blue dots in figures with color) regulation of core genes in $G_{Alert}$ induced by contralateral lower limb injury or intravenous (iv) HMGB1. FIG. 10B: Network map of gene ontology terms of differentially expressed cells during $G_{Alert}$ induction in muscle stem cells. FIG. 10C: Dose response of FR-HMGB1 in a $BaCl_2$ skeletal muscle injury model, with regeneration quantified by fiber cross-sectional area. The optimal dose was 0.75 mg/kg (28.75 nmol/kg) and was used in subsequent assays. FIG. 10D: Animals were dosed with FR-HMGB1 (optimal dose) at the varying timepoints after injection of $BaCl_2$ to assess the interval where treatment with FR-HMGB1 is effective post-injury. Values in FIG. 10C and FIG. 10D shown as mean±SEM in nested ANOVA with Holm-Sidak correction. FIG. 10E: Pharmacokinetics of HMGB1 in the circulation following administration of 0.75 mg/ml FR-HMGB1, fitted by nonlinear least squares to a two-phase exponential decay curve. FIG. 10F: Kaplan-Meier survival plot. 5 wk following MI FR-HMGB1=83%, PBS=52%. FIG. 10G: Ejection fraction over time calculated from serial MRI scans. Dotted line indicates ejection fraction in normal/sham surgery mice. FIG. 10H: Infarct size over time calculated from serial MRI scans. FIG. 10I: Representative mid-ventricular short-axis cine-MRI images at end-diastolic and end-systolic phases of the cardiac cycle 1 and 5 wk after MI. Blood in the chambers appears bright. FR-HMGB1 group shows preservation of heart function and maintenance of wall thickness (yellow arrows) with visible separation of right and left ventricles (red arrows) during systole. In contrast, in the PBS group, there is significant left ventricle dilation (white arrows) and very limited contraction between diastole and systole. n=10 per group. All MRI scans performed and assessed by a blinded observer. FIG. 10J: Mean muscle cross-section area at given time points after $BaCl_2$ muscle injured animals treated with PBS (black), 28.75 nM/kg of FR-HMGB1A-c001 (red) or dBB12L (green). N=5 per group and timepoint, nested ANOVA (Holm-Sidak post-hoc correction). A representative image at each point is shown in FIG. 15.

FIG. 11A: Peptide array of full-length CXCL12. "+" positions correspond to positive control 10-His peptides; the rest of the peptides comprise CXCL12 15-mers shifted two (2) residues in succession towards the C-terminus. The membrane was exposed to 1 uM HMGB1 (FR or 3S)-His6 (1-214), BoxA-His6 (8-78) and BoxB-His6 (94-162) for 24 hours. Bound protein was detected by anti-His-HRP conjugate chemoluminescence. A peptide of CXCL12 interacting with full length HMGB1 cannot interact with either Box A or Box B alone, confirming the requirement of the N-terminal segment of each Box domain (particularly, D4 in box A/D90 in box B): intensity of the spots pertaining to the common CXCL12 peptide is also markedly decreased upon binding to the Box domains alone when compared to FL-HMGB1. Binding to 3S seems to be of higher intensity than that to FR; this is likely due to protein oxidation during the assay, although this was not quantified due to the low concentration of protein used being unsuitable for ESI/TOF MS. BLI data, however, do suggest a lower off rate of CXCL12 from 3S than from FR-HMGB1. FIG. 11B: CXCL12 dimer (PDB 2J7Z) with the regions binding HMGB1 highlighted. Red: shared binding region. Blue: non-shared binding region.

FIG. 13A: Cumulative CSP of HMGB1 3S 1-184 (HMGB1A-c007) upon addition of 1:2 molar equivalents of CXCL12 in one step (1:1 HMG Box to CXCL12 ratio). Box A and Box B residues have been considered separate molecules for the purposes of median CSP calculation. Intensity of the green color in the bar graph indicates higher relative CSP. The sequence of each HMGB1 construct has been overlaid with the residue number; an empty column (no number) represents residues which could not be mapped in the parallel 3D 1H-15N HSQC/NOE/TOCSY experiments. The sequence of the residues corresponding to each box is in the middle of each condition, colored as per: Light blue, residues previously reported in the literature as involved in CXCL12 binding; red, residues weakly involved in the peptide array; purple, residues involved according to both published literature and peptide array. The sequences shown are represented in SEQ ID NOs: 6 and 7. FIG. 13B: 15N HSQC-HQMC peak spectra for (FIG. 13A) in 10 mM HEPES 150 mM NaCl pH 7.5 buffer. Protein concentrations are indicated in the spectra overlay. FIGS. 13C and 13D show 15N HSQC-HQMC peak spectra in 10 mM HEPES 150 mM NaCl pH 7.5 buffer. Protein concentrations are indicated in the spectra overlay. FIG. 13C: HMGB1A 94-162 (2-day experiment); FIG. 13D: HMGB1A 89-174 (6-day experiment; minor degradation occurs after day 4).

DETAILED DESCRIPTION OF THE INVENTION

Figure 1A:
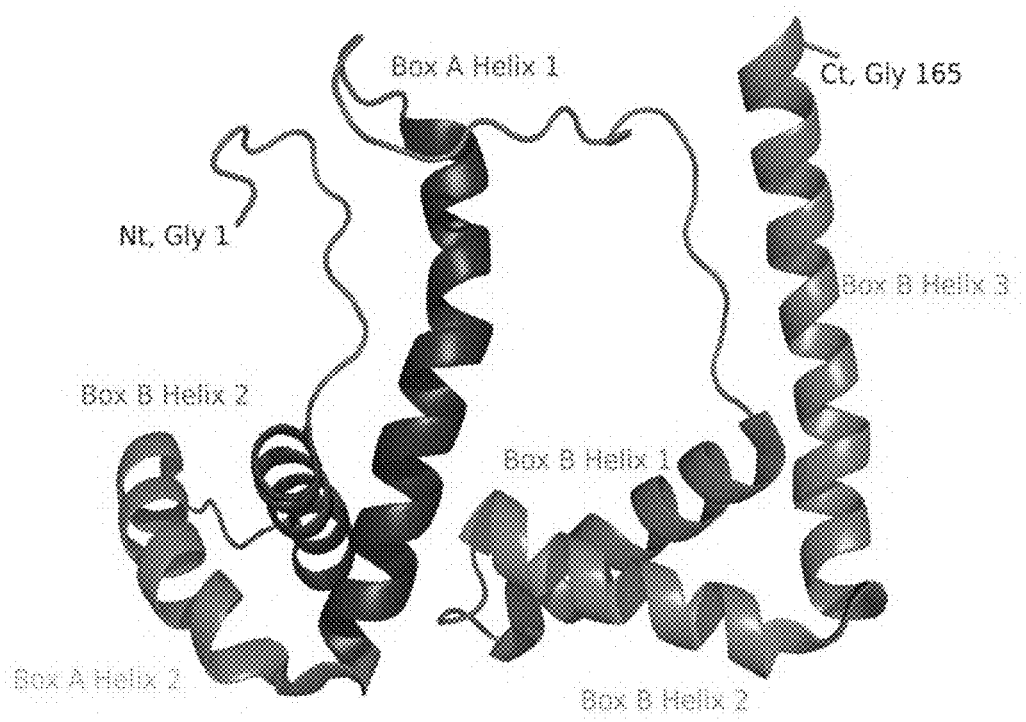
FIGS. 1A-1C show a schematic of the HMGB1 structure and locations of known immunogenic activities.

This invention provides a polypeptide represented by the following formula:

$$H_2N-A-X-B-A-X-B-HOOC$$

wherein each A represents consecutive amino acids, the sequence of which
  (1) is a sequence of four amino acids
    (a) identical to the sequence of amino acids 90-93 of wild type human HMGB1 (SEQ ID NO: 1), or
    (b) which differs from the sequence of (a) in respect to one or more amino acids; and
  (2) has at its amino terminal end, between one and six consecutive amino acids,
  the sequence of which
    (a) is identical to the sequence of the corresponding one to six amino acids preceding amino acid 90 in wild type human HMGB1, or
    (b) differs from the sequence of (a) in respect to one or more amino acids;
  and
  (3) optionally has a methionine at the amino terminus,
wherein each A may be the same or different;
wherein each X represents consecutive amino acids, the sequence of which is identical to the sequence of amino acids 94-162 of wild type human HMGB1;
wherein each B represents consecutive amino acids, the sequence of which
  (1) is a sequence of five or six amino acids
    (a) identical to the sequence of amino acids 163-168 of wild type human HMGB1, (b) identical to the sequence of amino acids 163-167 of wild type human HMGB1, (c) the sequence of (a) in which any one of amino acids 163, 167, or 168 is changed to any other amino acid;

(d) the sequence of (b) in which any one of amino acids 163 or 167 is changed to any other amino acid;

(e) the sequence of (a) or (b) in which amino acid 164 is changed from lysine to arginine; or (f) the sequence of (a) or (b) in which amino acid 165 is changed from glycine to alanine, serine or threonine;

(g) the sequence of (a) or (b) in which amino acid 166 is changed from lysine to arginine; or (h) the sequence of (a) or (b) in combination with the changes in (e) and (f), (e) and (g), (f) and (g), or (e), (f) and (g);

(i) the sequence of (a), (b), or (c) in combination with the changes in one or more of (e), (f), and (g); or (j) the sequence of (d) in combination with the changes in one or more of (e), (f), and (g); and (2) has at its carboxy terminal end, between one and six consecutive amino acids, the sequence of which (a) is identical to the sequence of the corresponding one to six amino acids following amino acid 168 in wild type human HMGB1, (b) is identical to the sequence of the corresponding one to six amino acids following amino acid 167 in wild type human HMGB1, (c) differs at one or more positions from the sequence of the corresponding one to six amino acids following amino acid 168 in wild type human HMGB1, or (d) differs at one or more positions from the sequence of the corresponding one to six amino acids following amino acid 167 in wild type human HMGB1, and wherein each B may be the same or different; and wherein each - represents a peptide bond between each of A and X, X and B, B and A, A and X, and X and B;

with the proviso that in the B-A between the two Xs, the number of amino acids must be at least 12; and with the additional proviso that in the B at the carboxy terminal end of the polypeptide, the one to six consecutive amino acids of (2) may be absent.

In some embodiments, the methionine is present at the amino terminus of the polypeptide.

In other embodiments, A has at its amino terminal end, the amino acid corresponding to amino acid 89 of wild type HMGB1 (SEQ ID NO: 1).

In some embodiments, in B(2), B has at its carboxy terminal end, six amino acids corresponding to amino acids 169-174 of wild type human HMGB1.

In some embodiments, the number of amino acids in the B-A between the two Xs is at least 13. In such embodiments, the number of amino acids in the B-A between the two Xs is up to 22, more preferably up to 21, 20, 19, 18, 17, 16, 15, or 14.

In other embodiments, the number of amino acids in the B-A between the two Xs is between 12 and 22 inclusive.

In yet further embodiments, the number of amino acids in the B-A between the two Xs is between 13 and 22 inclusive. In some embodiments the number of amino acids in the B-A between the two Xs is between 13 and 21 inclusive, more preferably between 13 and 20 inclusive, more preferably between 13 and 19 inclusive, more preferably between 13 and 18 inclusive, more preferably between 13 and 17 inclusive, more preferably between 13 and 16 inclusive, more preferably between 13 and 15 inclusive, more preferably between 13 and 14 inclusive.

In some embodiments, the sequence of (2)(c) or (2)(d) of either B or of both Bs differs at the one or more positions by the presence of a glycine, serine, proline, arginine, lysine, aspartic acid, glutamic acid, or histidine amino acid residue instead of the amino acid residue present at such position or positions in naturally occurring HMG1.

In some embodiments, the sequence of (2)(c) or (2)(d) of either B or of both Bs is or comprises GSGSG (SEQ ID NO: 175).

In other embodiments, the GSGSG (SEQ ID NO: 175) has been inserted into the region between the sequence of the B and the sequence of the A between the two Xs.

In yet further embodiments, the order or number of the glycine and serine residues has been altered within the SEQ ID NO: 175 peptide sequence. As non-limiting examples, the sequence of (2)(c) or (2)(d) may be or comprise any of GSSSG (SEQ ID NO: 176), GSSGS (SEQ ID NO: 177), or GGSGG (SEQ ID NO: 178).

In some embodiments, the amino acids of (2)(c) or (2)(d) of either B or of both Bs lack a defined secondary structure, or have a turn or random coil secondary structure.

In some embodiments, either A or both As are five consecutive amino acids.

In some embodiments, the five consecutive amino acids have a sequence identical to the sequence of amino acids 89-93 of wild type human HMGB1.

In some embodiments, a) the A between the Xs is five consecutive amino acids and the B between the Xs is at least seven consecutive amino acids;

b) the A between the Xs is six consecutive amino acids and the B between the Xs is at least six consecutive amino acids;

c) the A between the Xs is seven consecutive amino acids and the B between the Xs is at least six consecutive amino acids;

d) the A between the Xs is eight consecutive amino acids and the B between the Xs is at least six consecutive amino acids;

e) the A between the Xs is nine consecutive amino acids and the B between the Xs is at least six consecutive amino acids; or f) the A between the Xs is ten consecutive amino acids and the B between the Xs is at least six consecutive amino acids.

In some embodiments, a) the B between the Xs is six consecutive amino acids and the A between the Xs is at least six consecutive amino acids;

b) the B between the Xs is seven consecutive amino acids and the A between the Xs is at least five consecutive amino acids;

c) the B between the Xs is eight consecutive amino acids and the A between the Xs is at least five consecutive amino acids;

d) the B between the Xs is nine consecutive amino acids and the A between the Xs is at least five consecutive amino acids;

e) the B between the Xs is ten consecutive amino acids and the A between the Xs is at least five consecutive amino acids;

f) the B between the Xs is eleven consecutive amino acids and the A between the Xs is at least five consecutive amino acids; or g) the B between the Xs is twelve consecutive amino acids and the A between the Xs is at least five consecutive amino acids.

This invention also provides a composition comprising any of the polypeptides of the invention and a carrier.

In some embodiments, the polypeptide is present in a therapeutically or prophylactically effective amount and the carrier is a pharmaceutically acceptable carrier.

This invention also provides methods of treating a subject suffering from, or at risk for developing, a condition which would be alleviated by promoting regeneration of a tissue or cells that rely upon CXCR4$^+$ cells for repair which comprise administering to the subject a polypeptide or composition of the invention in an amount or dose effective to promote regeneration of the tissue or cells, that is, achieve a therapeutic or prophylactic effective dose of the pharmaceutical composition of the invention in a subject in need thereof.

In some embodiments, the condition is an acute injury.

In a currently preferred embodiment, the polypeptide is administered within 5 hours, preferably within 4 hours, more preferably within 3 hours, even more preferably within 2 hours and most preferably within 1 hour of the acute injury.

In some embodiments, the condition is a chronic condition.

In some embodiments, the polypeptide is administered repeatedly at a daily, weekly, monthly, or yearly interval.

In some embodiments, the acute injury is myocardial infarction. In some embodiments, the tissue is cardiac tissue or myocardium.

In some embodiments, the acute injury is stroke, spinal cord injury, or peripheral nerve injury.

In a currently preferred embodiment, the polypeptide is administered within 5 hours of the myocardial infarction. In some embodiments, the polypeptide is administered within 5 hours, preferably within 4 hours, more preferably within 3 hours, even more preferably within 2 hours and most preferably within 1 hour of the myocardial infarction.

In a currently preferred embodiment, the polypeptide is administered within 5 hours of the stroke, spinal cord injury, or peripheral nerve injury. In some embodiments, the polypeptide is administered within 5 hours, preferably within 4 hours, more preferably within 3 hours, even more preferably within 2 hours and most preferably within 1 hour of the stroke, spinal cord injury, or peripheral nerve injury.

In some embodiments, the acute injury is a fracture, joint replacement or bone fusion.

In some embodiments, the tissue is a bone.

In some embodiments, the acute injury is a skeletal muscle injury, joint injury or ligament injury.

In some embodiments, the condition involves liver damage. In some embodiments the tissue is liver tissue.

In some embodiments, the chronic condition is non-alcoholic steatohepatitis, liver cirrhosis or infective hepatitis.

In some embodiments, the chronic condition involves damage to the brain or other parts of the central nervous system.

In some embodiments, the chronic condition is Parkinson's disease, dementia, multiple sclerosis, motor neuron disease or peripheral nerve injury.

In some embodiments, the chronic condition involves a chronic joint injury.

In some embodiments, the chronic joint injury is inflammatory arthritis or osteoarthritis.

In some embodiments, the condition involves damage to the lung.

In some embodiments, the acute injury is a viral infection of the lungs, bacterial infection of the lungs, fungal infection of the lungs, or mechanical injury to the lungs.

In some embodiments, the viral infection of the lungs is an infection by severe acute respiratory syndrome coronavirus 2 (SARS-CoV-2).

In some embodiments, the mechanical injury is a ventilator-induced injury.

In some embodiments, the chronic condition is idiopathic pulmonary fibrosis (IPF), chronic obstructive pulmonary disease, or emphysema.

In some embodiments, the condition involves the gut.

In some embodiments, the acute injury is a surgical injury to the gut.

In some embodiments, the chronic injury is inflammatory bowel disease, Crohn's disease, or ulcerative colitis.

In some embodiments, the condition involves damage to the skin.

In some embodiments, the acute injury is a burn or a surgical injury of the skin.

In some embodiments, the chronic condition is a skin ulcer, diabetic ulcer, venous ulcer, arterial ulcer, or pressure ulcer.

In some embodiments, the condition involves the pancreas and the cells are islet cells.

In some embodiments, the condition is diabetes.

In some embodiments, the condition is neutropenia following chemotherapy and the tissue is bone marrow.

In some embodiments, the acute injury is chemotherapy, and optionally the polypeptide is administered before or within 5 hours of administration of the chemotherapy.

In some embodiments, the polypeptide is administered before the acute injury.

In some embodiments, the polypeptide is administered after the acute injury.

In some embodiments, the condition is kidney failure and the tissue is kidney tissue.

In some embodiments, the chronic condition is a disease that results in chronic renal failure.

In some embodiments, the acute injury is elective surgery and the polypeptide is administered before, during or within 5 hours after the surgery.

In some embodiments, the acute injury is a sport or military combat injury.

In some embodiments, the chronic condition is a chronic skeletal muscle condition.

In some embodiments, the chronic skeletal muscle condition is a muscular dystrophy such as Duchenne macular dystrophy, sarcopenia, or disuse atrophy.

This invention provides a polypeptide represented by the following formula:

H$_2$N-A-X-B-A-X-B-HOOC wherein A represents consecutive amino acids, the sequence of which (1) includes a sequence identical to the sequence of amino acids 90-93 of wild type HMGB1, (2) has at its amino terminal end, between one and six consecutive amino acids, the sequence of which is identical to the sequence of the corresponding one to six amino acids preceding amino acid 90 in wild type HMGB1, and optionally (3) has a methionine at the amino terminus;

wherein X represents consecutive amino acids, the sequence of which is identical to the sequence of amino acids 94-162 of wild type HMGB1; and wherein B represents consecutive amino acids, the sequence of which (1) includes a sequence identical to the sequence of amino acids 163-168 of wild type HMGB1 and (2) has at its carboxy terminal end, between one and six consecutive amino acids, for example, 1, 2, 3, 4, 5, or 6 amino acids, the sequence of which is identical to the sequence of the corresponding one to six amino acids following amino acid 168 in wild type HMGB1; and wherein each - represents a peptide bond between each of A and X, X and B, B and A, A and X, and X and B.

In some embodiments, the methionine is present at the amino terminus of the polypeptide.

In other embodiments, A has at its amino terminal end, one amino acid corresponding to amino acid 89 of wild type HMGB1.

In some embodiments, B has at its carboxy terminal end, six amino acids the sequence of which corresponds to the sequence of amino acids 169-174 of wild type HMGB1.

This invention also provides a composition comprising the polypeptide of any one of the provided embodiments and a carrier.

In some embodiments, the polypeptide is present in a therapeutically or prophylactically effective amount and the carrier is a pharmaceutically acceptable carrier.

This invention also provides methods of treating a subject suffering from, or at risk for developing, a condition which would be alleviated by promoting regeneration of a tissue or cells that rely upon CXCR4⁺ cells for repair which comprise administering to the subject the polypeptide of any one of the provided embodiments in an amount effective to promote regeneration of the tissue or cells, that is, a therapeutically or prophylactically effective dose of the pharmaceutical composition of the invention.

In certain embodiments, the condition is myocardial infarction and the tissue is a cardiac tissue, particularly, myocardium.

In a currently preferred embodiment, the polypeptide is administered within 5 hours, preferably within 4 hours, more preferably within 3 hours, even more preferably within 2 hours and most preferably within 1 hour of the myocardial infarction.

In some embodiments, the condition is a fracture and the tissue is a bone.

In other embodiments, the condition involves liver damage and the tissue is liver tissue.

In yet further embodiments, the condition involves damage to the brain or nervous system and includes stroke, Parkinson's disease and dementia.

In some embodiments, the condition involves damage to the lung.

In yet further embodiments, the condition involves the gut and includes surgery and inflammatory bowel disease.

In some embodiments, the condition involves damage to the skin and includes surgical procedures, burns and ulcers.

In additional embodiments, the condition involves the pancreas including type 1 diabetes and the cells are islet cells.

In further embodiments, the condition is neutropenia, for example, neutropenia following chemotherapy and the tissue is bone marrow.

In some embodiments, the condition is kidney failure and the tissue is kidney tissue.

Terms

In order to facilitate an understanding of the invention, except as otherwise expressly provided herein, each of the following terms shall have the meaning set forth below.

As used herein, "engineered" means a non-naturally occurring compound that has been created based upon changing a naturally occurring compound. An engineered polypeptide may include amino acids corresponding to amino acids of a naturally occurring polypeptide and amino acids that vary in identity or location from those of a naturally occurring polypeptide. Such an engineered polypeptide may also be referred to as an "analogue" or "derivative" of the naturally occurring polypeptide.

As used herein, "stem cell" means any unspecialized cell that has the potential to develop into many different cell types in the body, including without limitation hemopoietic stem cells.

As used herein, the term "effective amount" means an amount of a polypeptide of the invention that is capable of achieving a desired result, for example, alleviating a condition or one or more symptoms associated with a condition, for example, an acute or chronic tissue injury. The specific amount or dose of a polypeptide administered according to this invention will, of course, be determined by the particular manner of treating or preventing the condition, for example, the route of administration, the physiological state of the subject, and the severity of the condition being treated. For example, an engineered HMGB1 polypeptide administered to a subject is preferably in the form of a composition comprising a therapeutically or prophylactically effective amount of the engineered HMGB1 polypeptide.

The phrase "pharmaceutically acceptable" refers to those compounds, materials, compositions, or dosage forms which are, within the scope of sound medical judgment, suitable for use in human beings and animals without excessive toxicity, irritation, allergic response, or other problems or complications, commensurate with a reasonable benefit/risk ratio. The phrase "pharmaceutically acceptable carrier" as used herein means a pharmaceutically acceptable material, composition or vehicle, such as a liquid or solid filler, diluent, excipient, or solvent encapsulating material. The choice of any specific pharmaceutically acceptable carriers is well within the knowledge of those skilled in the art. Accordingly, there is a wide variety of suitable carries available and routinely used in pharmaceutical compositions.

It should be understood that the terms "a" and "an" as used herein refer to "one or more" of the enumerated components.

As used herein, all numerical ranges provided are intended to expressly include the endpoints and consistent with context all numbers that fall between the endpoints of range.

Further non-limiting details are described in the following Experimental Details section which is set forth to aid in an understanding of the invention but is not intended to, and should not be construed to, limit in any way the scope of the invention disclosed.

Experimental Details

Figure 2A:
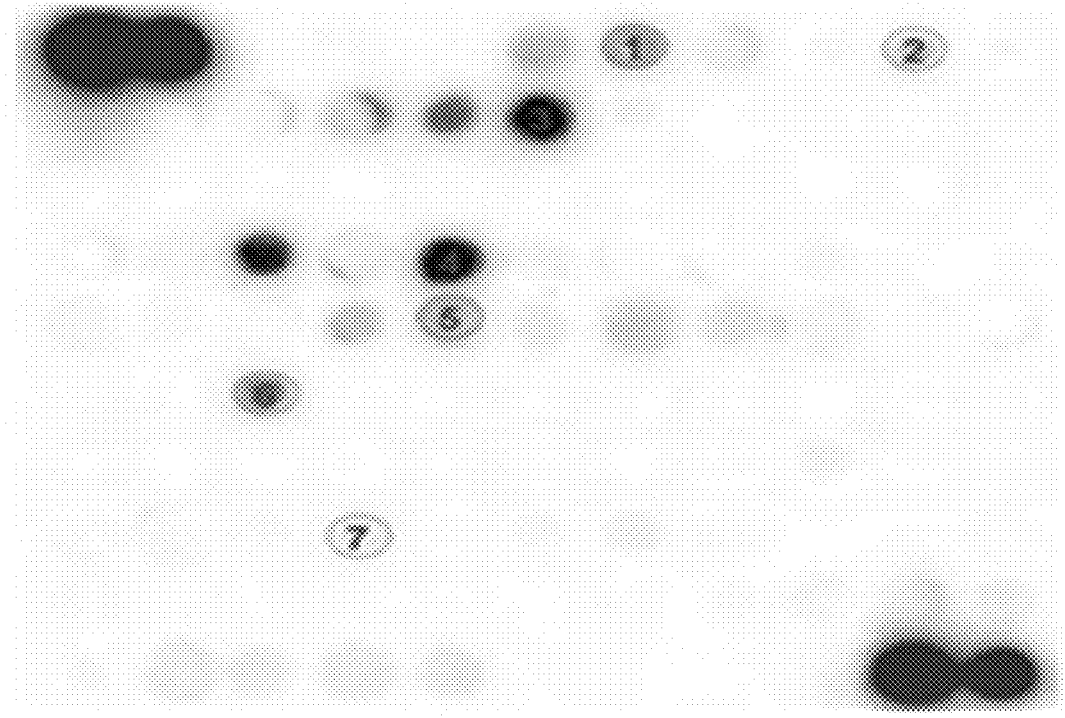
FIGS. 2A-2F show conserved residues in each HMG Box domain are critical for CXCL12 binding.
Figure 2B:
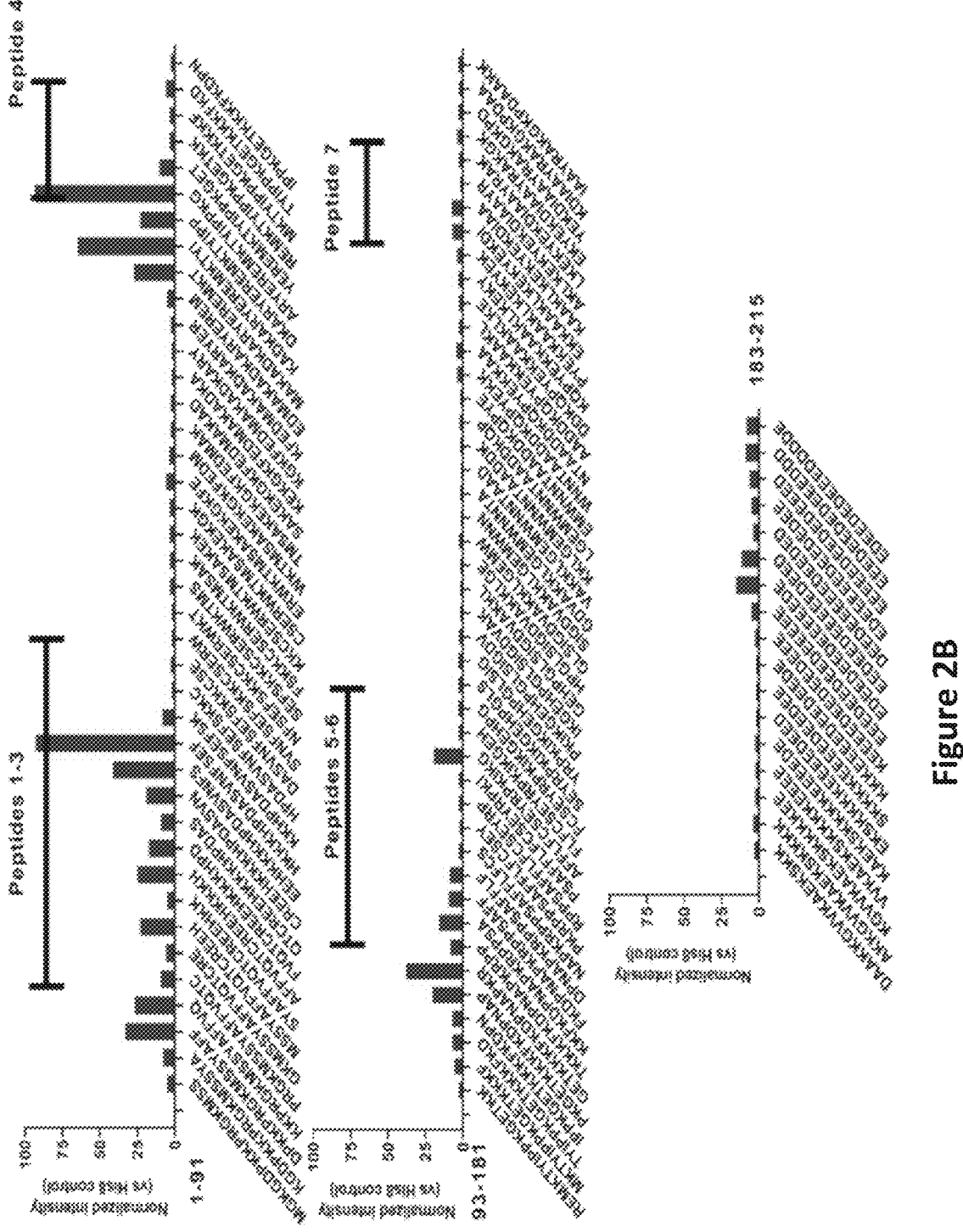

Results
Identification of Amino Acids and Motifs in HMGB1 Involved in CXCL12 Binding Before considering which residues of FR-HMGB1 can be mutated or deleted to eliminate proinflammatory signaling, it is essential to map the amino acids and motifs involved in binding to CXCL12. We used peptide SPOT arrays, [42] where overlapping peptides covering the sequence of one of the target proteins (HMGB1) are assessed by immunoblotting for their capacity to bind CXCL12. Two main binding sites were identified (FIG. 2A and FIG. 2B). The first encompassed α-helix I and part of helix II of each HMG Box (peptides 1-3 in Box A, peptides 5-6 in Box B), overlapping the glycyrrhizin binding site [43]. The second region (peptide 4 in Box A and 7 in B) was located at the C-terminal half of α-helix III. In each HMG Box, the first CXCL12 binding peptide (helices I and II) had much greater intensity of the spots, indicating potentially higher affinity for CXCL12.

Figure 2C:
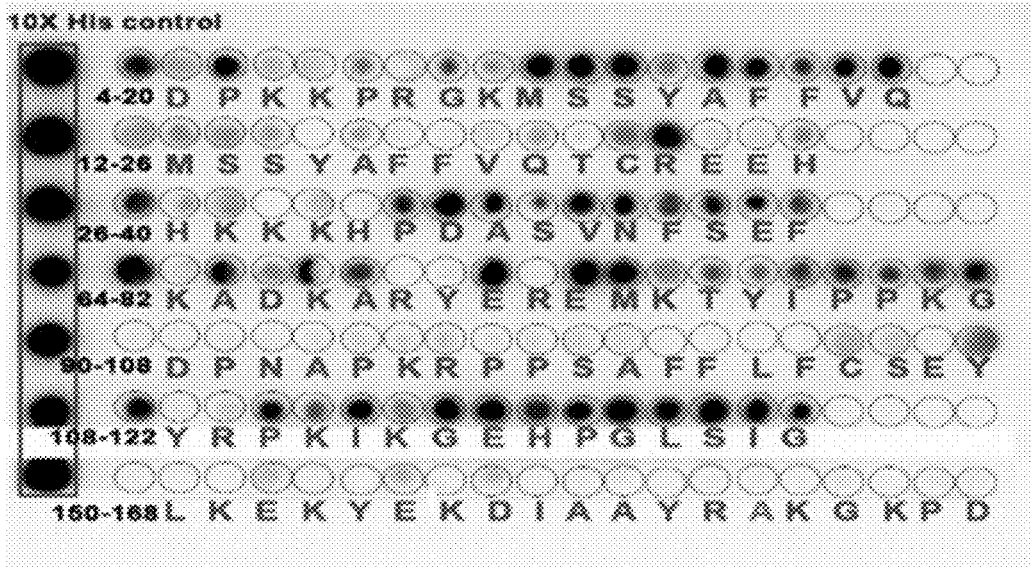
Figure 2D:
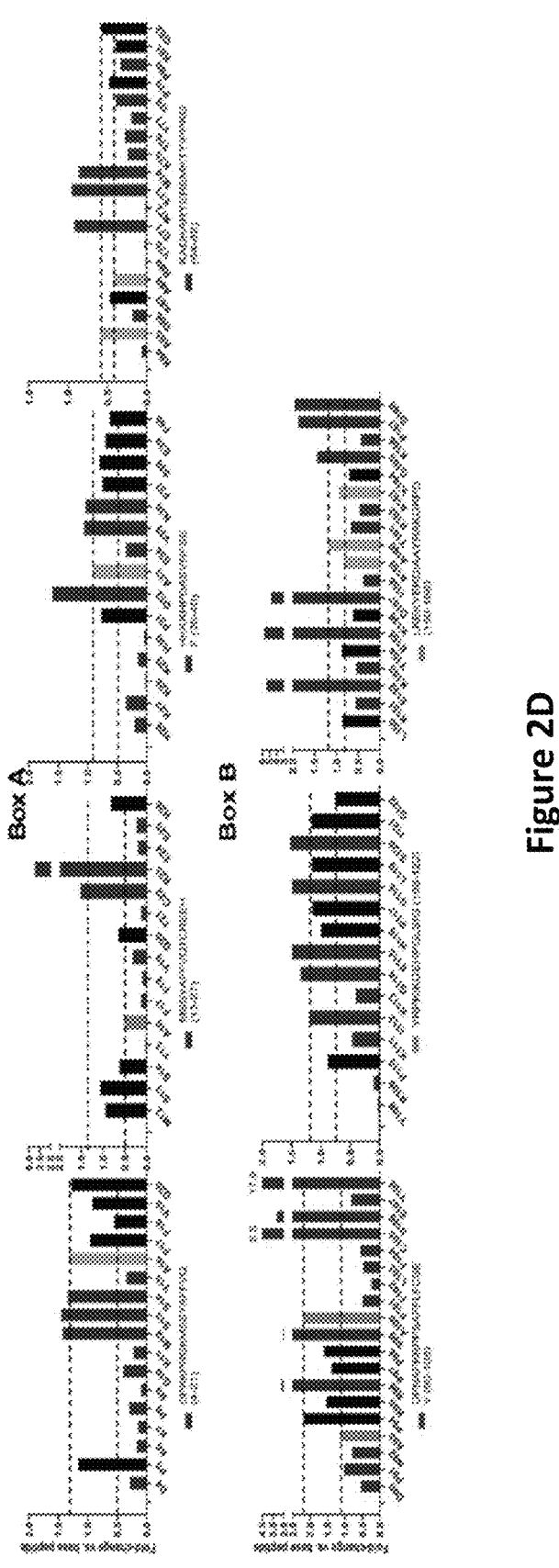
Figures 2E, 2F:
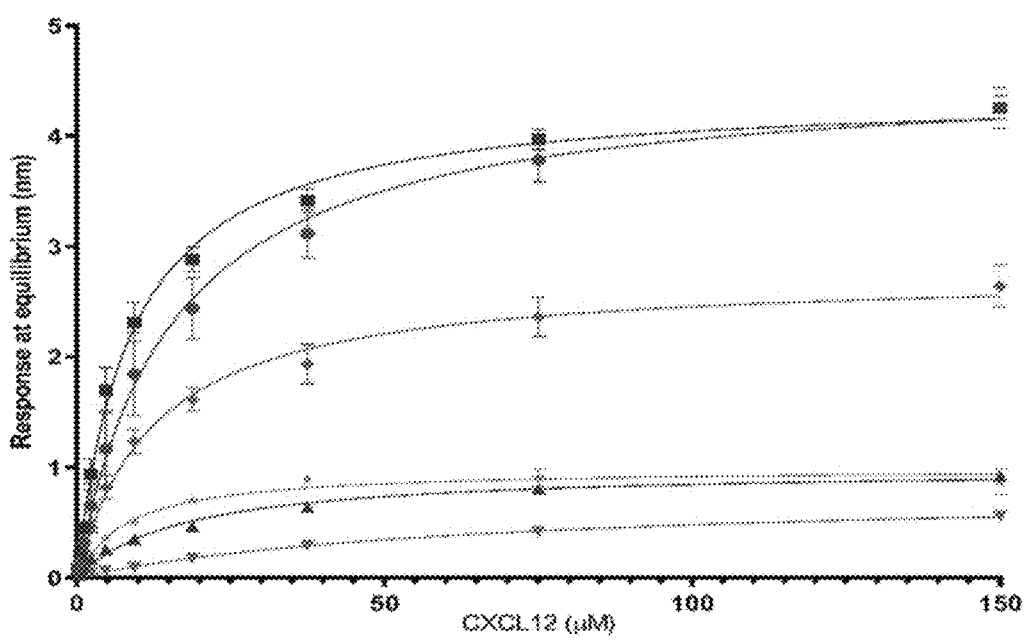

Next, to identify the amino acids that directly contribute to CXCL12 interaction, we generated a second peptide array where each amino acid within the CXCL12 binding peptides was substituted with alanine, This confirmed the critical role of several residues (FIG. 2C and FIG. 2D). Contrary to published data where the CXCL12 has only been shown to interact with the helical segments of the HMG Boxes [44-46], we found that part of the flexible N-terminal flanking region of each box ($D_{-4}$-$P_{-3}$-$X_{-2}$-$X_{-1}$, where the subscript number indicates relative position to the first residue in each HMG Box—Pro 9 in A, and Pro 94 in B), as well as C-terminal residues (Ile 78-Pro 80 for Box A and Ala 163-Asp168 for Box B), are also involved (FIG. 2E). This was confirmed with a reverse peptide array (FIG. 11) in which CXCL12 peptides were probed for binding to HMGB1. Full-length FR- and 3S-HMGB1 bound to peptides containing sequences covering the whole β-sheet of CXCL12, whereas HMGB1 Box constructs alone (8-78 Box A) or (94-162 Box B), without the flanking flexible region [47], only interacted with the peptides covering the N-terminal strand of the β-sheet.

To further confirm the role of these flexible regions, we used biolayer interferometry (BLI) to assess binding of CXCL12 to HMGB1 constructs with different boundaries. We generated either full HMG Box constructs comprising the entire HMG Box with the flanking regions (HMGB1 1-88 for Box A, HMGB1 89-174 for Box B) [48] and helical-only HMG Box constructs comprising the core HMG Box alone, without the flexible flanking residues (HMGB1 9-78, HMGB1 94-162). These were compared to full-length HMGB1 constructs (1-214), both FR-HMGB1 and non-oxidizable (3S)-HMGB1, the latter sharing the CXCL12-binding properties of the wild-type protein [14]. As expected, the helical-only constructs had lower CXCL12 affinity and binding capacity compared to full HMG Box constructs with intact flanking regions due to much faster dissociation rates. In contrast, affinities of CXCL12 for full-length FR- or 3S-HMGB1 and full HMG Box constructs were comparable to each other and greater than for the helical-only constructs (FIG. 2E and FIG. 2F).

Figure 3:
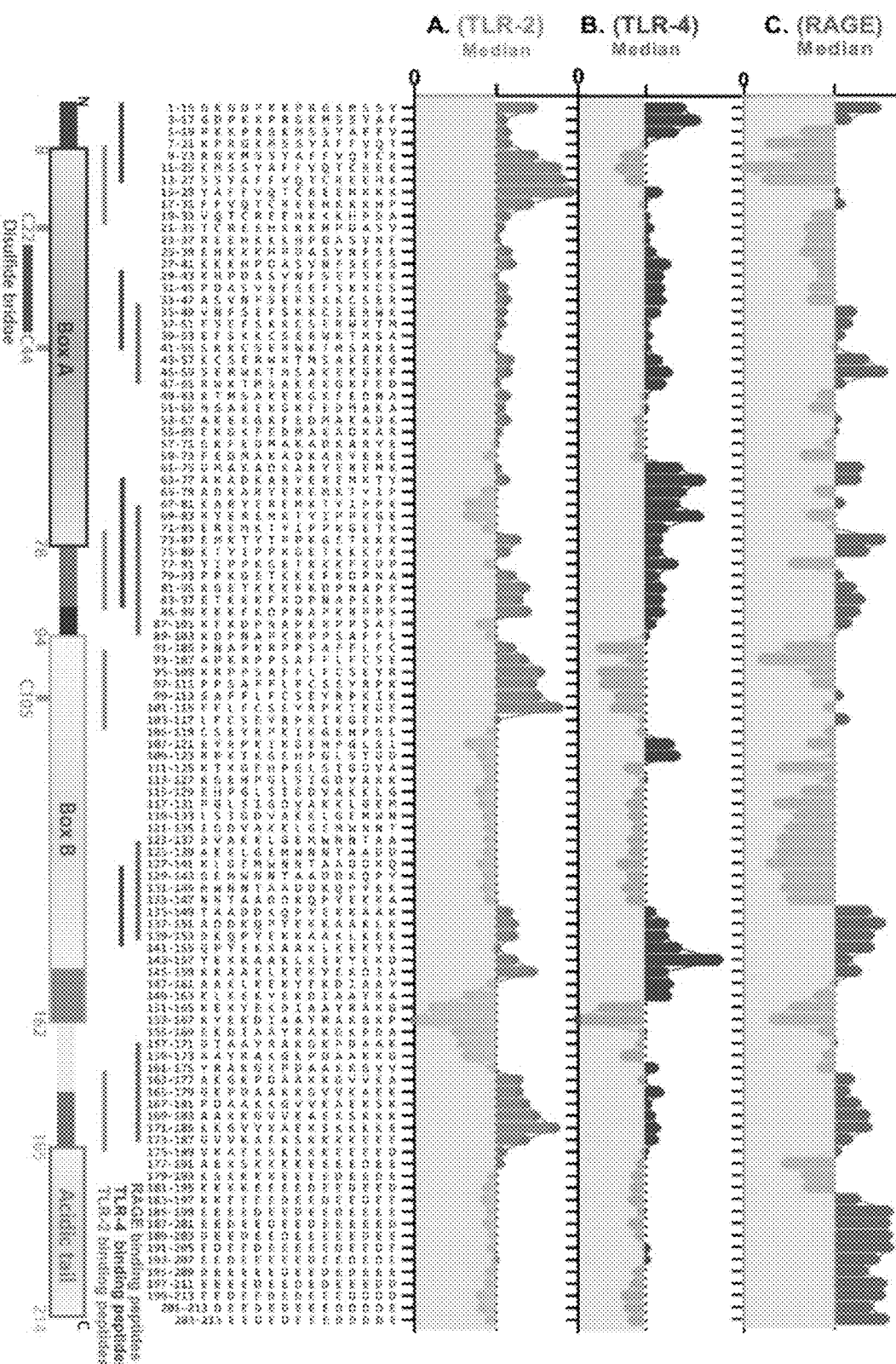
FIG. 3 shows the binding of DAMP receptors to HMGB1 analyzed via peptide arrays. Intensity densitogram of Cel-luSpot™ arrays with HMGB1 15-mer peptides baited with TLR-2 (orange), TLR-4 (red) or RAGE (green). Intensity normalized from 0 (empty spots) to 100 (highest control) and averaged across two membranes for each target. A schematic representation of HMGB1 is shown to the left of the peptide sequences. TLR-2 (A) binding peptide sequences within HMGB1 occupy similar positions across Box A and Box B with another binding region just before the acidic tail. Unlike CXCL12, the binding pattern for TLR-4 (B) and RAGE (C) differs between the two Boxes, with TLR-4 binding peptides clustered mostly in Box A and the linker, and RAGE binding peptide sequences in the C-terminal end of Box B and the flexible region preceeding the acid tail.

Identification of Amino Acids and Motifs in HMGB1 Involved in TLR-2, TLR-4 and RAGE Binding Next, we probed the HMGB1 peptide arrays against each of the proinflammatory receptors (TLR-2, TLR-4 and RAGE) To account for nonspecific binding, the normalized signal from unbaited arrays was subtracted from the baited arrays We found that TLR-2 bound to a peptide in HMGB1 in Box A and Box B (FIG. 3, section A) that coincides with the glycyrrhizin binding site in both HMG Boxes (FIG. 1B) [49]. In addition, TLR-2 also bound to the linker region between the two Boxes, the peptide immediately adjacent to the acidic tail of HMGB1 and the C-terminal regions to each HMG Box, extending beyond the residues that bound CXCL12. Interestingly, the binding interface for TLR-2 within Box A is within the alpha helices which twist upon oxidation [50] to adopt a different 3D configuration (FIG. 4, section A).

Figure 4:
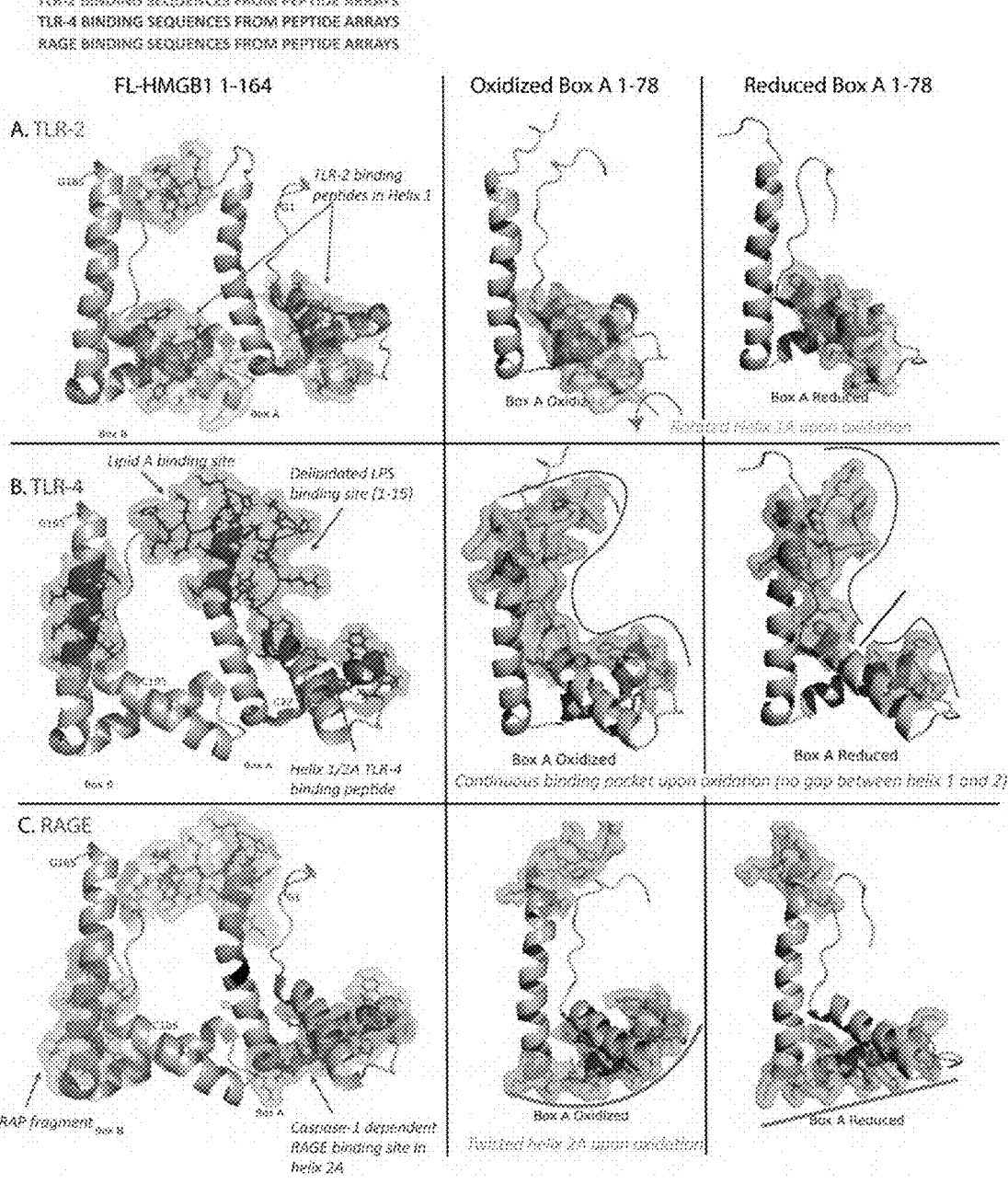
FIG. 4 shows a representation of DAMP-receptor binding peptides and changes in their configuration dependent on the oxidation status of Cys22-Cys44 in Box A. Surface representation of the binding peptides described in FIG. 3 overlaid on the published Pymol NMR structure of HMGB1 (PDB 2YRQ). A) TLR-2, B) TLR-4, C) RAGE. Cyan: cysteine residues. Pink (A only), glycyrrhizin binding residues contained in a TLR-2 binding site. Black (C only), Caspase-1 site reported to result in RAGE-mediated immune tolerance induced by HMGB1. Peptides binding after residue 164 in HMGB1 are not shown in any of the figures as they are absent in the available protein structures. In all three cases, the positioning of peptides within Box A is affected by oxidation.

Peptides binding to TLR-4 (FIG. 3, section B) form a binding pocket in Box A that is only continuous when Box A is oxidized (FIG. 4, section B). These include the delipidated LPS binding segment and the region bordering the Lipid A binding region within Box A [51].

Our spot array data for RAGE (FIG. 3, section C) confirmed the role of peptides previously shown to modulate RAGE activity [39][52](FIG. 4, section C), namely Rage Antagonistic Peptide (RAP) between positions 149-182, and the Caspase-1 activated site in Helix 2 of Box A. However, in contrast to previous studies where activity was only seen following Caspase-1 cleavage of HMGB1 [39], we observed that the Box A site is solvent-accessible in a full-length Box A and that its positioning is affected by the bending of Helix 2 in Box A on oxidation.

Taken together, these data show that binding of HMGB1 to all three proinflammatory receptors involves distinct regions in each of the HMG Boxes, and the spatial arrangement within Box A is dependent on oxidation. In addition, the sequences in the inter-Box linker and those preceding the acidic tail have high affinity for all three proinflammatory receptors. Therefore, substitution or elimination of these sequences would effectively reduce binding to all these proinflammatory receptors.

CXCL12 Binds to a Concave Pocket on the Underside of Each HMG Box as Shown by Peptide Array and NMR (578)

We next used NMR to confirm, from a structural perspective, the amino acid residues in HMGB1 involved in CXCL12 binding. We used FR-HMGB1 94-162 and 89-174 to represent HMG Boxes with and without the flanking regions, as well as 3S HMGB1 1-184. Non-oxidizable 3S-HMGB1 was used instead of native full-length FR-HMGB1 as the time required for obtaining a full set of 3D spectra at 750 MHz ($^{15}$N HSQC-TOCSY/NOESY and associated $^{15}$N HSQC spectra) would result in oxidation of the latter.

CXCL12 titration of HMGB1 Box B 94-162 (FIG. 5A) resulted in changes in cumulative chemical shift perturbation (CSP) or peak height changes ($I/I_0$), of several residues at both the C-terminal and N-terminal binding regions identified in the peptide arrays. For the Box B construct that included the flanking regions, both the median CSP and mean volume change were significantly higher, confirming that several residues (D90, G165, K166) in these flanking regions are involved in CXCL12 binding. Residues not affected by CXCL12 binding in the helical-only (94-162) construct, such as Y154, D157 and I158, and which were identified as being involved in CXCL12 binding in the peptide arrays, demonstrated significant CSP in the full HMG Box construct (89-174), indicative of improved binding when the flanking regions were present. In addition, we observed CSP changes for residues not identified in the peptide arrays (A147, M131, A169, K172, G173) in the construct with the flanking regions. Other residues that have not been previously identified but were flagged as being potentially important in the peptide arrays did not display either CSP or volume changes upon addition of CXCL12 (C105, E107, Y108). Consequently, this group of residues was reclassified as being not critical for CXCL12 binding. Surprisingly, in contrast to published data [53], residues A100, I112, L119 and A136 in either Box B construct failed to produce significant CSP changes, although residues (S99, K113) that are very close to some of these were affected.

Figure 11A:
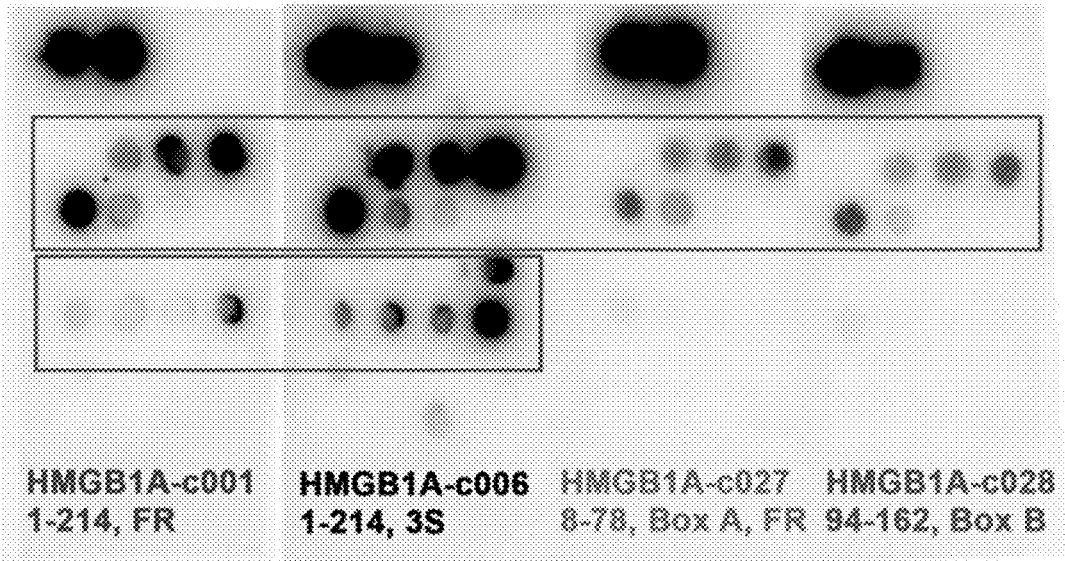
FIGS. 11A-11B show results of a peptide array of CXCL12 peptides interacting with HMGB1.
Figure 11B:
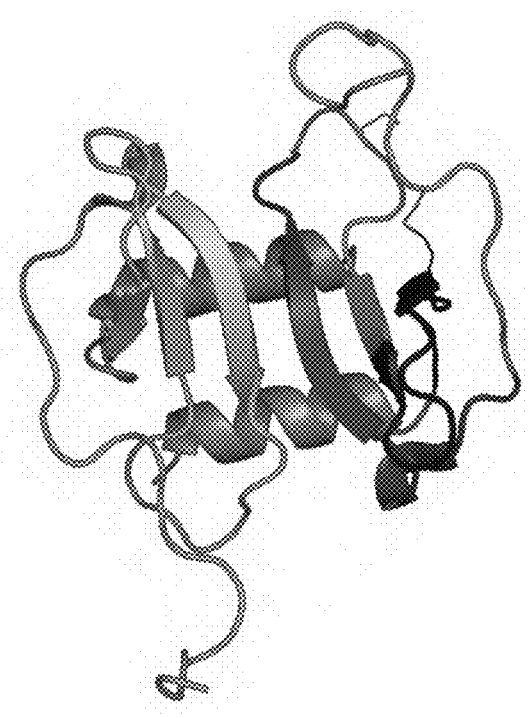
Figure 12:
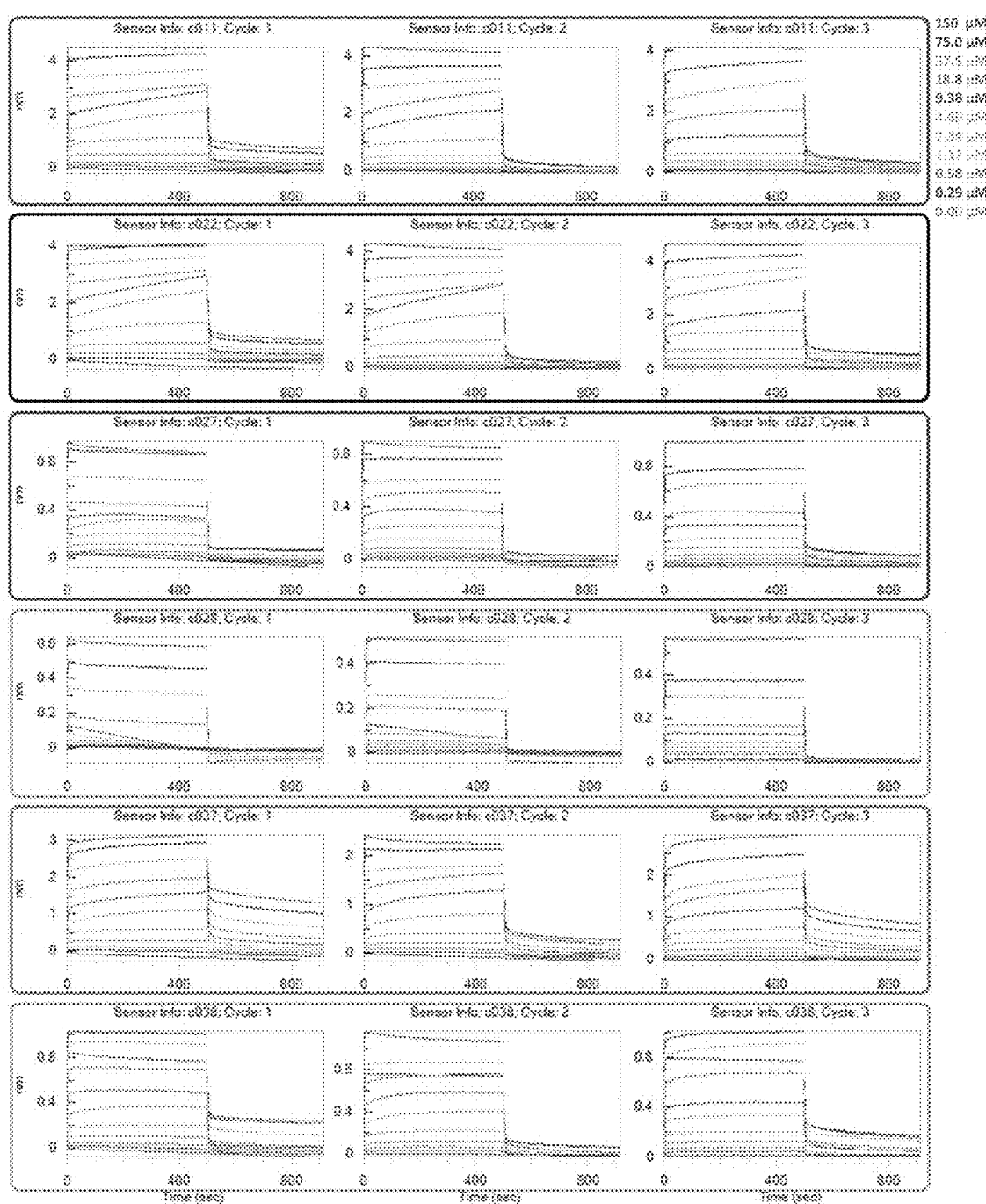
FIG. 12 shows interferograms in BLI of CXCL12 binding to immobilized HMGB1 constructs. Biotinylated HMGB1 constructs were immobilized on streptavidin-coated Octet biosensors and dipped in rising concentration of CXCL12. Interferograms are colored according to CXCL12 concentration (key in top right). Each set of three replicates (cycles) for a given sensor is surrounded by a colored overlay according to construct. FR FL-HMGB1 (c011), black: 3S-FL HMGB1 (c022), purple: FR-HMGB1 Box A 8-78 (c027), brown: FR-HMGB1 Box B 94-162 (c028), pink: FR-HMGB1 Box A 1-88 (c037), grey: FR-HMGB1 Box B 90-162 (c038).
Figure 13A:
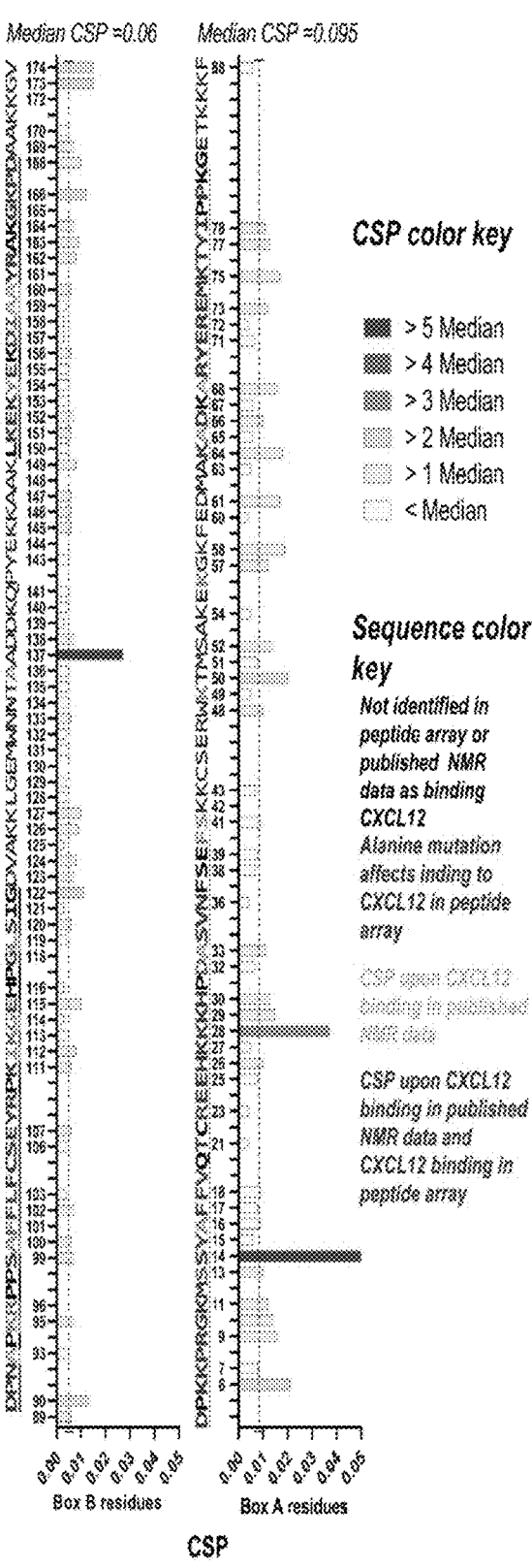
FIGS. 13A-13D show NMR validation of residues involved in CXCL12 binding.
Figure 13B:
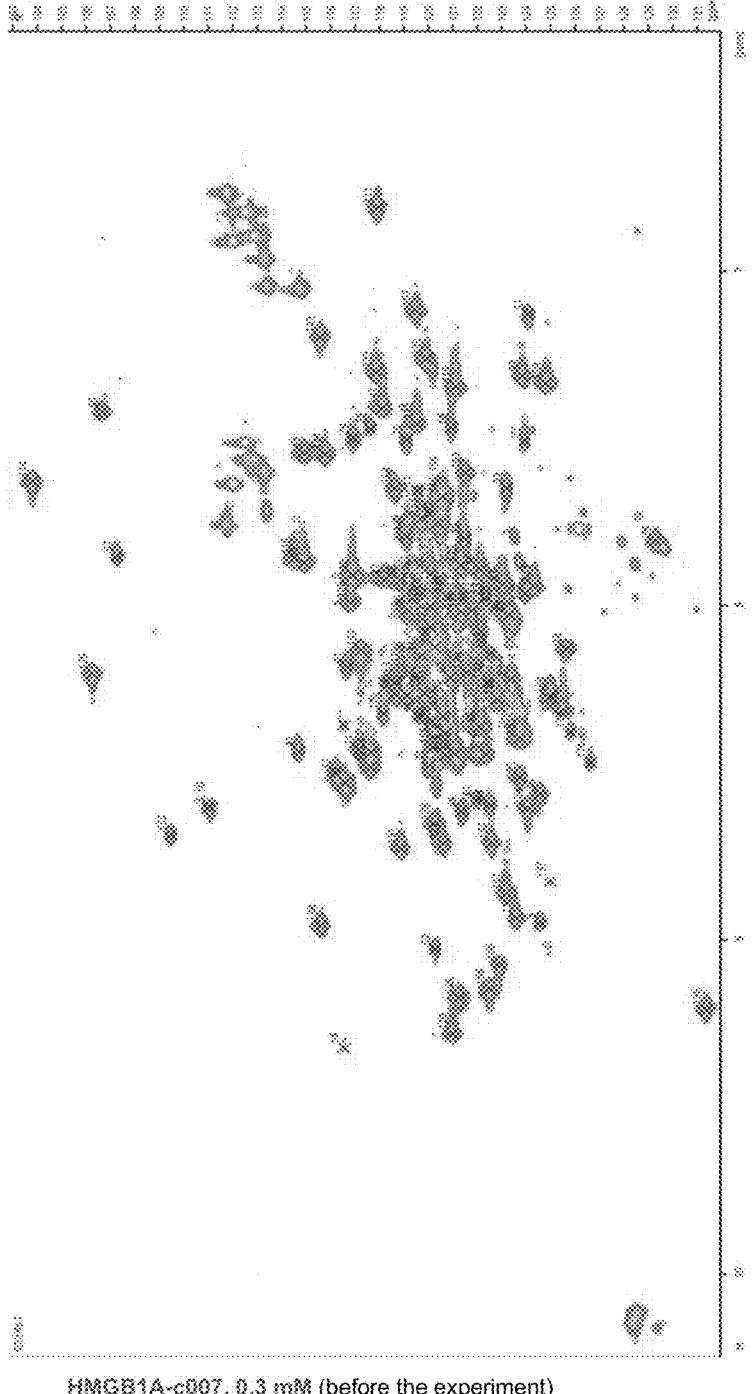
Figure 13C:
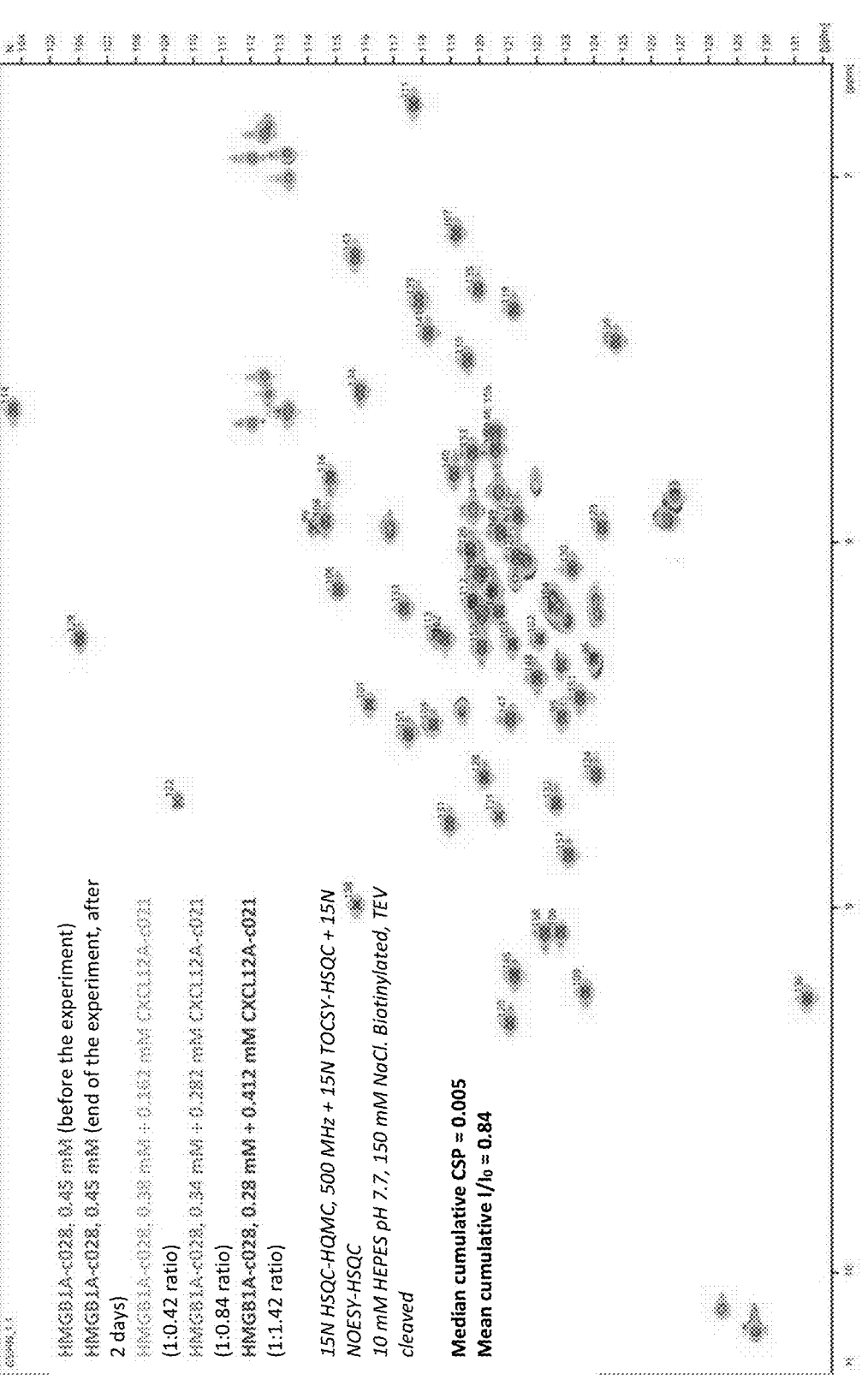
Figure 13D:
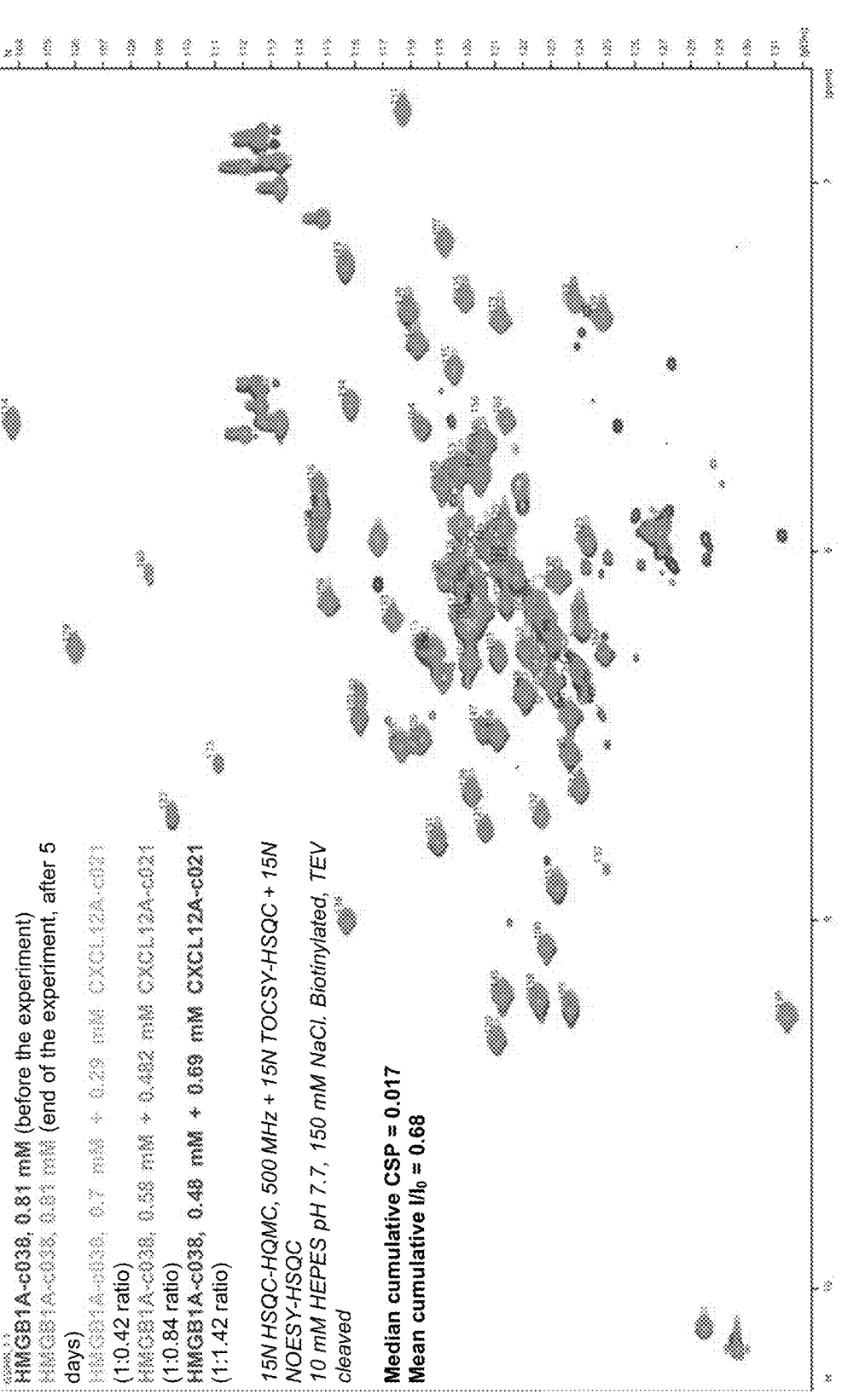
Figure 14:
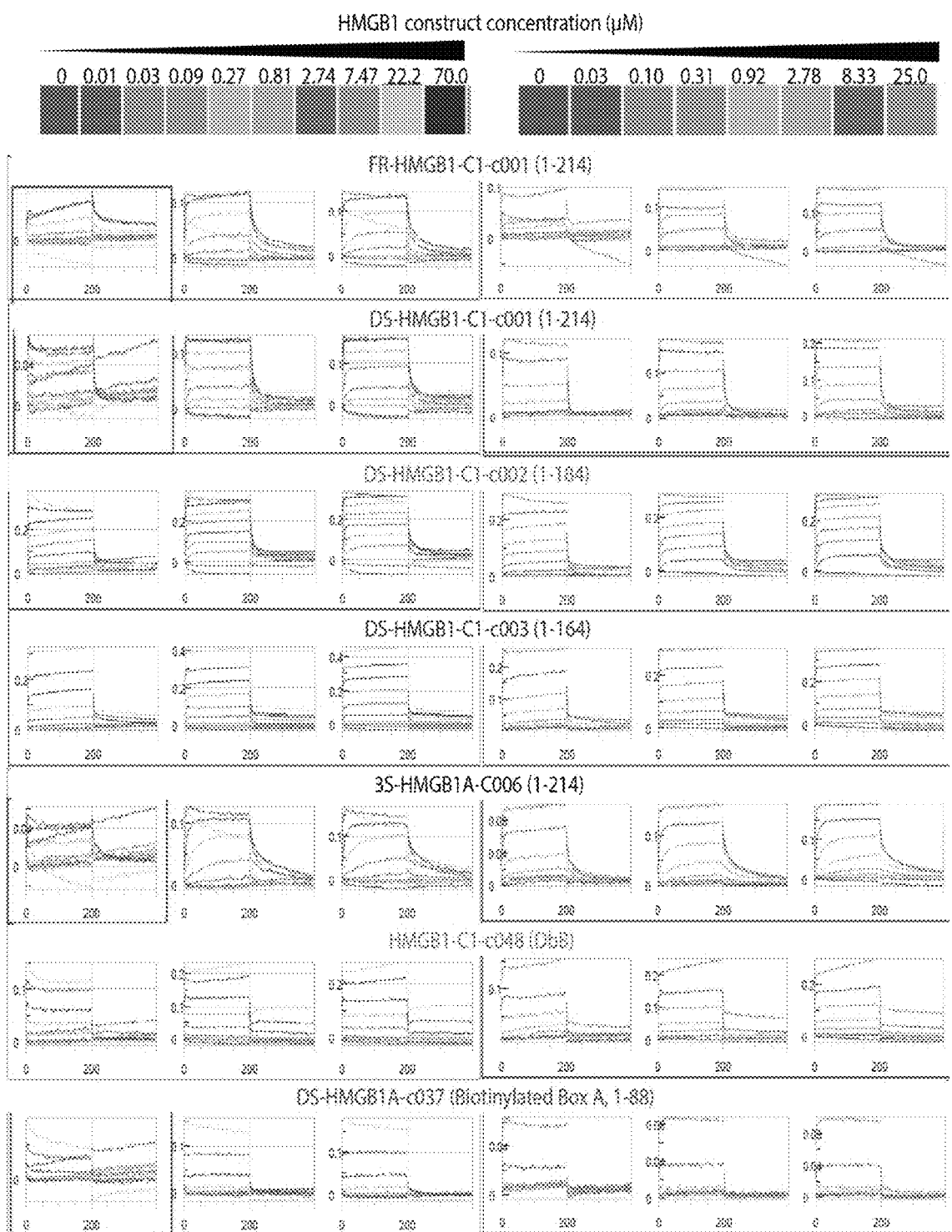
FIG. 14 shows interferograms in BLI of HMGB1 constructs binding to immobilized Fc-RAGE. RAGE-Fc was immobilized in the surface of AHC sensors and dipped in rising concentration of different HMGB1 constructs. Two experiments were run with different concentration ranges: the three columns of graphs in the left, 0 to 22.22 μM HMGB1 over 9 steps; on the right, 0 to 25 μM over 7 steps. Both are color-coded by concentration (top). Colors indicate the specific construct concentration. Each graph corresponds to a single sensor (replicate). Interferograms surrounded by a red rectangle had data points excluded due to poor quality (e.g. drift).
Figure 15:
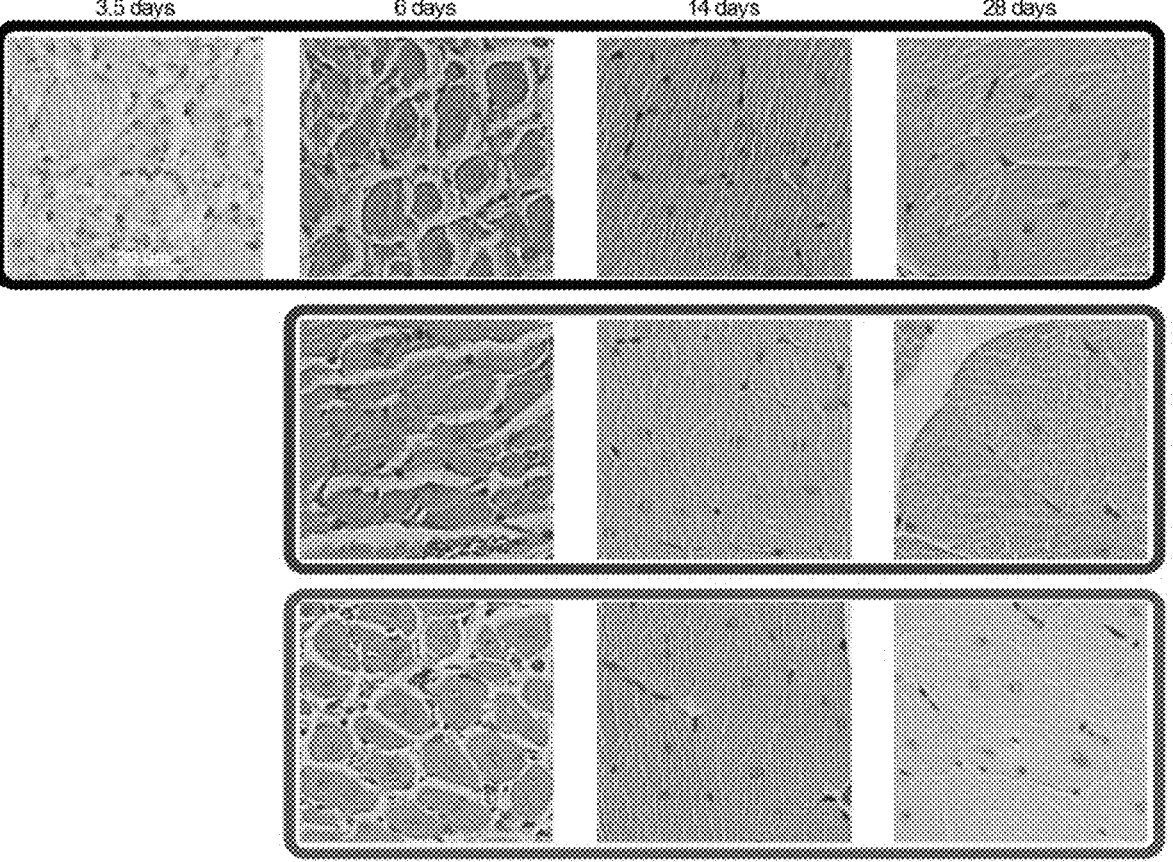
FIG. 15 shows histological images of regenerating muscle in response to FR-HMGB1 (red) or dBB12L (green) compared to PBS control (black), from FIG. 10.
Figure 16:
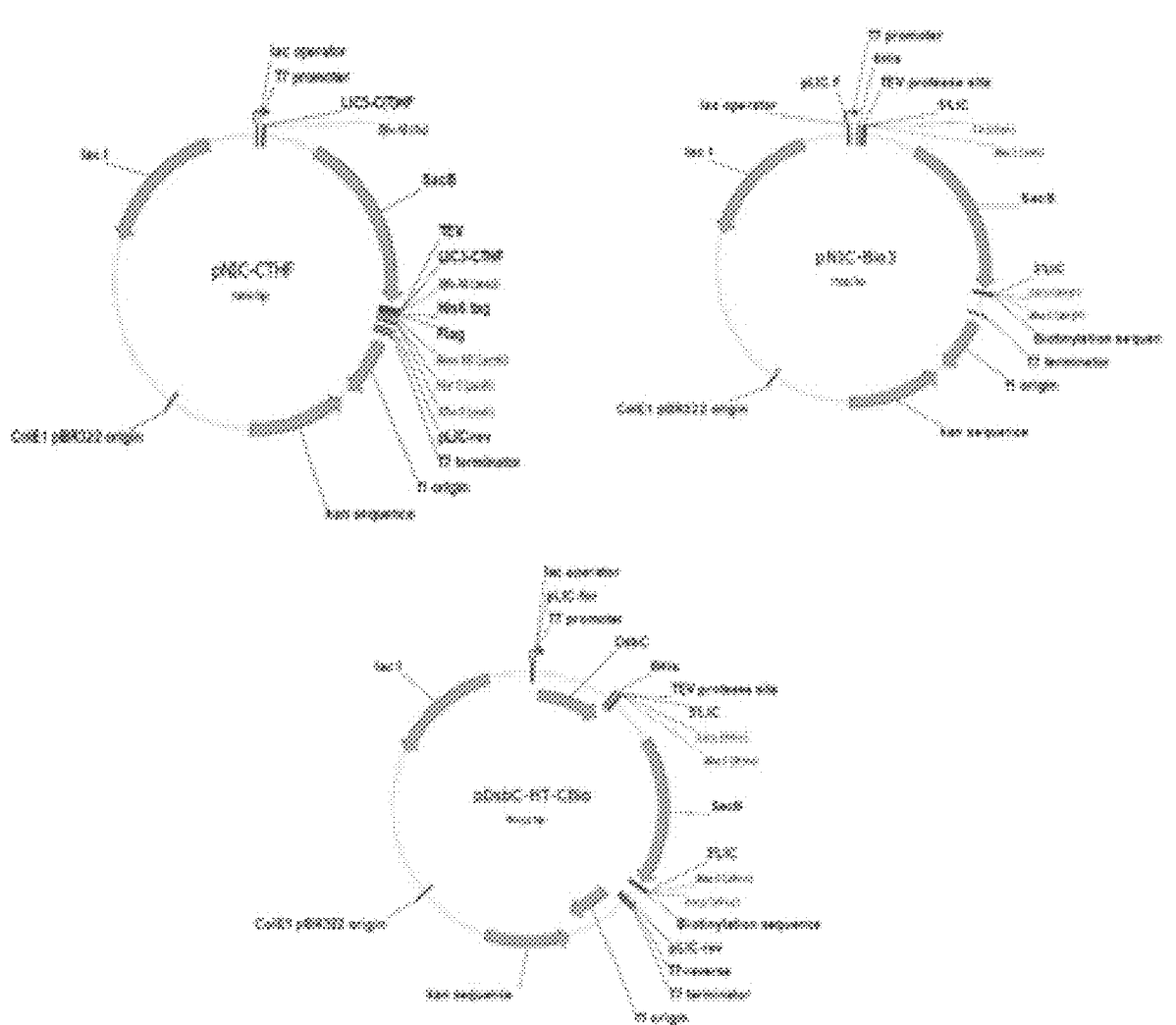
FIG. 16 shows plasmid vector maps. Vector maps with features and restriction sites. TEV: Tobacco etch virus protease recognition site. 6-His: 10/6-histidine residue affinity epitope. FLAG: FLAG affinity epitope. StrepTag: StreptactinXT affinity epitope. SacB: Levansucrase precursor (negative selection in the presence of sucrose). pLIC: Annealing sites for sequencing primers used in colony screening. All plasmids contain kanamycin resistance (50 μg/mL).

When the NMR experiment was repeated with 3S-HMGB1 1-184, CSP changes upon CXCL12 addition were below the threshold for detection for most residues due to a lower signal to noise ratio. However, we were able to still observe binding to some residues over the median CSP change. Residues corresponding to HMG Box B showed overall weaker CSP changes compared to those in Box A. This could represent a more fluid equilibrium, consistent with the faster association and dissociation rates for Box B (FIG. 2F). This allowed us to also denote residues such as H30, D32 or S34 in Box A identified in the peptide array as false positives (FIG. 11). Whilst K89 in Box B 89-174 showed high CSP, this is the third residue from the N-terminus (after the TEV cleavage leftover N-terminal residues—Ser-Met-). In the experiments with 3S HMGB1 1-184, where it is in the middle of the flexible linker, it did not demonstrate increased CSP changes. Therefore, the changes associated with this residue in Box B alone are likely related to its position at the N-terminus potentially permitting high conformational flexibility.

Figure 1B:
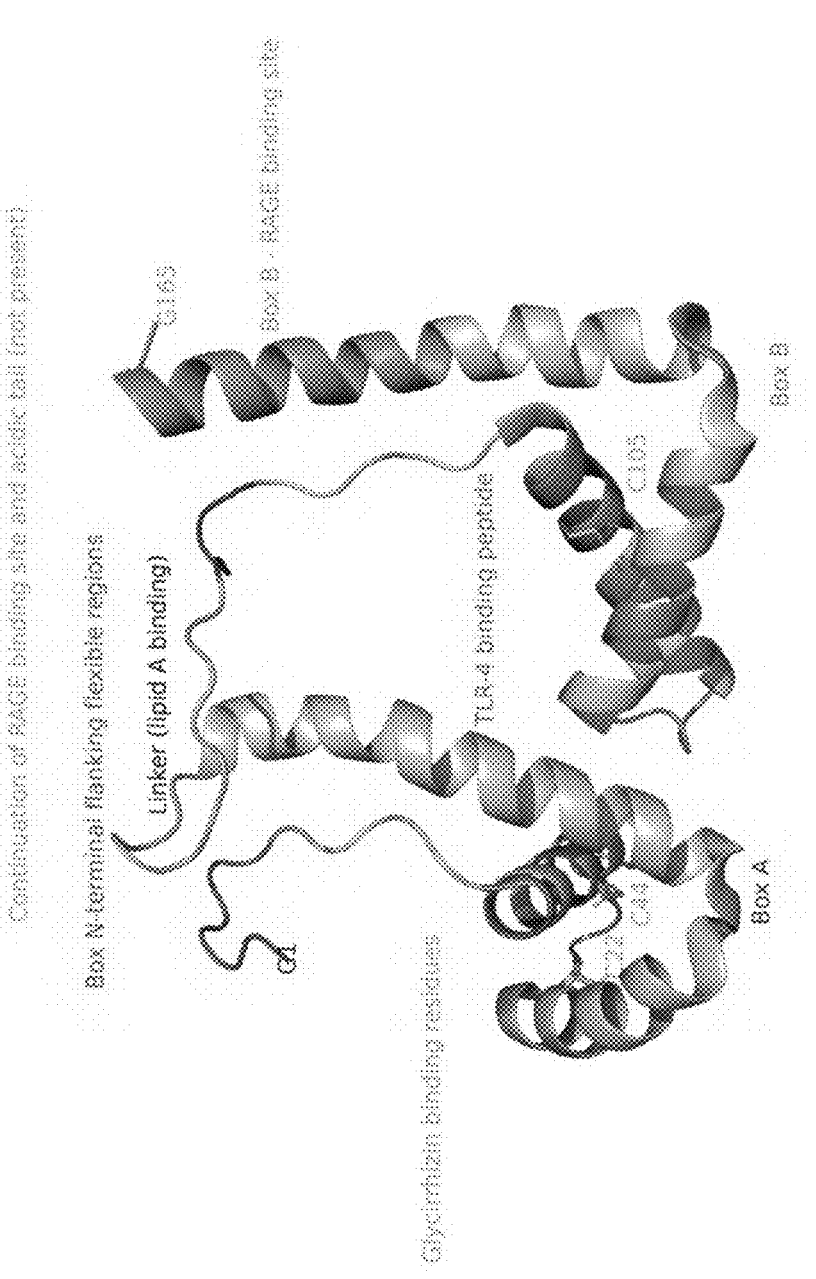
Figure 1C:
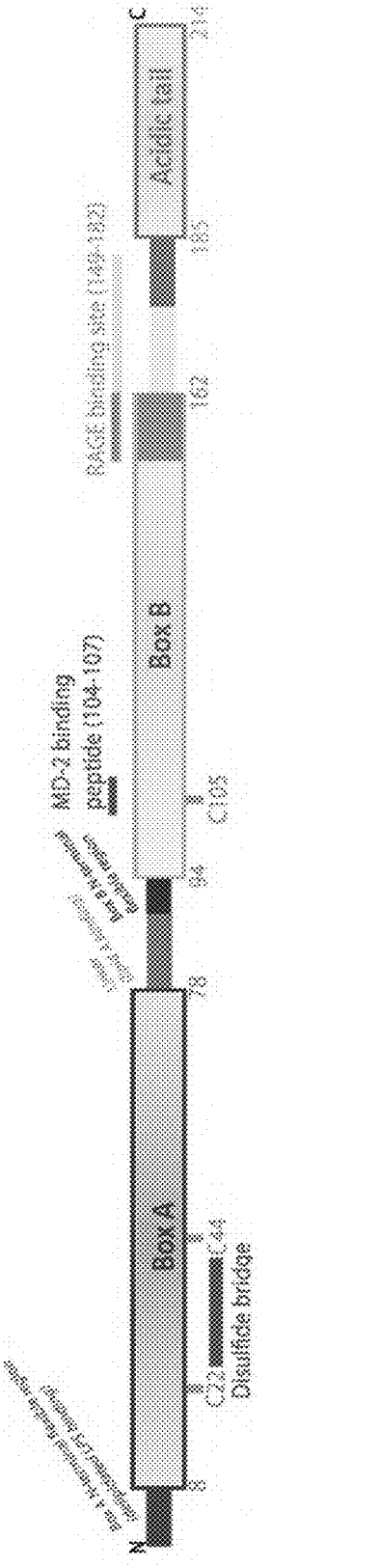
Figures 6A, 6B:
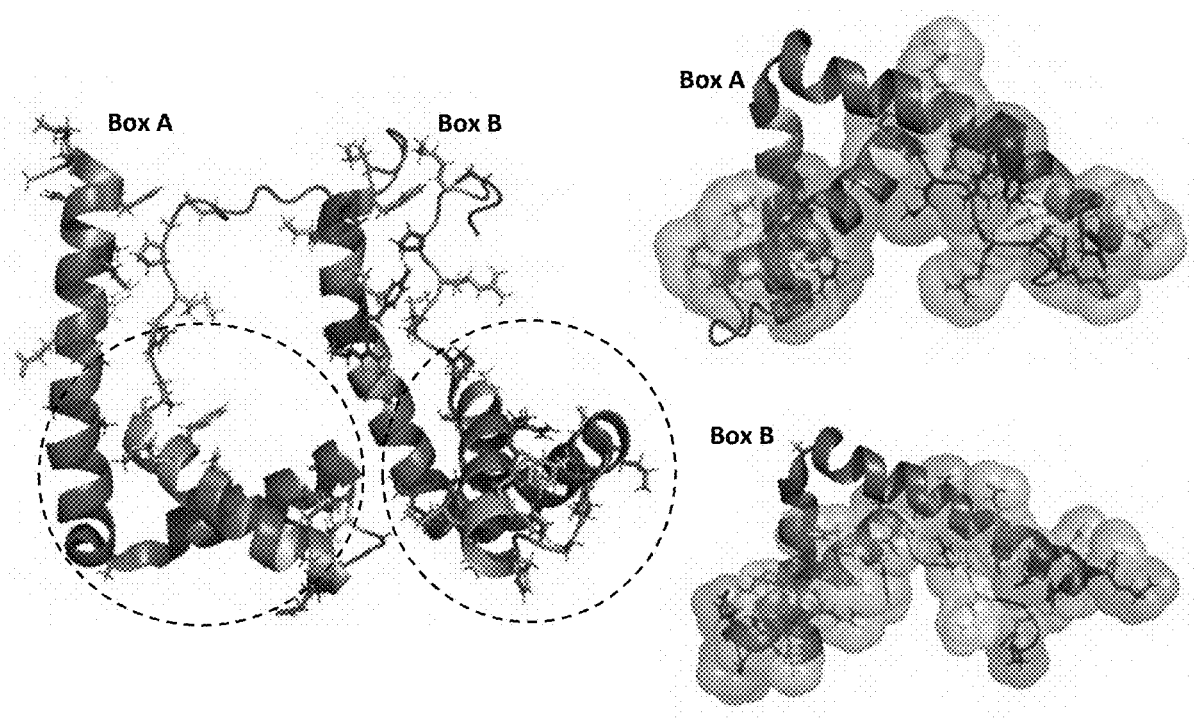
FIGS. 6A-6C show design of dBB12L construct to eliminate RAGE, TLR-2 and TLR-4 signaling.
Figure 6C:
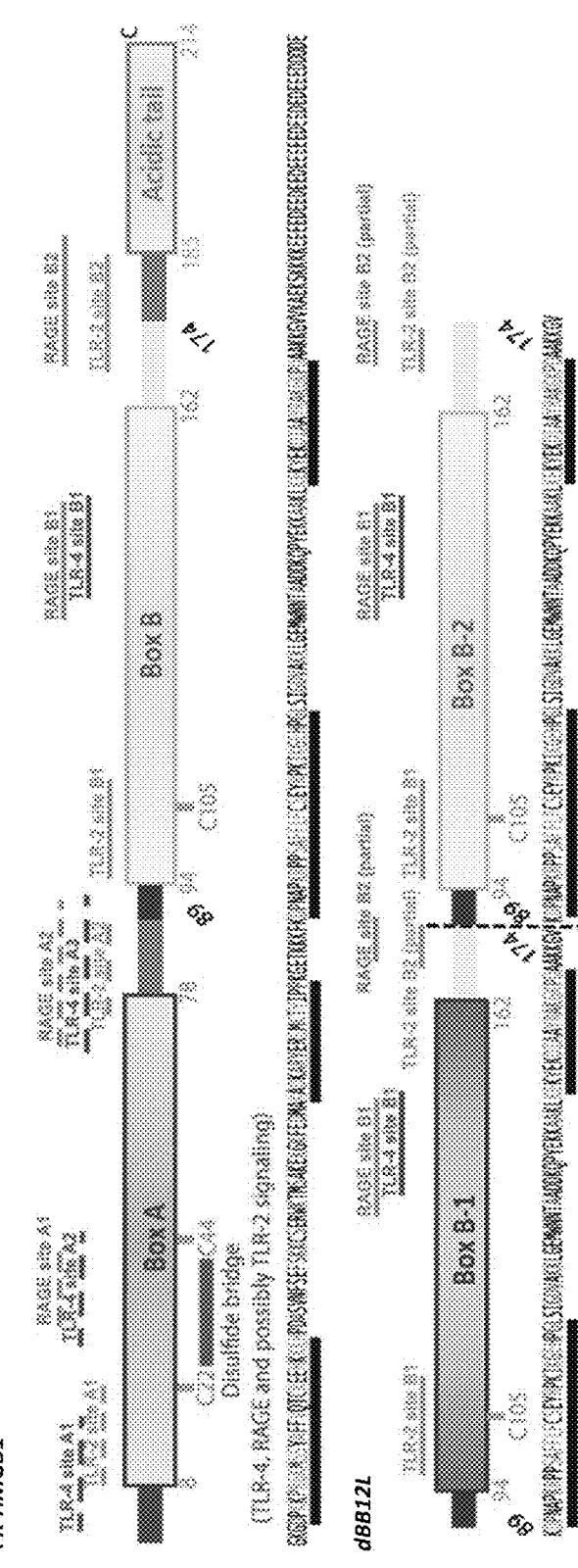

Design of a Double Box B HMGB1 Construct that Retains CXCL12 Binding Whilst Eliminating Proinflammatory Signaling We combined the data from the peptide arrays, alanine substitution and NMR, and mapped them onto the NMR structure of HMGB1 (FIG. 6A and FIG. 6B, PDB 2YRQ), to identify the residues involved in binding CXCL12. We found they form concave pocket on the underside of each HMG Box. These two pockets also contain the described binding site for glycyrrhizin, which inhibits HMGB1-CXCL12 binding [43]. Surprisingly, the distribution of peptides within each HMG Box that interact with CXCL12 is similar between both HMG Boxes and form almost identical binding pockets (FIG. 6B1). Furthermore, the HMG Box A and B are each capable of binding one CXCL12 monomer with equivalent affinity and binding of a monomer of CXCL12 does not require cooperation between the two Box domains. In contrast, binding to the proinflammatory receptors requires cooperation between the two Box domains. Therefore, we hypothesized that an engineered HMGB1 construct where Box A is substituted by another Box B (i.e. 1-88 replaced by 89-174) would effectively bind two CXCL12 monomers to present to a CXCR4 membrane dimer but would be unable to signal through TLR-2, TLR-4 or RAGE. We further reduced the propensity for binding to RAGE by deleting the RAGE-binding sequence in Box B (175-184). Replacing the Box A sequence for Box B also replaces the LPS glycan-binding peptide for the LPS lipid A binding peptide [51]. Therefore, this engineered construct dBB12L (FIG. 6C) comprised the following segments of the native HMGB1 protein: flexible N-terminal region (from HMGB1 89-93), first Box B (from HMGB1 94-162), 12-residue linker C-terminal of native Box B (from HMGB1 163-174), and second Box B (from HMGB1 94-162). The linker length of 12 residues in this dBB12L is similar to the 10 amino acids in the linker of native HMGB1 and included residues 172 and 173 which showed changes in CSP on CXCL12 binding.

Figures 7B, 7C:
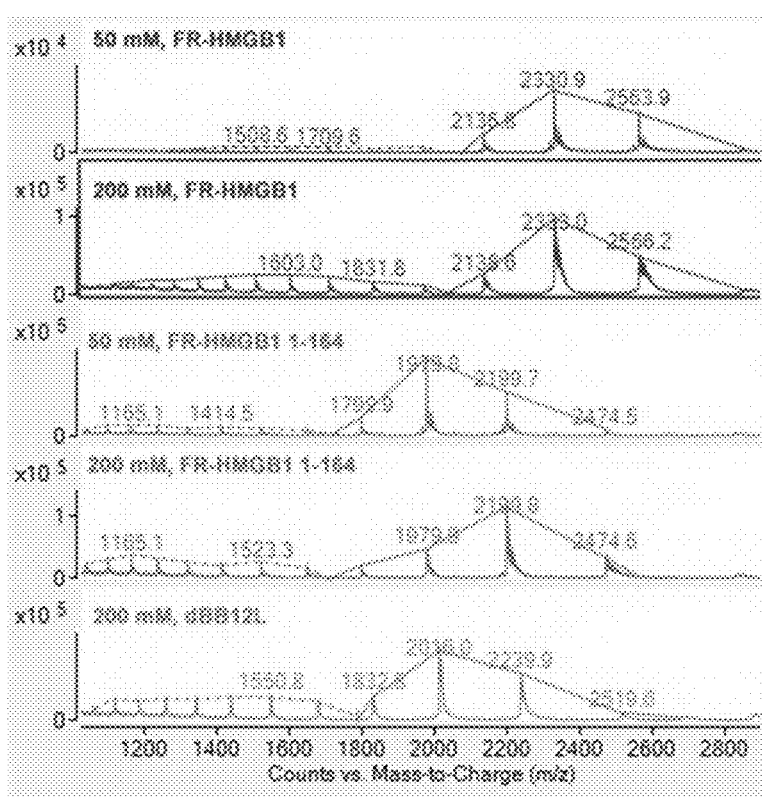
Figure 7D:
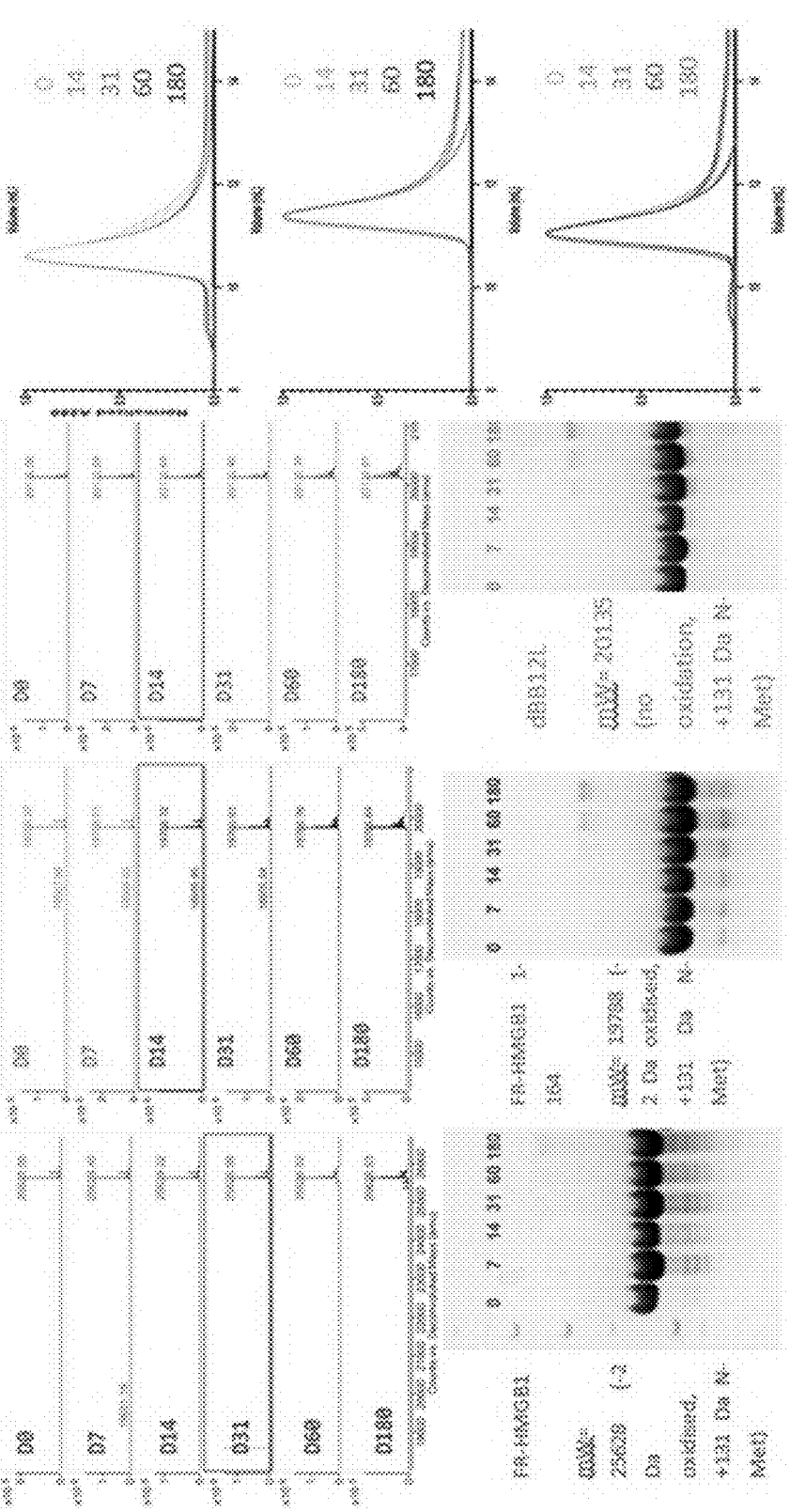

We compared the thermostability of dBB12L and wild-type HMGB1 across a variety of buffer conditions using differential scanning fluorimetry (DSF) and solvent accessible surface area (SASA) determination by both native mass spectrometry (native ESI/MS) and size exclusion chromatography (SEC). dBB12L had similar stability and surface charge profiles to FR-HMGB1 1-164, which also contains two HMG Box domains and no C-terminal acid tail. Thermostability trends across different buffer conditions were similar for all constructs (FIG. 7A), with lower $Tm_{50}$ for buffers with pH close to the isoelectric point (9.9 for tail-less constructs as dBB12L or 1-164, and 6 for FL-HMGB1). All constructs were equally stable in PBS, purification buffers, and saline solution, with $Tm_{50} \sim 50^\circ$ C. However, we observed different optimal ionic strength and pH ranges for FR-HMGB1/FR-HMGB1 1-164 compared to dBB12L. In native ESI/MS, all three HMGB1 constructs had similar charge state distributions, with a compact monomer as the main species and a second species with higher SASA representing an extended monomer conformation (FIG. 7B and FIG. 7C). The extended monomer was more prevalent for tail-less constructs or at higher ionic strength. Average monomer SASA values observed in native ESI/MS (FIG. 7C) agreed with those derived from SEC or published NMR structures (PDB 2YRQ; HMGB1 1-164). Compact FL-HMGB1 monomer SASA matched computational models of FL-HMGB1 in water [46]. Storage up to 180 days did not affect SEC profiles (always monodisperse at equal RV), degradation, or aggregation (FIG. 7D). Taken together, these data show that dBB12L has a similar folding and stability to native FR-HMGB1 in clinically relevant solutions.

dBB12L Construct has Greatly Reduced Affinity for RAGE and Cannot Signal Through TLR-2 or TLR-4

Figure 8A:
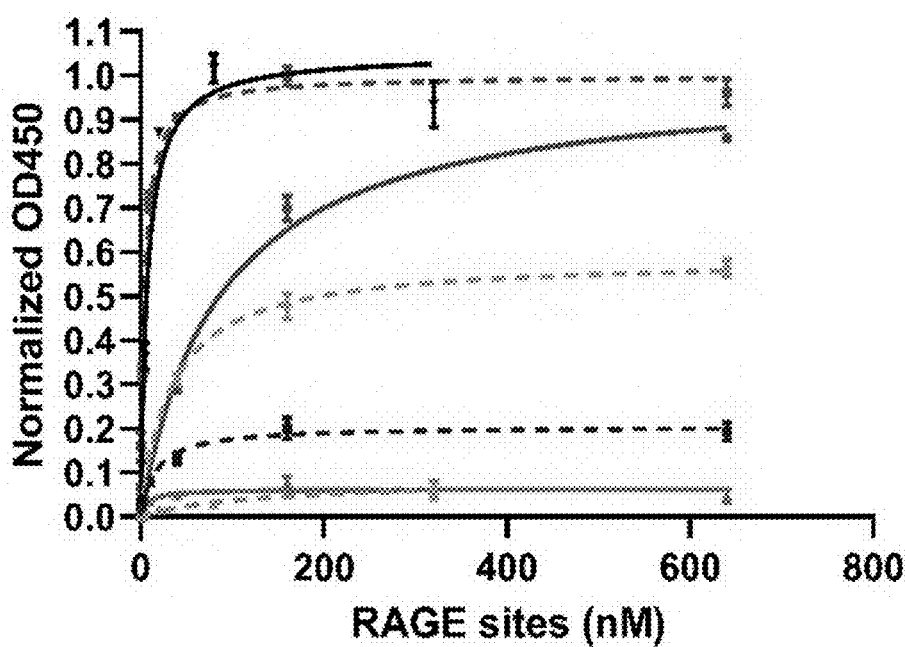
FIG. 8A-8F show dBB12L has reduced binding to RAGE and does not signal through TLR-2 or TLR-4.

Next, we evaluated whether dBB12L had decreased TLR-2, TLR-4 signaling and RAGE binding, whilst preserving HMGB1-mediated regeneration. Due to the lack of an established signaling assay for RAGE, we assessed the binding of RAGE to HMGB1 using real-time kinetics (BLI) and an endpoint assay (ELISA). ELISA-based affinity measurements (FIG. 8A) showed that 3S-, FR- and DS-HMGB1 at equilibrium bound similar amounts of RAGE, with DS-HMGB1 and 3S-HMGB1 having significantly higher affinity compared to FR-HMGB1. In contrast, dBB12L did not bind RAGE. Three additional HMGB1 constructs were tested, DS-HMGB1 1-184, which has an intact RAGE binding peptide and oxidized Box A but no acidic tail and therefore has all the requisites for RAGE binding; DS-HMGB1 1-164, which lacks a significant portion of the RAGE binding peptide but retains an oxidized Box A; and DS-Box A alone. We found that DS-HMGB1 1-184 bound RAGE, but with reduced capacity and affinity compared to full-length DS-HMGB1. By comparison, DS-HMGB1 1-164 had greatly diminished RAGE binding capacity compared to full-length DS-HMGB1 but still higher than dBB12L, whilst DS Box A 1-88 (full HMG Box construct with flanking regions) was unable to bind RAGE.

Figure 8B:
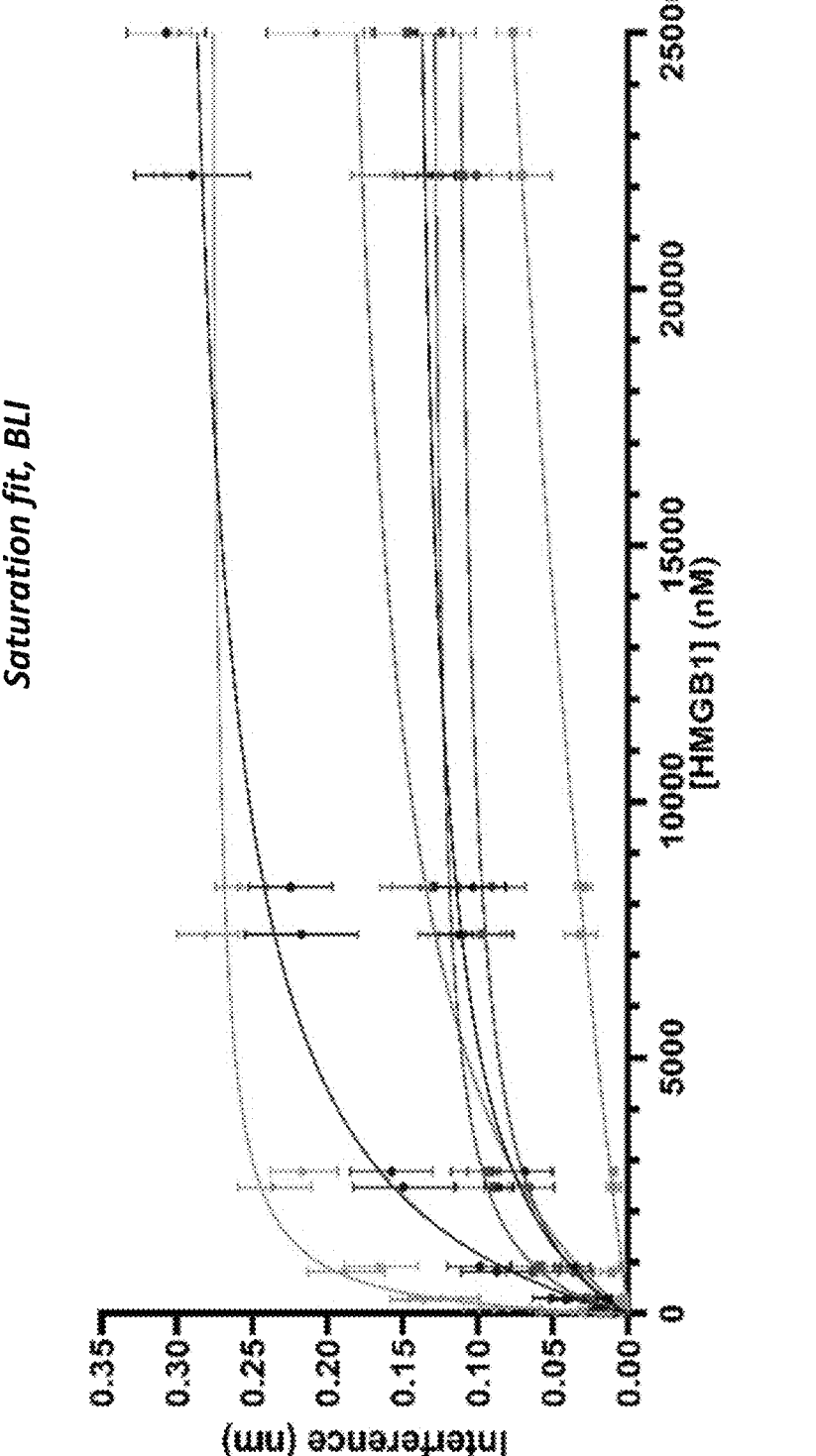
Figures 8C, 8D:
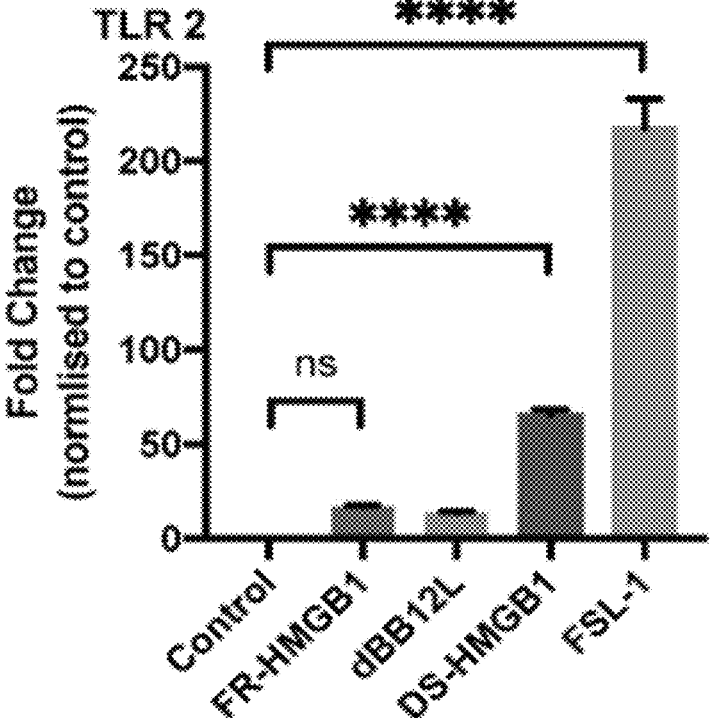

Kinetics analysis using BLI were consistent with the ELISA results (FIG. 8B), with two exceptions. In BLI (FIG. 8C) DS-HMGB1 1-184 had much higher RAGE binding affinity than all other constructs, albeit with a slightly faster dissociation rate, compared to ELISA where it had lower affinity than DS-HMGB1. 3S-HMGB1, whilst binding equivalent amounts of RAGE to DS- or FR-HMGB1, had similar affinity to FR-HMGB1 but much slower overall kinetic rates, whereas in ELISA it had affinity and binding capacity equivalent to DS-HMGB1. The higher RAGE affinity of DS-HMGB1 compared to FR in both assays was due to a much faster association rate ($k_{on}$), whereas dissociation rates ($k_{off}$) were nearly identical for these two redox forms. In contrast, dBB12L, which had an association rate closer to DS-HMGB1, exhibited very unstable binding due to a very high dissociation rate. DS-HMGB1 1-164 also had a faster RAGE binding equilibrium with overall lower binding affinity than full length DS-HMGB1, albeit with higher affinity than dBB12L-HMGB1. The deletion of both the final 10 residues in Box B (175-184) and the disulfide bridge in Box A by substituting it with Box B in dBB12L resulted in unstable binding of RAGE.

Figure 8E:
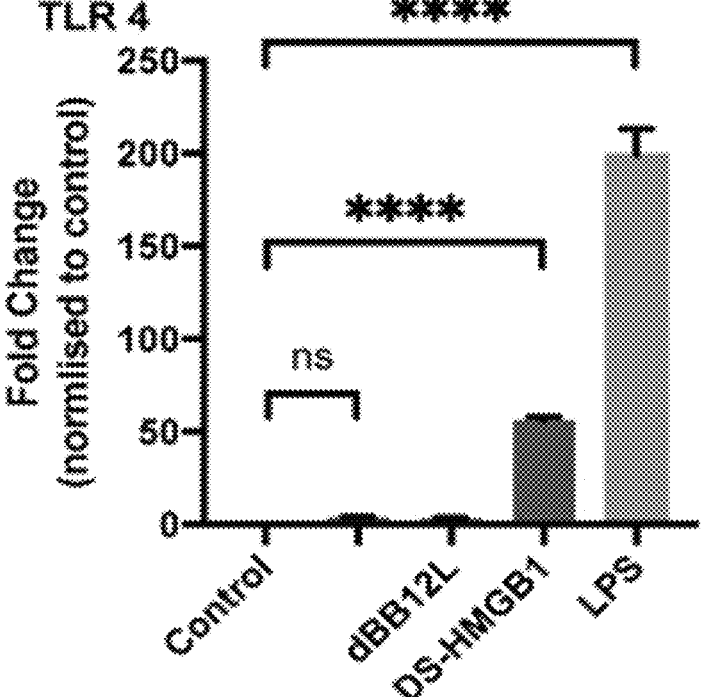
Figure 8F:
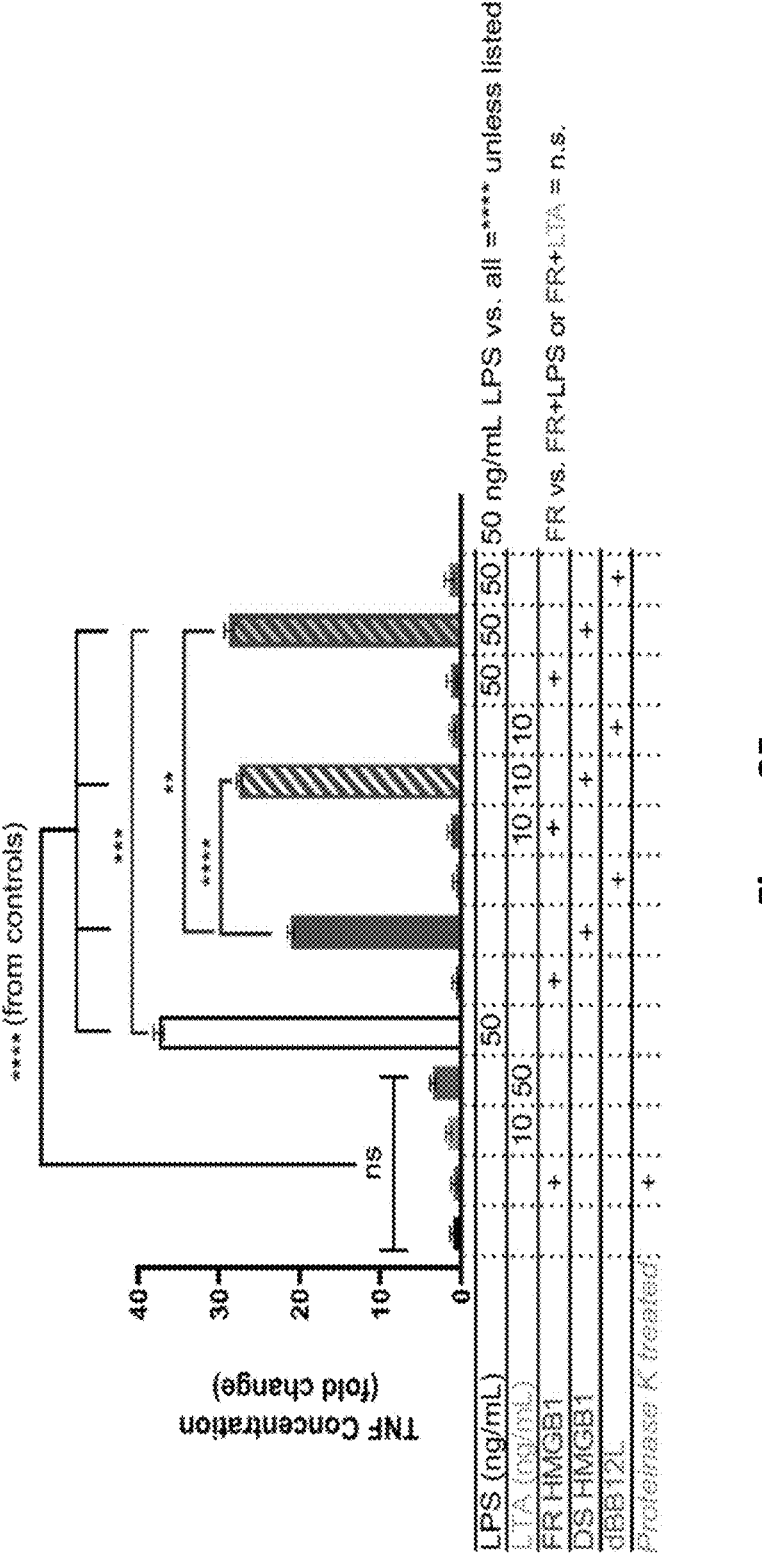
Figure 9:
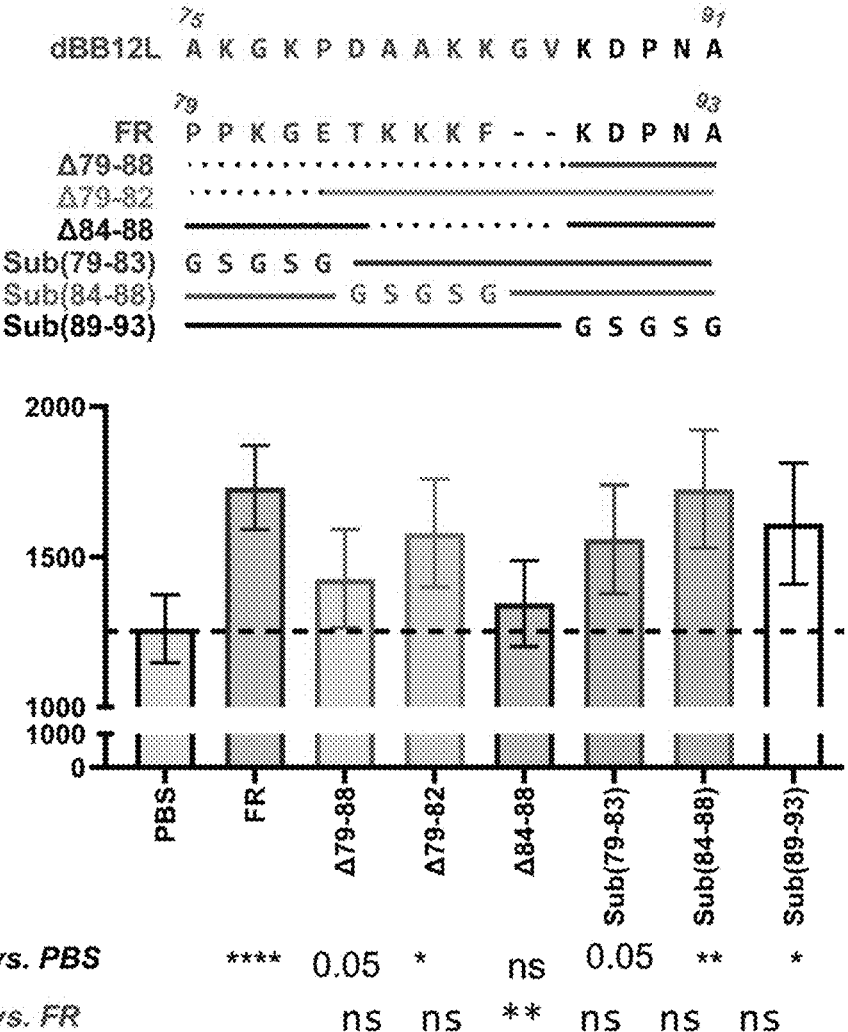
FIG. 9 shows the effects of modification of the linker on regenerative activity of FR-HMGB1. The dBB12L sequence shown in the alignment is provided by residues 75-91 of SEQ ID NO: 2. The FR-HMGB1 sequence shown in the alignment ("FR") is provided by residues 79-93 of SEQ ID NO: 1. The "Sub(79-83)", "Sub(84-88)", and "Sub(89-93)" sequences shown in the alignment are provided by SEQ ID NO: 175.

HMGB1 binds TLR-2, TLR-4, and RAGE and signaling from all receptors converges to the NF-κβ pathway [25]. Consequently, it is difficult to attribute downstream proinflammatory cytokine production to each receptor. Therefore, we first evaluated TLR-specific signaling using NF-κβ reporter cell lines engineered to express either TLR-2 or TLR-4 and their co-receptors. Disulfide HMGB1 promoted NF-kB signaling via TLR-2 (FIG. 8D) and TLR-4 (FIG. 8E). In contrast, dBB12L failed to signal in either cell type. Next, we confirmed the effects of the various HMGB1 constructs on primary human monocytes. It has been reported that DS-HMGB1 synergizes with TLR-2 ligands such as lipoteichoic acid (LTA) to promote proinflammatory signaling [32]. We confirmed that DS-HMGB1 acted synergistically with LTA to promote higher TNF production than LTA or DS-HMGB1 alone. In contrast, dBB12L or FR-HMGB1 did not exhibit this synergistic effect and failed to elicit TNF secretion greater than media alone (FIG. 8F). No synergistic response has been described with DS-HMGB1 and the TLR-4 ligand LPS. When combined with LPS, DS-HMGB1 promoted TNF expression by primary human monocytes to the same extent as LPS alone. In contrast, FR-HMGB1 or dBB12L alone did not promote TNF production. However, when combined with LPS, FR-HMGB1 or dBB12L reduced TNF expression compared to LPS alone.

Taken together, these data show that dBB12L does not signal via TLR-2 or TLR-4, even in the presence of their cognate ligands, has greatly decreased affinity for RAGE and reduces LPS-mediated pro-inflammatory signaling.

The dBB12L Construct has Pro-Regenerative Activity Comparable to that of FR-HMGB1

Figure 10A:
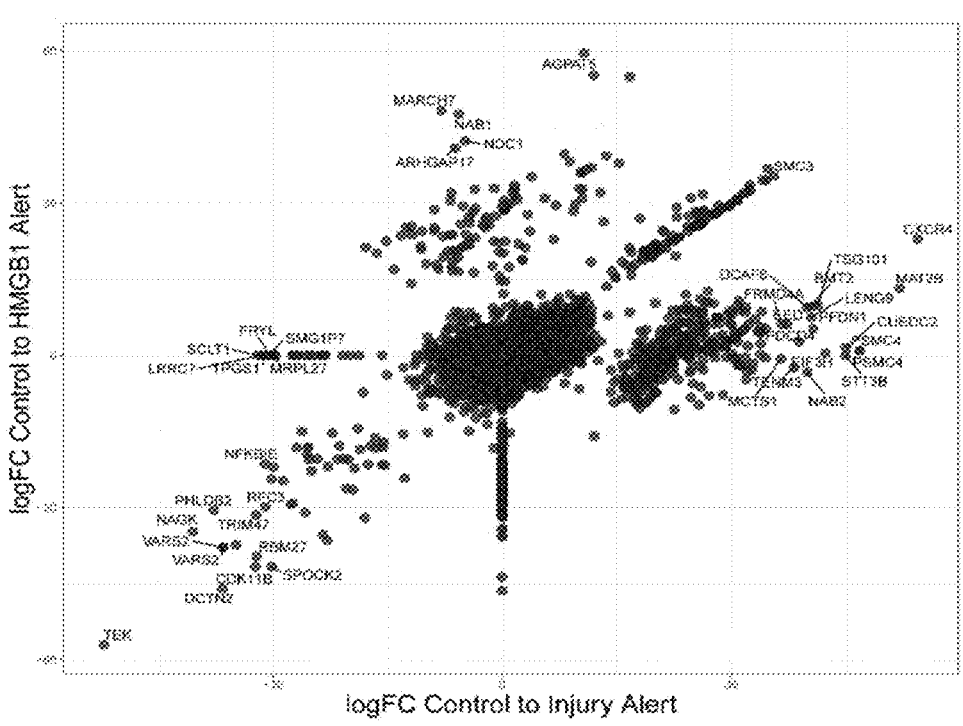
FIGS. 10A-10J show the regenerative effects of optimal doses of dBB-HMGB1 and FR-HMGB1 are identical to those of an activating injury.
Figure 10B:
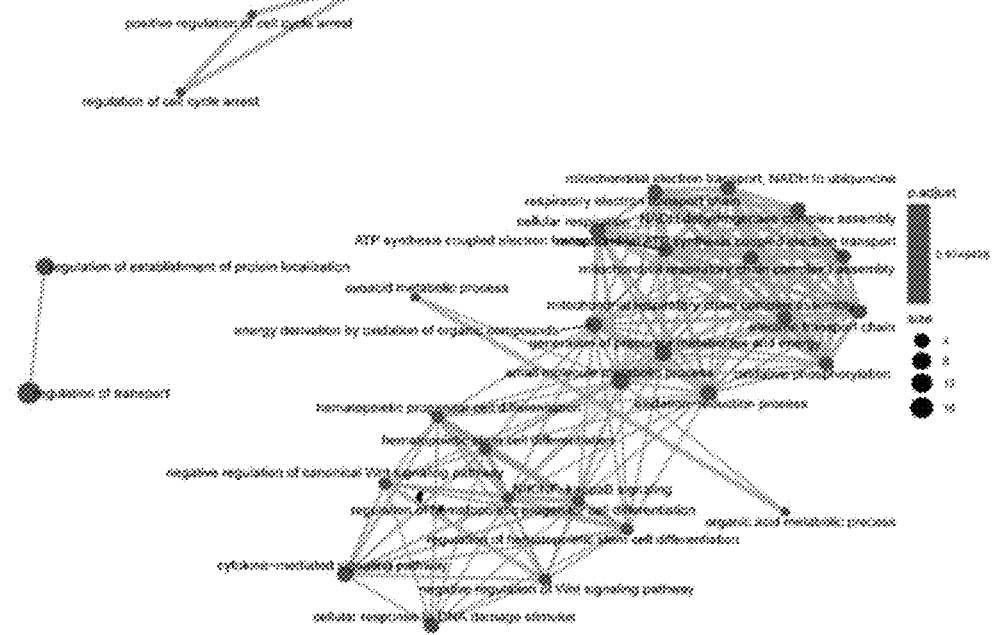

Distant injury has previously been shown to transition stem cells to $G_{Alert}$ [13]. Therefore, we first compared the transcriptomic response of skeletal muscle stem cells to FR-HMGB1 or injury to the contralateral limb. The genes up- and down-regulated by FR-HMGB1 or distant injury were remarkably similar (FIG. 10A), with the major pathways upregulated being those associated with $G_{Alert}$ [8,13], including mitochondrial metabolism, oxidative phosphorylation and cell cycle (FIG. 10B). Interestingly, CXCR4 was one of the most highly upregulated genes.

Figure 10C:
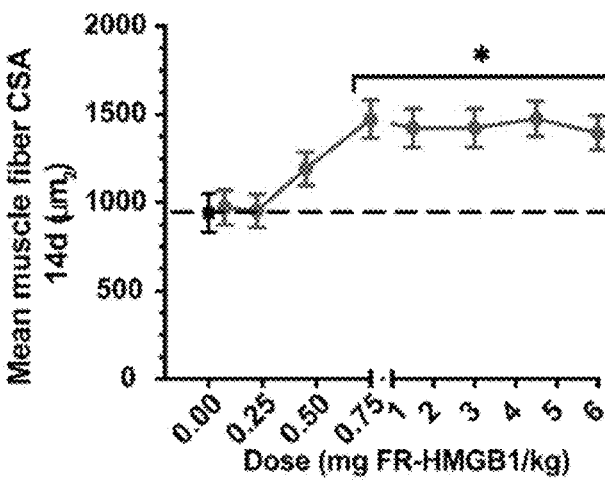
Figure 10D:
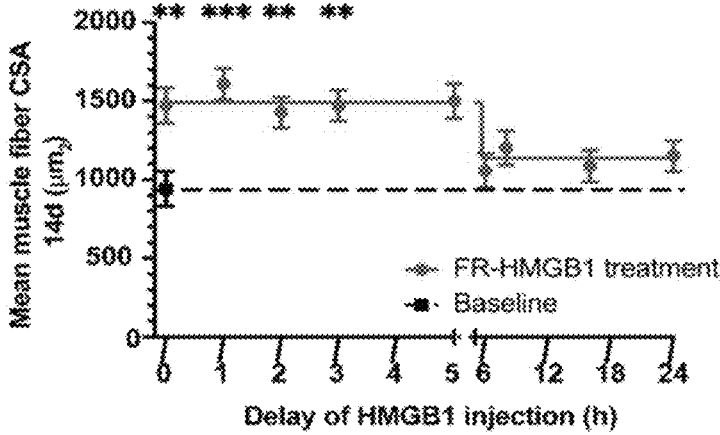
Figure 10E:
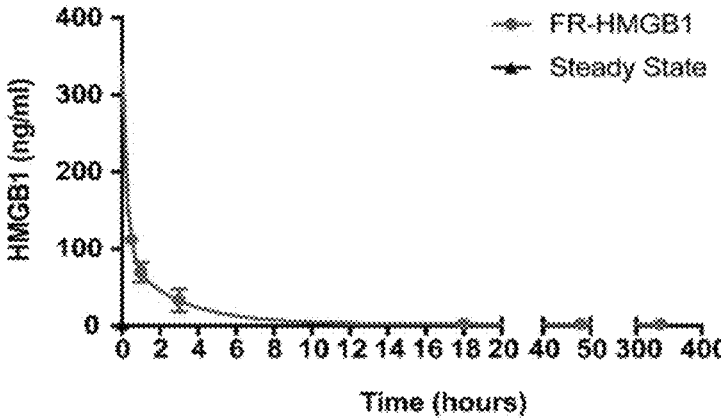

Next, we determined the optimal in vivo treatment dose for FR-HMGB1 using a validated murine model of skeletal muscle injury [8,13]. We found that 0.75 mg/kg (29 nmol/kg) resulted in the maximal response, with no further improvement in regenerative activity with higher doses (FIG. 10C). We also assessed the optimal time for administration in vivo after injury. FR-HMGB1 was found to be effective in promoting repair when injected up to 5 h post-injury (FIG. 10D). We then assessed the half-life of FR-HMGB1 in the circulation following iv administration. We found that there was an initial rapid clearance (t1/2≈11 min) followed by subsequent slower clearance rate (t1/2≈120 min) (FIG. 10E). This would be consistent with the half-life of 25 min in humans [54], with the protein being cleared by binding to haptoglobin [55,56].

Figure 10F:
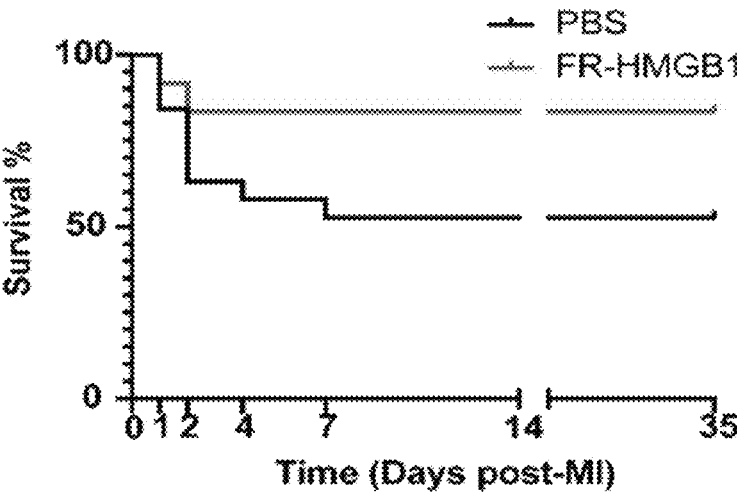
Figure 10G:
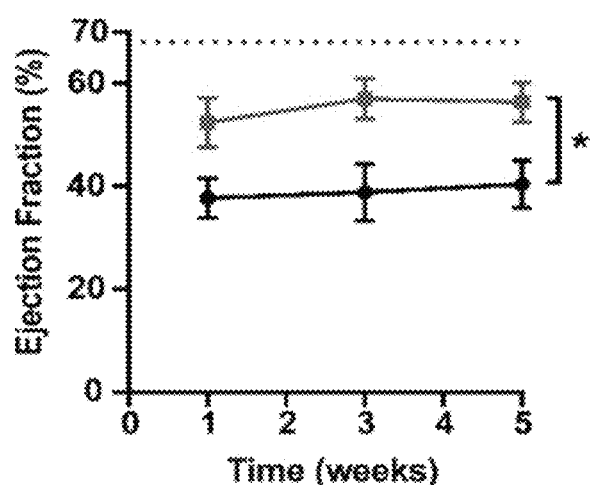
Figure 10H:
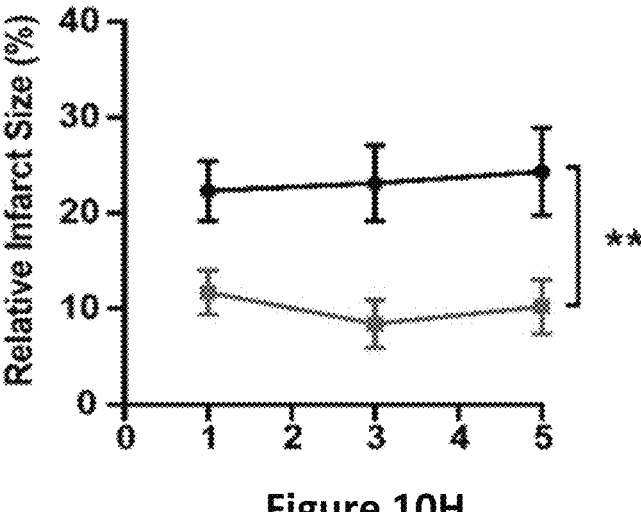
Figure 10I:
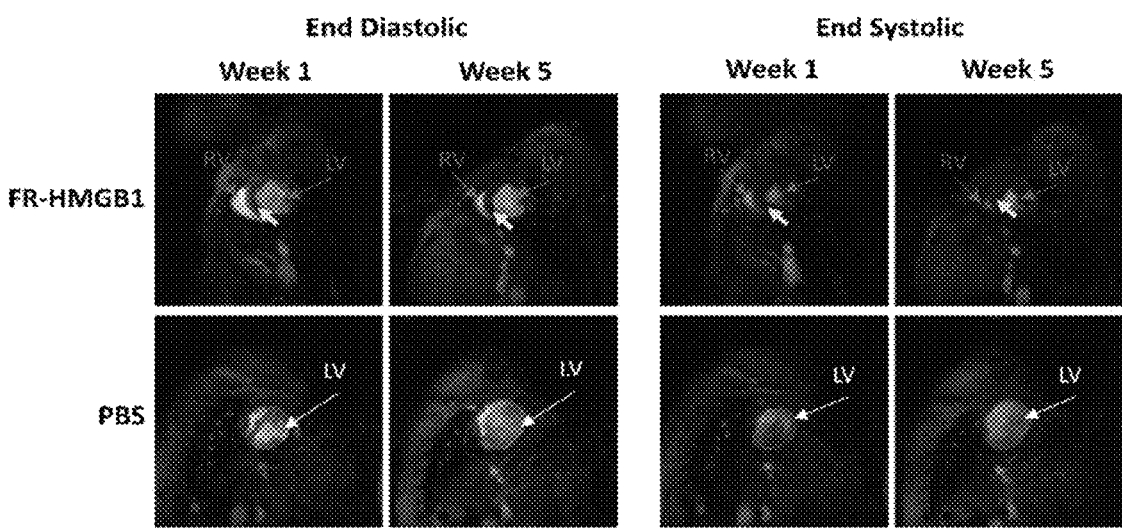

We have previously shown that FR-HMGB1 accelerates regeneration of skeletal muscle, bone and blood following injury by promoting the transition of stem and progenitor cells to $G_{Alert}$ [8]. There is a small population of progenitor cells in the mammalian heart [57] and the majority of new cardiomyocytes following injury are derived from existing cardiomyocytes [58]. To ascertain the efficacy of FR-HMGB1 on tissues that do not rely on resident stem and progenitor cells for regeneration, we assessed whether administration of FR-HMGB1 on cardiac regeneration. We found that iv injection at the time of myocardial infarction resulted in enhanced survival (83% in mice treated with FR-HMGB1 compared to 52% in PBS controls) (FIG. 10F) and approximately 60% reduction in infarct size as assessed by serial MRI scans over 5 weeks (FIG. 10H) and 16% improvement in overall left ventricular ejection fraction (FIG. 10G).

Figure 10J:
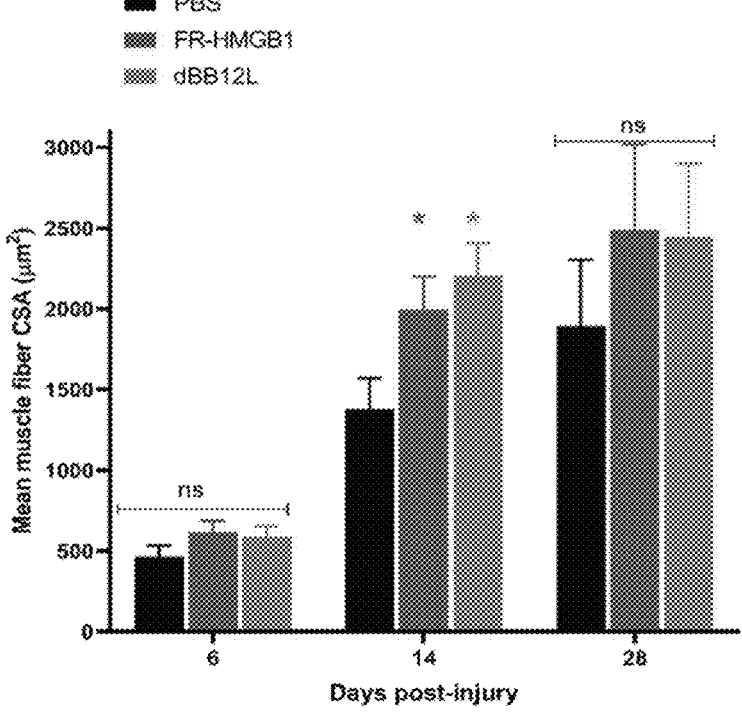

Next, we assessed the efficacy of dBB12L compared to FR-HMGB1 in promoting skeletal muscle regeneration in vivo. Mice injected with optimal doses (29 nM/kg) of FR-HMGB1 or dBB12L exhibited accelerated regeneration equally following injury (FIG. 10J), as determined by an increase in the mean cross-sectional area of regenerating muscle fibers with central nuclei [8,13]. This was most apparent at day 14, as previously described for FR-HMGB1 [8].

Finally, we assessed the role of the flexible region between HMG Boxes in the regenerative process. We first tested whether alterations in this linker region of wild type human FR-HMGB1 affected protein stability. We found that reducing the linker length to 13 amino acid residues or less led to a decrease in $Tm_{50}$ indicating that the linker length plays a key role in protein folding and stability. Furthermore, deletion of the first two prolines in the linker region completely abrogated expression. This indicates that the linker length likely also governs protein folding and stability. We then tested in vivo regenerative activity of the constructs with variations in their linkers (Figure). We found that deletion of the entire linker (A79-88) resulted in loss of regenerative activity and deletion of the first four linker residues (A79-82) led to some loss of regenerative activity. Whilst deletion of the central region (A84-88) resulted in complete loss of tissue regeneration, surprisingly substitution of residues 84-88 with a sequence of generic flexible amino acid residues restored full regenerative activity. Substitution of the DPNA peptide before the second Box B domain also adversely affected regenerative activity.

Discussion

HMGB1 Needs to be Modified in Order to be Used as a Tissue Repair Therapeutic

Therapies based on administration of exogenous stem cells to promote repair of solid organs have failed to deliver on the initial promise [6,59], and killed cells are just as effective by triggering an immune response [60]. An alternative, potentially more effective approach, would be to target endogenous regenerative repair processes, including resident stem and progenitor cells [61,62]. Inhibition of prostaglandin dehydrogenase is a promising approach [7], although progress through to clinical translation has been slow [63]. Administration of growth factors has also been described [64,65] but is limited by in vivo proteolysis [66]. Currently, there is no approved therapeutic for promoting regeneration and accelerating repair of multiple tissues.

We previously showed that exogenous administration of FR-HMGB1 is effective in accelerating regeneration of bone, skeletal muscle and blood by transitioning resident stem and progenitor cells to $G_{Alert}$, when they are able to readily respond to the appropriate activating factors released on tissue injury to effect repair [8]. However, there is accumulating evidence supporting the conversion of FR-HMGB1 into DS-HMGB1 in vivo locally at the site of injury [15,16]. Therefore, the potential for deleterious proinflammatory signaling precludes the use of native FR-HMGB1 as a therapeutic. DS-HMGB1 can signal through TLR-4 [29, 35], TLR-2 [32,33,35] or RAGE [37,67] to converge on NF-κβ [25,68], leading to synergistic expression of proinflammatory cytokines [69,70]. Therefore, development of HMGB1 as a therapeutic is crucially dependent on engineering the molecule to eliminate signaling via all three receptors.

Box A and Box B Bind CXCL12 Independently

The regenerative activities of FR-HMGB1 are crucially dependent on the formation of a heterocomplex with CXCL12 and signaling via CXCR4. Whilst it is known that CXCL12 binds to HMG Boxes [44,71], the precise structural motifs involved remain unknown [53,72]. It is also unclear whether this signaling involves homodimers of CXCL12 monomers, which promote chemotaxis [73-75]. By combining the data from our forward (FIG. 2A and FIG. 2B) and reverse peptide arrays (FIG. 11), alanine substitution arrays (FIG. 2C and FIG. 2D), and NMR experiments (FIG. 5A and FIG. 5B), we were able to identify the residues [76] involved in HMGB1-CXCL12 interaction. We identified a common pattern of HMGB1 peptides binding CXCL12 that occupy concave pockets on the underside of Box A and Box B. Using BLI (FIG. 2E and FIG. 2F) we identified the role of the flanking flexible regions by BLI in CXCL12 binding. Furthermore, as we used HEPES buffer during BLI and NMR experiments to prevent CXCL12 dimerization [77], we concluded that each Box is able to bind monomeric CXCL12 without the requisite for cooperation between the Box domains and that dimerization of CXCL12 is not a requisite for complex formation.

Design of the Engineered dBB12L Construct that does not Signal Via TLR-2 or TLR-4 or Bind RAGE, Whilst Retaining Full Pro-Regenerative Properties We observed a similar mirroring across HMG Boxes of the regions in HMGB1 involved in TLR-2 binding (FIG. 3, section A and FIG. 4, section A), but found that the disulfide form of HMGB1 is more capable of signaling through TLR-2 (FIG. 8D and FIG. 8F) This indicates that, unlike with CXCL12 (two identical HMG Boxes in the reduced molecule), TLR-2 signaling requires two different HMG Boxes (one in the reduced and another in the oxidized conformation). TLR-4 has long been known to preferentially bind oxidized HMGB1 Box A. We identified a clear binding pocket for TLR-4 on HMGB1 that overlaps with the LPS binding segments (1-15, 80-96) and is only continuous when Box A is oxidized. In addition to both Box A and B, RAGE binding requires an intact sequence before the acidic tail and oxidation of Box A enhances RAGE binding. Interestingly, in all cases the linker region of HMGB1 appears to be involved in binding to the proinflammatory receptors.

With this detailed understanding, we were able to design a construct to eliminate proinflammatory signaling via TLR-4 and TLR-2 and RAGE whilst preserving CXCL12 binding. This construct consisted of two HMG Box B domains in tandem separated by a linker of similar length to that of wild-type HMGB1 (dBB12L). The absence of Box A in dBB12L precludes oxidation and hence the rearrangement of the observed binding interfaces for TLR-2 (rotation of Helix 3), RAGE (bending of Helix 2) and TLR-4 (continuous binding surface), whilst permitting binding to two CXCL12 monomers via the two Box B domains. We found that dBB12L was as stable as 1-164 FR-HMGB1 or full-length FR-HMGB1, with no aggregation or degradation on storage for prolonged periods of time.

Whilst DS-HMGB1 alone can bind and signal via TLR-4/MD-2 [28], it can also facilitate signaling via LPS by substituting for LPS-binding protein (LBP), which binds LPS and promotes transfer and recognition to TLR-4/MD-2 [51]. Deletion of Box A in our dBB12L construct effectively precluded signaling via TLR-4. Interestingly, we observed that both FR-HMGB1 and dBB12L decrease TNF expression by monocytes on exposure to LPS. This could be due to these proteins binding LPS but are unable to transfer it to TLR-4/MD2 due to the lack of oxidized Box A, unlike DS-HMGB1, which can effectively substitute for residual LBP [51] present in the serum of the culture medium [78].

There is controversy as to whether HMGB1 can induce TLR-2 signaling on its own [34,35] or requires a co-ligand to induce activity, and also whether this response is dependent on the redox state of the protein [32,33]. Available data [32][33] suggest that that HMGB1 alone can signal through TLR-2 but a co-ligand is required to induce higher levels of response. We found that DS-HMGB1 alone was able to signal via TLR-2 and the effect was enhanced in the presence of LTA in serum-containing media. However, there was no response to FR-HMGB1 or dBB12L, which did not synergize with LTA. This would suggest that, as with TLR-4, oxidized Box A with a disulfide bridge is necessary for TLR-2 mediated responses and that TLR-2 co-ligands synergize with DS-HMGB1, potentially by displacing the acidic tail to promote TLR-2 interaction.

A RAGE binding peptide within HMGB1 (residues 149-182) has been previously described [37]. A similar motif is also present in other RAGE ligands such as S100 proteins, and homologous peptides to these sequences are effective antagonists of HMGB1-mediated RAGE signaling [38,52]. The acidic tail of HMGB1 shares residues with the RAGE binding peptide [40] and has been proposed as a regulator of RAGE interaction, analogous to its role in TLR-2 binding. However, only the disulfide form of HMGB1 has been linked to prothrombotic activities via RAGE [36]. We observed that the RAGE binding peptide in Box A [39], which was previously thought to require Caspase-1 processing for activity, is exposed in the intact HMGB1 when in solution and alters its conformation upon oxidation of the disulfide. We found that constructs lacking a complete RAGE binding peptide 149-182, including dBB12L, were unable to bind RAGE in the ELISA assay. In contrast DS-HMGB1, and interestingly also 3S-HMGB1, were able to bind RAGE better than FR-HMGB1. Our BLI data showed that dBB12L has lower affinity for RAGE compared to FR-HMGB1 and DS-HMGB1. Whilst dBB12L had a three-fold higher association rate than FR-HMGB1, potentially due to the presence of two partial RAGE binding domains in this construct, the dissociation rate was five-fold greater. The ELISA data represent the binding status at equilibrium and, therefore, reflects the balance between the association and dissociation rates. For instance, 3S-HMGB1, which has an affinity for RAGE similar to FR-HMGB1 in BLI, shows a much higher apparent affinity in ELISA similar to DS-HMGB1 due to a dissociation rate much lower than that of FR-HMGB1 or DS-HMGB1. This increased RAGE binding may in part account for the increased fibrosis seen in mouse models of myocardial infarction compared to controls, whereas FR-HMGB1 promoted regeneration and improved function [31]. Using SPR others have also shown that binding of HMGB1 to RAGE likely requires two distinct binding sites, one of which varies according to the oxidation status [20]. We found that the affinity for RAGE for DS-HMGB1 using BLI ($K_d$=0.2-1.3 μM) was similar to that previously reported using SPR (0.1 [79]—0.65 μM [36]), these studies also reporting high affinity for 3S-HMGB1. Our BLI data also show that loss of the acidic tail increases the affinity of HMGB1 for RAGE by greatly increasing the association rate, whereas truncation of the RAGE binding peptide or reduction of Box A greatly increased dissociation rates. Interestingly, oxidized Box A alone is incapable of binding RAGE, suggesting that the interaction is fully stabilized by the RAGE binding peptide, and the acidic tail negatively regulates this binding by competing with residues within the RAGE binding peptide

[40]. The absence of Box A together with truncation of the RAGE binding peptide in dBB12L results in greatly reduced RAGE affinity.

The transcriptomic changes induced by FR-HMGB1 in skeletal muscle stem cells are very similar to those induced by distant injury and upregulation of CXCR4 expression by HMBG1 would potentially enhance its effects. Our data showing that FR-HMGB1 is only effective if administered up to 5 h post injury would be consistent with it acting by transitioning stem cells to $G_{Alert}$. At later time points the stem cells will have been fully activated [80]. We confirmed that dBB12L retains regenerative activity in vivo equivalent to FR-HMGB1. Importantly, we found that FR-HMGB1 administered intravenously at the time of myocardial infarction resulted in improved survival, reduction in infarct size and improved left ventricular ejection fraction. Based on these data we would predict that administration of dBB12L would also promote regeneration of tissues that rely on stem cells for repair such as bone, skeletal muscle and blood, as well as tissues where regeneration is predominantly reliant on mature cell populations such as cardiomyocytes in the heart. We also predict that dBB12L is likely to be effective if administered up to 5 h after injury. This is important as the median time for admission to hospital following MI in the USA is 3 h [81]. Approximately 800,000 people in the USA suffer from myocardial infarction every year [81] and approximately 20% go on to develop cardiac failure. Despite US healthcare expenditure for heart failure of >$30 billion in 2012, projected to increase to $70 Bn by 2030, 5-year survival is only ~60%, which is worse than most cancers [81]. Based on our data we predict that administration of dBB12L within 5 h of the event will enhance survival of patients experiencing a myocardial infarction, and through reduction in infarct size and preservation of ejection fraction, reduce the incidence and severity of cardiac failure. Others have shown in mouse [31,82,83] and sheep [84] models that direct injection of FR-HMGB1 into the myocardium in the peri-infarct area 4 h after infraction is effective in promoting cardiac repair. Our data demonstrating the efficacy of iv administration are important as this route is readily applicable for clinical use.

Based on our data using constructs with different linker lengths and linker substitutions, alternative constructs to dBB12L with similar activity profiles can also be designed. These could include the following variations:

1) Residues equivalent to positions 169-174 (i.e. "AAKKGV," shown as residues 167-172 of SEQ ID NO: 2) at the C terminus of the second B Box in our double Box B construct could be eliminated altogether or substituted as described below (3). We would also envisage that substituting the equivalent residues at the C terminus of the first B Box domain in the double Box B construct would further help eliminate any potential binding to TLR-2.

2) Our current dBB12L construct contains 12 amino acid residues corresponding to positions 163-174 of the native HMGB1 sequence at the C terminus of the first Box B domain. With the additional 5 amino acids at the N terminus of the second B Box that we have found to be critical for CXCL12 binding, this gives an overall inter Box linker length of 17 amino acids. Constructs with linker length less than 13 amino acid residues have lower regenerative activity and thermostability indicative of unstable molecular folding. Therefore, we would predict that the optimal linker length would be 13-20 amino acids. The loss of regenerative activity of constructs with shorter linkers may also be related to an inability to adopt the appropriate conformation to present two CXCL12 monomers to a CXCR4 dimer.

3) Deletion of the linker affects the regenerative effect differently depending on the deleted positions: deletion of residues 79-82 (11 residues including the beginning of Box B) resulted in a molecule with decreased regenerative effect whilst deletion of residues 84-88 led to complete loss of regenerative activity. We also found that substitution of amino acids 84-88 with a sequence of generic flexible amino acids (GSGSG (SEQ ID NO: 175)) in the inter Box linker after the C terminus of Box A did not adversely affect in vivo regenerative activity. This region was not involved in CXCL12 binding in in our peptide arrays or NMR. Therefore, in our next generation molecules this region could be substituted with a linker of between 13 and 17 residues with any of the following modifications:

a) Substitution of any, or all, residues equivalent to positions 168-174 (last 7 residues in the linker) in wild type human HMGB1 for any of the following:

A random sequence of amino acids such that this region can adopt either no specific secondary structure, coil-turn structures, or alpha helical conformations, with the first two being preferred.

Substitution of the amino acids (e.g., Lys↔Arg, aliphatic to aliphatic substitutions).

Flexible amino acid sequences [85] such as Gly-Ser, or turn-inducing residues such as Pro.

Charged residues to improve solubility.

b) Substitution of any, or all residues equivalent to positions 163-167 by any of the options in (3a) or point deletion of individual residues. However, we anticipate that substitution of K164, G165 or K166 is likely to affect CXCL12 binding capacity, as substitution or deletion of residues equivalent to this region on wild type HMGB1 led to reduction in regenerative activity. Therefore, those would likely need to be substituted with more chemically similar residues.

c) Substitution of any, or all, residues in the immediate 5 amino acids before Box B, including the D-P-X-X motif. Whilst this resulted in loss of some regenerative activity, it is possible that this region is only required as a flexible extension of the HMG Box as it is positioned parallel to the third alpha helix.

The above amino acid sequences will be designed with the intention of reducing proinflammatory activities (by removal of specific epitopes to e.g., further reduce the affinity for RAGE, LPS, and other DAMP/PAMPs), improve protein stability and folding, or introduction of chemical functionalization (e.g. Click chemistry or unnatural amino acids), with the overriding objective of preserving CXCL12 binding capacity to the modified HMG Box domains including the altered linkers. Whilst more profound modifications to the HMG Box core domain are also possible, these would be more likely to disrupt the structure of the HMG Box domains and therefore the CXCL12 binding pockets.

Our data show that whilst the peptides involved in binding CXCL12 are mirrored in Box A and Box B, this is not the case with the proinflammatory receptors, as each Box and the adjacent domains are involved in the binding to TLR-2, TLR-4 or RAGE. The loss of Box A and its C-terminal linker in dBB12L accounts for the absence of signaling via all three proinflammatory receptors. TLR-2 and RAGE binding and signaling is further impaired by the truncation of the binding sequences before the C-terminal acidic tail and the fact that the binding regions in oxidized Box A has been replaced by those equivalent in Box B. Box B adopts a different surface arrangement than Box A when it is oxidized and therefore is unable to effectively bind to TLR4, TLR-2 or RAGE. Importantly, the double Box B construct maintains regenerative activity equivalent to FR-HMGB1. Taken together these data show that the double Box B constructs described above can be developed as clinical therapeutics.

In conclusion, the sites of HMGB1 critical for CXCL12 binding were mapped and a construct (dBB12L) that does not signal via TLR-2 or TLR-4 and fails to effectively bind RAGE was designed. FR-HMGB1 transitions stem cells to $G_{Alert}$ in a manner similar to distant injury despite a short half-life and is effective when administered up to 5 hours after injury. Furthermore, dBB12L promotes tissue regeneration in vivo as effectively as FR-HMGB1. Accordingly, dBB12L can be developed for clinical translation.

SUMMARY

Reduced High Mobility Group Box 1 (HMGB1) protein binds to CXC Ligand 12 (CXCL12) and signals through CXC Receptor 4 (CXCR4) to promote tissue regeneration and accelerates repair by transitioning stem and progenitor cells to $G_{Alert}$. However, local conversion of FR-HMGB1 to the disulfide form (DS-HMGB1) may result in deleterious inflammation through signalling via Toll-Like Receptors 2 and 4, and the Receptor for Advanced Glycation End Products (RAGE). Therefore, it is important to engineer the molecule to eliminate these potentially deleterious proinflammatory effects when considering HMGB1 for use in clinical practice.

We have identified the residues involved in formation of the HMGB1-CXCL12 heterocomplex using a combination of peptide arrays, biolayer interferometry and nuclear magnetic resonance. In addition, we used peptide arrays to define the peptide sequences required for the binding of TLR-2, RAGE, TLR-4. Based on these data we designed a construct comprising two HMG B Boxes in tandem (dBB12L). This has similar regenerative capacity, stability and conformation to wild-type fully-reduced HMGB1, does not signal through TLR-2 or TLR-4, even in the presence of their co-ligands, and has greatly decreased RAGE binding. We also describe a series of other double Box B constructs that would have similar attributes.

A comprehensive review of the patent landscape and the scientific literature has identified U.S. Patent Application Publication US 2015/0203551 A1, which describes the substitution of cysteines with serines to prevent TLR-4 signalling; however, this construct has been shown to lead to excessive cardiac fibrosis following MI [14]. Furthermore, this construct has a slower dissociation for RAGE compared to FR-HMGB1, resulting in RAGE remaining bound for longer after equilibrium, as shown herein in FIG. 8B); therefore these substitutions were avoided in our constructs. U.S. Patent Application Publication US 2009/0069227 A9 stipulates that HMGB1 constructs that promote stem cell migration and proliferation must include amino acids 1-187 (0-186 in our data, with 0 being the N-terminal Met) and U.S. Pat. No. 9,623,078 refers to peptides limited to amino acids 1-44 (0-43 for our data) for cardiac regeneration. U.S. Patent Application Publication US 2009/0202500 A1 discloses methods for tissue repair but only refers to full-length (1-215) wild-type HMGB1 (0-214 for our data). The dBB12L construct presented herein has no RAGE binding or TLR-4/2 signalling, is 177 amino acids long, and includes amino acid substitutions that have not been previously described. Therefore, the constructs presented herein do not fall within the scope of the prior art.

Clinical Applications

This invention provides polypeptides and methods to harness endogenous regenerative processes to enhance tissue repair. The polypeptides function similarly to fully reduced wild type HMGB1 which promotes tissue regeneration by forming a heterocomplex with two CXCL12 molecules, which in turn signals via CXCR4, likely two adjacent CXCR4 receptors on the cell surface.

Our data show that a polypeptide of the invention (dBB12L) acts in a similar way. Therefore, it is contemplated that dBB12L will promote the regeneration of tissues that rely on CXCR4+ cells for repair. Such tissues include tissues where repair is primarily dependent on stem and progenitor cells, such as skeletal muscle and the haemopoietic system, as well tissues where repair is largely dependent on existing mature cells, e.g., cardiomyocytes in the adult mammalian heart.

Potential Clinical Indications:

Heart following myocardial infarction. This indication is ripe for a clinical trial. Globally, ischemic heart disease affects 153 million people (101), with the loss of >105,000,000 Disability Adjusted Life Years in 2017 (102). Every year 205,000 people in the UK (103) and 805,000 in USA suffer from myocardial infarction (MI), 38% of them experiencing ST-elevation MI (STEMI) (101). Following MI, approximately 30-40% of individuals develop heart failure, affecting 38 million worldwide. Despite US healthcare expenditure for heart failure of >$30 billion in 2012, projected to increase to $70 Bn by 2030, 5-year survival is only ~60%, which is worse than most cancers (101). The main target population are patients following MI, especially those at risk of developing heart failure (104). A novel therapeutic that limits cardiac damage, promotes regeneration following MI and prevents the development of heart failure would dramatically reduce morbidity and mortality, and massively reduce healthcare burden. Definitive data using an established (105-108) permanent ligation murine MI model that reliably leads to cardiomyocyte necrosis (109) show that a single iv dose of FR-HMGB1 at the time of injury leads to enhanced survival (83% for animals treated with FR-HMGB1 compared to 52% in the group treated with PBS placebo), and compared to controls, ~16% improvement of absolute cardiac ejection fraction and ~60% reduction in infarct size compared to PBS controls over 5 weeks (FIG. 10F).

In a skeletal injury model, the optimal dose of FR-HMGB1 was 0.75 mg/kg (FIG. 10C) and is effective even if administered iv up to 5 hours post injury (109) (FIG. 10D), despite a very short half-life (FIG. 10E). Following myocardial infarction, reperfuion of the ischemic cardiac muscle should be achieved as soon as possible. For example, following STEMI patients should undergo percutaneous intervention. Data show that administration of HMGB1 as soon as possible and maximally up to 5 hours post-injury will preserve the damaged myocardium and promote regeneration.

While native FR-HMGB1 promotes functional recovery post MI (FIGS. 10F-10I), local conversion to the disulfide form promotes thrombus formation and propagation via RAGE, TLR-2 and TLR-4 (110). Constructs reported by others such as 3S-HMGB1 that retain RAGE binding (FIG. 8B) result in excessive fibrosis and impairment of function following MI (111). FR-HMGB1 also binds RAGE, albeit to a lesser extent than DS-HMGB1 and, therefore, would not be suitable for clinical use. HMGB1 signalling via TLR-2 plays a key role in ischaemia reperfusion injury following myocardial infarction (112) and thrombosis (110), The inventors a have shown the key role of TLR-2 in human atherosclerosis (113). TLR-4 signalling is also crucial in myocardial reperfusion injury (114). The redox conditions in the ischemic and inflamed microcirculation of the damaged heart following myocardial infarction will promote conversion of FR-HMGB1 to the disulfide form (DS-HMGB1), which is a central mediator of thrombosis (110). There is no approved therapy for promoting cardiac regeneration following MI. Reports purporting to show regenerative effect of hematopoietic stem cells have been discredited (115), and killed cells are just as effective by triggering an immune response (116). Even with other cell types, including pluripotential stem cells, significant challenges remain, including arrhythmogenesis, immunosuppression, scalability, batch variability, delivery, long-term viability and efficacy (115, 117). Large scale trials of cell-based therapies showed no significant improvement in function, with arrhythmias reported in patients (118-120).

The absence of a significant stem population (121) and limited epicardial progenitor cells (122) in the adult heart, together with an understanding that the majority of new cardiomyocytes following injury are derived from existing cardiomyocytes, has shifted focus to promoting regeneration by manipulating endogenous pathways (121). This includes adenoviral transduction of multiple transcription factors (105, 108), manipulation of developmental pathways such as Hippo (106) or Meis1 (123), addition of growth factors such as neuregulin (124), IGF/HGF (125) or FSTL1 (126), or manipulation of miRNAs (127). These approaches have significant shortcomings: adenoviral transduction and growth factors (IFGF1/HGF) require intracardiac injection or topical patch application (FSTL1), manipulation of developmental pathways carries oncogenic risk (128) and viral transduction of miRNA199-a in pigs resulted in fatal arrhythmias (127). An alternative strategy for stimulating cardiac regeneration by promoting clearance of immune cells requires repeated injection of VEGF-C (129). Inhibition of MAP4K4 promotes myocardial survival and limits infarct size, but there was no regenerative effect (130). To date, none of these strategies have progressed to clinical trials.

This invention provides a unique solution which targets endogenous processes to promote cardiomyocyte survival and regeneration of multiple tissues. It overcomes the many hurdles associated with cell therapies, including anti-fibrotic CAR T cells (131), such as prohibitive expense (132, 133). Since FR-HMGB1 acts via the cell surface receptor CXCR4, it is not expected to have off target effects associated with targeting intracellular processes, e.g. by adenoviral transduction of transcription factors or miRNA. HMGB1 inhibition increased infarct size following ischemia reperfusion injury (134) and whilst local upregulation (135, 136) or intramyocardial injection of FR-HMGB1 has been shown to be effective in both mice (111, 137, 138) and sheep (139), our data indicate iv administration is efficacious and more likely to reach all target cells. The engineered double Box B construct of the invention which avoids deleterious proinflammatory signaling should be safe.

A group in Milan described an HMGB1 analogue (3S-HMGB1) where 3 cysteines are replaced with serines to negate TLR-4 signaling (140). Whilst they claimed that 3S-HMGB1 is superior to FR-HMGB1 in promoting tissue regeneration (141), the present inventors have not found this to be the case (142). Importantly, 3S-HMGB1 promoted fibrosis in a murine MI model, with deterioration in cardiac function, whereas FR-HMGB1 promoted tissue regeneration and improved left ventricular ejection fraction (111). The inventors have found that 3S-HMGB1 remains bound to RAGE for longer than either DS-HMGB1 or FR-HMGB1 (FIG. 7A). Therefore, whilst FR-HMGB1, 3S-HMGB1 and DS-HMGB1 bind equivalent amounts of RAGE at equilibrium, over time levels of RAGE bound by 3S-HMGB1 are comparable to the proinflammatory disulfide HMGB1 (DS-HMGB1) and higher than to FR-HMGB1. The inventors double Box B construct eliminates undesirable proinflammatory signaling whilst retaining regenerative activity equivalent to FR-HMGB1.

Additional Applications:

Fractures. Fractures occur following injury. However, one of the commonest skeletal 'injuries' is joint replacement or arthroplasty. The inventors propose that dBB12 can be used to promote healing following fracture or arthroplasty, thereby reducing the risk of potential complications such as loosening of components.

Brain and nervous system. dBB12L may be used to improve patient outcomes following stroke. Other potential indications include Parkinson's disease and dementia.

Lung. dBB12L is contemplated to improve outcomes following lung injury, for example, following Covid-19 or in patients with idiopathic pulmonary fibrosis.

Liver. 30% of people in the USA are estimated to suffer from non-alcoholic liver disease. 60% of these go on to develop non-alcoholic steatohepatitis and 20% of those develop liver cirrhosis. Treatments are being developed to limit and prevent liver damage from tehse conditions. The inventors propose that dBB12L to be used in combination with these treatments to promote liver regeneration.

Gut. dBB12L may be used to promote healing of the gut, for example, following surgery or patients with inflammatory bowel disease such as ulceractive colitis in combination with treatments to control inflammation.

Kidney. dBB12L may be used to promote regeneration of the kideny, thereby potentially avoiding the need for dialysis or kidney transplantation.

Skin. dBB12L may be used to promote wound healing eg following surgery, burns or patients with ulcers eg diabetic ulders.

Pancreas. dBB12L may be used to improve outcomes in patients with type 1 diabetes mellitus by promoting regeneration of islet cells.

Bone marrow. dBB12L may promote regeneration of the haemopoetic system e.g. following chemotherapy, thereby preventing severe potentially life threatening neutropenia.

The inventors have previously shown that FR-HMGB1 is effective even if adminsitered up to 2 weeks before injury (142). Since dBB12L is equally efficacious to FR-HMGB1 (FIG. 10J) it is contemplated that this polypeptide may be used prophylactically, for example, by the military or for sports injuries or before elective surgery or chemotherapy.

Materials and Methods

*E. coli* Strains

Mach-1 T1R cells (Invitrogen, no antibiotic resistance or induction, BL21(DE3)-R3-pRARE2 (in-house BL21 derivative, chloramphenicol resistance 36 µg/mL, T7-polymerase lac induction [86]) and BL21(DE3)-R3-pRARE2-BirA (in vivo biotinylation derivative of the above, additional spectinomycin resistance 50 µg/mL) were sourced from chemically competent stocks made in-house.

Bacterial Culture Media

SOC: 20 g/L tryptone, 5 g/L yeast extract, 0.5 g/L NaCl, 0.1862 g/L KCl were autoclaved and supplemented with 4.132 g/L $MgCl_2$ and 20 mM glucose.

LB (Luria Bertani): 10 g/L tryptone, 5 g/L yeast extract, 10 g/L NaCl, pH 7.2, autoclave sterilized. 2% w/v agar powder was added to make LB agar plates.

TB (Terrific Broth): 12 g/L tryptone, 24 g/L yeast extract, 4 g/L glycerol, 12.5 g/L $K_2HPO_4$, 2.35 g/L $KH_2PO_4$, autoclave-sterilized.

TB supplement: 1.6% w/v glycerol, 1% glucose, 25 mM $(NH_4)_2SO_4$, 10 mM $MgSO_4$, 10× trace metals, 0.22 μM sterile filtered.

Trace metal solution: 50 mM $FeCl_3$ (13.5 g/L), 20 mM $CaCl_2$ (2.94 g/L), 10 mM $MnCl_2$ (1.96 g/L), 10 mM $ZnSO_4$ (2.88 g/L), 2 mM $CoCl_2$ (0.48 g/L), 2 mM $CuCl_2$ (0.34 g/L), and 2 mM $NiCl_2$ (0.48 g/L), in 0.1 M HCl, 0.22 μM sterile-filtered.

M9 minimal medium: 16 g/L $Na_2HPO_4$, 4 g/L $K_2HPO_4$, 1 g/L NaCl, pH 7.2-7.3 and 2.5 g/L $FeSO_4$, 0.25 mg/L $ZnCl_2$, 0.05 mg/L $CuSO_4$, 0.25 g/L EDTA, 1 mM $MgSO_4$ were autoclaved and supplemented with 4 g/L glucose, 1 g/L U-99% $^{15}NH_4Cl$ (Cambridge Isotopes), 0.3 mM $CaCl_2$), 1.5 mg/L D-biotin and 1.5 mg/L Thiamine-HCL from sterile filtered stocks.

Plasmids

Plasmids were sourced from the SGC libraries [86]. All plasmids contain a 6×His tag with a TEV-cleavage site; pNIC-Bio3 and pDsbC-HT-CBio also have C-terminal biotinylation epitopes (which can be removed with a stop codon). Plasmid DNA was linearized by restriction enzyme digestion: BfuA1 (3 h, 60° C.) for pNIC-CTHF or BsaI (2 h, 37° C.). Cut vector DNA was purified with a PureLink PCR kit and treated with T4 DNA polymerase (NEB M0203) in the presence of 0.25 mM dGTP (pNIC-CTHF) or dCTP as per manufacturer protocols.

Cloning

HMGB1 constructs sourced from the Mammalian Gene Collection (Mach1 cells) were amplified via PCR: a program of 95° C./10', 25×(95° C./30", 52° C./1', 0.5-1.5' at 68° C.), 68° C./10' was used. Reaction consisted of 5 μL Herculase II buffer, 1 μM of each primer, 6 μg/mL plasmid template, 1 μM dNTP mixture and 1 unit Herculase II polymerase (Agilent 600679; supplied with buffer and 100 μM dNTP stocks) in 25 μL final volume. PCR products were purified before further use (PureLink kit, ThermoFisher K310001).

Amplified coding sequences (alleles) were cloned into the destination vector via ligation independent cloning (LIC). The insert was treated with T4 DNA polymerase in the presence of a cognate nucleotide to that used for the vector (10 μL reaction volume), and 2 μL was mixed with 1 μL of treated vector and annealed for 30'. 40 μL ice-cold Mach-1 cells (for storage) or 20 μL BL21(DE3)-R3-pRARE2/BL21 (DE3)-R3-pRARE2-BirA cells (for expression) were added and heat-shocked for 45" at 42° C. before chilling in ice. Recovery was performed for 2 h in SOC medium at 37° C. prior to plating on selective media with 5% sucrose and antibiotics. After 24 h, positive colonies were picked and screened with MyTaq polymerase according to manufacturer protocols with specific sequencing primer pairs for bands of the correct molecular weight. Positive transformants were grown overnight in 1 mL of 2×LB (double concentration of LB) with antibiotics and stocked with 12% glycerol v/v at −80° C.

Figure 17:
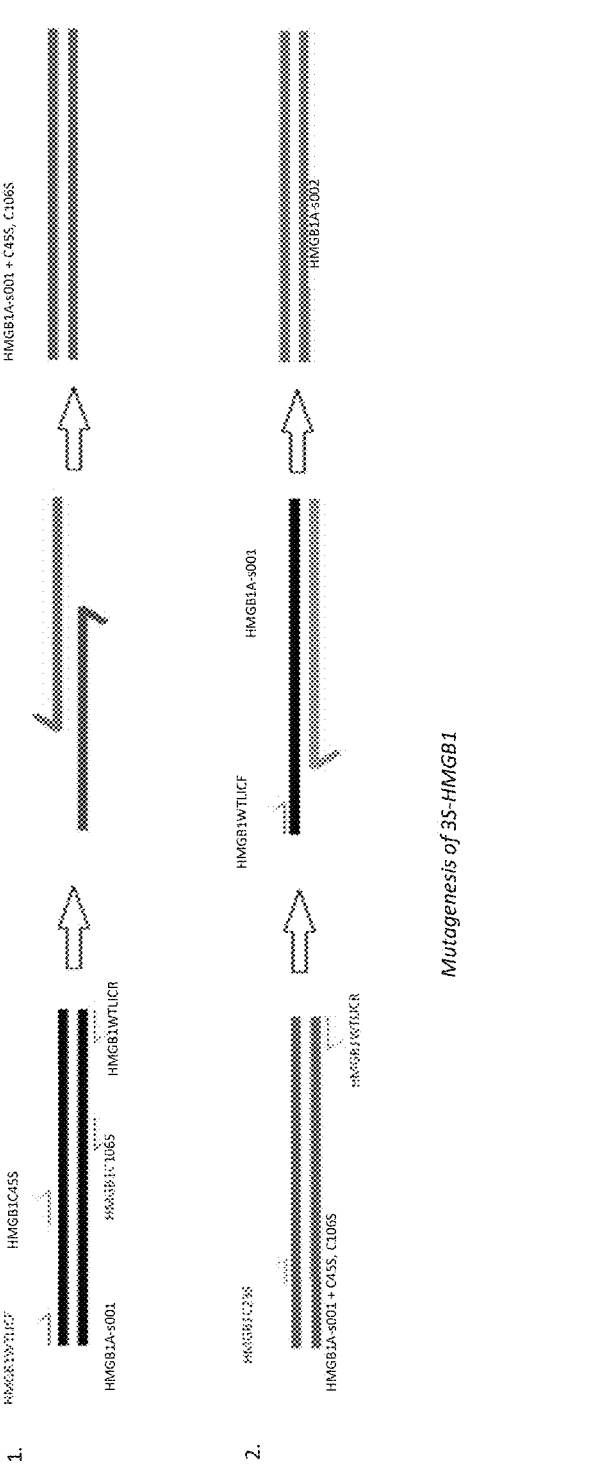
FIG. 17 shows process to generate 3S-HMGB1.

3S-HMGB1 mutant sequence was generated in a similar manner. PCR was performed separately to generate a S23-S45 and a S106 fragment, which were annealed via PCR; 5 μL of each purified PCR product substituted the primers and template in this reaction. The process is summarized in FIG. 17.

CXCL12 constructs were cloned with an in-frame SUMO protease site N-terminal to the mature protein to allow for periplasmic secretion with an N-terminal fusion protein in the pDsbC-HT-CBio vector (DsbC-SUMO-CXCL12) to avoid addition of N-terminal residues to the protein which could affect its activity [87,88] whilst obtaining folded, oxidized CXCL12 via the DsbC fusion protein system [89]. A detailed table of primers and vectors used for each construct, boundaries, expression strains, and base pairs/amino acid sequences can be found in the Supplemental Methods section. All mutants were verified by sequencing (SourceBioscience). The sequence for HMGB1-dBB was designed in silico by codon-optimizing a Box B 89-174 sequence according to E. coli BL21-DE3 genome (assembly ASM956v1) placed after the native HMGB1 Box B sequence, and synthetized in vitro by Twist Bioscience (San Francisco, USA) cloned in pNIC-CTHF.

Recombinant Protein Expression 20 mL of overnight culture of HMGB1-expression strain transformants, grown from a fresh agar plate streak, were inoculated into 1 L of TB (or M9) medium with supplement and allowed to grow up to OD 2.0 at 37° C. with 0.45 RCF orbital shaking (OD 0.6 for M9 medium). Precultures used for production of $^{15}N$ labelled HMGB1 were first spun down at 1000 RCF for 5' and washed in M9 medium. Once the target OD was reached, were cooled to 18° C. before addition of 0.5 mM or 0.25 mM IPTG (for HMGB1 and CXCL12 proteins respectively) and grown for 16 h before harvesting at 4000 RCF. For biotinylated proteins, 10 mM D-biotin in PBS was added before induction and again 1 h before cell harvesting.

Recombinant HMGB1 Purification

Pellets of induced HMGB1-expressing cells were resuspended at 14 g/L in 1 M NaCl, 5% glycerol, 50 mM HEPES pH 7.5, 10 mM Imidazole (Buffer A) supplemented with 1:1000 protease inhibitors (Calbiochem Set III, Merck 539134), 3 μg/mL Benzonase-MBP, 1 mM $MgSO_4$, 0.5 mg/L lysozyme (Sigma L6876) and 0.5% v/v Triton-X100 before freezing at −80° C.; from this point onwards all steps took place at 4° C. Thawed pellets were spun down at 6780 RCF for 45' and the supernatant was loaded into pre-equilibrated nickel-His GraviTrap (GE Healthcare) 1 mL columns. After drip-through, columns were washed with 10 CV of 1 M NaCl, 50 mM HEPES pH 7.5 and 1.5 CV of 0.4 M NaCl, 20 mM HEPES pH 7.5, 1 mM $MgSO_4$, and 3 μg/mL Benzonase-MBP solution to digest remaining DNA for 30'. Contaminants were washed with 15 CV of 0.5 M NaCl, 5% glycerol, 50 mM HEPES pH 7.5 (Buffer B) supplemented with 30 mM imidazole before elution directly into a PD-10 column (GE Healthcare; equilibrated in Buffer B+20 mM imidazole) with 2.5 mL of Buffer B+500 mM imidazole. Proteins were eluted from the column with 3.5 mL of Buffer B+20 mM imidazole before tag removal with 1:20 OD TEV-GST protease over 16 hours.

Proteases and further contaminants were removed by recirculating the protein solutions over the same GraviTrap column used to purify initially (equilibrated in Buffer B+20 mM imidazole). For biotinylated proteins, streptavidin-XT resin was used instead to select biotinylated molecules only: after 30' of incubation in the resin, sample was allowed to drip through, washed with 30 CV of buffer A and 1 CV of buffer B+100 mM D-biotin, and eluted by incubation in 3 CV of the same buffer for 2 h. Proteins were further purified by size exclusion chromatography (SEC) (Superdex S75 10/300-0.35 mL/min or 16/600-1.2 mL/min flow rate) in either 10 mM HEPES pH 7.5+150 mM NaCl for biophysics work or cell-culture grade PBS for cell and animal work. Recombinant proteins were flash-frozen for storage, adding 1 mM TCEP in the case of reduced HMGB1 proteins.

Recombinant CXCL12 Purification

Outer membranes of cells expressing DsbC-SUMO-CXCL12 were lysed by osmotic shock [90]. Pellets were resuspended at 40 g/L in 1 M sucrose, 0.2 M Tris-HCl pH 8.0, 1 mM EDTA, 1 mg/mL lysozyme, 2× cOmplete protease inhibitor set (COEDTAF-RO, Roche), 50 mM Imidazole and 3 μg/mL benzonase. This was stirred for 45' at room temperature before adding 4 volumes of ice-cold 18.2 mΩ water and mixed for a further 10' before adding 1 mM MgSO4. This was centrifuged for 1 h at 16000 RCF, 4° C., and the supernatant loaded at 10 mL/min into Ni-NTA Superflow columns (Qiagen, 30761) on an Akta Xpress FPLC system; 1 column was used for every 6 L of cells. Proteins were eluted via an imidazole gradient (10-25 mM over 10 CV, and 25-500 mM over 8 CV) in Buffer B, and 1:10 OD of Ulp-1 protease were added before dialysis in 100 volumes of 0.2 M NaCl, 20 mM HEPES pH 8.0 (Buffer Ac) overnight. On the next day, the protein was loaded into CaptoS columns (CaptoS ImpAct, GE 17-3717-47) at 2.3 mL/min and eluted in a gradient of 0.2-1.5 M NaCl in 20 mM HEPES pH 8.0 to separate cut CXCL12 from DsbC and Ulp-1. Proteins were further purified via SEC in the same way as HMGB1 and flash-frozen for storage.

Removal of Endotoxins

Endotoxin was removed in all cases before size-exclusion chromatography via phase separation with Triton Tx-114 [91]. A 2% v/v of TX-114 was added to recombinant protein solutions, homogenized for 20' with orbital shaking at 2000 RCF at 4° C., and separated for 5' at 37° C. before pelleting the detergent phase at 8000 RCF, 10', 25° C. The supernatant was mixed with 5% w/v of SM-2 Biobeads (BioRad, 152-8920), cleaned with 2% TX-114 for 2 h and regenerated with 30 CV of methanol, 30 CV of endotoxin-free 18.2 mΩ water and 30 CV of endotoxin-free PBS. This was incubated for 4 h at room temperature to adsorb remaining Triton and PEG [92] before injection onto a sanitized SEC system (with 0.5 M NaOH contact over 12 h, followed by 0.2 M acetic acid/20% ethanol contact over 6 h and equilibration in cell-culture grade PBS) to fully remove leftover polymer contaminants whilst performing size exclusion. The absence of Triton and PEG was verified by lack of their respective charge state species in ESI/QTOF-MS mass spectrometry [93]. LPS content of the recombinant proteins was assessed via the LAL method (GenScript ToxinSensor L000350). Samples were approved for cell and animal use when they contained <4 EU LPS/mg protein.

Enzyme Production

TEV-GST protease (GST-fusion protein), Benzonase-MBP, and Ulp-1 protease were produced from transformants in storage at the SGC collection [86]; all had 200 μg/mL ampicillin resistance. TEV and Ulp-1 were purified as per the protocols described for HMGB1 with only one IMAC step, whereas Benzonase-MBP was purified from outer membrane lysates obtained as with CXCL12 and isolated with use of amylose resin (NEB, E0821) as per manufacturer protocols. In both cases, the resulting proteins were concentrated to 10 mg/mL in 50 mM HEPES pH 7.5, 0.3 M NaCl, 10% glycerol. GST-TEV protease and Ulp-1 were flash-frozen with liquid nitrogen and supplemented with 0.5 mM TCEP during purification; Benzonase-MBP was supplemented with 50% glycerol and 2 mM MgCl₂ and stored at −20° C.

Peptide Arrays

For alanine scanning and the initial HMGB1 and CXCL12 arrays, membranes with the identified peptides in the original membrane, the full HMGB1 sequence, or CXCL12 (Uniprot P48061, excluding secretion signal) were printed by Dr. Sarah Picaud at the SGC upon request following published protocols [42]. The membranes were rehydrated at 20-25° C. with 95% and 70% ethanol, equilibrated with PBST (PBS 1X+0.05% Tween-20, 3×), and blocked with 10% BSA/PBST for 8 h. 1 μM of the partner His-tagged protein construct was added (in PBS) and allowed to bind for 24 h at 4° C. Excess BSA and protein was removed with 3 washes in PBST; all washes lasted 1' unless otherwise stated. To detect bound proteins, the membranes were treated with 1:3000 dilution of Qiagen anti-Penta His HRP conjugate (Qiagen 34460) and excess antibody removed with 3 washes in PBST for 20'.

For the TLR-2, TLR-4 and RAGE peptide arrays, CelluSpot arrays were used instead (IntaVis, [94]) The membranes were baited with either CXCL12 or either of the three receptors in fusion with the CH domain of IgG (1530-TR, 9149-TR, 1145-RG, BioTechne) above, then probed with Anti-CXCL12 antibody (PA5-17238, Invitrogen). Bound IgG, whether by the Fc fusion proteins or anti CXCL12, was then detected with 0.25 μg/mL anti-human IgG CH2 domain antibody (NBP2-68464, custom conjugated to HRP). A series of peptides covering human IgG CH2 domain were used as controls (Uniprot P01857, 11-223) were used as controls: the highest intensity spot was used as 100% signal threshold.

Bound antibody was in all cases via chemiluminescence (Pierce ECL substrate—32109): the membrane was covered in substrate solution and placed between two clear plastic sheets before incremental imaging at 2' intervals in a LAS-4000 camera. The intensity of the peptides in each membrane was measured in ImageJ and normalized to the controls and blank spots (100%-0%). Residues whose mutation to alanine resulted in higher intensity changes than those observed for alanine positions in the sequence were considered as significant contributors to CXCL12 binding.

Biolayer Interferometry (BLI)

Pre-hydrated streptavidin Octet Biosensors (ForteBio 18-5019) were coated with 4 μM solutions of biotinylated HMGB1 proteins in 10 mM HEPES, pH 7.5, 150 mM NaCl (Base buffer-BB) plus, 0.5 mM TCEP (60" baseline, 60" binding). Nonspecific binding was minimized by incubation for 3' in BB+1% BSA+0.05% Tween-20 (Kinetics Buffer, KB) prior to kinetics assays. Interaction with CXCL12 was measured by performing incremental immersion of the sensors in solutions with increasing CXCL12 concentration (0-150 μM, in 1:2 dilutions) in KB (60" baseline, 500" association, 420" dissociation, 180" reduction in BB+0.5 mM TCEP). An OctetRed 384 instrument was used for these experiments. Kinetics data were extracted with DataAnalysis 9.0 (ForteBio). Response at equilibrium $R_{Eq}$ was plotted against concentration in a Michaelis-Menten saturation plot to calculate kD/$B_{max}$ (saturation plot of concentration against rEq). Kinetic rates (association rate; $k_{on}$ and dissociation rate; $k_{off}$) were derived from the direct measurements of each parameter from all the association and dissociation steps in the interferogram, and fitted to a horizontal line (mean) across all measurements. Data from each replicate run were pooled in the same manner to calculate the overall mean. For measuring RAGE binding kinetics to HMGB1, 15 μg/mL RAGE-Fc in PBS+0.1% BSA+0.02% Tween-20 was immobilized on the surface of anti-IgG biosensors (AHC, 18-5060) over 30" and dipped in serial concentrations of each HMGB1 construct (60" baseline, 200" association/dissociation) and fitted in the same manner to derive kinetic parameters.

US 12,624,074 B2

35

36

Nuclear Magnetic Resonance (NMR)

$^{15}$N-labelled recombinant HMGB1 constructs in 10 mM HEPES 150 mM NaCl pH 7.5 (identical buffering and ionic strength to BLI experiments) were supplemented with 5% v/v D$_2$O, and pipetted with a glass Pasteur pipette into a 5 mm Shigeimi tube, sealed with paraffin. Final volumes were >330 μL. CXCL12 was added in the same buffer and final volumes were adjusted to avoid modification of the referencing. Signal locking, tube shimming, and nuclei tuning were manually performed via Bruker TopSpin software. Water signal was suppressed by acquiring a $^1$H spectra with power level 1 (P1)=estimated pulse calibration (pulsecal). When a single peak was observed, a P1 value of 4 times the initial was used as a baseline and adjusted until a symmetric peak could be observed in the $^1$H spectrum. NMR experiments were performed after these calibration steps ($^1$H-NMR, $^{15}$N-HSQC, $^{15}$N-NOESY-HSQC, $^{15}$N-TOCSY-HSQC Peaks in $^{15}$N-HSQC spectra were assigned based on published NMR tables for HMGB1 1-184 (BMRB 15418) and our own NOESY/TOCSY data for each construct analyzed. To measure CXCL12 binding, the chemical shift position and volume of identified peaks was tracked across different molar equivalences of CXCL12 (these are listed in the relevant image) via CCPNMR 3.0 Analyze's Chemical Shift Tracking module. For peak intensity changes, the median intensity change in each set was considered as a baseline. Full chemical shift tables and experiment parameters are detained at the end of this section.

Mass Spectrometry

For protein identification via MS/MS and tryptic digest, bands from SDS-PAGE gels were excised and submitted to the SGC open access MS platform and analysed by Dr. Rod Chalk, Dr. Tiago Moreira and Oktawia Borkowska, as published [93,95]. Data analysis (peptide mapping) to annotate protein identity was performed with the MASCOT search engine, against the Uniprot (reference protein sequences) and SGC (construct sequence) databases. Native ESI/MS experiments were performed by manual injection in volatile buffer (50 or 200 mM ammonium acetate, pH 6.5) into an ESI/QTOF instrument (Agilent Q-TOF 6545) at 360 μL/h. Signal was acquired for at least 10 counts (30 sec) once a steady ionic stream was observed in the total ion chromatogram. For denaturing experiments, samples were diluted to 1 mg/mL in 0.2% formic acid and injected via HPLC (Agilent 1100 HPLC) and eluted in a mobile phase of formic acid/methanol, as described [93]. Each continuous distribution of charge states was considered a distinct conformation; charge states (Z) were assigned according to the formula where mW=(mW/Z-proton mass)*Z. Surface areas were derived from the formulas proposed in the literature [96,97] which resulted in the formula ln(SASA)=ln(M/Z) *0.6897-4.063 for native MS and ln(SASA)=ln(M/Z) *0.9024-5.9013 for denatured samples. At least three independent injections were performed for all MS samples. All solutions in these experiments were made with HPLC water (electrochemical grade) and solvents.

SEC Surface Area Quantitation

To correlate SEC chromatograms with surface area, standard sets with known structures (BioRad 1511901) were run through a Superdex 75 μg, 10/300 column used in these experiments. SASA for the proteins contained in these and the GE-supplied calibration curve standards were derived from published PDB structures (BSA, 3V03; Ovalbumin, 1JTI; Myoglobin, 2V1I; RNAseA, 1A5P; Aprotinin, 1NAG; Vitamin B12, 3BUL) and correlated with retention volume by nonlinear least squares fitting (SASA=331.2*RV$^2$– 1.19e4*RV+1.08e5). All experiments compared between HMGB1 samples were performed in the same buffer as native MS (200 mM ammonium acetate, pH 6.5); injections were performed at 1 mg/mL to avoid saturation of signal and all samples were eluted at 0.4 mL/min.

RAGE Binding ELISA Assay 384-well protein-binding ELISA plates (Santa Cruz Biotechnology, sc-206072) were coated with 50 μL of 40 nM solutions in PBS (+0.5 mM TCEP for FR-HMGB1 constructs) of HMGB1 constructs for 24 h, at 4° C., including FL/DS HMGB1 full-length controls and blank, with 4 replicates of each. Nonspecific binding was blocked by incubation with 10% BSA in PBS for 2 h, at 20-25° C. A concentration range of RAGE-Fc chimera protein (Bio-Techne, 1145-RG; 0-640 nM in 1:4 dilutions) was added in 10% BSA/PBS and allowed to bind for 2 h, at 4° C. Bound FC chimera was detected by incubation with Anti-Human IgG HRP (Agilent Dako P021402-2) diluted 1:10000 in 10% BSA/PBS for 2 h, at 20-25° C. Between each of these 3 steps, the plate was washed with 100 μL PBST, three times. To detect bound antibody, 25 μL of TMB substrate (ThermoFisher N301) was added to each well; the reaction was allowed to develop in the dark until the FL-DS-HMGB1 control developed a clear concentration-dependent color gradient before stopping the reaction with 25 μL of 0.5 M H$_2$SO$_4$. OD 450 was measured as a readout (FluoStar OMEGA, BMG Labtech) and plotted as a saturation fit against 2×RAGE-Fc concentration (as the chimera is a RAGE dimer).

TLR-4 and TLR-2-Mediated NF-κB Signaling Reporter Assay

HEK-Dual cells (Invivogen) expressing human TLR-2 and CD14 or murine TLR-4, MD-2 and CD14 were maintained in DMEM (Gibco), supplemented with 10% FBS (Gibco), 1% L-Glutamine (Gibco), and 1% penicillin/streptomycin (Gibco), in standard tissue culture conditions (37° C.; 5% CO2). To determine if FR-HMGB1, DS-HMGB1 and dBB12L induces activation of TLR-4 and TLR-2 signaling, 104 TLR-4 and TLR-2 HEK-Dual cells were plated in triplicate into wells of a 96 well plate and stimulated with 10 μg/mL 1 HMGB1 and (X concentration) FSL-1 for TLR-2 and 10 ng/mL LPS for TLR-4. 24 hours after stimulation, NF-κβ activity was determined my measuring the induced levels of secreted embryonic alkaline phosphatase (SEAP).

Monocyte Total NF-κB Secretion Assay

Human monocytes (StemCell Technologies) were maintained in DMEM (Gibco), supplemented with 10% FBS (Gibco) in standard tissue culture conditions (37° C.; 5% CO2). To determine if FR-HMGB1, DS-HMGB1 and dBB12L induces proinflammatory cytokine production, 105 human monocytes were plated in triplicate into wells of a 96-well plate and stimulated with 10 μg/mL HMGB1 and 50 ng/mL LPS or 10 ng/mL LTA. 24 h after stimulation, TNF levels were determined by Enzyme-linked immunosorbent assays (ELISA) (Abcam).

Transcriptomic Analysis

Mice were treated systemically with an i.v. injection of 30 μg FR-HMGB1 in 50 μL of PBS vehicle, or PBS only control. Injury cell are from BaCl$_2$ injured mice as described below. Alert cells are from the uninjured contralateral side of BaCl$_2$ injured mice. Murine muscle stem cells (mMuSCs) were defined and freshly isolated according to previously reported protocols. Muscle cell suspensions were created by mincing thigh muscles and enzymatically digesting with collagenase 800 U/ml (Worthington-Biochem) and dispase 1 U/mL (Gibco). Thereafter, all suspensions were strained through 70 μm and 40 μm filters (Greiner Bio-One) and stained with respective antibodies. mMuSC, CD31⁻CD45⁻ Sca-1⁻ VCAM1⁺, were isolated by fluorescence activated cell sorting (FACS) using BD FACSAria III machine. RNA, extracted from freshly FACS isolated mMuSCs, was sent to RNA-seq analysis using Lexogen 3' kit library prep and sequenced using HiSeq400 (Illumina). FASTQ files were assessed using FASTQC followed by the generation of TPM values with kallisto v0.42.4. TPM values were summed to obtain gene-level expression values using tximport and differential expression analysis was undertaken with DeSEQ2. GO enrichment of differentially expressed genes was performed using the R package 'clusterProfiler'[98] with a Benjamini-Hochberg multiple testing adjustment and a false-discovery rate cut-off of 0.1. Visualization was performed using the R packages 'ggplot2' and 'igraph'.

In Vivo Mouse Muscle Injury Model

C57BL/6 inbred mouse strain, females of 11-12 weeks of age were purchased from Charles River UK and housed in the local Biological Safety Unit (BSU) at the Kennedy Institute. Acclimatization period was 1-2 weeks. All protocols performed on live animals have been approved by the UK Home Office (PPL 30/3330 and PPL P12F5C2AF) as well as the local animal facility named persons and are registered under the appropriate project and personal licenses under ASPA regulations. All consumables were surgically certified; recombinant proteins were endotoxin-free. Surgeries were done in a clean environment separate from culling facilities. All animals were monitored for 6 h post-operatively, and daily for the following 3 days; monitoring was then transferred to the NVS/NACWO.

Surgeries were performed as described previously ([8, 13]). Animals were anesthetized by aerosolized 2% isoflurane, given analgesia, transferred to a warming pad and the right lower hindlimb was disinfected with povidone iodine and the tail with 70% ethanol if intravenous injection was performed. 50 µL of 1.2% BaCl₂ (Sigma) was injected into and along the length of the tibialis anterior (TA) muscle to induce cell death. Mice were euthanized and lower limbs removed at the times indicated, fixed in 4% paraformaldehyde (Santa Cruz Biotechnology) for 24 h. The TA muscles were dissected and further fixed for 24 h before being embedded in paraffin and sectioned. Sections (5 µm) were stained with hematoxylin and eosin to identify fibers with central nuclei and imaged with an Olympus BX51 using a 10× ocular/40× objective lens. The cross-sectional area (CSA) of the fibers from at least 4 images per mice was manually measured using the FIJI distribution of ImageJ2 software (NIH). Data were grouped per mice. Mice were injected with HMGB1 constructs (46 nM/kg, resuspended in PBS) or PBS vehicle control intramuscularly or intravenously at the time of injury or after injury for the optimal time administration of HMGB1 constructs after injury.

In Vivo Mouse Cardiac Injury Model

C57BL/6 female mice were subject to surgery between 10-14 weeks old, with body weight between 25-30 g. All mice had either an intravenous injection of FR-HMGB1 (46 nM/kg, resuspended in PBS) or vehicle control just before surgery. Buprenorphine (buprenorphine hydrochloride; Vetergesic) was delivered as a 0.015 mg ml solution via intraperitoneal injection at 20 min before the procedure to provide analgesia. They were anaesthetized with 2.5% isoflurane and externally ventilated via an endotracheal tube. Cardiac injury was induced by permanent ligation of the left anterior descending coronary artery (LAD) via a thoracotomy. Experimenters were blind to treatment groups for subsequent cardiac cine-MRI and analysis. Mice were housed and maintained in a controlled environment. All surgical and pharmacological procedures were performed in accordance with the Animals (Scientific Procedures) Act 1986, UK.

Cardiac Cine-MRI and Analysis

Cardiac cine-MRI was performed post-LAD ligation at 7T using a Varian DDR system. Briefly, mice were anaesthetised with 2% isoflurane in 02, and positioned supine in a custom animal handling system with homeothermic control. Prospectively gated proton cardiac images were acquired with a partial Fourier accelerated spoiled gradient echo CINE sequence (TR 5.9 ms, TE 2.2 ms, 30 kHz bandwidth, 30° F.A, approximately 20-30 frames gated to the R wave with a 4 ms postlabel delay; 20% partial acquisition; 4 averages) with a 72 mm volume transmit/4 channel surface receive coil (Rapid Biomedical GmbH) in order to acquire two and four chamber long-axis views and a short axis stack for functional quantification (128×128 matrix; 25.6 mmˆ2 FOV; 0.2 mm resolution in-plane). Non-acquired partial Fourier data was reconstructed via the method of projection onto convex sets prior to a simple, cartesian, DFT. Blinded image analysis was performed using ImageJ (NIH). Left ventricular mass, volumes and ejection fraction were calculated as previously described[1]. The relative infarct size was calculated from the average of the endocardial and epicardial circumferential lengths of the thinned, akinetic region of all slices, measured at diastole, and expressed as a percentage of the total myocardial surface [99].

Statistical Analysis

All calculations were performed with GraphPad Prism (v. 8.41). For kinetics experiments (BLI/RAGE ELISA), all fits were performed via nonlinear least squares. For the RAGE ELISA, as each concentration of RAGE was independent from the rest of the wells, all data were considered as one kinetics fit; in BLI however each sensor was considered an independent fit for the purposes of calculation. Comparisons between parameters were performed via the AUC method. Mouse muscle injury model data were analyzed as a nested ANOVA, where each sub-column comprises all the muscle CSA values for a given animal, and each group contains all the animals in order to separate biological variation from treatment effect. If the equal variance assumption could not be met in either case data were analyzed via a Kruskal-Wallis test; for nested ANOVA equal numbers of data from each animal would be randomly selected to avoid skewing. Any other data were analyzed via one-way ANOVA if the heteroskedasticity plot and Q/Q plot supported the equal variance assumption [100]; these were also verified by Spearman's Test. For multivariate experiments (e.g. cardiac experiments) a two-factor ANOVA was used under the same assumptions (no dataset violated heteroskedasticity in this case). Post-hoc comparisons were weighted by Holms-Sidak correction (ANOVA family tests) or Dunn's method (Kruskal-Wallis). The test selected in each case is noted under each figure legend. Significance legends: n.s; not significant, *; $p<0.033$, ; $p<0.002$, *; $p<0.0002$, ****; $p<0.0001$.

NMR Chemical Shift Tables

Figure 5A:
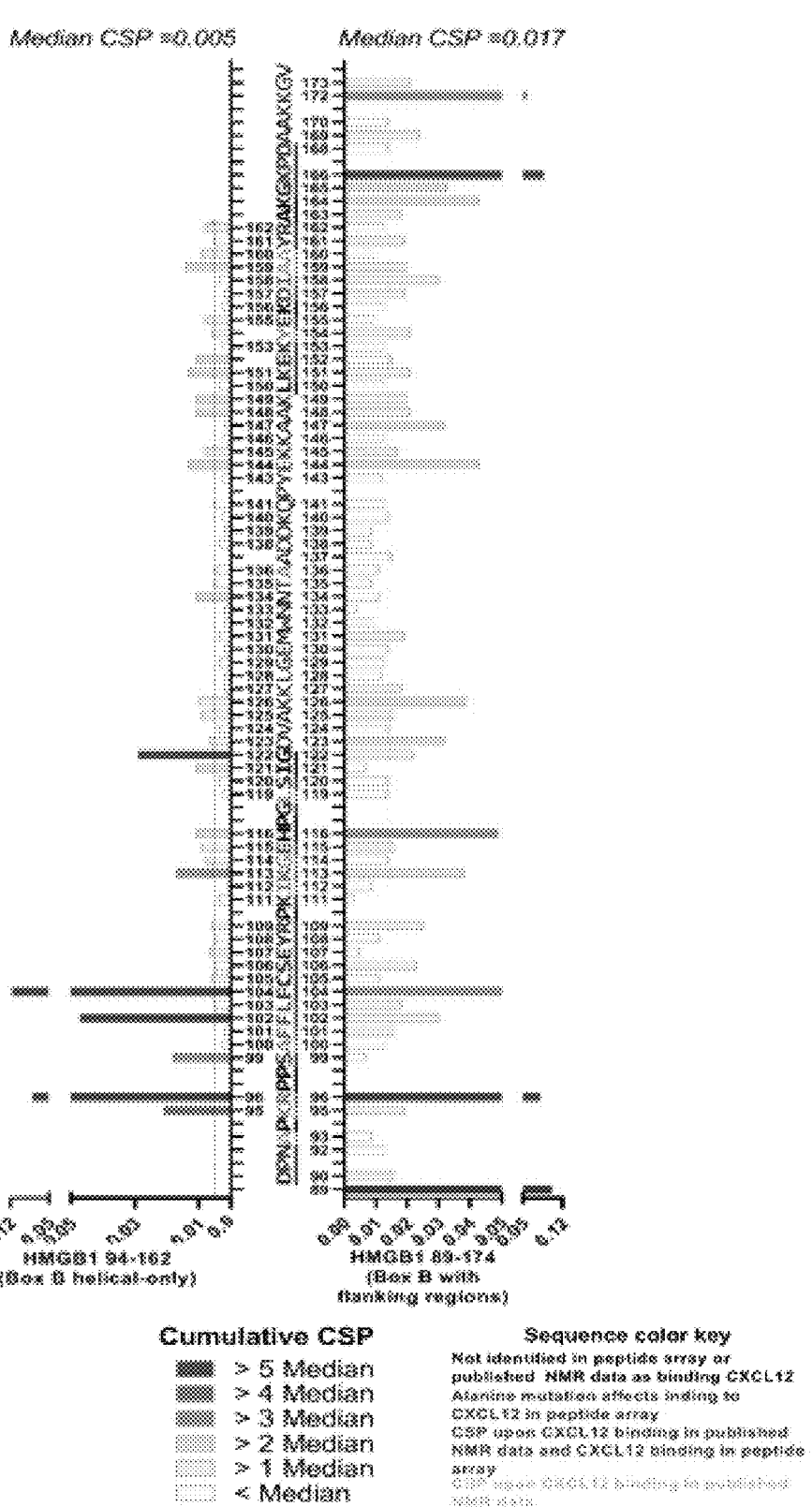
FIGS. 5A-5B show NMR validation of residues involved in CXCL12 binding.
Figure 5B:
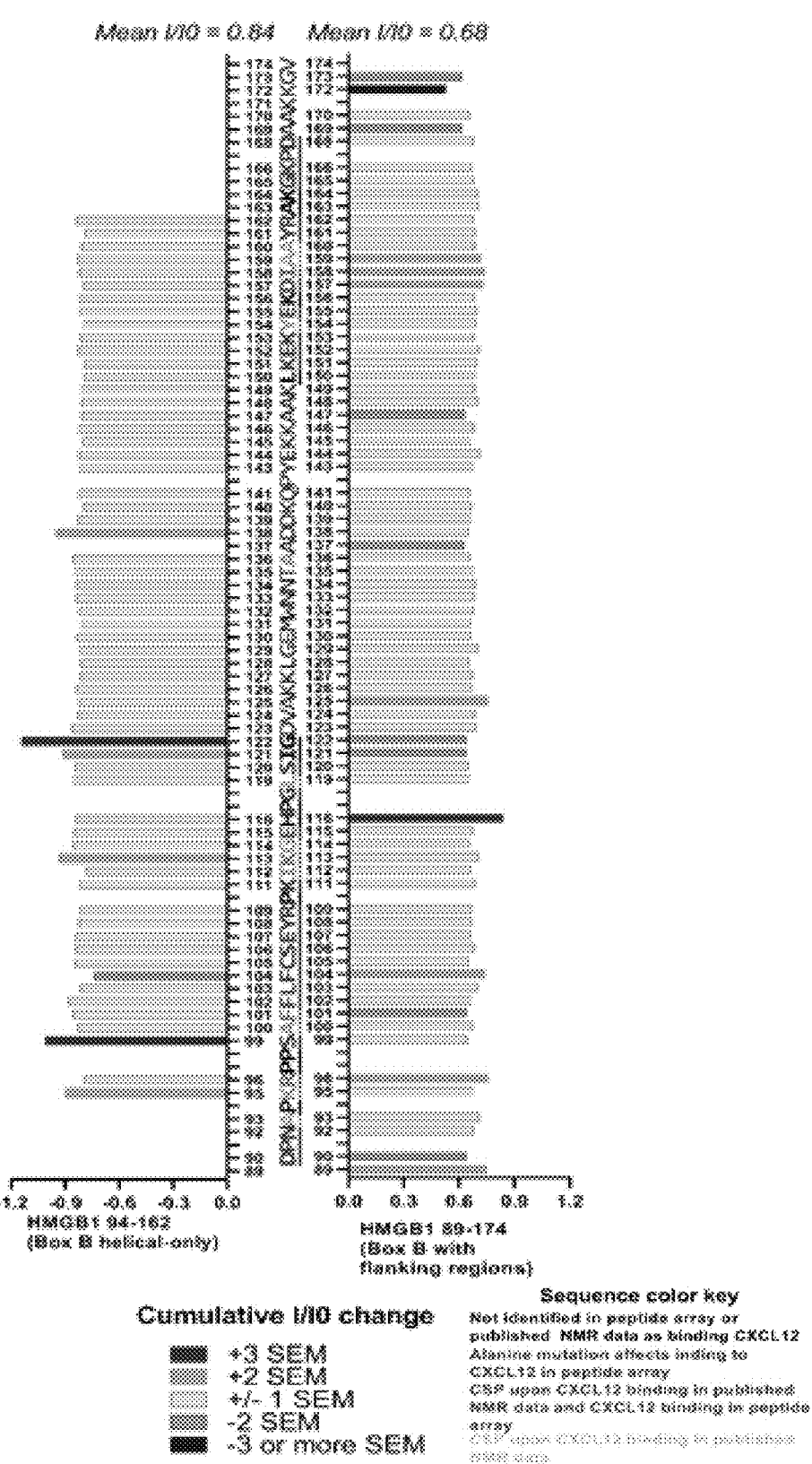

HMGB1-c028 (94-162, Biotinylated) Titration with CXCL12A-c021 at 0, 0.42, 0.82 and 1.42 molar equivalents, FIGS. 5A-5B.

Due to protein amount limitations, titration was performed by sequential addition of CXCL12 to HMGB1 samples, resulting in sample dilution. As the calculations in the chemical shift tracking module in CCPNMR are independent of peak, this does not alter the results; the median change has been indicated in the volume comparisons.

| BROKER AVIII HD 500, 5 MM CPTCI 1H-13C/15N/D Z-GRD PROBE | |
|---|---|
| $^1$H frequency (Hz) | 500.01233645 |
| $^1$H sweep width (ppm) | 11.9044681870088 |
| $^1$H sweep width (Hz) | 5952.38095238095 |
| $^1$HN sweep width (ppm) | 10.9286921061064 |
| $^{15}$N frequency (Hz) | 50.6715211382702 |
| $^{15}$N sweep width (ppm) | 32.0372585410812 |
| $^{15}$N sweep width (Hz) | 1623.37662337662 |
| Water suppression gradient pulse width (Hz) | 2336.45 |
| Buffer | 10 mM HEPES, pH 7.5, 150 mM NaCl |

Baseline 1 (Day 1)

| Experiment type | 2D $^1$H-$^{15}$N HSQC |
|---|---|
| HMGB1 construct and concentration | 0.45 mM, HMGB1-c028 (Box B 94-162), C-terminal Avi tag |
| CXCL12 construct and concentration | 0 mM |
| Temperature | 25° C. |
| Volume | 300 μL |
| Sample pH (after adjusting) | 7.7 |
| Number of scans | 8 |

| Assign | F1 position | F2 position | LW F1 (Hz) | LW F2 (Hz) | Height |
|---|---|---|---|---|---|
| BoxBFL.95.LYS.N | 8.47816 | 122.87351 | 16.67468 | 12.22962 | 10886431 |
| BoxBFL.96.ARG.N | 8.30965 | 123.9316 | 14.96291 | 11.62421 | 144139104 |
| BoxBFL.99.SER.N | 7.95885 | 114.22726 | 22.5074 | 15.03176 | 16802856 |
| BoxBFL.100.ALA.N | 9.0643 | 122.83852 | 12.15917 | 12.63149 | 138071536 |
| BoxBFL.101.PHE.N | 8.44324 | 116.14361 | 13.00283 | 12.61897 | 92877416 |
| BoxBFL.102.PHE.N | 8.26304 | 122.13933 | 14.85477 | 12.7452 | 88662424 |
| BoxBFL.103.LEU.N | 8.27748 | 121.1555 | 13.77712 | 12.44091 | 112430712 |
| BoxBFL.104.PHE.N | 8.15422 | 122.51526 | 17.30965 | 12.77095 | 208687344 |
| BoxBFL.105.CYS.N | 8.49978 | 118.38542 | 12.79441 | 13.0002 | 114087696 |
| BoxBFL.106.SER.N | 8.12921 | 115.05247 | 11.81293 | 12.01762 | 185743392 |
| BoxBFL.107.GLU.N | 7.15444 | 119.18761 | 15.14408 | 11.95417 | 174642688 |
| BoxBFL.108.TYR.N | 7.944 | 114.61662 | 17.02596 | 12.46204 | 118306368 |
| BoxBFL.109.ARG.N | 9.23012 | 123.69626 | 13.5621 | 12.34021 | 130691488 |
| BoxBFL.111.LYS.N | 6.80053 | 117.70067 | 15.27665 | 12.39016 | 143073536 |
| BoxBFL.112.ILE.N | 8.1617 | 119.74645 | 14.25943 | 12.83013 | 126874280 |
| BoxBFL.113.LYS.N | 8.24755 | 118.47981 | 17.01044 | 13.8802 | 71528184 |
| BoxBFL.114.GLY.N | 7.6363 | 103.71903 | 15.16014 | 12.02905 | 120973232 |
| BoxBFL.115.GLU.N | 7.50091 | 119.58688 | 15.18257 | 12.11395 | 146458640 |
| BoxBFL.116.HIS.N | 7.8198 | 114.78302 | 14.39534 | 11.92497 | 117505296 |
| BoxBFL.119.LEU.N | 7.36285 | 121.19842 | 12.72385 | 11.91713 | 222764784 |
| BoxBFL.120.SER.N | 9.31614 | 121.05943 | 13.74707 | 12.14133 | 126779632 |
| BoxBFL.121.ILE.N | 8.7484 | 120.66613 | 14.38154 | 12.69317 | 61496764 |
| BoxBFL.122.GLY.N | 8.70938 | 109.44017 | 17.19009 | 12.98604 | 15080434 |
| BoxBFL.123.ASP.N | 7.96042 | 124.28299 | 14.86623 | 12.46038 | 123154200 |
| BoxBFL.124.VAL.N | 8.63541 | 124.07082 | 13.35656 | 11.92144 | 172075232 |
| BoxBFL.125.ALA.N | 7.92766 | 121.34983 | 12.19988 | 11.82723 | 225860864 |
| BoxBFL.126.LYS.N | 8.01853 | 119.68738 | 12.11349 | 12.34419 | 232838720 |
| BoxBFL.127.LYS.N | 8.03865 | 121.30632 | 12.54305 | 12.01855 | 257706416 |
| BoxBFL.128.LEU.N | 8.6442 | 120.16728 | 12.9965 | 12.28793 | 158055184 |
| BoxBFL.129.GLY.N | 8.26246 | 106.03693 | 14.92945 | 11.88241 | 144422592 |
| BoxBFL.130.GLU.N | 8.07143 | 123.2476 | 13.07349 | 12.04715 | 202424016 |
| BoxBFL.131.MET.N | 8.77019 | 118.9603 | 12.65128 | 12.17389 | 190716976 |
| BoxBFL.132.TRP.N | 8.7155 | 122.68159 | 13.66438 | 12.0197 | 125464952 |
| BoxBFL.133.ASN.N | 8.17909 | 117.36655 | 11.90513 | 11.83855 | 191488080 |
| BoxBFL.134.ASN.N | 7.58752 | 115.82865 | 19.62284 | 12.10783 | 166835600 |
| BoxBFL.135.THR.N | 7.30723 | 119.95451 | 15.53231 | 12.28047 | 175465168 |
| BoxBFL.136.ALA.N | 9.24925 | 131.44171 | 12.05279 | 11.8376 | 183664944 |
| BoxBFL.138.ASP.N | 8.99204 | 115.70293 | 13.82959 | 13.53115 | 66696728 |
| BoxBFL.139.ASP.N | 7.33843 | 117.87656 | 17.35284 | 12.00825 | 172632800 |
| BoxBFL.140.LYS.N | 7.8113 | 119.11469 | 15.11934 | 12.32708 | 144059264 |
| BoxBFL.141.GLN.N | 7.42681 | 118.19987 | 12.23114 | 12.40879 | 203757632 |
| BoxBFL.143.TYR.N | 7.21691 | 115.66054 | 15.9391 | 12.2 | 135669520 |
| BoxBFL.144.GLU.N | 8.18987 | 120.68771 | 12.95833 | 12.4239 | 148173872 |
| BoxBFL.145.LYS.N | 9.18301 | 121.23245 | 13.19779 | 12.25029 | 171717696 |
| BoxBFL.146.LYS.N, BoxBFL.156.LYS.N | 7.69692 | 120.57372 | 12.71031 | 12.47383 | 196874368 |
| BoxBFL.147.ALA.N | 8.48249 | 121.09351 | 12.35114 | 12.39023 | 191332288 |
| BoxBFL.148.ALA.N | 8.36965 | 122.00069 | 12.19025 | 12.15233 | 220547328 |
| BoxBFL.149.LYS.N | 7.97224 | 120.72971 | 13.19222 | 12.42346 | 213554816 |
| BoxBFL.150.LEU.N | 8.28652 | 120.07973 | 14.56355 | 13.14455 | 145004448 |
| BoxBFL.151.LYS.N | 8.42411 | 123.51065 | 12.54219 | 12.56125 | 167598160 |
| BoxBFL.152.GLU.N | 8.08663 | 119.9904 | 12.53193 | 12.7395 | 223413808 |
| BoxBFL.153.LYS.N | 7.75259 | 119.74852 | 13.195 | 12.42426 | 187833136 |
| BoxBFL.154.TYR.N | 8.13041 | 120.47623 | 13.12379 | 12.69255 | 159451584 |
| BoxBFL.155.GLU.N | 8.52484 | 117.50521 | 13.60921 | 12.71924 | 154408976 |
| BoxBFL.157.ASP.N | 8.85459 | 123.10409 | 12.45843 | 12.23066 | 174923680 |
| BoxBFL.158.ILE.N | 9.0667 | 122.28071 | 13.73538 | 12.53844 | 157092272 |
| BoxBFL.159.ALA.N | 7.45046 | 124.74939 | 12.51372 | 12.04599 | 200120928 |
| BoxBFL.160.ALA.N | 7.74386 | 120.563 | 14.38809 | 12.29212 | 198915568 |

-continued

| Assign | F1 position | F2 position | LW F1 (Hz) | LW F2 (Hz) | Height |
|---|---|---|---|---|---|
| BoxBFL.161.TYR.N | 8.20147 | 120.05331 | 14.39746 | 13.18223 | 167227632 |
| BoxBFL.162.ARG.N | 8.26383 | 118.79358 | 13.15573 | 12.41703 | 173894048 |

3D Experiments (Day 1)

These spectra are not shown due to their 3D nature; data available if requested. Sample is that of Baseline 1.

| Experiment type | 3D, $^{15}$N EDITED $^1$H-$^1$H TOCSY-HSQC, THROUGH-SPACE INTERACTION |
|---|---|
| Temperature | 25° C. |
| Volume | 300 μL |
| Number of scans | 12 |

| Experiment type | 3D, $^{15}$N EDITED $^1$H-$^1$H NOESY-HSQC, THROUGH-BOND INTERACTION |
|---|---|
| Temperature | 25° C. |
| Volume | 300 μL |
| Number of scans | 16 |

0.42 Molar Ratio CXCL12/HMG Box (Day 2)

| Experiment type | 2D $^1$H-$^{15}$N HSQC |
|---|---|
| HMGB1 construct and concentration | 0.38 mM, U-15N HMGB1A-c028 (Box B 94-162), C-terminal biotinylation tag (300 μL of 0.45 mM stock) |
| CXCL12 construct and concentration | 0.162 mM, CXCL12A-c021, wt 1-67, no tag (50 μL of 1.14 mM stock) |
| Volume | 350 μL |
| Sample pH (after adjusting) | 7.71 |
| Temperature | 25° C. |
| Number of scans | 8 |

| Assign | F1 position | F2 position | LW F1 (Hz) | LW F2 (Hz) | Height |
|---|---|---|---|---|---|
| BoxBFL.95.LYS.N | 8.47806 | 122.8889 | 15.74549 | 12.59893 | 1.04E+08 |
| BoxBFL.96.ARG.N | 8.31955 | 123.9958 | 15.32754 | 11.79906 | 1.23E+08 |
| BoxBFL.99.SER.N | 7.95975 | 114.213 | 18.91249 | 16.00748 | 19314842 |
| BoxBFL.100.ALA.N | 9.06482 | 122.8403 | 12.12244 | 12.51287 | 1.23E+08 |
| BoxBFL.101.PHE.N | 8.44328 | 116.1449 | 14.02058 | 12.94259 | 83270120 |
| BoxBFL.102.PHE.N | 8.2626 | 122.1026 | 14.57979 | 12.61002 | 83484184 |
| BoxBFL.103.LEU.N | 8.27876 | 121.1543 | 13.21545 | 12.41884 | 98850448 |
| BoxBFL.104.PHE.N | 8.1723 | 122.6037 | 17.85543 | 16.70344 | 1.63E+08 |
| BoxBFL.105.CYS.N | 8.49894 | 118.3888 | 12.67018 | 13.00159 | 1.03E+08 |
| BoxBFL.106.SER.N | 8.12904 | 115.0558 | 11.922 | 12.17556 | 1.66E+08 |
| BoxBFL.107.GLU.N | 7.15246 | 119.1841 | 15.05754 | 12.02976 | 1.54E+08 |
| BoxBFL.108.TYR.N | 7.94272 | 114.6176 | 17.11915 | 12.55614 | 1.04E+08 |
| BoxBFL.109.ARG.N | 9.23036 | 123.7013 | 13.06226 | 12.53714 | 1.15E+08 |
| BoxBFL.111.LYS.N | 6.79969 | 117.703 | 15.74346 | 12.62776 | 1.25E+08 |
| BoxBFL.112.ILE.N | 8.1614 | 119.7481 | 15.19044 | 12.89975 | 1.06E+08 |
| BoxBFL.113.LYS.N | 8.25273 | 118.4894 | 16.03035 | 15.20607 | 71142304 |
| BoxBFL.114.GLY.N | 7.63597 | 103.7241 | 14.57231 | 12.02882 | 1.1E+08 |
| BoxBFL.115.GLU.N | 7.49968 | 119.5819 | 15.16195 | 12.5197 | 1.35E+08 |
| BoxBFL.116.HIS.N | 7.82235 | 114.787 | 15.19416 | 11.98251 | 1.02E+08 |
| BoxBFL.119.LEU.N | 7.3624 | 121.2015 | 12.53706 | 12.04396 | 2.03E+08 |
| BoxBFL.120.SER.N | 9.31525 | 121.061 | 13.81227 | 12.2652 | 1.13E+08 |
| BoxBFL.121.ILE.N | 8.74925 | 120.6769 | 12.5753 | 12.7098 | 61919540 |
| BoxBFL.122.GLY.N | 8.71207 | 109.4584 | 25.89949 | 13.91125 | 16954762 |
| BoxBFL.123.ASP.N | 7.95784 | 124.2831 | 14.47967 | 12.59113 | 1.13E+08 |
| BoxBFL.124.VAL.N | 8.63489 | 124.0688 | 13.34502 | 12.07557 | 1.51E+08 |
| BoxBFL.125.ALA.N | 7.92846 | 121.3424 | 11.96993 | 12.06949 | 1.99E+08 |
| BoxBFL.126.LYS.N | 8.01973 | 119.6945 | 12.24395 | 12.62986 | 2.08E+08 |
| BoxBFL.127.LYS.N | 8.03911 | 121.3059 | 12.17418 | 12.02556 | 2.24E+08 |
| BoxBFL.128.LEU.N | 8.64346 | 120.1657 | 12.73252 | 12.33711 | 1.36E+08 |
| BoxBFL.129.GLY.N | 8.26155 | 106.0419 | 14.87585 | 12.01202 | 1.26E+08 |
| BoxBFL.130.GLU.N | 8.07094 | 123.248 | 12.8194 | 12.1305 | 1.81E+08 |
| BoxBFL.131.MET.N | 8.77033 | 118.9628 | 12.47681 | 12.18055 | 1.65E+08 |
| BoxBFL.132.TRP.N | 8.71521 | 122.6821 | 13.43252 | 12.15419 | 1.09E+08 |
| BoxBFL.133.ASN.N | 8.17879 | 117.3654 | 11.81466 | 11.94108 | 1.72E+08 |
| BoxBFL.134.ASN.N | 7.58738 | 115.8377 | 20.34615 | 11.95454 | 1.47E+08 |
| BoxBFL.135.THR.N | 7.30659 | 119.9511 | 15.61869 | 12.3645 | 1.57E+08 |
| BoxBFL.136.ALA.N | 9.2484 | 131.4382 | 11.79903 | 12.0221 | 1.7E+08 |
| BoxBFL.138.ASP.N | 8.99068 | 115.7088 | 13.61787 | 13.15666 | 66921064 |
| BoxBFL.139.ASP.N | 7.33797 | 117.8781 | 18.54773 | 12.14095 | 1.52E+08 |
| BoxBFL.140.LYS.N | 7.81083 | 119.1164 | 14.67427 | 12.45762 | 1.24E+08 |

-continued

| Assign | F1 position | F2 position | LW F1 (Hz) | LW F2 (Hz) | Height |
|---|---|---|---|---|---|
| BoxBFL.141.GLN.N | 7.42677 | 118.2031 | 12.06407 | 12.71254 | 1.77E+08 |
| BoxBFL.143.TYR.N | 7.21631 | 115.6619 | 15.45741 | 12.35014 | 1.19E+08 |
| BoxBFL.144.GLU.N | 8.18784 | 120.6799 | 13.13889 | 12.30444 | 1.27E+08 |
| BoxBFL.145.LYS.N | 9.183 | 121.238 | 13.17983 | 12.43273 | 1.47E+08 |
| BoxBFL.146.LYS.N, | | | | | |
| BoxBFL.156.LYS.N | 7.69709 | 120.5754 | 12.94948 | 12.65531 | 1.73E+08 |
| BoxBFL.147.ALA.N | 8.48271 | 121.0951 | 12.06422 | 12.53668 | 1.63E+08 |
| BoxBFL.148.ALA.N | 8.37014 | 122.0096 | 12.01385 | 12.60817 | 1.9E+08 |
| BoxBFL.149.LYS.N | 7.97339 | 120.7383 | 13.42094 | 12.64648 | 1.82E+08 |
| BoxBFL.150.LEU.N | 8.28676 | 120.0845 | 14.4103 | 13.05275 | 1.22E+08 |
| BoxBFL.151.LYS.N | 8.42457 | 123.5222 | 12.66033 | 12.96606 | 1.42E+08 |
| BoxBFL.152.GLU.N | 8.08704 | 119.9998 | 12.5224 | 13.21315 | 1.98E+08 |
| BoxBFL.153.LYS.N | 7.75272 | 119.7489 | 13.27981 | 12.63584 | 1.63E+08 |
| BoxBFL.154.TYR.N | 8.12892 | 120.4783 | 12.99281 | 12.73019 | 1.34E+08 |
| BoxBFL.155.GLU.N | 8.52395 | 117.5111 | 13.25587 | 12.99665 | 1.34E+08 |
| BoxBFL.157.ASP.N | 8.85469 | 123.1047 | 12.50397 | 12.25568 | 1.51E+08 |
| BoxBFL.158.ILE.N | 9.06751 | 122.2825 | 13.25933 | 12.71521 | 1.38E+08 |
| BoxBFL.159.ALA.N | 7.44862 | 124.7591 | 12.4575 | 12.38733 | 1.75E+08 |
| BoxBFL.160.ALA.N | 7.7427 | 120.5687 | 14.46225 | 12.64065 | 1.71E+08 |
| BoxBFL.161.TYR.N | 8.19946 | 120.0547 | 15.35591 | 13.74534 | 1.39E+08 |
| BoxBFL.162.ARG.N | 8.2623 | 118.7997 | 12.52352 | 12.69996 | 1.54E+08 |

0.84 molar ratio CXCL12/HMG Box (Day 2)

| Experiment type | 2D $^1$H-$^{15}$N HSQC |
|---|---|
| HMGB1 construct and concentration | 0.337 mM, U-15N HMGB1A-c028 (Box B 94-162), C-terminal biotinylation tag (300 µL of 0.45 mM stock) |
| CXCL12 construct and concentration | 0.285 mM, CXCL12A-c021, wt 1-67, no tag (100 µL of 1.14 mM stock) |
| Volume | 350 µL |
| Sample pH (after adjusting) | 7.73 |
| Temperature | 25° C. |
| Number of scans | 8 |

| F1 assign | F1 position | F2 position | LW F1 (Hz) | LW F2 (Hz) | Height |
|---|---|---|---|---|---|
| BoxBFL.95.LYS.N | 8.47806 | 122.8889 | 15.74549 | 12.59893 | 1.04E+08 |
| BoxBFL.96.ARG.N | 8.31955 | 123.9958 | 15.32754 | 11.79906 | 1.23E+08 |
| BoxBFL.99.SER.N | 7.95975 | 114.213 | 18.91249 | 16.00748 | 19314842 |
| BoxBFL.100.ALA.N | 9.06482 | 122.8403 | 12.12244 | 12.51287 | 1.23E+08 |
| BoxBFL.101.PHE.N | 8.44328 | 116.1449 | 14.02058 | 12.94259 | 83270120 |
| BoxBFL.102.PHE.N | 8.2626 | 122.1026 | 14.57979 | 12.61002 | 83484184 |
| BoxBFL.103.LEU.N | 8.27876 | 121.1543 | 13.21545 | 12.41884 | 98850448 |
| BoxBFL.104.PHE.N | 8.1723 | 122.6037 | 17.85543 | 16.70344 | 1.63E+08 |
| BoxBFL.105.CYS.N | 8.49894 | 118.3888 | 12.67018 | 13.00159 | 1.03E+08 |
| BoxBFL.106.SER.N | 8.12904 | 115.0558 | 11.922 | 12.17556 | 1.66E+08 |
| BoxBFL.107.GLU.N | 7.15246 | 119.1841 | 15.05754 | 12.02976 | 1.54E+08 |
| BoxBFL.108.TYR.N | 7.94272 | 114.6176 | 17.11915 | 12.55614 | 1.04E+08 |
| BoxBFL.109.ARG.N | 9.23036 | 123.7013 | 13.06226 | 12.53714 | 1.15E+08 |
| BoxBFL.111.LYS.N | 6.79969 | 117.703 | 15.74346 | 12.62776 | 1.25E+08 |
| BoxBFL.112.ILE.N | 8.1614 | 119.7481 | 15.19044 | 12.89975 | 1.06E+08 |
| BoxBFL.113.LYS.N | 8.25273 | 118.4894 | 16.03035 | 15.20607 | 71142304 |
| BoxBFL.114.GLY.N | 7.63597 | 103.7241 | 14.57231 | 12.02882 | 1.1E+08 |
| BoxBFL.115.GLU.N | 7.49968 | 119.5819 | 15.16195 | 12.5197 | 1.35E+08 |
| BoxBFL.116.HIS.N | 7.82235 | 114.787 | 15.19416 | 11.98251 | 1.02E+08 |
| BoxBFL.119.LEU.N | 7.3624 | 121.2015 | 12.53706 | 12.04396 | 2.03E+08 |
| BoxBFL.120.SER.N | 9.31525 | 121.061 | 13.81227 | 12.2652 | 1.13E+08 |
| BoxBFL.121.ILE.N | 8.74925 | 120.6769 | 12.5753 | 12.7098 | 61919540 |
| BoxBFL.122.GLY.N | 8.71207 | 109.4584 | 25.89949 | 13.91125 | 16954762 |
| BoxBFL.123.ASP.N | 7.95784 | 124.2831 | 14.47967 | 12.59113 | 1.13E+08 |
| BoxBFL.124.VALN | 8.63489 | 124.0688 | 13.34502 | 12.07557 | 1.51E+08 |
| BoxBFL.125.ALA.N | 7.92846 | 121.3424 | 11.96993 | 12.06949 | 1.99E+08 |
| BoxBFL.126.LYS.N | 8.01973 | 119.6945 | 12.24395 | 12.62986 | 2.08E+08 |
| BoxBFL.127.LYS.N | 8.03911 | 121.3059 | 12.17418 | 12.02556 | 2.24E+08 |
| BoxBFL.128.LEU.N | 8.64346 | 120.1657 | 12.73252 | 12.33711 | 1.36E+08 |
| BoxBFL.129.GLY.N | 8.26155 | 106.0419 | 14.87585 | 12.01202 | 1.26E+08 |
| BoxBFL.130.GLU.N | 8.07094 | 123.248 | 12.8194 | 12.1305 | 1.81E+08 |
| BoxBFL.131.MET.N | 8.77033 | 118.9628 | 12.47681 | 12.18055 | 1.65E+08 |
| BoxBFL.132.TRP.N | 8.71521 | 122.6821 | 13.43252 | 12.15419 | 1.09E+08 |

-continued

| F1 assign | F1 position | F2 position | LW F1 (Hz) | LW F2 (Hz) | Height |
|---|---|---|---|---|---|
| BoxBFL.133.ASN.N | 8.17879 | 117.3654 | 11.81466 | 11.94108 | 1.72E+08 |
| BoxBFL.134.ASN.N | 7.58738 | 115.8377 | 20.34615 | 11.95454 | 1.47E+08 |
| BoxBFL.135.THR.N | 7.30659 | 119.9511 | 15.61869 | 12.3645 | 1.57E+08 |
| BoxBFL.136.ALA.N | 9.2484 | 131.4382 | 11.79903 | 12.0221 | 1.7E+08 |
| BoxBFL.138.ASP.N | 8.99068 | 115.7088 | 13.61787 | 13.15666 | 66921064 |
| BoxBFL.139.ASP.N | 7.33797 | 117.8781 | 18.54773 | 12.14095 | 1.52E+08 |
| BoxBFL.140.LYS.N | 7.81083 | 119.1164 | 14.67427 | 12.45762 | 1.24E+08 |
| BoxBFL.141.GLN.N | 7.42677 | 118.2031 | 12.06407 | 12.71254 | 1.77E+08 |
| BoxBFL.143.TYR.N | 7.21631 | 115.6619 | 15.45741 | 12.35014 | 1.19E+08 |
| BoxBFL.144.GLU.N | 8.18784 | 120.6799 | 13.13889 | 12.30444 | 1.27E+08 |
| BoxBFL.145.LYS.N | 9.183 | 121.238 | 13.17983 | 12.43273 | 1.47E+08 |
| BoxBFL.146.LYS.N, BoxBFL.156.LYS.N | 7.69709 | 120.5754 | 12.94948 | 12.65531 | 1.73E+08 |
| BoxBFL.147.ALA.N | 8.48271 | 121.0951 | 12.06422 | 12.53668 | 1.63E+08 |
| BoxBFL.148.ALA.N | 8.37014 | 122.0096 | 12.01385 | 12.60817 | 1.9E+08 |
| BoxBFL.149.LYS.N | 7.97339 | 120.7383 | 13.42094 | 12.64648 | 1.82E+08 |
| BoxBFL.150.LEU.N | 8.28676 | 120.0845 | 14.4103 | 13.05275 | 1.22E+08 |
| BoxBFL.151.LYS.N | 8.42457 | 123.5222 | 12.66033 | 12.96606 | 1.42E+08 |
| BoxBFL.152.GLU.N | 8.08704 | 119.9998 | 12.5224 | 13.21315 | 1.98E+08 |
| BoxBFL.153.LYS.N | 7.75272 | 119.7489 | 13.27981 | 12.63584 | 1.63E+08 |
| BoxBFL.154.TYR.N | 8.12892 | 120.4783 | 12.99281 | 12.73019 | 1.34E+08 |
| BoxBFL.155.GLU.N | 8.52395 | 117.5111 | 13.25587 | 12.99665 | 1.34E+08 |
| BoxBFL.157.ASP.N | 8.85469 | 123.1047 | 12.50397 | 12.25568 | 1.51E+08 |
| BoxBFL.158.ILE.N | 9.06751 | 122.2825 | 13.25933 | 12.71521 | 1.38E+08 |
| BoxBFL.159.ALA.N | 7.44862 | 124.7591 | 12.4575 | 12.38733 | 1.75E+08 |
| BoxBFL.160.ALA.N | 7.7427 | 120.5687 | 14.46225 | 12.64065 | 1.71E+08 |
| BoxBFL.161.TYR.N | 8.19946 | 120.0547 | 15.35591 | 13.74534 | 1.39E+08 |
| BoxBFL.162.ARG.N | 8.2623 | 118.7997 | 12.52352 | 12.69996 | 1.54E+08 |

1.43 Molar Ratio CXCL12/HMG Box (Day 2)

| Experiment type | 2D $^1$H-$^{15}$N HSQC |
|---|---|
| HMGB1 construct and concentration | 0.28 mM, U-15N HMGB1A-c028 (Box B 94-162), C-terminal biotinylation tag, 300 μL of 0.45 mM stock |
| CXCL12 construct and concentration | 0.412 mM, CXCL12A-c021, wt 1-67, no tag, 170 μL of 1.14 mM stock |
| Temperature | 25° C. |
| Volume | 350 μL |
| Sample pH (after adjusting) | 7.69 |
| Number of scans | 8 |

| F1 assign | F1 position | F2 position | LW F1 (Hz) | LW F2 (Hz) | Height |
|---|---|---|---|---|---|
| BoxBFL.95.LYS.N | 8.47778 | 122.9103 | 15.37565 | 12.39804 | 80050272 |
| BoxBFL.96.ARG.N | 8.33007 | 124.0602 | 14.92746 | 12.00118 | 82355536 |
| BoxBFL.99.SER.N | 7.96392 | 114.2034 | N/A | N/A | 14006653 |
| BoxBFL.100.ALA.N | 9.06578 | 122.8423 | 12.95809 | 12.6583 | 87116544 |
| BoxBFL.101.PHE.N | 8.44289 | 116.1454 | 13.47969 | 12.85253 | 61494512 |
| BoxBFL.102.PHE.N | 8.26155 | 122.0515 | 14.49526 | 12.56936 | 63868476 |
| BoxBFL.103.LEU.N | 8.28051 | 121.1503 | 14.84782 | 12.62126 | 65927464 |
| BoxBFL.104.PHE.N | 8.18982 | 122.6828 | 20.78995 | 15.31712 | 1E+08 |
| BoxBFL.105.CYS.N | 8.49843 | 118.3925 | 13.1053 | 13.13926 | 70645200 |
| BoxBFL.106.SER.N | 8.1287 | 115.0622 | 12.0922 | 12.5294 | 1.18E+08 |
| BoxBFL.107.GLU.N | 7.15039 | 119.185 | 14.99568 | 11.952 | 1.12E+08 |
| BoxBFL.108.TYR.N | 7.9412 | 114.6199 | 17.85822 | 12.78123 | 73545448 |
| BoxBFL.109.ARG.N | 9.23053 | 123.7071 | 13.66025 | 13.12308 | 78615272 |
| BoxBFL.111.LYS.N | 6.79981 | 117.7058 | 16.96135 | 12.39598 | 86118672 |
| BoxBFL.112.ILE.N | 8.16151 | 119.7459 | 14.73583 | 13.27134 | 71542432 |
| BoxBFL.113.LYS.N | 8.25631 | 118.4871 | 16.07722 | 14.62748 | 55390008 |
| BoxBFL.114.GLY.N | 7.63682 | 103.7319 | 15.93962 | 12.34204 | 83576064 |
| BoxBFL.115.GLU.N | 7.49983 | 119.5699 | 15.3896 | 12.37429 | 96911488 |
| BoxBFL.116.HIS.N | 7.82619 | 114.7906 | 14.24248 | 12.35403 | 74137880 |
| BoxBFL.119.LEU.N | 7.36266 | 121.2025 | 12.44261 | 12.21601 | 1.49E+08 |
| BoxBFL.120.SER.N | 9.31408 | 121.062 | 12.93199 | 12.44319 | 84698824 |
| BoxBFL.121.ILE.N | 8.75038 | 120.6813 | 14.48357 | 12.89635 | 45051028 |
| BoxBFL.122.GLY.N | 8.71118 | 109.4804 | 16.4655 | 14.14866 | 16957850 |
| BoxBFL.123.ASP.N | 7.95741 | 124.2905 | 15.0023 | 12.39813 | 80795464 |
| BoxBFL.124.VAL.N | 8.63479 | 124.0656 | 13.47634 | 12.10198 | 1.07E+08 |

-continued

| F1 assign | F1 position | F2 position | LW F1 (Hz) | LW F2 (Hz) | Height |
|---|---|---|---|---|---|
| BoxBFL.125.ALA.N | 7.92779 | 121.3329 | 13.01599 | 12.5379 | 1.33E+08 |
| BoxBFL.126.LYS.N | 8.02119 | 119.7027 | 12.30924 | 12.8741 | 1.48E+08 |
| BoxBFL.127.LYS.N | 8.03986 | 121.3062 | 12.4847 | 12.16844 | 1.55E+08 |
| BoxBFL.128.LEU.N | 8.64351 | 120.1664 | 12.98093 | 12.34936 | 95774424 |
| BoxBFL.129.GLY.N | 8.26062 | 106.0395 | 14.57273 | 12.29455 | 88870768 |
| BoxBFL.130.GLU.N | 8.07098 | 123.2514 | 12.85049 | 12.30451 | 1.28E+08 |
| BoxBFL.131.MET.N | 8.77103 | 118.9657 | 12.95376 | 12.1418 | 1.15E+08 |
| BoxBFL.132.TRP.N | 8.71439 | 122.6801 | 14.10342 | 12.19979 | 76116600 |
| BoxBFL.133.ASN.N | 8.17827 | 117.365 | 12.53999 | 12.19573 | 1.2E+08 |
| BoxBFL.134.ASN.N | 7.58849 | 115.8472 | 19.64464 | 11.72657 | 1.07E+08 |
| BoxBFL.135.THR.N | 7.30642 | 119.9458 | 15.21751 | 12.24418 | 1.12E+08 |
| BoxBFL.136.ALA.N | 9.24753 | 131.4348 | 12.65711 | 12.04662 | 1.19E+08 |
| BoxBFL.138.ASP.N | 8.99115 | 115.7039 | 12.95325 | 13.45469 | 55523416 |
| BoxBFL.139.ASP.N | 7.33717 | 117.8755 | 17.56433 | 12.18072 | 1.09E+08 |
| BoxBFL.140.LYS.N | 7.80982 | 119.1179 | 15.67278 | 12.39083 | 82706752 |
| BoxBFL.141.GLN.N | 7.42724 | 118.2084 | 12.20378 | 12.60333 | 1.22E+08 |
| BoxBFL.143.TYR.N | 7.21658 | 115.6631 | 17.78092 | 12.5108 | 80885808 |
| BoxBFL.144.GLU.N | 8.18558 | 120.6672 | 12.65054 | 12.60763 | 91853544 |
| BoxBFL.145.LYS.N | 9.1835 | 121.244 | 13.52547 | 12.49804 | 1.01E+08 |
| BoxBFL.146.LYS.N, | | | | | |
| BoxBFL.156.LYS.N | 7.69757 | 120.5767 | 13.43106 | 13.08878 | 1.22E+08 |
| BoxBFL.147.ALA.N | 8.48332 | 121.097 | 12.54408 | 12.70391 | 1.12E+08 |
| BoxBFL.148.ALA.N | 8.37158 | 122.0199 | 12.14356 | 12.99704 | 1.29E+08 |
| BoxBFL.149.LYS.N | 7.97496 | 120.7468 | 12.94812 | 12.72338 | 1.28E+08 |
| BoxBFL.150.LEU.N | 8.28799 | 120.0826 | 13.26184 | 13.21101 | 83975808 |
| BoxBFL.151.LYS.N | 8.42544 | 123.5327 | 13.10847 | 12.87192 | 96388256 |
| BoxBFL.152.GLU.N | 8.08805 | 120.0097 | 13.34088 | 13.96487 | 1.37E+08 |
| BoxBFL.153.LYS.N | 7.75361 | 119.7537 | 13.4631 | 12.86615 | 1.13E+08 |
| BoxBFL.154.TYR.N | 8.12773 | 120.4857 | 13.65716 | 12.83688 | 92183904 |
| BoxBFL.155.GLU.N | 8.522 | 117.5173 | 12.9949 | 13.07435 | 92028096 |
| BoxBFL.157.ASP.N | 8.85612 | 123.1054 | 13.64785 | 12.54087 | 99610256 |
| BoxBFL.158.ILE.N | 9.06839 | 122.2825 | 13.74015 | 12.91936 | 94902504 |
| BoxBFL.159.ALA.N | 7.44725 | 124.7733 | 12.59718 | 12.9055 | 1.24E+08 |
| BoxBFL.160.ALA.N | 7.74231 | 120.5797 | 15.01396 | 13.34523 | 1.18E+08 |
| BoxBFL.161.TYR.N | 8.19948 | 120.0505 | 15.71875 | 13.97336 | 94945976 |
| BoxBFL.162.ARG.N | 8.26146 | 118.804 | 12.47976 | 12.94011 | 1.12E+08 |

Baseline 2 (Day 2)

| Experiment type | 2D $^1$H-$^{15}$N HSQC |
|---|---|
| HMGB1 construct and concentration | 0.45 mM, HMGB1-c028 (Box B 94-162), C-terminal biotinylation tag |
| CXCL12 construct and concentration | 0 mM |
| Temperature | 25° C. |
| Volume | 300 μL |
| Sample pH (after adjusting) | 7.7 |
| Number of scans | 8 |

| F1 assign | F1 position | F2 position | LW F1 (Hz) | LW F2 (Hz) | Height |
|---|---|---|---|---|---|
| BoxBFL.95.LYS.N | 8.47836 | 122.87041 | 15.45555 | 12.31895 | 1.15E+08 |
| BoxBFL.96.ARG.N | 8.30905 | 123.928 | 14.69757 | 11.67602 | 1.52E+08 |
| BoxBFL.99.SER.N | 7.95323 | 114.2133 | 15.92668 | 15.37737 | 19244536 |
| BoxBFL.100.ALA.N | 9.06443 | 122.8375 | 12.04384 | 12.58362 | 1.45E+08 |
| BoxBFL.101.PHE.N | 8.44327 | 116.1467 | 13.37094 | 12.57032 | 99456376 |
| BoxBFL.102.PHE.N | 8.26291 | 122.1401 | 13.91643 | 12.69516 | 93582568 |
| BoxBFL.103.LEU.N | 8.27739 | 121.1559 | 13.54853 | 12.32854 | 1.2E+08 |
| BoxBFL.104.PHE.N | 8.15312 | 122.5067 | 16.98582 | 12.61768 | 2.23E+08 |
| BoxBFL.105.CYS.N | 8.49958 | 118.3879 | 12.45479 | 13.04816 | 1.23E+08 |
| BoxBFL.106.SER.N | 8.12962 | 115.053 | 11.71118 | 11.95992 | 2.01E+08 |
| BoxBFL.107.GLU.N | 7.15443 | 119.1857 | 15.15976 | 11.875 | 1.85E+08 |
| BoxBFL.108.TYR.N | 7.94312 | 114.6181 | 16.58447 | 12.32968 | 1.25E+08 |
| BoxBFL.109.ARG.N | 9.2303 | 123.6965 | 13.1266 | 12.39272 | 1.36E+08 |
| BoxBFL.111.LYS.N | 6.80044 | 117.7026 | 15.51854 | 12.47282 | 1.51E+08 |
| BoxBFL.112.ILE.N | 8.16214 | 119.7445 | 14.38896 | 12.72125 | 1.33E+08 |
| BoxBFL.113.LYS.N | 8.24788 | 118.4867 | 17.04567 | 13.89265 | 75341960 |
| BoxBFL.114.GLY.N | 7.63545 | 103.7167 | 16.12903 | 11.9801 | 1.23E+08 |
| BoxBFL.115.GLU.N | 7.50084 | 119.5887 | 15.33825 | 12.18563 | 1.53E+08 |

-continued

| F1 assign | F1 position | F2 position | LW F1 (Hz) | LW F2 (Hz) | Height |
|---|---|---|---|---|---|
| BoxBFL.116.HIS.N | 7.81992 | 114.7797 | 14.07903 | 12.00191 | 1.27E+08 |
| BoxBFL.119.LEU.N | 7.36245 | 121.1993 | 12.49408 | 11.92292 | 2.35E+08 |
| BoxBFL.120.SER.N | 9.31637 | 121.0591 | 13.96408 | 12.31166 | 1.32E+08 |
| BoxBFL.121.ILE.N | 8.74889 | 120.6692 | 14.04081 | 13.00014 | 64885424 |
| BoxBFL.122.GLY.N | 8.71247 | 109.452 | 14.17681 | 13.60233 | 17286296 |
| BoxBFL.123.ASP.N | 7.95965 | 124.2811 | 13.89649 | 12.49605 | 1.34E+08 |
| BoxBFL.124.VAL.N | 8.63524 | 124.0725 | 13.34482 | 12.04966 | 1.82E+08 |
| BoxBFL.125.ALA.N | 7.92792 | 121.3503 | 11.86774 | 11.79008 | 2.42E+08 |
| BoxBFL.126.LYS.N | 8.01841 | 119.6864 | 11.86371 | 12.33853 | 2.45E+08 |
| BoxBFL.127.LYS.N | 8.03849 | 121.3063 | 12.1092 | 12.01079 | 2.71E+08 |
| BoxBFL.128.LEU.N | 8.64384 | 120.1687 | 12.82931 | 12.23453 | 1.65E+08 |
| BoxBFL.129.GLY.N | 8.26299 | 106.0359 | 14.80106 | 11.90484 | 1.55E+08 |
| BoxBFL.130.GLU.N | 8.07168 | 123.2465 | 12.61599 | 12.00749 | 2.15E+08 |
| BoxBFL.131.MET.N | 8.76967 | 118.9613 | 12.58221 | 12.16772 | 2E+08 |
| BoxBFL.132.TRP.N | 8.71566 | 122.6842 | 13.26303 | 12.06045 | 1.35E+08 |
| BoxBFL.133.ASN.N | 8.17935 | 117.3676 | 11.78966 | 11.94741 | 2.04E+08 |
| BoxBFL.134.ASN.N | 7.58744 | 115.8288 | 20.03676 | 12.02406 | 1.76E+08 |
| BoxBFL.135.THR.N | 7.30721 | 119.9545 | 14.90053 | 12.28766 | 1.9E+08 |
| BoxBFL.136.ALA.N | 9.2491 | 131.4409 | 11.88622 | 11.94243 | 1.93E+08 |
| BoxBFL.138.ASP.N | 8.99179 | 115.703 | 14.27261 | 13.33337 | 68493488 |
| BoxBFL.139.ASP.N | 7.33887 | 117.8767 | 18.17146 | 11.95364 | 1.82E+08 |
| BoxBFL.140.LYS.N | 7.81148 | 119.1162 | 15.20448 | 12.14857 | 1.5E+08 |
| BoxBFL.141.GLN.N | 7.4268 | 118.1975 | 11.86842 | 12.43174 | 2.19E+08 |
| BoxBFL.143.TYR.N | 7.21681 | 115.6633 | 16.06949 | 12.06739 | 1.45E+08 |
| BoxBFL.144.GLU.N | 8.19039 | 120.6913 | 12.43979 | 12.40533 | 1.6E+08 |
| BoxBFL.145.LYS.N | 9.18288 | 121.2343 | 13.02849 | 12.2664 | 1.81E+08 |
| BoxBFL.146.LYS.N, | | | | | |
| BoxBFL.156.LYS.N | 7.69649 | 120.5726 | 12.4096 | 12.47784 | 2.08E+08 |
| BoxBFL.147.ALA.N | 8.48223 | 121.0936 | 11.71767 | 12.54903 | 2.05E+08 |
| BoxBFL.148.ALA.N | 8.36946 | 122.0011 | 12.08468 | 12.21854 | 2.33E+08 |
| BoxBFL.149.LYS.N | 7.9718 | 120.7293 | 12.63602 | 12.4563 | 2.26E+08 |
| BoxBFL.150.LEU.N | 8.28613 | 120.0804 | 13.87273 | 13.26832 | 1.52E+08 |
| BoxBFL.151.LYS.N | 8.42463 | 123.5087 | 12.67228 | 12.49152 | 1.76E+08 |
| BoxBFL.152.GLU.N | 8.08647 | 119.9901 | 12.2303 | 12.58471 | 2.36E+08 |
| BoxBFL.153.LYS.N | 7.75247 | 119.748 | 13.27241 | 12.43002 | 1.97E+08 |
| BoxBFL.154.TYR.N | 8.13017 | 120.4741 | 12.9694 | 12.56059 | 1.68E+08 |
| BoxBFL.155.GLU.N | 8.52488 | 117.5048 | 13.26926 | 12.59952 | 1.65E+08 |
| BoxBFL.157.ASP.N | 8.85488 | 123.1048 | 12.53023 | 12.19821 | 1.85E+08 |
| BoxBFL.158.ILE.N | 9.06773 | 122.2845 | 12.97983 | 12.55507 | 1.7E+08 |
| BoxBFL.159.ALA.N | 7.45038 | 124.7516 | 12.10878 | 12.01767 | 2.17E+08 |
| BoxBFL.160.ALA.N | 7.74351 | 120.5631 | 14.03576 | 12.41792 | 2.12E+08 |
| BoxBFL.161.TYR.N | 8.20134 | 120.056 | 14.08572 | 13.06065 | 1.75E+08 |
| BoxBFL.162.ARG.N | 8.26373 | 118.7947 | 12.78627 | 12.3573 | 1.81E+08 |

HMGB1-c038 (89-174, Biotinylated) Titration with CXCL12A-c021 at 0, 0.42, 0.82 and 1.42 Molar Equivalents, FIGS. 5A-5B Due to protein amount limitations, titration was performed by sequential addition of CXCL12 to HMGB1 samples, resulting in sample dilution. As the calculations in the chemical shift tracking module in CCPNMR are independent of peak, this does not alter the results; the median change has been indicated in the volume comparisons.

| | BROKER AVIII HD 500, 5 MM CPTCI 1H-13C/15N/D Z-GRD PROBE |
|---|---|
| $^1$H frequency (Hz) | 500.01233645 |
| $^1$H sweep width (ppm) | 11.9044681870088 |
| $^1$H sweep width (Hz) | 5952.38095238095 |
| $^1$HN sweep width (ppm) | 10.9286921061064 |
| $^{15}$N frequency (Hz) | 50.6715211382702 |
| $^{15}$N sweep width (ppm) | 32.0372585410812 |
| $^{15}$N sweep width (Hz) | 1623.37662337662 |
| Water suppression gradient pulse width (Hz) | 2336.45 |
| Buffer | 10 mM HEPES, pH 7.5, 150 mM NaCl |

| Experiment type | 2D $^1$H-$^{15}$N HSQC |
|---|---|
| HMGB1 construct and concentration | 0.81 mM, HMGB1-c038 (Box B 89-174), C-terminal biotinylation tag |

-continued

| Experiment type | 2D ¹H-¹⁵N HSQC |
|---|---|
| CXCL12 construct and concentration | 0 mM |
| Temperature | 25° C. |
| Volume | 300 μL |
| Sample pH (after adjusting) | 7.8 |
| Number of scans | 8 |

| Assign | F1 position | F2 position | LW F1 (Hz) | LW F2 (Hz) | Height |
|---|---|---|---|---|---|
| BoxBFL.89.LYS.H | 8.22877 | 123.15 | 13.43706 | 11.76465 | 2.84E+08 |
| BoxBFL.90.ASP.H | 8.06507 | 119.1836 | 17.47528 | 13.0415 | 71477080 |
| BoxBFL.92.ASN.H | 8.38837 | 116.1932 | 26.72516 | 13.63039 | 40775376 |
| BoxBFL.93.ALA.H | 7.31759 | 123.8361 | 12.03289 | 11.75968 | 2.88E+08 |
| BoxBFL.95.LYS.H | 8.54394 | 123.6499 | 15.56655 | 12.66447 | 1.57E+08 |
| BoxBFL.96.ARG.H | 8.31244 | 123.9103 | 13.30976 | 11.8029 | 3.19E+08 |
| BoxBFL.99.SER.H | 7.89322 | 114.8385 | 12.94573 | 13.41732 | 83696192 |
| BoxBFL.100.ALA.H | 9.06159 | 122.8259 | 12.5281 | 12.3534 | 1.5E+08 |
| BoxBFL.101.PHE.H | 8.44257 | 116.1455 | 14.2976 | 12.88207 | 1.18E+08 |
| BoxBFL.102.PHE.H | 8.26477 | 122.1713 | 14.09453 | 12.29629 | 2.95E+08 |
| BoxBFL.103.LEU.H | 8.27759 | 121.1528 | 15.09128 | 13.06243 | 1.22E+08 |
| BoxBFL.104.PHE.H | 8.13387 | 122.4785 | 13.88173 | 12.22486 | 2.22E+08 |
| BoxBFL.105.CYS.H | 8.50131 | 118.3952 | 14.09029 | 13.6882 | 1.26E+08 |
| BoxBFL.106.SER.H | 8.1324 | 115.0572 | 11.86819 | 12.2455 | 2.18E+08 |
| BoxBFL.107.GLU.H | 7.15821 | 119.2011 | 15.07209 | 12.23544 | 1.97E+08 |
| BoxBFL.108.TYR.H | 7.94721 | 114.6268 | 17.12946 | 12.56173 | 1.29E+08 |
| BoxBFL.109.ARG.H | 9.22527 | 123.6917 | 14.35796 | 12.40158 | 1.33E+08 |
| BoxBFL.111.LYS.H | 6.80367 | 117.7105 | 15.83919 | 12.77867 | 1.48E+08 |
| BoxBFL.112.ILE.H | 8.16585 | 119.7589 | 15.93766 | 14.10622 | 1.3E+08 |
| BoxBFL.113.LYS.H | 8.24667 | 118.3979 | 14.18155 | 12.282 | 1.95E+08 |
| BoxBFL.114.GLY.H | 7.6419 | 103.7578 | 15.9097 | 12.86625 | 1.49E+08 |
| BoxBFL.115.GLU.H | 7.50312 | 119.5592 | 15.3641 | 12.25047 | 1.76E+08 |
| BoxBFL.116.HIS.H | 7.82141 | 114.7108 | 15.60333 | 12.79576 | 1.45E+08 |
| BoxBFL.119.LEU.H | 7.36645 | 121.1961 | 12.25315 | 11.84566 | 2.79E+08 |
| BoxBFL.120.SER.H | 9.31869 | 121.0561 | 13.67984 | 12.45399 | 1.5E+08 |
| BoxBFL.121.ILE.H | 8.7507 | 120.6719 | 13.37699 | 12.68743 | 93999208 |
| BoxBFL.122.GLY.H | 8.71122 | 109.4492 | 18.2158 | 13.7384 | 40704368 |
| BoxBFL.123.ASP.H | 7.96237 | 124.2817 | 14.31821 | 13.03276 | 1.64E+08 |
| BoxBFL.124.VAL.H | 8.6379 | 124.0546 | 13.5712 | 12.12567 | 1.86E+08 |
| BoxBFL.125.ALA.H | 7.93334 | 121.344 | 12.65998 | 12.7035 | 2.76E+08 |
| BoxBFL.126.LYS.H | 8.02273 | 119.6775 | 12.14567 | 12.20318 | 2.67E+08 |
| BoxBFL.127.LYS.H | 8.04282 | 121.3008 | 13.53438 | 16.44289 | 2.72E+08 |
| BoxBFL.128.LEU.H | 8.64819 | 120.1742 | 13.66523 | 12.49721 | 1.57E+08 |
| BoxBFL.129.GLY.H | 8.26351 | 106.0328 | 15.35471 | 12.18689 | 1.69E+08 |
| BoxBFL.130.GLU.H | 8.07435 | 123.2474 | 13.07314 | 12.31509 | 2.26E+08 |
| BoxBFL.131.MET.H | 8.77512 | 118.9617 | 13.39615 | 12.51007 | 2.05E+08 |
| BoxBFL.132.TRP.H | 8.71654 | 122.6792 | 14.56383 | 12.46287 | 1.3E+08 |
| BoxBFL.133.ASN.H | 8.17988 | 117.3613 | 12.44756 | 12.16788 | 2.1E+08 |
| BoxBFL.134.ASN.H | 7.59333 | 115.8407 | 17.61059 | 12.39088 | 1.9E+08 |
| BoxBFL.135.THR.H | 7.31004 | 119.9467 | 15.60722 | 12.12025 | 2.02E+08 |
| BoxBFL.136.ALA.H | 9.25013 | 131.437 | 12.17023 | 12.15813 | 2.27E+08 |
| BoxBFL.137.ALA.H | 8.85817 | 124.999 | 15.52392 | 16.42924 | 11136171 |
| BoxBFL.138.ASP.H | 8.99358 | 115.7103 | 13.01277 | 13.43146 | 1.17E+08 |
| BoxBFL.139.ASP.H | 7.34269 | 117.8836 | 17.65566 | 12.28682 | 1.93E+08 |
| BoxBFL.140.LYS.H | 7.81346 | 119.1053 | 15.13034 | 12.58181 | 1.53E+08 |
| BoxBFL.141.GLN.H | 7.43127 | 118.216 | 12.22585 | 12.9068 | 2.03E+08 |
| BoxBFL.143.TYR.H | 7.21936 | 115.67 | 15.42101 | 12.81604 | 1.43E+08 |
| BoxBFL.144.GLU.H | 8.1673 | 120.3573 | 19.36893 | 15.09454 | 2.23E+08 |
| BoxBFL.145.LYS.H | 9.19147 | 121.2642 | 13.950/3 | 13.10497 | 1.73E−08 |
| BoxBFL.146.LYS.H, BoxBFL.156.LYS.H | 7.70091 | 120.5702 | 14.84964 | 12.91125 | 3.78E+08 |
| BoxBFL.147.ALA.H | 8.47542 | 120.5044 | 16.38659 | 13.35601 | 61059660 |
| BoxBFL.148.ALA.H | 8.38049 | 122.0622 | 13.43968 | 12.61324 | 2.27E+08 |
| BoxBFL.149.LYS.H | 7.98075 | 120.7812 | 13.45082 | 13.37624 | 2.21E+08 |
| BoxBFL.150.LEU.H | 8.29642 | 120.0874 | 14.65693 | 13.57267 | 1.39E+08 |
| BoxBFL.151.LYS.H | 8.4373 | 123.66 | 13.67398 | 13.22858 | 1.71E+08 |
| BoxBFL.152.GLU.H | 8.0907 | 120.0978 | 14.82538 | 13.76241 | 2.37E+08 |
| BoxBFL.153.LYS.H | 7.76448 | 119.7662 | 14.67797 | 13.05371 | 1.95E+08 |
| BoxBFL.154.TYR.H | 8.14526 | 120.4576 | #VALUE! | #VALUE! | 1.83E+08 |
| BoxBFL.155.GLU.H | 8.52465 | 117.6406 | 14.85626 | 13.30374 | 1.65E+08 |
| BoxBFL.157.ASP.H | 8.90183 | 123.2173 | 13.33878 | 13.30286 | 1.79E+08 |
| BoxBFL.158.ILE.H | 9.20351 | 122.5498 | 13.98115 | 12.71351 | 1.81E+08 |
| BoxBFL.159.ALA.H | 7.36561 | 124.8259 | 12.81959 | 12.53986 | 2.31E+08 |
| BoxBFL.160.ALA.H | 7.78333 | 120.4019 | 13.47788 | 13.29924 | 2.25E+08 |
| BoxBFL.161.TYR.H | 8.19889 | 120.0636 | 16.81491 | 18.13778 | 2.19E+08 |

-continued

| Assign | F1 position | F2 position | LW F1 (Hz) | LW F2 (Hz) | Height |
|---|---|---|---|---|---|
| BoxBFL.162.ARG.H | 8.26173 | 118.8178 | 12.98114 | 12.65685 | 1.88E+08 |
| BoxBFL.163.ALA.H | 7.63926 | 121.3704 | 13.43373 | 12.39034 | 1.48E+08 |
| BoxBFL.164.LYS.H | 7.65612 | 118.3003 | 14.35415 | 12.33745 | 1.22E+08 |
| BoxBFL.165.GLY.H | 8.05505 | 108.6412 | 27.92431 | 13.8698 | 20239174 |
| BoxBFL.166.LYS.H | 8.04195 | 121.5844 | 15.77089 | 13.22022 | 4.24E+08 |
| BoxBFL.168.ASP.H | 8.4885 | 121.098 | 12.61027 | 13.02291 | 1.96E+08 |
| BoxBFL.169.ALA.H | 8.27056 | 124.8752 | 14.6408 | 13.13492 | 53273208 |
| BoxBFL.170.ALA.H | 8.13312 | 121.3951 | 14.00858 | 12.18198 | 1.5E+08 |
| BoxBFL.172.LYS.H | 8.4277 | 124.6737 | 7.48588 | 9.20329 | 3518457 |
| BoxBFL.173.GLY.H | 8.57505 | 111.1121 | 15.89317 | 13.54035 | 25440228 |

3D Experiments (Day 1-5)

These spectra are not shown due to their 3D nature; data available if requested. Sample is that of Baseline 1.

| Experiment type | 3D, $^{15}$N EDITED $^1$H-$^1$H TOCSY-HSQC, THROUGH-SPACE INTERACTION |
|---|---|
| Temperature | 25° C. |
| Volume | 300 μL |
| Number of scans | 32 |

| Experiment type | 3D, $^{15}$N EDITED $^1$H-$^1$H NOESY-HSQC, THROUGH-BOND INTERACTION |
|---|---|
| Temperature | 25° C. |
| Volume | 300 μL |
| Number of scans | 32 |

0.42 Molar Ratio CXCL12/HMG Box (Day 5)

| Experiment type | 2D $^1$H-$^{15}$N HSQC |
|---|---|
| HMGB1 construct and concentration | 0.7 mM, HMGB1-c038 (Box B 94-162), C-terminal biotinylation tag (285 μL of 0.8 mM stock) |
| CXCL12 construct and concentration | 0.29 mM, CXCL12A-c021, wt 1-67, no tag (41 μL of 1.8 mM stock) |
| Volume | 25° C. |
| Sample pH (after adjusting) | 320 μL |
| Temperature | 7.8 |
| Number of scans | 32 |

| Assign | F1 position | F2 position | LW F1 (Hz) | LW F2 (Hz) | Height |
|---|---|---|---|---|---|
| BoxBFL.89.LYS.H | 8.23317 | 123.6882 | 15.99121 | 13.36991 | 8.54E+08 |
| BoxBFL.90.ASP.H | 8.07425 | 119.195 | 17.03548 | 12.94404 | 3.32E+08 |
| BoxBFL.92.ASN.H | 8.39252 | 116.22 | 20.52278 | 13.76841 | 1.57E+08 |
| BoxBFL.93.ALA.H | 7.32309 | 123.8461 | 13.23603 | 12.04781 | 8.1E+08 |
| BoxBFL.95.LYS.H | 8.55152 | 123.6861 | 15.235 | 12.47899 | 5.7E+08 |
| BoxBFL.96.ARG.H | 8.33348 | 124.0077 | 14.64892 | 11.53036 | 6.66E+08 |
| BoxBFL.99.SER.H | 7.89458 | 114.8324 | 17.06332 | 13.29929 | 3.9E+08 |
| BoxBFL.100.ALA.H | 9.07237 | 122.8303 | 12.45091 | 12.65528 | 6.1E+08 |
| BoxBFL.101.PHE.H | 8.45267 | 116.1672 | 12.95977 | 12.54238 | 5.08E+08 |
| BoxBFL.102.PHE.H | 8.2712 | 122.1831 | 13.80017 | 13.34009 | 8.34E+08 |
| BoxBFL.103.LEU.H | 8.28642 | 121.127 | 15.05638 | 12.72235 | 4.44E+08 |
| BoxBFL.104.PHE.H | 8.154 | 122.5034 | 15.15558 | 12.55092 | 4.93E+08 |
| BoxBFL.105.CYS.H | 8.50821 | 118.3965 | 13.60565 | 14.11493 | 5.43E+08 |
| BoxBFL.106.SER.H | 8.14042 | 115.0895 | 12.31066 | 12.82245 | 7.92E+08 |
| BoxBFL.107.GLU.H | 7.1606 | 119.2044 | 15.04631 | 12.06946 | 7.79E+08 |
| BoxBFL.108.TYR.H | 7.95517 | 114.6331 | 17.1485 | 12.51247 | 5.1E+08 |
| BoxBFL.109.ARG.H | 9.24196 | 123.7109 | 14.77907 | 12.44116 | 5.14E+08 |
| BoxBFL.111.LYS.H | 6.80383 | 117.7113 | 16.35257 | 12.50023 | 5.75E+08 |
| BoxBFL.112.ILE.H | 8.17228 | 119.7666 | 15.12234 | 13.68265 | 5.3E+08 |
| BoxBFL.113.LYS.H | 8.26058 | 118.4342 | 14.68114 | 12.6851 | 5.11E+08 |
| BoxBFL.114.GLY.H | 7.64965 | 103.7836 | 14.15269 | 12.03673 | 6.32E+08 |
| BoxBFL.115.GLU.H | 7.50893 | 119.5449 | 15.10884 | 12.14579 | 7E+08 |
| BoxBFL.116.HIS.H | 7.83669 | 114.7278 | #VALUE! | #VALUE! | 3.31E+08 |
| BoxBFL.119.LEU.H | 7.37631 | 121.2095 | 11.82599 | 11.95517 | 1.11E+09 |
| BoxBFL.120.SER.H | 9.32759 | 121.0738 | 13.32814 | 12.27617 | 6.4E+08 |
| BoxBFL.121.ILE.H | 8.75541 | 120.6669 | 13.45308 | 12.74538 | 4.21E+08 |
| BoxBFL.122.GLY.H | 8.72192 | 109.4783 | 18.02792 | 13.29589 | 1.9E+08 |
| BoxBFL.123.ASP.H | 7.97614 | 124.3289 | 15.78848 | 12.93298 | 5.54E+08 |
| BoxBFL.124.VAL.H | 8.6467 | 124.0535 | 13.39795 | 11.91108 | 7.39E+08 |
| BoxBFL.125.ALA.H | 7.93311 | 121.3373 | 20.94036 | 12.50751 | 7.5E+08 |

-continued

| Assign | F1 position | F2 position | LW F1 (Hz) | LW F2 (Hz) | Height |
|---|---|---|---|---|---|
| BoxBFL.126.LYS.H | 8.03459 | 119.7401 | 12.11644 | 12.969 | 9.82E+08 |
| BoxBFL.127.LYS.H | 8.05395 | 121.3131 | 13.08531 | 12.0213 | 1.04E+09 |
| BoxBFL.128.LEU.H | 8.65647 | 120.1666 | 12.77726 | 12.56328 | 6.48E+08 |
| BoxBFL.129.GLY.H | 8.26041 | 106.0026 | 16.56723 | 12.47707 | 5.83E+08 |
| BoxBFL.130.GLU.H | 8.0809 | 123.2669 | 12.42406 | 12.29425 | 8.83E+08 |
| BoxBFL.131.MET.H | 8.78921 | 118.9705 | 13.20277 | 12.33316 | 7.89E+08 |
| BoxBFL.132.TRP.H | 8.71893 | 122.6622 | 13.85963 | 12.75907 | 4.98E+08 |
| BoxBFL.133.ASN.H | 8.18222 | 117.3634 | 13.90003 | 12.0061 | 7.53E+08 |
| BoxBFL.134.ASN.H | 7.6005 | 115.8484 | 17.9579 | 11.96318 | 7.22E+08 |
| BoxBFL.135.THR.H | 7.31604 | 119.9459 | 15.68761 | 11.89589 | 7.84E+08 |
| BoxBFL.136.ALA.H | 9.25887 | 131.4427 | 12.04897 | 11.90835 | 9.4E+08 |
| BoxBFL.137.ALA.H | 8.86544 | 124.9937 | 18.19465 | 14.33638 | 71698952 |
| BoxBFL.138.ASP.H | 9.00067 | 115.712 | 12.28957 | 13.24047 | 5.28E+08 |
| BoxBFL.139.ASP.H | 7.34953 | 117.8877 | 17.87632 | 12.18195 | 7.56E+08 |
| BoxBFL.140.LYS.H | 7.82254 | 119.1251 | 15.16611 | 12.34065 | 6.15E+08 |
| BoxBFL.141.GLN.H | 7.44009 | 118.2284 | 11.84562 | 12.39199 | 8.33E+08 |
| BoxBFL.143.TYR.H | 7.22876 | 115.6684 | 16.28895 | 12.57946 | 5.48E+08 |
| BoxBFL.144.GLU.H | 8.18291 | 120.313 | 24.30189 | 16.31598 | 7.26E+08 |
| BoxBFL.145.LYS.H | 9.20235 | 121.2804 | 13.87277 | 13.31669 | 6.47E+08 |
| BoxBFL.146.LYS.H, BoxBFL.156.LYS.H | 7.70895 | 120.5874 | 14.10502 | 13.01551 | 1.38E+09 |
| BoxBFL.147.ALA.H | 8.48426 | 120.552 | 16.0703 | 14.31819 | 2.91E+08 |
| BoxBFL.148.ALA.H | 8.39134 | 122.0914 | 13.96231 | 13.19139 | 7.81E+08 |
| BoxBFL.149.LYS.H | 7.99377 | 120.7978 | 13.72404 | 13.22412 | 7.88E+08 |
| BoxBFL.150.LEU.H | 8.30338 | 120.106 | 14.84471 | 13.15063 | 5.18E+08 |
| BoxBFL.151.LYS.H | 8.44582 | 123.6944 | 13.55023 | 13.11479 | 6.01E+08 |
| BoxBFL.152.GLU.H | 8.10037 | 120.1197 | 14.86852 | 13.77938 | 8.15E+08 |
| BoxBFL.153.LYS.H | 7.77409 | 119.7673 | 13.08363 | 13.46475 | 7.36E+08 |
| BoxBFL.154.TYR.H | 8.15602 | 120.4585 | 24.22866 | 16.12356 | 6.94E+08 |
| BoxBFL.155.GLU.H | 8.53056 | 117.6515 | 13.90664 | 13.6262 | 5.87E+08 |
| BoxBFL.157.ASP.H | 8.91261 | 123.2303 | 14.37862 | 13.03578 | 5.44E+08 |
| BoxBFL.158.ILE.H | 9.21552 | 122.5667 | 15.94888 | 12.94384 | 4.83E+08 |
| BoxBFL.159.ALA.H | 7.36871 | 124.8542 | 14.00455 | 12.99954 | 6.93E+08 |
| BoxBFL.160.ALA.H | 7.79079 | 120.4098 | 13.48341 | 13.45411 | 7.53E+08 |
| BoxBFL.161.TYR.H | 8.20906 | 120.0582 | 17.84468 | 15.5777 | 8.17E+08 |
| BoxBFL.162.ARG.H | 8.26922 | 118.8094 | 13.23997 | 12.86921 | 7.66E+08 |
| BoxBFL.163.ALA.H | 7.64365 | 121.401 | 13.62381 | 13.15062 | 4.69E+08 |
| BoxBFL.164.LYS.H | 7.66395 | 118.3578 | 14.08222 | 14.60296 | 3.61E+08 |
| BoxBFL.165.GLY.H | 8.06949 | 108.6489 | 23.00117 | 14.26944 | 84792952 |
| BoxBFL.166.LYS.H | 8.06804 | 121.6875 | 16.22206 | 12.67618 | 1.02E+09 |
| BoxBFL.168.ASP.H | 8.49698 | 121.1145 | 12.93091 | 12.80312 | 7.46E+08 |
| BoxBFL.169.ALA.H | 8.27748 | 124.8788 | 14.08935 | 13.77469 | 2.91E+08 |
| BoxBFL.170.ALA.H | 8.13889 | 121.4079 | 15.50116 | 12.51434 | 5.16E+08 |
| BoxBFL.172.LYS.H | 8.44213 | 124.8148 | 14.07011 | 12.03688 | 79426568 |
| BoxBFL.173.GLY.H | 8.58133 | 111.1267 | 16.71041 | 13.95112 | 1.23E+08 |

0.84 Molar Ratio CXCL12/HMG Box (Day 5)

| Experiment type | 2D ¹H-¹⁵N HSQC |
|---|---|
| HMGB1 construct and concentration | 0.58 mM, HMGB1-c038 (Box B 94-162), C-terminal biotinylation tag (285 µL of 0.8 mM stock) |
| CXCL12 construct and concentration | 0.482 mM, CXCL12A-c021, wt 1-67, no tag (104 µL of 1.8 mM stock) |

-continued

| Experiment type | 2D ¹H-¹⁵N HSQC |
|---|---|
| Volume | 25° C. |
| Sample pH (after adjusting) | 320 µL |
| Temperature | 7.8 |
| Number of scans | 32 |

| Assign | F1 position | F2 position | LW F1 (Hz) | LW F2 (Hz) | Height |
|---|---|---|---|---|---|
| BoxBFL.89.LYS.H | 8.22679 | 122.98562 | 19.92847 | 15.30362 | 6.04E+08 |
| BoxBFL.90.ASP.H | 8.07636 | 119.19941 | 17.45582 | 13.22061 | 2.24E+08 |
| BoxBFL.92.ASN.H | 8.39239 | 116.22614 | 23.07716 | 14.06705 | 1.06E+08 |
| BoxBFL.93.ALA.H | 7.32259 | 123.8468 | 13.46498 | 12.02831 | 6.25E+08 |
| BoxBFL.95.LYS.H | 8.55168 | 123.69223 | 15.31781 | 12.58495 | 4.41E+08 |
| BoxBFL.96.ARG.H | 8.34299 | 124.0494 | 14.88799 | 11.9875 | 4.06E+08 |
| BoxBFL.99.SER.H | 7.89423 | 114.84247 | #VALUE! | #VALUE! | 3.07E+08 |
| BoxBFL.100.ALA.H | 9.07369 | 122.83003 | 11.94043 | 12.61474 | 5.02E+08 |
| BoxBFL.101.PHE.H | 8.45401 | 116.1693 | 13.37439 | 12.53442 | 3.98E+08 |
| BoxBFL.102.PHE.H | 8.27231 | 122.15451 | 13.98629 | 14.5081 | 5.11E+08 |
| BoxBFL.103.LEU.H | 8.28889 | 121.12078 | 14.37061 | 12.72043 | 3.73E+08 |
| BoxBFL.104.PHE.H | 8.16438 | 122.51969 | 15.78414 | 13.39462 | 2.93E+08 |

-continued

| Assign | F1 position | F2 position | LW F1 (Hz) | LW F2 (Hz) | Height |
|---|---|---|---|---|---|
| BoxBFL.105.CYS.H | 8.50866 | 118.40024 | 13.19461 | 13.85193 | 4.4E+08 |
| BoxBFL.106.SER.H | 8.1423 | 115.09842 | 11.9209 | 12.43735 | 6.58E+08 |
| BoxBFL.107.GLU.H | 7.16005 | 119.20473 | 14.95609 | 12.03505 | 6.36E+08 |
| BoxBFL.108.TYR.H | 7.95609 | 114.63347 | 16.8564 | 12.6025 | 4.15E+08 |
| BoxBFL.109.ARG.H | 9.24419 | 123.71548 | 14.94347 | 12.70613 | 4.15E+08 |
| BoxBFL.111.LYS.H | 6.80375 | 117.70835 | 16.02119 | 12.42776 | 4.77E+08 |
| BoxBFL.112.ILE.H | 8.17303 | 119.76733 | 15.02702 | 13.64763 | 4.37E+08 |
| BoxBFL.113.LYS.H | 8.26665 | 118.45194 | 14.62975 | 13.06685 | 3.35E+08 |
| BoxBFL.114.GLY.H | 7.64978 | 103.7787 | 14.53777 | 12.13962 | 5.15E+08 |
| BoxBFL.115.GLU.H | 7.50983 | 119.55375 | 15.22445 | 11.99963 | 5.72E+08 |
| BoxBFL.116.HIS.H | 7.84327 | 114.73761 | #VALUE! | #VALUE! | 2.63E+08 |
| BoxBFL.119.LEU.H | 7.37738 | 121.21246 | 11.7834 | 12.0448 | 9.01E+08 |
| BoxBFL.120.SER.H | 9.32827 | 121.07659 | 13.31064 | 12.27752 | 5.09E+08 |
| BoxBFL.121.ILE.H | 8.7561 | 120.66594 | 13.60291 | 12.71327 | 3.22E+08 |
| BoxBFL.122.GLY.H | 8.72507 | 109.47718 | 17.30426 | 13.44831 | 1.43E+08 |
| BoxBFL.123.ASP.H | 7.97787 | 124.33699 | 16.31857 | 12.97771 | 4.33E+08 |
| BoxBFL.124.VAL.H | 8.6484 | 124.05721 | 12.86612 | 11.89578 | 6.24E+08 |
| BoxBFL.125.ALA.H | 7.92439 | 121.32801 | 19.18773 | 11.92173 | 6.11E+08 |
| BoxBFL.126.LYS.H | 8.0362 | 119.75212 | 12.45829 | 12.85125 | 7.81E+08 |
| BoxBFL.127.LYS.H | 8.05575 | 121.31674 | 12.43276 | 12.04567 | 8.57E+08 |
| BoxBFL.128.LEU.H | 8.65767 | 120.16374 | 13.11087 | 12.67279 | 5.26E+08 |
| BoxBFL.129.GLY.H | 8.25962 | 105.99904 | 16.21275 | 12.32688 | 4.86E+08 |
| BoxBFL.130.GLU.H | 8.08214 | 123.27002 | 12.67708 | 12.37817 | 7.09E+08 |
| BoxBFL.131.MET.H | 8.79146 | 118.97292 | 13.56391 | 12.24356 | 6.42E+08 |
| BoxBFL.132.TRP.H | 8.71828 | 122.65646 | 13.66393 | 12.75142 | 4.11E+08 |
| BoxBFL.133.ASN.H | 8.1825 | 117.36324 | 13.94004 | 11.96683 | 6.19E+08 |
| BoxBFL.134.ASN.H | 7.60102 | 115.8515 | 19.86751 | 11.87762 | 5.95E+08 |
| BoxBFL.135.THR.H | 7.31691 | 119.94345 | 15.84212 | 11.78759 | 6.45E+08 |
| BoxBFL.136.ALA.H | 9.25983 | 131.44194 | 11.68396 | 11.88563 | 7.59E+08 |
| BoxBFL.137.ALA.H | 8.86664 | 124.98894 | 17.53135 | 14.89353 | 51062092 |
| BoxBFL.138.ASP.H | 9.0022 | 115.71168 | 12.51951 | 13.18965 | 4.13E+08 |
| BoxBFL.139.ASP.H | 7.3505 | 117.8869 | 19.06678 | 12.10936 | 6.11E+08 |
| BoxBFL.140.LYS.H | 7.82332 | 119.12697 | 14.98048 | 12.40774 | 4.99E+08 |
| BoxBFL.141.GLN.H | 7.44172 | 118.2299 | 11.81727 | 12.36063 | 6.81E+08 |
| BoxBFL.143.TYR.H | 7.23052 | 115.66761 | 15.72802 | 12.52565 | 4.53E+08 |
| BoxBFL.144.GLU.H | 8.17729 | 120.35761 | 20.14083 | 15.18319 | 5.71E+08 |
| BoxBFL.145.LYS.H | 9.20417 | 121.2843 | 13.91087 | 13.13152 | 5.12E+08 |
| BoxBFL.146.LYS.H, BoxBFL.156.LYS.H | 7.70982 | 120.59018 | 14.12825 | 13.12581 | 1.11E+09 |
| BoxBFL.147.ALA.H | 8.48613 | 120.5644 | 16.41386 | 14.34424 | 2.09E+08 |
| BoxBFL.148.ALA.H | 8.39403 | 122.09686 | 13.11396 | 13.17476 | 6.52E+08 |
| BoxBFL.149.LYS.H | 7.99631 | 120.80367 | 13.52788 | 13.03509 | 6.35E+08 |
| BoxBFL.150.LEU.H | 8.30472 | 120.10823 | 15.05319 | 13.15084 | 4.31E+08 |
| BoxBFL.151.LYS.H | 8.44699 | 123.70209 | 13.71114 | 13.30569 | 4.8E+08 |
| BoxBFL.152.GLU.H | 8.10211 | 120.12205 | 13.45462 | 13.68813 | 6.67E+08 |
| BoxBFL.153.LYS.H | 7.77558 | 119.76647 | 13.7091 | 13.64753 | 5.96E+08 |
| BoxBFL.154.TYR.H | 8.15632 | 120.46388 | 21.61287 | 16.30266 | 5.62E+08 |
| BoxBFL.155.GLU.H | 8.53123 | 117.6528 | 13.66215 | 13.47564 | 4.65E+08 |
| BoxBFL.157.ASP.H | 8.91586 | 123.23537 | 14.3729 | 12.90289 | 4.42E+08 |
| BoxBFL.158.ILE.H | 9.21936 | 122.58191 | 16.30721 | 13.2986 | 3.82E+08 |
| BoxBFL.159.ALA.H | 7.36846 | 124.86417 | 13.94085 | 12.75957 | 5.54E+08 |
| BoxBFL.160.ALA.H | 7.79128 | 120.4108 | 13.753 | 13.44963 | 5.87E+08 |
| BoxBFL.161.TYR.H | 8.21265 | 120.05605 | 16.82215 | 14.29685 | 6.46E+08 |
| BoxBFL.162.ARG.H | 8.27145 | 118.80874 | 12.38965 | 12.75367 | 6.47E+08 |
| BoxBFL.163.ALA.H | 7.64337 | 121.40884 | 14.1601 | 13.35172 | 3.57E+08 |
| BoxBFL.164.LYS.H | 7.66408 | 118.38396 | 14.21213 | 14.54701 | 2.69E+08 |
| BoxBFL.165.GLY.H | 8.07305 | 108.67299 | 20.01365 | 13.50363 | 59059740 |
| BoxBFL.166.LYS.H | 8.07769 | 121.72575 | 15.87162 | 13.20124 | 6.24E+08 |
| BoxBFL.168.ASP.H | 8.4982 | 121.11929 | 12.80238 | 12.73258 | 6.09E+08 |
| BoxBFL.169.ALA.H | 8.28032 | 124.89477 | 15.56254 | 15.33651 | 1.81E+08 |
| BoxBFL.170.ALA.H | 8.14155 | 121.40211 | 15.22818 | 12.63552 | 3.56E+08 |
| BoxBFL.172.LYS.H | 8.44239 | 124.80508 | 14.17767 | 12.23471 | 67949384 |
| BoxBFL.173.GLY.H | 8.58353 | 111.11154 | 15.74456 | 14.03704 | 74405800 |

1.43 Molar Ratio CXCL12/HMG Box (Day 5)

| Experiment type | 2D $^1$H-$^{15}$N HSQC |
|---|---|
| HMGB1 construct and concentration | 0.48 mM, HMGB1-c038 (Box B 94-162), C-terminal biotinylation tag (285 µL of 0.8 mM stock) |
| CXCL12 construct and concentration | 0.69 mM, CXCL12A-c021, wt 1-67, no tag (171 µL of 1.8 mM stock) |

-continued

| Experiment type | 2D $^1$H-$^{15}$N HSQC |
|---|---|
| Temperature | 25° C. |
| Volume | 320 µL |
| Sample pH (after adjusting) | 7.8 |
| Number of scans | 32 |

| Assign | F1 position | F2 position | LW F1 (Hz) | LW F2 (Hz) | Height |
|---|---|---|---|---|---|
| BoxBFL.89.LYS.H | 8.21895 | 122.9077 | 18.92121 | 17.02404 | 5.39E+08 |
| BoxBFL.90.ASP.H | 8.07743 | 119.2044 | 17.38461 | 13.70778 | 1.57E+08 |
| BoxBFL.92.ASN.H | 8.39578 | 116.2228 | 22.65251 | 14.06046 | 78748568 |
| BoxBFL.93.ALA.H | 7.3206 | 123.844 | 13.85399 | 11.97782 | 5.01E+08 |
| BoxBFL.95.LYS.H | 8.55161 | 123.6949 | 15.60312 | 12.56883 | 3.5E+08 |
| BoxBFL.96.ARG.H | 8.34894 | 124.0718 | 15.43549 | 12.28544 | 2.6E+08 |
| BoxBFL.99.SER.H | 7.89399 | 114.8337 | #VALUE! | #VALUE! | 2.52E+08 |
| BoxBFL.100.ALA.H | 9.07401 | 122.83 | 12.0362 | 12.69173 | 4.12E+08 |
| BoxBFL.101.PHE.H | 8.45444 | 116.1709 | 13.37824 | 12.49155 | 3.25E+08 |
| BoxBFL.102.PHE.H | 8.27168 | 122.1244 | 14.24496 | 16.08647 | 3.25E+08 |
| BoxBFL.103.LEU.H | 8.28943 | 121.1158 | 14.34292 | 12.71141 | 3.12E+08 |
| BoxBFL.104.PHE.H | 8.17112 | 122.5365 | 17.78199 | 16.29353 | 1.94E+08 |
| BoxBFL.105.CYS.H | 8.50875 | 118.4054 | 12.72396 | 13.22091 | 3.64E+08 |
| BoxBFL.106.SER.H | 8.14279 | 115.1046 | 11.79716 | 12.39792 | 5.45E+08 |
| BoxBFL.107.GLU.H | 7.15923 | 119.2044 | 15.5058 | 12.08644 | 5.2E+08 |
| BoxBFL.108.TYR.H | 7.95617 | 114.6327 | 17.84136 | 12.54391 | 3.41E+08 |
| BoxBFL.109.ARG.H | 9.24629 | 123.7188 | 14.08981 | 12.70662 | 3.49E+08 |
| BoxBFL.111.LYS.H | 6.8034 | 117.7047 | 16.29311 | 12.28933 | 4E+08 |
| BoxBFL.112.ILE.H | 8.17337 | 119.7674 | 14.76928 | 13.50054 | 3.6E+08 |
| BoxBFL.113.LYS.H | 8.27134 | 118.4462 | #VALUE! | #VALUE! | 2.17E+08 |
| BoxBFL.114.GLY.H | 7.64931 | 103.7749 | 14.43105 | 12.23031 | 4.15E+08 |
| BoxBFL.115.GLU.H | 7.50986 | 119.5617 | 14.96744 | 11.95792 | 4.69E+08 |
| BoxBFL.116.HIS.H | 7.87127 | 114.7661 | 19.92977 | 12.94964 | 2.92E+08 |
| BoxBFL.119.LEU.H | 7.37742 | 121.2158 | 11.72553 | 12.11307 | 7.45E+08 |
| BoxBFL.120.SER.H | 9.32858 | 121.0789 | 13.18459 | 12.45593 | 4.18E+08 |
| BoxBFL.121.ILE.H | 8.7553 | 120.6649 | 13.54667 | 12.77952 | 2.56E+08 |
| BoxBFL.122.GLY.H | 8.72559 | 109.4867 | 18.08209 | 13.61802 | 1.03E+08 |
| BoxBFL.123.ASP.H | 7.98069 | 124.3565 | 15.26493 | 12.68456 | 3.59E+08 |
| BoxBFL.124.VAL.H | 8.6488 | 124.0599 | 12.70186 | 11.8932 | 5.19E+08 |
| BoxBFL.125.ALA.H | 7.92234 | 121.3274 | 19.67901 | 12.01544 | 5.27E+08 |
| BoxBFL.126.LYS.H | 8.03667 | 119.7712 | 12.36815 | 13.1321 | 6.59E+08 |
| BoxBFL.127.LYS.H | 8.05631 | 121.3212 | 12.09821 | 12.05342 | 7.14E+08 |
| BoxBFL.128.LEU.H | 8.65776 | 120.1602 | 13.10106 | 12.67615 | 4.37E+08 |
| BoxBFL.129.GLY.H | 8.25895 | 105.9973 | 16.02096 | 12.32461 | 4.1E+08 |
| BoxBFL.130.GLU.H | 8.08217 | 123.2734 | 12.61882 | 12.35737 | 5.86E+08 |
| BoxBFL.131.MET.H | 8.79223 | 118.9771 | 12.92803 | 12.14025 | 5.33E+08 |
| BoxBFL.132.TRP.H | 8.71806 | 122.6543 | 13.59301 | 12.72152 | 3.45E+08 |
| BoxBFL.133.ASN.H | 8.18174 | 117.3624 | 14.1966 | 12.05599 | 5.03E+08 |
| BoxBFL.134.ASN.H | 7.60142 | 115.8532 | 19.14308 | 11.90938 | 4.93E+08 |
| BoxBFL.135.THR.H | 7.31694 | 119.9423 | 15.52944 | 11.84047 | 5.33E+08 |
| BoxBFL.136.ALA.H | 9.25989 | 131.4404 | 11.56485 | 11.90864 | 6.26E+08 |
| BoxBFL.137.ALA.H | 8.86475 | 125.0108 | 16.06168 | 15.67273 | 35378044 |
| BoxBFL.138.ASP.H | 9.00211 | 115.711 | 12.86091 | 13.34747 | 3.22E+08 |
| BoxBFL.139.ASP.H | 7.35096 | 117.8866 | 19.0693 | 12.15302 | 5.06E+08 |
| BoxBFL.140.LYS.H | 7.82374 | 119.1295 | 14.6706 | 12.41802 | 4.18E+08 |
| BoxBFL.141.GLN.H | 7.44219 | 118.232 | 11.85067 | 12.27391 | 5.63E+08 |
| BoxBFL.143.TYR.H | 7.23072 | 115.6698 | 15.74818 | 12.51927 | 3.75E+08 |
| BoxBFL.144.GLU.H | 8.17663 | 120.3647 | 19.90498 | 14.8137 | 4.57E+08 |
| BoxBFL.145.LYS.H | 9.20511 | 121.2878 | 14.30353 | 13.0189 | 4.26E+08 |
| BoxBFL.146.LYS.H, BoxBFL.156.LYS.H | 7.71006 | 120.5924 | 14.14949 | 13.23139 | 9.14E+08 |
| BoxBFL.147.ALA.H | 8.48712 | 120.5785 | 16.9957 | 14.34865 | 1.49E+08 |
| BoxBFL.148.ALA.H | 8.39484 | 122.1015 | 12.93976 | 12.98248 | 5.41E+08 |
| BoxBFL.149.LYS.H | 7.99731 | 120.8071 | 13.2779 | 13.16866 | 5.32E+08 |
| BoxBFL.150.LEU.H | 8.3049 | 120.1088 | 14.94034 | 13.2186 | 3.55E+08 |
| BoxBFL.151.LYS.H | 8.4477 | 123.7082 | 13.98336 | 13.38566 | 3.93E+08 |
| BoxBFL.152.GLU.H | 8.10253 | 120.1254 | 13.30973 | 13.69574 | 5.51E+08 |
| BoxBFL.153.LYS.H | 7.77618 | 119.767 | 13.49419 | 13.56752 | 4.88E+08 |
| BoxBFL.154.TYR.H | 8.15722 | 120.4673 | 22.68082 | 16.71144 | 4.54E+08 |
| BoxBFL.155.GLU.H | 8.53108 | 117.6557 | 13.40247 | 13.49932 | 3.86E+08 |
| BoxBFL.157.ASP.H | 8.91702 | 123.2376 | 13.94689 | 12.93051 | 3.63E+08 |
| BoxBFL.158.ILE.H | 9.22334 | 122.5976 | 15.59077 | 13.35733 | 3.16E+08 |
| BoxBFL.159.ALA.H | 7.36744 | 124.8739 | 13.98725 | 12.61412 | 4.56E+08 |
| BoxBFL.160.ALA.H | 7.79157 | 120.411 | 13.64762 | 13.47195 | 4.83E+08 |
| BoxBFL.161.TYR.H | 8.21447 | 120.0592 | 16.95219 | 14.11511 | 5.1E+08 |
| BoxBFL.162.ARG.H | 8.27207 | 118.8079 | 12.06017 | 12.68513 | 5.39E+08 |
| BoxBFL.163.ALA.H | 7.64246 | 121.4127 | 13.9688 | 13.29345 | 2.85E+08 |
| BoxBFL.164.LYS.H | 7.66442 | 118.4079 | 14.86267 | 15.95431 | 2.05E+08 |
| BoxBFL.165.GLY.H | 8.07387 | 108.6809 | 24.49469 | 14.82814 | 37366064 |
| BoxBFL.166.LYS.H | 8.08076 | 121.7464 | 18.19369 | 13.05761 | 3.83E+08 |
| BoxBFL.168.ASP.H | 8.49868 | 121.1201 | 12.66135 | 12.73158 | 5.01E+08 |
| BoxBFL.169.ALA.H | 8.28128 | 124.9183 | 14.6585 | 15.5819 | 1.24E+08 |
| BoxBFL.170.ALA.H | 8.14173 | 121.3982 | 16.83083 | 12.7598 | 2.45E+08 |
| BoxBFL.172.LYS.H | 8.44324 | 124.8133 | 14.79008 | 12.58927 | 50445744 |
| BoxBFL.173.GLY.H | 8.57949 | 111.0939 | 20.28256 | 15.57476 | 46002192 |

Baseline 2 (Day 5)

-continued

| Experiment type | 2D $^1$H-$^{15}$N HSQC |
| --- | --- |
| HMGB1 construct and concentration | 0.8 mM, HMGB1-c038 (Box B 94-162), C-terminal biotinylation tag |
| CXCL12 construct and concentration | 0 mM |

| Experiment type | 2D $^1$H-$^{15}$N HSQC |
| --- | --- |
| Temperature | 25° C. |
| Volume | 285 μL |
| Sample pH (after adjusting) | 7.8 |
| Number of scans | 32 |

| Assign | F1 position | F2 position | LW F1 (Hz) | LW F2 (Hz) | Height |
| --- | --- | --- | --- | --- | --- |
| BoxBFL.89.LYS.H | 8.23102 | 123.1415 | 14.76968 | 12.01671 | 1.13E+09 |
| BoxBFL.90.ASP.H | 8.06917 | 119.1829 | 17.02515 | 12.22975 | 3.96E+08 |
| BoxBFL.92.ASN.H | 8.38929 | 116.2163 | 20.63226 | 13.77677 | 2.02E+08 |
| BoxBFL.93.ALA.H | 7.32084 | 123.8384 | 14.33885 | 11.63902 | 8.9E+08 |
| BoxBFL.95.LYS.H | 8.5478 | 123.6697 | 15.96042 | 12.62552 | 6.07E+08 |
| BoxBFL.96.ARG.H | 8.3189 | 123.9301 | 14.50868 | 11.3829 | 1.03E+09 |
| BoxBFL.99.SER.H | 7.89207 | 114.8246 | 15.31161 | 12.80624 | 3.66E+08 |
| BoxBFL.100.ALA.H | 9.06739 | 122.8207 | 14.07546 | 12.19279 | 5.84E+08 |
| BoxBFL.101.PHE.H | 8.44676 | 116.1525 | 14.74864 | 12.91541 | 4.61E+08 |
| BoxBFL.102.PHE.H | 8.26698 | 122.1883 | 14.22121 | 12.44991 | 1.11E+09 |
| BoxBFL.103.LEU.H | 8.28133 | 121.1339 | 16.10868 | 12.48103 | 4.42E+08 |
| BoxBFL.104.PHE.H | 8.13782 | 122.4713 | 14.37141 | 12.44314 | 7.5E+08 |
| BoxBFL.105.CYS.H | 8.50419 | 118.3867 | 15.14844 | 14.2131 | 4.87E+08 |
| BoxBFL.106.SER.H | 8.13524 | 115.0683 | 13.16398 | 12.31969 | 7.42E+08 |
| BoxBFL.107.GLU.H | 7.15834 | 119.1995 | 15.9825 | 11.95677 | 7.25E+08 |
| BoxBFL.108.TYR.H | 7.9497 | 114.6278 | 17.47581 | 12.33864 | 4.82E+08 |
| BoxBFL.109.ARG.H | 9.23234 | 123.6965 | 16.59866 | 12.29412 | 4.81E+08 |
| BoxBFL.111.LYS.H | 6.80327 | 117.711 | 16.90439 | 12.46518 | 5.6E+08 |
| BoxBFL.112.ILE.H | 8.16856 | 119.7594 | 16.15624 | 13.91137 | 4.88E+08 |
| BoxBFL.113.LYS.H | 8.24926 | 118.3993 | 14.3358 | 12.1708 | 6.95E+08 |
| BoxBFL.114.GLY.H | 7.64664 | 103.781 | 15.76333 | 12.14132 | 5.87E+08 |
| BoxBFL.115.GLU.H | 7.50528 | 119.5289 | 15.88641 | 12.53165 | 6.74E+08 |
| BoxBFL.116.HIS.H | 7.82554 | 114.7129 | 17.52591 | 12.91339 | 4.1E+08 |
| BoxBFL.119.LEU.H | 7.37163 | 121.1972 | 13.24197 | 11.65462 | 1.03E+09 |
| BoxBFL.120.SER.H | 9.32283 | 121.0625 | 15.14154 | 12.10113 | 5.93E+08 |
| BoxBFL.121.ILE.H | 8.7522 | 120.6657 | 14.87619 | 12.56095 | 4.04E+08 |
| BoxBFL.122.GLY.H | 8.71514 | 109.4591 | 18.21003 | 13.47553 | 2E+08 |
| BoxBFL.123.ASP.H | 7.96996 | 124.3035 | 16.15828 | 12.66772 | 5.78E+08 |
| BoxBFL.124.VAL.H | 8.64104 | 124.0413 | 14.34107 | 12.30741 | 7.01E+08 |
| BoxBFL.125.ALA.H | 7.93386 | 121.3372 | 15.70871 | 12.46088 | 8.51E+08 |
| BoxBFL.126.LYS.H | 8.02815 | 119.7021 | 13.46969 | 12.7483 | 9.18E+08 |
| BoxBFL.127.LYS.H | 8.0478 | 121.2943 | 14.12423 | 15.42969 | 9.72E+08 |
| BoxBFL.128.LEU.H | 8.65186 | 120.1671 | 14.50135 | 12.59408 | 5.79E+08 |
| BoxBFL.129.GLY.H | 8.26077 | 106.0107 | 16.79447 | 12.54485 | 5.75E+08 |
| BoxBFL.130.GLU.H | 8.07653 | 123.2546 | 14.00815 | 12.1069 | 8.25E+08 |
| BoxBFL.131.MET.H | 8.7821 | 118.9601 | 14.7908 | 12.21398 | 7.26E+08 |
| BoxBFL.132.TRP.H | 8.71726 | 122.6675 | 15.33509 | 12.4674 | 4.67E+08 |
| BoxBFL.133.ASN.H | 8.17966 | 117.3578 | 14.21937 | 12.09116 | 7.35E+08 |
| BoxBFL.134.ASN.H | 7.59622 | 115.839 | 17.11067 | 12.24948 | 7.11E+08 |
| BoxBFL.135.THR.H | 7.31205 | 119.9435 | 16.01333 | 11.84476 | 7.59E+08 |
| BoxBFL.136.ALA.H | 9.25411 | 131.4374 | 13.61094 | 12.00251 | 8.78E+08 |
| BoxBFL.137.ALA.H | 8.86096 | 124.9828 | 16.96746 | 13.9175 | 82783192 |
| BoxBFL.138.ASP.H | 8.99667 | 115.7095 | 14.2258 | 12.81374 | 5.22E+08 |
| BoxBFL.139.ASP.H | 7.34551 | 117.8838 | 17.77517 | 12.06753 | 7.26E+08 |
| BoxBFL.140.LYS.H | 7.81795 | 119.1111 | 16.26883 | 12.4296 | 5.8E+08 |
| BoxBFL.141.GLN.H | 7.4356 | 118.2188 | 13.44592 | 12.84284 | 7.56E+08 |
| BoxBFL.143.TYR.H | 7.22342 | 115.6648 | 17.19563 | 12.6802 | 5.23E+08 |
| BoxBFL.144.GLU.H | 8.17886 | 120.3107 | 24.6535 | 15.3662 | 8.3E+08 |
| BoxBFL.145.LYS.H | 9.19676 | 121.2667 | 15.33294 | 12.93118 | 6.33E+08 |
| BoxBFL.146.LYS.H, BoxBFL.156.LYS.H | 7.70415 | 120.5771 | 15.33781 | 12.75619 | 1.39E+09 |
| BoxBFL.147.ALA.H | 8.47838 | 120.5221 | 16.72412 | 13.05465 | 3.2E+08 |
| BoxBFL.148.ALA.H | 8.38608 | 122.0761 | 15.38089 | 12.69376 | 7.72E+08 |
| BoxBFL.149.LYS.H | 7.98664 | 120.7873 | 15.37662 | 13.186 | 7.8E+08 |
| BoxBFL.150.LEU.H | 8.29876 | 120.0933 | 15.78188 | 13.31339 | 5.08E+08 |
| BoxBFL.151.LYS.H | 8.44117 | 123.678 | 14.86959 | 12.979 | 6.28E+08 |
| BoxBFL.152.GLU.H | 8.09634 | 120.1123 | 17.64454 | 13.74299 | 8.61E+08 |
| BoxBFL.153.LYS.H | 7.76844 | 119.7644 | 14.87574 | 12.75453 | 7.39E+08 |
| BoxBFL.154.TYR.H | 8.14945 | 120.4238 | #VALUE! | #VALUE! | 7.23E+08 |
| BoxBFL.155.GLU.H | 8.52687 | 117.6413 | 15.0031 | 13.04017 | 6.17E+08 |
| BoxBFL.157.ASP.H | 8.906 | 123.2206 | 15.30218 | 13.15 | 6.04E+08 |
| BoxBFL.158.ILE.H | 9.20733 | 122.5499 | 17.72024 | 12.87546 | 5.48E+08 |
| BoxBFL.159.ALA.H | 7.36719 | 124.835 | 14.8669 | 12.75735 | 7.55E+08 |
| BoxBFL.160.ALA.H | 7.78634 | 120.3982 | 14.86213 | 13.04298 | 7.84E+08 |
| BoxBFL.161.TYR.H | 8.20162 | 120.0455 | 17.64211 | 17.63803 | 8.72E+08 |
| BoxBFL.162.ARG.H | 8.26363 | 118.8125 | 15.04827 | 12.83358 | 7.06E+08 |

-continued

| Assign | F1 position | F2 position | LW F1 (Hz) | LW F2 (Hz) | Height |
|---|---|---|---|---|---|
| BoxBFL.163.ALA.H | 7.64059 | 121.3835 | 14.5465 | 12.45633 | 5.34E+08 |
| BoxBFL.164.LYS.H | 7.65996 | 118.3228 | 15.81194 | 12.97592 | 4.19E+08 |
| BoxBFL.165.GLY.H | 8.0589 | 108.6345 | 19.5729 | 13.76712 | 1.13E+08 |
| BoxBFL.166.LYS.H | 8.04566 | 121.5924 | 15.74549 | 13.70187 | 1.31E+09 |
| BoxBFL.168.ASP.H | 8.49244 | 121.104 | 14.18502 | 12.88319 | 7.2E+08 |
| BoxBFL.169.ALA.H | 8.2712 | 124.8749 | 14.52477 | 12.28691 | 3.58E+08 |
| BoxBFL.170.ALA.H | 8.13452 | 121.4021 | 14.64616 | 11.71461 | 6.15E+08 |
| BoxBFL.172.LYS.H | 8.42733 | 124.7554 | 12.80903 | 10.72519 | 46624344 |
| BoxBFL.173.GLY.H | 8.57669 | 111.124 | 19.67674 | 13.22967 | 1.55E+08 |

HMGB1A-c007 (3S, 1-184) with 1:2 molar ratio CXCL12 (1:1 molar ratio CXCL12 to HMG Box), in 10 mM HEPES pH 7.5 150 mM NaCl, FIGS. 13A-13D

| | |
|---|---|
| | BRUKER BIOSPIN 750 MHZ BROKER AVANCE SPECTROMETER WITH 5 MM TCI CRYOPROBE |
| $^1$H frequency (Hz) | 749.91352 |
| $^1$H sweep width (ppm) | 12.122609 |
| $^1$H sweep width (Hz) | 9090.9090 |
| $^1$HN sweep width (ppm) | 12.122609 |
| $^{15}$N frequency (Hz) | 75.99661 |
| $^{15}$N sweep width (ppm) | 32.01577 |
| $^{15}$N sweep width (Hz) | 2433.09002 |
| Water suppression gradient pulse width (Hz) | 3527.31 |

Baseline 1 (Day 1)

| Experiment type | 2D $^1$H-$^{15}$N HSQC |
|---|---|
| HMGB1 construct and concentration | 0.30 mM, HMGB1-c007 (3S 1-184), TEV-cleaved (200 µL 0.45 mM stock + 185 µL buffer) |
| CXCL12 construct and concentration | 0 mM |
| Temperature | 25° C. |
| Volume | 350 µL |
| Sample pH (after adjusting) | 7.66 |
| Number of scans | 16 |
| Buffer | 10 mM HEPES, pH 7.5 |

| F1 Assign | F1 position | F2 position | LW F1 (Hz) | LW F2 (Hz) | Height |
|---|---|---|---|---|---|
| TL.3.GLY.H, TL.10.GLY.H | 8.6061 | 111.0604 | 24.6728 | 23.8470 | 4.24E+06 |
| TL.6.LYS.H | 8.3808 | 120.7275 | 19.3276 | 19.0515 | 1.26E+07 |
| TL.7.LYS.H | 7.9672 | 123.9738 | 18.9452 | 18.4814 | 1.22E+07 |
| TL.9.ARG.H | 8.9422 | 124.5857 | 30.5185 | 22.5922 | 2.68E+06 |
| TL.11.LYS.H | 7.6533 | 119.5407 | 18.7001 | 20.1359 | 3.98E+06 |
| TL.13.SER.H, TL.26.HIS.H | 8.1990 | 119.2086 | 26.4193 | 23.6946 | 6.96E+06 |
| TL.14.SER.H | 9.3037 | 116.5728 | 17.7398 | 20.7154 | 1.52E+06 |
| TL.15.TYR.H | 7.9749 | 122.3508 | 21.5872 | 20.0836 | 9.77E+06 |
| TL.16.ALA.H | 7.8898 | 122.0710 | 18.6785 | 21.9854 | 1.16E+07 |
| TL.17.PHE.H | 8.3224 | 118.1346 | 25.4892 | 18.2495 | 5.66E+06 |
| TL.18.PHE.H | 8.1246 | 125.6475 | 19.4733 | 26.9249 | 6.38E+06 |
| TL.21.THR.H | 8.1820 | 116.6683 | 21.3497 | 19.6855 | 7.47E+06 |
| TL.23.ARG.H | 8.9337 | 123.5827 | 19.6637 | 19.5765 | 1.34E+07 |
| TL.25.GLU.H | 8.3297 | 119.6119 | 17.9559 | 20.8464 | 4.41E+06 |
| TL.27.LYS.H | 7.9199 | 118.2035 | 17.4027 | 24.5903 | 1.32E+07 |
| TL.28.LYS.H | 7.4656 | 117.6101 | 21.4259 | 22.0467 | 2.19E+06 |
| TL.29.LYS.H | 7.5008 | 116.9197 | 26.2391 | 24.4263 | 3.84E+06 |
| TL.30.HIS.H | 7.9045 | 116.8771 | 21.2366 | 19.0908 | 3.22E+07 |

-continued

| F1 Assign | F1 position | F2 position | LW F1 (Hz) | LW F2 (Hz) | Height |
|---|---|---|---|---|---|
| TL.32.ASP.H | 8.5014 | 116.2147 | 21.6349 | 20.6257 | 1.15E+07 |
| TL.33.ALA.H | 7.6405 | 123.1947 | 27.1908 | 18.4877 | 6.05E+06 |
| TL.36.ASN.H | 8.5631 | 124.5616 | 21.3601 | 19.8298 | 1.05E+07 |
| TL.38.SER.H | 8.5266 | 116.5707 | 20.6963 | 19.7437 | 1.75E+07 |
| TL.39.GLU.H | 7.8017 | 121.4763 | 24.3844 | 20.7391 | 5.60E+06 |
| TL.41.SER.H | 8.4328 | 114.6754 | 21.9986 | 19.2519 | 7.61E+06 |
| TL.43.LYS.H | 7.9047 | 120.0881 | 24.5054 | 21.5027 | 8.26E+06 |
| TL.48.TRP.H | 8.6119 | 121.3719 | 27.7321 | 19.6527 | 6.67E+06 |
| TL.49.LYS.H | 7.5392 | 114.9177 | 22.4466 | 26.2994 | 6.95E+06 |
| TL.50.THR.H | 7.4184 | 106.6545 | 19.9202 | 26.9454 | 3.55E+06 |
| TL.51.MET.H | 7.1286 | 124.1028 | 34.8660 | 19.9547 | 3.59E+06 |
| TL.52.SER.H | 9.0214 | 120.2824 | 25.7658 | 22.2592 | 3.14E+06 |
| TL.54.LYS.H | 8.2612 | 118.6673 | 21.4006 | 20.8276 | 1.72E+07 |
| TL.55.GLU.H, TL.146.LYS.H, TL.156.LYS.H | 7.6743 | 120.5743 | 39.0944 | 20.4649 | 4.08E+07 |
| TL.57.GLY.H | 7.8481 | 107.2718 | 24.8060 | 21.1106 | 4.92E+06 |
| TL.58.LYS.H | 7.9240 | 118.8658 | 23.1257 | 30.2328 | 5.35E+06 |
| TL.60.GLU.H | 8.4408 | 121.0589 | 18.5170 | 21.8991 | 2.43E+07 |
| TL.61.ASP.H | 8.5793 | 121.9550 | 25.9461 | 21.0215 | 2.41E+06 |
| TL.63.ALA.H | 8.0272 | 123.2985 | 18.8092 | 20.8840 | 3.01E+07 |
| TL.64.LYS.H | 8.5925 | 122.4879 | 24.6164 | 26.1814 | 3.30E+06 |
| TL.65.ALA.H | 7.9334 | 123.0276 | 19.4945 | 20.6248 | 1.77E+07 |
| TL.66.ASP.H | 8.3419 | 120.0786 | 22.2268 | 23.0110 | 5.95E+06 |
| TL.67.LYS.H | 8.2124 | 120.8922 | 19.2067 | 21.7276 | 1.54E+07 |
| TL.68.ALA.H | 7.4653 | 120.9539 | 26.2159 | 21.1243 | 4.51E+06 |
| TL.71.GLU.H | 8.4294 | 117.1838 | 20.4156 | 25.0309 | 7.16E+06 |
| TL.72.ARG.H | 8.0622 | 120.1074 | 18.6953 | 20.2934 | 2.46E+07 |
| TL.73.GLU.H | 8.4749 | 120.0201 | 22.5415 | 19.5028 | 9.11E+06 |
| TL.74.MET.H | 8.4409 | 117.6522 | #VALUE! | #VALUE! | 6.40E+06 |
| TL.75.LYS.H | 7.5100 | 119.0899 | 22.5073 | 22.2834 | 3.08E+06 |
| TL.77.TYR.H | 7.5024 | 123.9352 | 30.9003 | 17.6211 | 3.53E+06 |
| TL.78.ILE.H | 7.8034 | 129.2718 | 20.0866 | 19.3005 | 1.72E+07 |
| TL.88.PHE.H | 8.3596 | 122.1156 | 17.9211 | 19.8933 | 2.66E+07 |
| TL.89.LYS.H | 8.2181 | 123.3632 | 21.8312 | 19.6249 | 1.19E+07 |
| TL.90.ASP.H | 8.0110 | 119.1287 | 20.5283 | 23.7061 | 9.96E+06 |
| TL.93.ALA.H | 7.3090 | 123.8485 | 18.6517 | 18.5426 | 2.41E+07 |
| TL.95.LYS.H | 8.5094 | 123.7507 | 19.5433 | 18.6325 | 1.67E+07 |
| TL.99.SER.H | 7.8684 | 114.9049 | 20.2451 | 19.8589 | 2.20E+07 |
| TL.100.ALA.H | 9.0706 | 122.9058 | 17.9269 | 19.6686 | 1.43E+07 |
| TL.102.PHE.H | 8.2289 | 122.4276 | 19.9106 | 19.5888 | 1.37E+07 |
| TL.103.LEU.H | 8.2529 | 120.0969 | 21.6806 | 25.4949 | 1.99E+07 |
| TL.104.PHE.H | 8.1450 | 122.5447 | 19.7785 | 17.8570 | 3.42E+06 |
| TL.106.SER.H | 7.9866 | 116.8141 | 16.6297 | 18.4050 | 2.77E+07 |
| TL.107.GLU.H | 7.1139 | 119.4856 | 18.6763 | 18.2751 | 2.77E+07 |
| TL.111.LYS.H | 6.8070 | 117.8973 | 20.9968 | 19.4882 | 1.97E+07 |
| TL.112.ILE.H | 8.1471 | 119.7094 | 19.6956 | 20.7896 | 2.21E+07 |
| TL.113.LYS.H | 8.2277 | 118.6620 | 18.9931 | 20.0020 | 2.62E+07 |
| TL.114.GLY.H | 7.6276 | 103.8053 | 19.2245 | 18.7965 | 2.17E+07 |
| TL.115.GLU.H | 7.4519 | 119.5050 | 19.0651 | 18.6530 | 2.50E+07 |
| TL.116.HIS.H | 7.8557 | 114.5584 | 21.3730 | 26.3315 | 1.95E+07 |
| TL.119.LEU.H | 7.3441 | 121.1282 | 16.9517 | 18.0939 | 4.11E+07 |
| TL.120.SER.H | 9.2783 | 120.9530 | 19.8514 | 19.2891 | 1.57E+07 |
| TL.121.ILE.H | 8.7093 | 120.6277 | 19.2620 | 19.2230 | 1.13E+07 |
| TL.122.GLY.H | 8.6846 | 109.4587 | 26.8288 | 22.3716 | 4.51E+06 |
| TL.123.ASP.H | 7.9382 | 124.3219 | 18.3663 | 18.7325 | 2.13E+07 |
| TL.124.VAL.H | 8.6040 | 124.0412 | 18.2886 | 18.7654 | 2.25E+07 |
| TL.125.ALA.H | 7.8785 | 121.3328 | 16.5530 | 19.1095 | 3.63E+06 |
| TL.126.LYS.H | 7.9989 | 119.7206 | 19.3006 | 19.3155 | 7.93E+07 |

-continued

| F1 Assign | F1 position | F2 position | LW F1 (Hz) | LW F2 (Hz) | Height |
|---|---|---|---|---|---|
| TL.127.LYS.H | 8.0145 | 121.3551 | 17.2034 | 17.8224 | 7.22E+07 |
| TL.128.LEU.H | 8.6505 | 120.2524 | 18.6803 | 18.7237 | 2.09E+07 |
| TL.129.GLY.H | 8.2032 | 106.2602 | 19.1920 | 18.8485 | 2.46E+07 |
| TL.131.MET.H | 8.7231 | 118.8760 | 18.0856 | 18.4060 | 2.38E+07 |
| TL.132.TRP.H | 8.7095 | 122.5759 | 19.0186 | 19.0721 | 1.59E+07 |
| TL.133.ASN.H | 8.1328 | 117.2422 | 19.0104 | 18.8528 | 3.15E+07 |
| TL.134.ASN.H | 7.5431 | 115.7695 | 19.1824 | 18.8449 | 2.98E+07 |
| TL.135.THR.H | 7.2603 | 119.9046 | 19.3742 | 19.5603 | 2.60E+07 |
| TL.136.ALA.H | 9.2045 | 131.3561 | 17.2667 | 18.5735 | 2.23E+07 |
| TL.137.ALA.H | 8.8342 | 124.9935 | 33.3526 | 21.2936 | 1.19E+06 |
| TL.138.ASP.H | 8.9528 | 115.6245 | 18.8620 | 19.6655 | 1.34E+07 |
| TL.139.ASP.H | 7.2986 | 117.8616 | 19.8829 | 18.6225 | 2.53E+07 |
| TL.140.ALA.H | 7.7883 | 119.0980 | 20.0357 | 19.4836 | 1.79E+07 |
| TL.141.GLN.H | 7.4069 | 118.1124 | 18.1893 | 19.2718 | 2.30E+07 |
| TL.143.TYR.H | 7.1940 | 115.5652 | 20.7215 | 19.7599 | 1.68E+07 |
| TL.145.LYS.H | 9.1712 | 121.2666 | 18.7285 | 20.6529 | 1.58E+07 |
| TL.147.ALA.H | 8.3287 | 120.5992 | 22.2428 | 21.8046 | 1.24E+07 |
| TL.149.LYS.H | 7.9709 | 120.8132 | 19.5777 | 23.5142 | 2.79E+07 |
| TL.150.LEU.H | 8.2579 | 119.8355 | 19.6870 | 24.4644 | 1.95E+07 |
| TL.151.LYS.H | 8.3943 | 123.7275 | 19.8464 | 22.6956 | 2.13E+07 |
| TL.152.GLU.H | 8.0005 | 120.0908 | 18.5048 | 18.9795 | 4.56E+07 |
| TL.153.LYS.H | 7.7378 | 119.7316 | 20.1171 | 19.9428 | 2.47E+07 |
| TL.154.TYR.H | 8.1211 | 120.2560 | 27.4207 | 25.0214 | 4.56E+07 |
| TL.155.GLU.H | 8.4779 | 117.6292 | 20.1839 | 20.3442 | 1.81E+07 |
| TL.157.ASP.H | 8.8596 | 123.1691 | 18.1489 | 19.7980 | 1.95E+07 |
| TL.158.ILE.H | 9.1467 | 122.4891 | 19.2484 | 19.6793 | 1.60E+07 |
| TL.159.ALA.H | 7.3324 | 124.8211 | 18.1448 | 19.5515 | 2.61E+07 |
| TL.160.ALA.H | 7.7523 | 120.3814 | 18.8194 | 20.3354 | 2.87E+07 |
| TL.162.ARG.H | 8.2660 | 119.1276 | 20.2383 | 21.2173 | 2.28E+07 |
| TL.163.ALA.H | 7.5998 | 121.5022 | 18.4569 | 19.0784 | 1.90E+07 |
| TL.164.LYS.H | 7.6444 | 118.6458 | 18.5535 | 19.1662 | 1.93E+07 |
| TL.166.LYS.H | 8.0107 | 121.8105 | 21.0399 | 22.8760 | 1.20E+07 |
| TL.168.ASP.H | 8.4217 | 120.2067 | 20.8680 | 20.3203 | 1.18E+07 |
| TL.169.ALA.H | 8.2713 | 124.9694 | 23.2824 | 19.9815 | 1.63E+07 |
| TL.170.ALA.H | 8.1977 | 121.6039 | 19.5714 | 19.2612 | 1.48E+07 |
| TL.174.VAL.H | 7.9243 | 119.5174 | 23.1927 | 24.7751 | 6.62E+06 |
| TL.175.VAL.H | 8.3105 | 125.5123 | 16.0756 | 16.4540 | 6.65E+07 |
| TL.176.LYS.H | 8.4655 | 126.6128 | 28.7022 | 20.5965 | 3.74E+06 |
| TL.177.ALA.H | 8.3773 | 125.8179 | 31.4688 | 20.8340 | 3.36E+06 |
| TL.178.GLU.H | 8.4450 | 120.6799 | #VALUE! | #VALUE! | 9.04E+06 |
| TL.179.LYS.H | 8.4425 | 122.3029 | 19.9586 | 24.6041 | 1.34E+07 |
| TL.185.GLU.H | 8.2782 | 122.8421 | 19.8975 | 21.0209 | 1.81E+07 |

3D Experiments (Day 1)

These spectra are not shown due to their 3D nature; data available if requested. Sample is that of Baseline 1.

| Experiment type | 3D, $^{15}$N EDITED $^1$H-$^1$H TOCSY-HSQC, THROUGH-SPACE INTERACTION (MAR. 1, 2019) |
|---|---|
| Temperature | 25° C. |
| Volume | 300 μL |
| Number of scans | 8 |

| Experiment type | 3D, $^{15}$N EDITED $^1$H-$^1$H NOESY-HSQC, THROUGH-BOND INTERACTION (FEB. 28, 2019) |
|---|---|
| Temperature | 25° C. |
| Volume | 300 μL |
| Number of scans | 16 |

Baseline 2 (Day 3)

| Experiment type | 2D $^1$H-$^{15}$N HSQC |
|---|---|
| HMGB1 construct and concentration | 0.30 mM, HMGB1-c007 (3S 1-184), TEV-cleaved (200 μL 0.45 mM stock + 185 μL buffer) |

-continued

| Experiment type | 2D $^1$H-$^{15}$N HSQC |
|---|---|
| CXCL12 construct and concentration | 0 mM |
| Temperature | 25° C. |
| Sample pH (after adjusting) | 7.66 |
| Volume | 350 μL |
| Number of scans | 16 |
| Buffer | 10 mM HEPES, pH 7.5 |

| F1 Assign | F1 position | F2 position | LW F1 (Hz) | LW F2 (Hz) | Height |
|---|---|---|---|---|---|
| TL.3.GLY.H, TL.10.GLY.H | 8.6065 | 111.0499 | 23.1613 | 23.4948 | 4.43E+06 |
| TL.6.LYS.H | 8.3807 | 120.7320 | 19.6417 | 18.6975 | 1.24E+07 |
| TL.7.LYS.H | 7.9677 | 123.9750 | 18.5170 | 18.1121 | 1.19E+07 |
| TL.9.ARG.H | 8.9453 | 124.5715 | 24.2572 | 23.7356 | 2.61E+06 |
| TL.11.LYS.H | 7.6528 | 119.5498 | 17.4576 | 20.3878 | 3.89E+06 |
| TL.13.SER.H, TL.26.HIS.H | 8.1991 | 119.1995 | 26.6500 | 22.3922 | 6.54E+06 |
| TL.14.SER.H | 9.2956 | 116.5826 | 16.8521 | 20.2197 | 1.33E+06 |
| TL.15.TYR.H | 7.9757 | 122.3477 | 21.7938 | 19.9370 | 9.68E+06 |
| TL.16.ALA.H | 7.8896 | 122.0725 | 19.8069 | 21.8309 | 1.12E+07 |
| TL.17.PHE.H | 8.3224 | 118.1373 | 25.3998 | 18.6893 | 5.67E+06 |
| TL.18.PHE.H | 8.1241 | 125.6449 | 20.5389 | 27.4613 | 6.00E+06 |
| TL.21.THR.H | 8.1825 | 116.6667 | 21.1937 | 19.7947 | 7.42E+06 |
| TL.23.ARG.H | 8.9329 | 123.5826 | 19.1345 | 19.5535 | 1.33E+07 |
| TL.25.GLU.H | 8.3294 | 119.6141 | 20.0289 | 20.5729 | 4.29E+06 |
| TL.27.LYS.H | 7.9196 | 118.2075 | 17.7875 | 24.4847 | 1.31E+07 |
| TL.28.LYS.H | 7.4656 | 117.5781 | 22.7406 | 23.1308 | 2.32E+06 |
| TL.29.LYS.H | 7.4989 | 116.9374 | 23.0209 | 25.0045 | 4.05E+06 |
| TL.30.HIS.H | 7.9042 | 116.8739 | 21.0887 | 18.9026 | 3.21E+07 |
| TL.32.ASP.H | 8.5004 | 116.2125 | 20.0730 | 20.5524 | 1.17E+07 |
| TL.33.ALA.H | 7.6424 | 123.1937 | 25.8311 | 18.9977 | 6.03E+06 |
| TL.36.ASN.H | 8.5629 | 124.5621 | 20.2634 | 20.1827 | 1.01E+07 |
| TL.38.SER.H | 8.5266 | 116.5762 | 20.3927 | 20.2102 | 1.75E+07 |
| TL.39.GLU.H | 7.8015 | 121.4813 | 25.4307 | 21.5986 | 5.49E+06 |
| TL.41.SER.H | 8.4315 | 114.6769 | 24.0654 | 18.8439 | 7.20E+06 |
| TL.43.LYS.H | 7.9025 | 120.0835 | 25.2682 | 22.0179 | 8.40E+06 |
| TL.48.TRP.H | 8.6129 | 121.3660 | 22.6050 | 19.2575 | 6.76E+06 |
| TL.49.LYS.H | 7.5396 | 114.9173 | 20.9942 | 25.1553 | 6.76E+06 |
| TL.50.THR.H | 7.4186 | 106.6388 | 24.1325 | 25.7242 | 3.44E+06 |
| TL.51.MET.H | 7.1310 | 124.1048 | 22.9068 | 19.6438 | 3.75E+06 |
| TL.52.SER.H | 9.0209 | 120.2880 | 28.9274 | 22.9000 | 2.95E+06 |
| TL.54.LYS.H | 8.2621 | 118.6676 | 20.9063 | 21.0484 | 1.74E+07 |
| TL.55.GLU.H, TL.146.LYS.H, TL.156.LYS.H | 7.6741 | 120.5737 | 35.8117 | 20.3103 | 4.07E+07 |
| TL.57.GLY.H | 7.8487 | 107.2598 | 28.3292 | 20.2673 | 4.70E+06 |
| TL.58.LYS.H | 7.9229 | 118.8497 | 24.2289 | 27.7675 | 5.26E+06 |
| TL.60.GLU.H | 8.4408 | 121.0595 | 18.5310 | 21.9295 | 2.41E+07 |
| TL.61.ASP.H | 8.5746 | 121.9512 | 28.9797 | 22.9634 | 2.66E+06 |
| TL.63.ALA.H | 8.0269 | 123.2962 | 18.7324 | 21.1710 | 2.95E+07 |
| TL.64.LYS.H | 8.5909 | 122.4962 | 24.9341 | 24.0694 | 2.94E+06 |
| TL.65.ALA.H | 7.9332 | 123.0304 | 20.3519 | 20.5074 | 1.74E+07 |
| TL.66.ASP.H | 8.3409 | 120.0857 | 22.2493 | 23.7054 | 5.80E+06 |
| TL.67.LYS.H | 8.2130 | 120.8955 | 19.6156 | 22.3669 | 1.54E+07 |
| TL.68.ALA.H | 7.4616 | 120.9561 | 37.9570 | 19.8115 | 4.30E+06 |
| TL.71.GLU.H | 8.4286 | 117.1801 | 21.4128 | 25.4454 | 6.76E+06 |
| TL.72.ARG.H | 8.0621 | 120.1083 | 18.7908 | 20.0752 | 2.45E+07 |
| TL.73.GLU.H | 8.4738 | 120.0142 | 23.7008 | 19.2906 | 8.71E+06 |
| TL.74.MET.H | 8.4409 | 117.6522 | #VALUE! | #VALUE! | 6.44E+06 |
| TL.75.LYS.H | 7.5068 | 119.0858 | 26.7860 | 22.3687 | 3.23E+06 |
| TL.77.TYR.H | 7.5032 | 123.9308 | 38.9311 | 17.2302 | 3.49E+06 |
| TL.78.ILE.H | 7.8036 | 129.2703 | 19.9513 | 19.4233 | 1.70E+07 |
| TL.88.PHE.H | 8.3595 | 122.1143 | 17.6506 | 19.7390 | 2.67E+07 |
| TL.89.LYS.H | 8.2182 | 123.3647 | 19.6893 | 20.1167 | 1.23E+07 |
| TL.90.ASP.H | 8.0126 | 119.1425 | 20.7630 | 25.2387 | 9.55E+06 |
| TL.93.ALA.H | 7.3090 | 123.8482 | 18.8016 | 18.5673 | 2.40E+07 |
| TL.95.LYS.H | 8.5090 | 123.7493 | 18.6872 | 18.3947 | 1.70E+07 |
| TL.99.SER.H | 7.8687 | 114.9053 | 20.2014 | 20.0612 | 2.21E+07 |
| TL.100.ALA.H | 9.0705 | 122.9049 | 17.6281 | 19.4111 | 1.43E+07 |
| TL.102.PHE.H | 8.2287 | 122.4261 | 20.3823 | 19.7821 | 1.38E+07 |
| TL.103.LEU.H | 8.2533 | 120.0963 | 22.3290 | 25.7323 | 1.99E+07 |

-continued

| F1 Assign | F1 position | F2 position | LW F1 (Hz) | LW F2 (Hz) | Height |
|---|---|---|---|---|---|
| TL.104.PHE.H | 7.9865 | 116.8146 | 16.6032 | 18.4916 | 2.71E+07 |
| TL.106.SER.H | 7.1139 | 119.4847 | 18.9087 | 18.2576 | 2.71E+07 |
| TL.107.GLU.H | 6.8074 | 117.8959 | 20.3505 | 19.3071 | 1.99E+07 |
| TL.111.LYS.H | 8.1473 | 119.7047 | 19.6728 | 20.5823 | 2.19E+07 |
| TL.112.ILE.H | 8.2277 | 118.6631 | 19.2041 | 19.9527 | 2.58E+07 |
| TL.113.LYS.H | 7.6278 | 103.8060 | 20.2430 | 18.4257 | 2.16E+07 |
| TL.114.GLY.H | 7.4522 | 119.5041 | 18.8464 | 18.7187 | 2.51E+07 |
| TL.115.GLU.H | 7.8558 | 114.5590 | 21.3428 | 26.4292 | 1.94E+07 |
| TL.116.HIS.H | 7.3444 | 121.1280 | 17.0541 | 18.0097 | 4.07E+07 |
| TL.119.LEU.H | 9.2779 | 120.9556 | 19.1260 | 18.9896 | 1.56E+07 |
| TL.120.SER.H | 8.7096 | 120.6282 | 19.3699 | 19.3593 | 1.16E+07 |
| TL.121.ILE.H | 8.6834 | 109.4592 | 23.3770 | 21.1555 | 4.56E+06 |
| TL.122.GLY.H | 7.9382 | 124.3228 | 18.0611 | 18.8783 | 2.14E+07 |
| TL.123.ASP.H | 8.6038| | 124.0408 | 18.3007 | 18.9123 | 2.25E+07 |
| TL.124.VAL.H | 7.8787 | 121.3329 | 16.2690 | 19.0869 | 3.68E+07 |
| TL.125.ALA.H | 7.9987 | 119.7210 | 19.0408 | 19.1946 | 7.83E+07 |
| TL.126.LYS.H | 8.0145 | 121.3562 | 17.2124 | 17.7746 | 7.14E+07 |
| TL.127.LYS.H | 8.6507 | 120.2533 | 18.8465 | 18.5636 | 2.06E+07 |
| TL.128.LEU.H | 8.2034 | 106.2583 | 19.1542 | 18.5945 | 2.46E+07 |
| TL.129.GLY.H | 7.9939 | 122.7099 | 31.0113 | 24.8633 | 2.83E+06 |
| TL.131.MET.H | 8.7234 | 118.8753 | 17.8826 | 18.2976 | 2.41E+07 |
| TL.132.TRP.H | 8.7097 | 122.5757 | 19.4286 | 19.1503 | 1.60E+07 |
| TL.133.ASN.H | 8.1327 | 117.2411 | 19.1545 | 18.7949 | 3.10E+07 |
| TL.134.ASN.H | 7.5430 | 115.7691 | 19.2434 | 18.7462 | 2.97E+07 |
| TL.135.THR.H | 7.2604 | 119.9055 | 18.9668 | 19.2131 | 2.62E+07 |
| TL.136.ALA.H | 9.2048 | 131.3556 | 16.6770 | 18.6275 | 2.27E+07 |
| TL.137.ALA.H | 8.8215 | 124.9797 | 28.9631 | 18.8998 | 9.53E+05 |
| TL.138.ASP.H | 8.9534 | 115.6244 | 19.3079 | 16.6390 | 1.34E+07 |
| TL.139.ASP.H | 7.2990 | 117.8613 | 19.5011 | 18.4882 | 2.54E+07 |
| TL.140.ALA.H | 7.7881 | 119.0997 | 19.6218 | 19.4625 | 1.80E+07 |
| TL.141.GLN.H | 7.4070 | 118.1139 | 18.2290 | 19.3873 | 2.28E+07 |
| TL.143.TYR.H | 7.1941 | 115.5640 | 20.6936 | 19.5627 | 1.75E+07 |
| TL.145.LYS.H | 9.1714 | 121.2694 | 18.9207 | 20.5145 | 1.55E+07 |
| TL.147.ALA.H | 8.3294 | 120.5969 | 21.2897 | 22.3662 | 1.25E+07 |
| TL.149.LYS.H | 7.9711 | 120.8080 | 19.0205 | 22.9038 | 2.77E+07 |
| TL.150.LEU.H | 8.2586 | 119.8352 | 19.6218 | 24.8315 | 1.93E+07 |
| TL.151.LYS.H | 8.3946 | 123.7260 | 20.5952 | 23.0334 | 2.12E+07 |
| TL.152.GLU.H | 8.0004 | 120.0915 | 18.6445 | 18.7793 | 4.53E+07 |
| TL.153.LYS.H | 7.7381 | 119.7331 | 20.2180 | 19.8851 | 2.46E+07 |
| TL.154.TYR.H | 8.1209 | 120.2560 | 28.0283 | 25.0515 | 4.45E+07 |
| TL.155.GLU.H | 8.4777 | 117.6292 | 19.6687 | 20.1632 | 1.81E+07 |
| TL.157.ASP.H | 8.8597 | 123.1714 | 18.3048 | 19.6916 | 1.96E+07 |
| TL.158.ILE.H | 9.1469 | 122.4919 | 19.3081 | 19.5812 | 1.61E+07 |
| TL.159.ALA.H | 7.3325 | 124.8205 | 17.9084 | 19.2404 | 2.59E+07 |
| TL.160.ALA.H | 7.7526 | 120.3794 | 18.6070 | 20.3336 | 2.91E+07 |
| TL.162.ARG.H | 8.2667 | 119.1253 | 20.5620 | 21.2604 | 2.28E+07 |
| TL.163.ALA.H | 7.5996 | 121.4996 | 18.4419 | 19.1701 | 1.89E+07 |
| TL.164.LYS.H | 7.6446 | 118.6434 | 18.3150 | 18.9990 | 1.94E+07 |
| TL.166.LYS.H | 8.0103 | 121.8118 | 20.8605 | 22.0326 | 1.21E+07 |
| TL.168.ASP.H | 8.4199 | 120.2046 | 21.4934 | 19.9990 | 1.18E+07 |
| TL.169.ALA.H | 8.2714 | 124.9725 | 23.9158 | 19.9230 | 1.64E+07 |
| TL.170.ALA.H | 8.1980 | 121.6044 | 19.8101 | 19.2270 | 1.50E+07 |
| TL.174.VAL.H | 7.9239 | 119.5328 | 23.8954 | 29.0599 | 6.20E+06 |
| TL.175.VAL.H | 8.3108 | 125.5127 | 16.0825 | 16.4752 | 6.74E+07 |
| TL.176.LYS.H | 8.4651 | 126.6236 | 22.4539 | 20.5401 | 4.14E+06 |
| TL.177.ALA.H | 8.3781 | 125.8126 | 25.5412 | 22.8124 | 3.71E+06 |
| TL.178.GLU.H | 8.4450 | 120.6799 | #VALUE! | #VALUE! | 9.25E+06 |
| TL.179.LYS.H | 8.4424 | 123.3058 | 19.6823 | 24.3392 | 1.27E+07 |
| TL.185.GLU.H | 8.2779 | 122.8405 | 19.1833 | 22.8993 | 1.91E+07 |

1:1 Molar Ratio CXCL12/HMG Box (1:2 ratio HMGB1A-c007/CXCL12A-c021, Day 4)

| Experiment type | 2D $^1$H-$^{15}$N HSQC |
|---|---|
| HMGB1 construct and concentration | 0.30 mM, HMGB1-c007 (3S 1-184), TEV-cleaved (200 μL 0.45 mM stock) |
| CXCL12 construct and concentration | 0.6 mM, CXCL12A-c021, wt 1-67, no tag (185 μL 1.14 mM stock) |
| Temperature | 25° C. |
| Volume | 350 μL |
| Sample pH (after adjusting) | 7.65 |
| Number of scans | 16 |
| Buffer | 10 mM HEPES, pH 7.5 |

| F1 Assign | F1 position | F2 position | LW F1 (Hz) | LW F2 (Hz) | Height |
|---|---|---|---|---|---|
| TL.3.GLY.H, TL.10.GLY.H | 8.6044 | 111.0338 | 27.0394 | 23.1335 | 5.94E+06 |
| TL.6.LYS.H | 8.3809 | 120.6948 | 22.5007 | 18.0287 | 1.34E+07 |
| TL.7.LYS.H | 7.9643 | 123.9632 | 20.3742 | 18.4134 | 1.54E+07 |
| TL.9.ARG.H | 8.9503 | 124.5797 | 31.7140 | 24.0875 | 3.87E+06 |
| TL.11.LYS.H | 7.6557 | 119.5615 | 16.0398 | 21.6463 | 5.42E+06 |
| TL.13.SER.H, TL.26.HIS.H | 8.2004 | 119.2105 | 23.4564 | 24.3179 | 1.04E+07 |
| TL.14.SER.H | 9.3238 | 116.5556 | 14.7611 | 15.5346 | 1.67E+06 |
| TL.15.TYR.H | 7.9778 | 122.3535 | 21.1121 | 19.3913 | 1.51E+07 |
| TL.16.ALA.H | 7.8925 | 122.0870 | 19.3520 | 22.0446 | 1.84E+07 |
| TL.17.PHE.H | 8.3240 | 118.1495 | 27.5926 | 18.0447 | 9.03E+06 |
| TL.18.PHE.H | 8.1278 | 125.6553 | 19.8250 | 26.5265 | 1.13E+07 |
| TL.21.THR.H | 8.1835 | 116.6724 | 21.5629 | 19.5787 | 9.24E+06 |
| TL.23.ARG.H | 8.9348 | 123.5796 | 18.8791 | 19.0832 | 2.40E+07 |
| TL.25.GLU.H | 8.3321 | 119.6265 | 22.0156 | 18.9298 | 6.69E+06 |
| TL.27.LYS.H | 7.9208 | 118.2122 | 17.2389 | 24.5277 | 2.00E+07 |
| TL.28.LYS.H | 7.4693 | 117.6188 | 20.5149 | 21.7352 | 3.16E+06 |
| TL.29.LYS.H | 7.5019 | 116.9291 | 20.0353 | 22.0649 | 5.99E+06 |
| TL.30.HIS.H | 7.9083 | 116.8927 | 20.9767 | 19.1705 | 5.23E+07 |
| TL.32.ASP.H | 8.5041 | 116.2183 | 21.3681 | 20.8293 | 1.80E+07 |
| TL.33.ALA.H | 7.6486 | 123.1983 | 33.3099 | 19.1418 | 7.80E+06 |
| TL.36.ASN.H | 8.5655 | 124.5629 | 18.7902 | 19.8770 | 1.75E+07 |
| TL.38.SER.H | 8.5296 | 116.5760 | 19.5825 | 19.3443 | 3.10E+07 |
| TL.39.GLU.H | 7.8000 | 121.4911 | 27.7099 | 20.3638 | 8.06E+06 |
| TL.41.SER.H | 8.4349 | 114.6887 | 23.1352 | 19.2946 | 1.18E+07 |
| TL.43.LYS.H | 7.9049 | 120.0830 | 25.4006 | 22.5369 | 1.19E+07 |
| TL.48.TRP.H | 8.6160 | 121.3765 | 22.4001 | 19.4978 | 1.10E+07 |
| TL.49.LYS.H | 7.5429 | 114.9206 | 21.7660 | 26.6768 | 1.04E+07 |
| TL.50.THR.H | 7.4225 | 106.6598 | 25.9188 | 26.8533 | 5.09E+06 |
| TL.51.MET.H | 7.1282 | 124.0983 | 25.1134 | 21.1386 | 5.30E+06 |
| TL.52.SER.H | 9.0270 | 120.2729 | 23.7729 | 19.7149 | 4.97E+06 |
| TL.54.LYS.H | 8.2637 | 118.6728 | 21.3251 | 20.6048 | 2.61E+07 |
| TL.55.GLU.H, TL.146.LYS.H, TL.156.LYS.H | 7.6767 | 120.5832 | 30.2398 | 20.3845 | 6.71E+07 |
| TL.57.GLY.H | 7.8522 | 107.2682 | 26.6428 | 20.8923 | 8.03E+06 |
| TL.58.LYS.H | 7.9244 | 118.8701 | 22.7163 | 29.6656 | 7.94E+06 |
| TL.60.GLU.H | 8.4437 | 121.0610 | 18.2434 | 20.3448 | 4.09E+07 |
| TL.61.ASP.H | 8.5815 | 121.9597 | 33.1388 | 21.6707 | 3.39E+06 |
| TL.63.ALA.H | 8.0294 | 123.2984 | 18.2389 | 19.6294 | 5.05E+07 |
| TL.64.LYS.H | 8.5980 | 122.5146 | 26.0412 | 25.2214 | 4.71E+06 |
| TL.65.ALA.H | 7.9368 | 123.0339 | 18.6025 | 19.9725 | 2.82E+07 |
| TL.66.ASP.H | 8.3457 | 120.0879 | 22.5058 | 23.2892 | 7.23E+06 |
| TL.67.LYS.H | 8.2154 | 120.8999 | 18.9826 | 22.1852 | 2.52E+07 |
| TL.68.ALA.H | 7.4697 | 120.9568 | 23.2933 | 19.0137 | 6.76E+06 |
| TL.71.GLU.H | 8.4315 | 117.1750 | 21.7295 | 26.3586 | 1.06E+07 |
| TL.72.ARG.H | 8.0645 | 120.1128 | 18.0569 | 19.4262 | 4.23E+07 |
| TL.73.GLU.H | 8.4787 | 120.0270 | 23.1364 | 19.3270 | 1.51E+07 |
| TL.74.MET.H | 8.4409 | 117.6522 | #VALUE! | #VALUE! | 9.83E+06 |
| TL.75.LYS.H | 7.5049 | 119.1098 | 31.7802 | 21.8213 | 4.59E+06 |
| TL.77.TYR.H | 7.5105 | 123.9396 | 38.1218 | 16.9483 | 4.14E+06 |
| TL.78.ILE.H | 7.8084 | 129.2854 | 19.5578 | 19.9301 | 2.60E+07 |
| TL.88.PHE.H | 8.3628 | 122.1204 | 16.9053 | 19.1178 | 4.49E+07 |
| TL.89.LYS.H | 8.2210 | 123.3706 | 19.7502 | 19.2731 | 2.10E+07 |
| TL.90.ASP.H | 8.0147 | 119.1518 | 21.2737 | 24.1312 | 1.43E+07 |
| TL.93.ALA.H | 7.3126 | 123.8531 | 19.3345 | 18.4537 | 3.57E+07 |
| TL.95.LYS.H | 8.5127 | 123.7578 | 18.2433 | 18.4107 | 2.55E+07 |
| TL.99.SER.H | 7.8719 | 114.9159 | 19.1639 | 18.9030 | 3.80E+07 |
| TL.100.ALA.H | 9.0737 | 122.9134 | 17.9203 | 18.9328 | 2.47E+07 |
| TL.102.PHE.H | 8.2316 | 122.4356 | 22.4797 | 20.9918 | 1.28E+07 |
| TL.103.LEU.H | 8.2553 | 120.1006 | 21.3513 | 23.9579 | 3.34E+07 |
| TL.104.PHE.H | 8.1434 | 122.5532 | 26.6494 | 18.4699 | 3.85E+06 |
| TL.106.SER.H | 7.9897 | 116.8195 | 16.1819 | 18.1182 | 4.66E+07 |
| TL.107.GLU.H | 7.1171 | 119.4906 | 17.8505 | 18.0469 | 4.73E+07 |
| TL.111.LYS.H | 6.8097 | 117.9049 | 19.8483 | 19.1076 | 3.40E+07 |
| TL.112.ILE.H | 8.1508 | 119.7121 | 19.4877 | 20.4021 | 3.72E+07 |
| TL.113.LYS.H | 8.2307 | 118.6666 | 18.3996 | 19.2564 | 4.37E+07 |
| TL.114.GLY.H | 7.6300 | 103.8047 | 18.7943 | 18.4306 | 3.60E+07 |
| TL.115.GLU.H | 7.4552 | 119.5222 | 19.2213 | 18.9640 | 4.04E+07 |
| TL.116.HIS.H | 7.8582 | 114.5580 | 20.7604 | 23.4804 | 3.16E+07 |
| TL.119.LEU.H | 7.3458 | 121.1340 | 16.1812 | 17.8123 | 6.86E+07 |
| TL.120.SER.H | 9.2812 | 120.9606 | 18.7787 | 19.3743 | 2.64E+07 |
| TL.121.ILE.H | 8.7114 | 120.6306 | 20.5564 | 19.1568 | 1.71E+07 |
| TL.122.GLY.H | 8.6882 | 109.4736 | 24.3584 | 20.5405 | 5.40E+06 |
| TL.123.ASP.H | 7.9414 | 124.3316 | 18.9583 | 18.7555 | 3.43E+07 |
| TL.124.VAL.H | 8.6075 | 124.0518 | 17.5597 | 18.0450 | 4.01E+07 |
| TL.125.ALA.H | 7.8803 | 121.3377 | 16.3135 | 18.8634 | 6.13E+07 |

-continued

| F1 Assign | F1 position | F2 position | LW F1 (Hz) | LW F2 (Hz) | Height |
|---|---|---|---|---|---|
| TL.126.LYS.H | 8.0024 | 119.7348 | 20.5705 | 18.3671 | 1.04E+08 |
| TL.127.LYS.H | 8.0190 | 121.3711 | 17.2894 | 17.8534 | 1.01E+08 |
| TL.128.LEU.H | 8.6532 | 120.2570 | 18.0062 | 18.2445 | 3.66E+07 |
| TL.129.GLY.H | 8.2053 | 106.2627 | 18.0361 | 18.4504 | 4.24E+07 |
| TL.131.MET.H | 8.7256 | 118.8819 | 16.6866 | 17.9953 | 4.34E+07 |
| TL.132.TRP.H | 8.7119 | 122.5814 | 18.4799 | 18.7626 | 2.80E+07 |
| TL.133.ASN.H | 8.1348 | 117.2495 | 17.4409 | 18.4657 | 5.40E+07 |
| TL.134.ASN.H | 7.5461 | 115.7741 | 19.5366 | 18.8391 | 4.91E+07 |
| TL.135.THR.H | 7.2627 | 119.9122 | 18.4851 | 18.5540 | 4.44E+07 |
| TL.136.ALA.H | 9.2071 | 131.3622 | 17.0411 | 18.2227 | 3.66E+07 |
| TL.137.ALA.H | 8.8274 | 124.9859 | 14.4547 | 22.1480 | 1.45E+06 |
| TL.138.ASP.H | 8.9571 | 115.6309 | 18.9345 | 19.4487 | 1.95E+07 |
| TL.139.ASP.H | 7.3010 | 117.8635 | 19.8679 | 18.2453 | 4.22E+07 |
| TL.140.ALA.H | 7.7905 | 119.1034 | 19.3181 | 18.7588 | 3.13E+07 |
| TL.141.GLN.H | 7.4097 | 118.1173 | 17.1880 | 18.8418 | 4.01E+07 |
| TL.143.TYR.H | 7.1967 | 115.5677 | 19.8319 | 19.1363 | 2.97E+07 |
| TL.145.LYS.H | 9.1741 | 121.2738 | 17.8887 | 20.0482 | 2.77E+07 |
| TL.147.ALA.H | 8.3318 | 120.6021 | 21.9785 | 20.7642 | 1.98E+07 |
| TL.149.LYS.H | 7.9737 | 120.8159 | 17.7823 | 22.3931 | 4.89E+07 |
| TL.150.LEU.H | 8.2612 | 119.8328 | 19.4856 | 23.9293 | 2.86E+07 |
| TL.151.LYS.H | 8.3980 | 123.7315 | 19.0907 | 22.3943 | 3.45E+07 |
| TL.152.GLU.H | 8.0036 | 120.1009 | 18.5759 | 18.4348 | 5.46E+07 |
| TL.153.LYS.H | 7.7406 | 119.7378 | 19.3471 | 19.4416 | 4.18E+07 |
| TL.154.TYR.H | 8.1247 | 120.2565 | 24.0128 | 22.4221 | 7.15E+07 |
| TL.155.GLU.H | 8.4809 | 117.6318 | 18.3609 | 19.8254 | 3.19E+07 |
| TL.157.ASP.H | 8.8614 | 123.1717 | 17.8349 | 19.3205 | 3.35E+07 |
| TL.158.ILE.H | 9.1480 | 122.4894 | 19.2904 | 19.2156 | 2.73E+07 |
| TL.159.ALA.H | 7.3355 | 124.8233 | 17.3550 | 19.1822 | 4.38E+07 |
| TL.160.ALA.H | 7.7549 | 120.3869 | 17.8564 | 19.8791 | 4.70E+07 |
| TL.162.ARG.H | 8.2685 | 119.1365 | 19.6143 | 21.0415 | 3.36E+07 |
| TL.163.ALA.H | 7.6030 | 121.5109 | 18.4123 | 19.0334 | 2.70E+07 |
| TL.164.LYS.H | 7.6483 | 118.6508 | 18.5044 | 19.7095 | 2.57E+07 |
| TL.166.LYS.H | 8.0157 | 121.7960 | 20.9936 | 22.5167 | 1.29E+07 |
| TL.168.ASP.H | 8.4254 | 120.2086 | 22.2976 | 21.9565 | 1.05E+07 |
| TL.169.ALA.H | 8.2750 | 124.9759 | 19.4096 | 19.6958 | 2.71E+07 |
| TL.170.ALA.H | 8.2009 | 121.6082 | 19.1281 | 18.5205 | 2.58E+07 |
| TL.174.VAL.H | 7.9258 | 119.5189 | 26.7477 | 26.1396 | 8.34E+06 |
| TL.175.VAL.H | 8.3137 | 125.5231 | 16.9953 | 16.9413 | 7.98E+07 |
| TL.176.LYS.H | 8.4697 | 126.6299 | 26.1100 | 20.5983 | 2.90E+06 |
| TL.177.ALA.H | 8.3806 | 125.7978 | 28.0424 | 18.8813 | 2.71E+06 |
| TL.178.GLU.H | 8.4483 | 120.7051 | #VALUE! | #VALUE! | 9.69E+06 |
| TL.179.LYS.H | 8.4452 | 122.3144 | 19.8139 | 22.4131 | 2.10E+07 |
| TL.185.GLU.H | 8.2803 | 122.8473 | 18.9947 | 20.4627 | 2.54E+07 |

REFERENCES

1. Weissman I L: Stem cells: Units of development, units of regeneration, and units in evolution. Cell 2000, 100:157-168.
2. Gratwohl A, Pasquini M C, Aljurf M, Atsuta Y, Baldomero H, Foeken L, Gratwohl M, Bouzas L F, Confer D, Frauendorfer K, et al.: One million haemopoietic stem-cell transplants: a retrospective observational study. Lancet Haematol 2015, 2:e91-e100.
3. Sharma R, Khristov V, Rising A, Jha B S, Dejene R, Hotaling N, Li Y, Stoddard J, Stankewicz C, Wan Q, et al.: Clinical-grade stem cell-derived retinal pigment epithelium patch rescues retinal degeneration in rodents and pigs. Sci Transl Med 2019, 11:1-14.
4. Ojeh N, Pastar I, Tomic-Canic M, Stojadinovic O: Stem cells in skin regeneration, wound healing, and their clinical applications. Int J Mol Sci 2015, 16:25476-25501.
5. Domb A J, Nudelman R: In vivo and in vitro elimination of aliphatic polyanhydrides. Biomaterials 1995, 16:319-23.
6. Trainor N, Pietak A, Smith T: Rethinking clinical delivery of adult stem cell therapies. Nat Biotechnol 2014, 32:729-735.
7. Zhang Y, Desai A, Yang S Y, Bae K B, Antczak M I, Fink S P, Tiwari S, Willis J E, Williams N S, Dawson D M, et al.: Inhibition of the prostaglandin-degrading enzyme 15-PGDH potentiates tissue regeneration. Science 2015, 348.
8. Lee G*, Espirito Santo, A. I.*, Zwingenberger Cai L, Vogl T, Feldmann M, Horwood N, J. K-K C, Nanchahal J: HMGB1 accelerates the regeneration of multiple tissues by transitioning stem cells to G(Alert). Proc Natl Acad Sci USA (*authors Contrib Equal to this Proj 2018, doi: 10.1073/pnas.1802893115.
9. Oppenheim J J, Yang D: Alarmins: Chemotactic activators of immune responses. Curr Opin Immunol 2005, 17:359-365.
10. Yang D, Rosa G De, Tewary P, Oppenheim J J: Alarmins Link Neutrophils and Dendritic Cells. Trends Immunol 2009, 30:531-537.
11. Belgrano F S, De Abreu Da Silva I C, Bastos De Oliveira F M, Fantappie M R, Mohana-Borges R: Role of the acidic tail of high mobility group protein B1 (HMGB1) in protein stability and DNA bending. PLoS One 2013, 8:1-12.
12. Joshi S R, Sarpong Y C, Peterson R C, Scovell W M: Nucleosome dynamics: HMGB1 relaxes canonical nucleosome structure to facilitate estrogen receptor binding. Nucleic Acids Res 2012, 40:10161-10171.
13. Rodgers J T, King K Y, Brett J O, Cromie M J, Charville G W, Maguire K K, Brunson C, Mastey N, Liu L, Tsai C-R, et al.: mTORC1 controls the adaptive transition of quiescent stem cells from G0 to G(Alert). Nature 2014, 509:393-6.
14. Venereau E, Casalgrandi M, Schiraldi M, Antoine D J, Cattaneo A, De Marchis F, Liu J, Antonelli A, Preti A, Raeli L, et al.: Mutually exclusive redox forms of HMGB1 promote cell recruitment or proinflammatory cytokine release. J Exp Med 2012, 209:1519-28.
15. Cecchinato V, D'Agostino G, Raeli L, Nerviani A, Schiraldi M, Danelon G, Manzo A, Thelen M, Ciurea A, Bianchi M E, et al.: Redox-Mediated Mechanisms Fuel Monocyte Responses to CXCL12/HMGB1 in Active Rheumatoid Arthritis. Front Immunol 2018, 9:1-12.
16. Ferrara M, Chialli G, Ferreira L M, Ruggieri E, Careccia G, Preti A, Piccirillo R, Bianchi M E, Sitia G, Venereau E: Oxidation of HMGB1 Is a Dynamically Regulated Process in Physiological and Pathological Conditions. Front Immunol 2020, 11:1-13.
17. Bonaldi T, Talamo F, Scaffidi P, Ferrera D, Porto A, Bachi A, Rubartelli A, Agresti A, Bianchi M E: Monocytic cells hyperacetylate chromatin protein HMGB1 to redirect it towards secretion. EMBO J 2003, 22:5551-5560.
18. Kim Y H, Kwak M S, Park J B, Lee S A, Choi J E, Cho H S, Shin J S: N-linked glycosylation plays a crucial role in the secretion of HMGB1. J Cell Sci 2016, 129:29-38.
19. Venereau E, Schiraldi M, Uguccioni M, Bianchi M E: HMGB1 and leukocyte migration during trauma and sterile inflammation. Mol Immunol 2013, 55:76-82.
20. Stark K, Philippi V, Stockhausen S, Busse J, Antonelli A, Miller M, Schubert I, Hoseinpour P, Chandraratne S, Von Bruhl M L, et al.: Disulfide HMGB1 derived from platelets coordinates venous thrombosis in mice—SM. Blood 2016, 128:2435-2449.
21. Teng W, He X, Shan L, Fan C, Peng S, Wang X, Shan Z, Wang W, Liu X, Liu S, et al.: Glycyrrhizin, a Direct HMGB1 Antagonist, Ameliorates Inflammatory Infiltration in a Model of Autoimmune Thyroiditis via Inhibition of TLR2-HMGB1 Signaling. Thyroid 2017, 27:722-731.
22. Vogel S, Bodenstein R, Chen Q, Feil S, Feil R, Rheinlaender J, Schaffer T E, Bohn E, Frick J S, Borst 0, et al.:

Platelet-derived HMGB1 is a critical mediator of thrombosis. *J Clin Invest* 2015, 125:4638-4654.

23. Maugeri N, Campana L, Gavina M, Covino C, De Metrio M, Panciroli C, Maiuri L, Maseri A, D'Angelo A, Bianchi M E, et al.: Activated platelets present high mobility group box 1 to neutrophils, inducing autophagy and promoting the extrusion of neutrophil extracellular traps. *J Thromb Haemost* 2014, 12:2074-2088.

24. Ahrens I, *Agrotis* A, Topcic D, Bassler N, Chen Y C, Bobik A, Bode C, Peter K: HMGB1 binds to activated platelets via platelet-expressed receptor for advanced glycation end products (RAGE) and is highly expressed in platelet rich coronary artery thrombi. *Thromb Haemost* 2015, 14:994-1003.

25. van Beijnum J R, Buurman W A, Griffioen A W: Convergence and amplification of toll-like receptor (TLR) and receptor for advanced glycation end products (RAGE) signaling pathways via high mobility group B1 (HMGB1). *Angiogenesis* 2008, 11:91-99.

26. Lotze M T, Tracey K J: High-mobility group box 1 protein (HMGB1): nuclear weapon in the immune arsenal. *Nat Rev Immunol* 2005, 5:331-42.

27. Sakaguchi M, Murata H, Yamamoto K, Ono T, Sakaguchi Y, Motoyama A, Hibino T, Kataoka K, Huh N: TIRAP, an adaptor protein for TLR2/4, transduces a signal from RAGE phosphorylated upon ligand binding. *PLoS One* 2011, 6:e23132.

28. He M, Bianchi M E, Coleman T R, Tracey K J, Al-abed Y, Unit C D, Biology C: Exploring the biological functional mechanism of the HMGB1/TLR4/MD-2 complex by surface plasmon resonance. [date unknown].

29. Yang H, Hreggvidsdottir H S, Palmblad K, Wang H, Ochani M, Li J, Lu B, Chavan S, Rosas-Ballina M, Al-Abed Y, et al.: A critical cysteine is required for HMGB1 binding to Toll-like receptor 4 and activation of macrophage cytokine release. *Proc Natl Acad Sci USA* 2010, 107:11942-7.

30. Tirone M, Tran N L, Ceriotti C, Gorzanelli A, Canepari M, Bottinelli R, Raucci A, Maggio S Di, Santiago C, Mellado M, et al.: High mobility group box 1 orchestrates tissue regeneration via CXCR4. *J Exp Med* 2018, doi:10.1084/jem.20160217.

31. Di Maggio S, Milano G, De Marchis F, D'Ambrosio A, Bertolotti M, Palacios B S, Badi I, Sommariva E, Pompilio G, Capogrossi M C, et al.: Non-oxidizable HMGB1 induces cardiac fibroblasts migration via CXCR4 in a CXCL12-independent manner and worsens tissue remodeling after myocardial infarction. *Biochim Biophys Acta —Mol Basis Dis* 2017, 1863:2693-2704.

32. Kwak M S, Lim M, Lee Y J, Lee H S, Kim Y H, Ho Youn J, Choi J E, Shin J-S: HMGB1 Binds to Lipoteichoic Acid and Enhances TNF-α and IL-6 Production through HMGB1-Mediated Transfer of Lipoteichoic Acid to CD14 and TLR2. *J Innate Immun* 2015, 7:405-416.

33. Aucott H, Sowinska A, Harris H E, Lundback P: Ligation of free HMGB1 to TLR2 in the absence of ligand is negatively regulated by the C-terminal tail domain. *Mol Med* 2018, 24:19.

34. Das N, Dewan V, Grace P M, Gunn R J, Tamura R, Tzarum N, Watkins L R, Wilson I A, Yin H: HMGB1 Activates Proinflammatory Signaling via TLR5 Leading to Allodynia. *Cell Rep* 2016, 17:1128-1140.

35. Yu M, Wang H, Ding A, Golenbock D T, Latz E, Czura C J, Fenton M J, Tracey K J, Yang H: HMGB1 signals through toll-like receptor (TLR) 4 and TLR2. *Shock* 2006, 26:174-179.

36. Stark K, Philippi V, Stockhausen S, Busse J, Antonelli A, Miller M, Schubert I, Hoseinpour P, Chandraratne S, Von Bruhl M L, et al.: Disulfide HMGB1 derived from platelets coordinates venous thrombosis in mice. *Blood* 2016, 128:2435-2449.

37. Huttunen H J, Fages C, Kuja-Panula J, Ridley A J, Rauvala H: Receptor for advanced glycation end products-binding COOH-terminal motif of amphoterin inhibits invasive migration and metastasis. *Cancer Res* 2002, 62:4805-4811.

38. Arumugam T, Ramachandran V, Gomez S B, Schmidt A M, Logsdon C D: S100P-derived RAGE antagonistic peptide reduces tumor growth and metastasis. *Clin Cancer Res* 2012, 18:4356-4364.

39. LeBlanc P M, Doggett T A, Choi J, Hancock M A, Durocher Y, Frank F, Nagar B, Ferguson T A, Saleh M: An immunogenic peptide in the A-box of HMGB1 protein reverses apoptosis-induced tolerance through RAGE receptor. *J Biol Chem* 2014, 289:7777-7786.

40. Anggayasti W L, Ogino K, Yamamoto E, Helmerhorst E, Yasuoka K, Mancera R L: The acidic tail of HMGB1 regulates its secondary structure and conformational flexibility: A circular dichroism and molecular dynamics simulation study. Comput Struct *Biotechnol J* 2020, 18:1160-1172.

41. Rauvala H, Rouhiainen A: Physiological and pathophysiological outcomes of the interactions of HMGB1 with cell surface receptors. *Biochim Biophys Acta —Gene Regul Mech* 2010, 1799:164-170.

42. Nady N, Min J, Kareta M S, Chedin F, Arrowsmith C H: A SPOT on the chromatin landscape?Histone peptide arrays as a tool for epigenetic research. *Trends Biochem Sci* 2008, 33:305-313.

43. Mollica L, De Marchis F, Spitaleri A, Dallacosta C, Pennacchini D, Zamai M, Agresti A, Trisciuoglio L, Musco G, Bianchi M E: Glycyrrhizin binds to high-mobility group box 1 protein and inhibits its cytokine activities. *Chem Biol* 2007, 14:431-41.

44. Schiraldi M, Raucci A, Mu5 oz LM, Livoti E, Celona B, Venereau E, Apuzzo T, De Marchis F, Pedotti M, Bachi A, et al.: {HMGB1}promotes recruitment of inflammatory cells to damaged tissues by forming a complex with {CXCL12} and signaling via {CXCR4.}. *J Exp Med* 2012, 209:551-563.

45. De Leo F, Quilici G, Tirone M, Mannella V, De Marchis F, Preti A, Gori A, Casalgrandi M, Mezzapelle R, Bianchi M, et al.: Diflunisal targets the HMGB1/CXCL12 heterocomplex and blocks immune cell recruitment. *bioRxiv* 2019, doi:10.1101/563890.

46. Fassi E M A, Sgrignani J, D'Agostino G, Cecchinato V, Garofalo M, Grazioso G, Uguccioni M, Cavalli A: Oxidation State Dependent Conformational Changes of HMGB1 Regulate the Formation of the CXCL12/HMGB1 Heterocomplex. Comput Struct *Biotechnol J* 2019, 17:886-894.

47. Bianchi M E, Falciola L, Ferrari S, Lilley D M: The DNA binding site of HMG1 protein is composed of two similar segments (HMG boxes), both of which have counterparts in other eukaryotic regulatory proteins. *Embo J* 1992, 11:1055-1063.

48. Li J, Wang H, Mason J M, Levine J, Yu M, Ulloa L, Czura C J, Tracey K J, Yang H: Recombinant HMGB1 with cytokine-stimulating activity. *J Immunol Methods* 2004, 289:211-223.

49. Girard J P: A Direct Inhibitor of HMGB1 Cytokine. *Chem Biol* 2007, 14:345-347.

50. Wang J, Tochio N, Takeuchi A, Uewaki J ichi, Kobayashi N, Tate S ichi: Redox-sensitive structural change in the A-domain of HMGB1 and its implication for the binding to cisplatin modified DNA. *Biochem Biophys Res Commun* 2013, 441:701-706.

51. Youn J H, Kwak M S, Wu J, Kim E S, Ji Y, Min H J, Yoo J H, Choi J E, Cho H S, Shin J S: Identification of lipopolysaccharide-binding peptide regions within HMGB1 and their effects on subclinical endotoxemia in a mouse model. *Eur J Immunol* 2011, 41:2753-2762.

52. Lee S, Piao C, Kim G, Kim J Y, Choi E, Lee M: Production and application of HMGB1 derived recombinant RAGE-antagonist peptide for anti-inflammatory therapy in acute lung injury. *Eur J Pharm Sci* 2018, 114:275-284.

53. De Leo F, Quilici G, Tirone M, Mannella V, De Marchis F, Preti A, Gori A, Casalgrandi M, Mezzapelle R, Bianchi M, et al.: Diflunisal targets the HMGB1/CXCL12 heterocomplex and blocks immune cell recruitment—SM. *bioRxiv* 2019, doi:10.1101/563890.

54. Ottestad W, Rognes I N, Pischke S E, Mollnes T E, Andersson U, Eken T: Biphasic Release of the Alarmin High Mobility Group Box 1 Protein Early After Trauma Predicts Poor Clinical Outcome. *Crit Care Med* 2019, 47:e614-e622.

55. Yang H, Wang H, Wang Y, Addorisio M, Li J, Postiglione M J, Chavan S S, Al-Abed Y, Antoine D J, Andersson U, et al.: The haptoglobin beta subunit sequesters HMGB1 toxicity in sterile and infectious inflammation. *J Intern Med* 2017, 282:76-93.

56. Yang H, Wang H, Levine Y A, Gunasekaran M K, Wang Y, Addorisio M, Zhu S, Li W, Li J, de Kleijn D P V, et al.: Identification of CD163 as an antiinflammatory receptor for HMGB1-haptoglobin complexes. JCI insight 2016, 1:1-14.

57. Smart N, Bollini S, Dube K N, Vieira J M, Zhou B, Davidson S, Yellon D, Riegler J, Price A N, Lythgoe M F, et al.: De novo cardiomyocytes from within the activated adult heart after injury. *Nature* 2011, 474:640-644.

58. Sadek H, Olson E N: Toward the Goal of Human Heart Regeneration. *Cell Stem Cell* 2020, 26:7-16.

59. Brooks M: Stem cell research: time for a dose of realism. BMJ2017, 356.

60. Vagnozzi R J, Maillet M, Sargent M A, Khalil H, Johansen A K Z, Schwanekamp J A, York A J, Huang V, Nahrendorf M, Sadayappan S, et al.: An acute immune response underlies the benefit of cardiac stem cell therapy. *Nature* 2020, 577:405-409.

61. Forbes S J, Rosenthal N: Preparing the ground for tissue regeneration: From mechanism to therapy. *Nat Med* 2014, 20:857-869.

62. Lane S W, Williams D A, Watt F M: Modulating the stem cell niche for tissue regeneration. *Nat Biotechnol* 2014, 32:795-803.

63. Antczak M I, Zhang Y, Wang C, Doran J, Naidoo J, Voruganti S, Williams N S, Markowitz S D, Ready J M: Inhibitors of 15-Prostaglandin Dehydrogenase To Potentiate Tissue Repair. *J Med Chem* 2017, 60:3979-4001.

64. Ren X, Zhao M, Lash B, Martino M M, Julier Z: Growth Factor Engineering Strategies for Regenerative Medicine Applications. *Front Bioeng Biotechnol* 2020, 7:1-9.

65. Yamakawa S, Hayashida K: Advances in surgical applications of growth factors for wound healing. *Burn Trauma* 2019, 7:1-13.

66. Mitchell A C, Briquez P S, Hubbell J A, Cochran J R: Engineering growth factors for regenerative medicine applications. *Acta Biomater* 2016, 30:1-12.

67. Hori 0, Brett J, Slattery T, Cao R, Zhang J, Chen J X, Stem D, Schmidt A M: The Receptor for Advanced Glycation End Products (RAGE) Is a Cellular Binding Site for Amphoterin. *J Biol Chem* 1995, 270:25752-25761.

68. Ibrahim Z A, Armour C L, Phipps S, Sukkar M B: RAGE and TLRs: Relatives, friends or neighbours?*Mol Immunol* 2013, 56:739-744.

69. Festoff B W, Sajja R K, van Dreden P, Cucullo L: HMGB1 and thrombin mediate the blood-brain barrier dysfunction acting as biomarkers of neuroinflammation and progression to neurodegeneration in Alzheimer's disease. *J Neuroinflammation* 2016, 13:1-12.

70. Hreggvidsdóttir HS, Lundberg A M, Aveberger A-C, Klevenvall L, Andersson U, Harris H E: High mobility group box protein 1 (HMGB1)-partner molecule complexes enhance cytokine production by signaling through the partner molecule receptor. *Mol Med* 2012, 18:224-30.

71. Livoti E: Experimentally validated computational docking to characterize protein-protein interactions. [date unknown].

72. Fassi E M A, Sgrignani J, D'Agostino G, Cecchinato V, Garfalo M, Grazioso G, Uguccioni M, Cavalli A: Oxidation state dependent conformational changes of HMGB1 regulates the formation of the CXCL12/HMGB1 heterocomplex. bioRxiv *Biochem* 2019, doi:10.1101/555946.

73. Drury L J, Ziarek J J, Gravel S, Veldkamp C T, Takekoshi T, Hwang S T, Heveker N, Volkman B F, Dwinell M B: Monomeric and dimeric CXCL12 inhibit metastasis through distinct CXCR4 interactions and signaling pathways. *Proc Natl Acad Sci USA* 2011, 108:17655-17660.

74. Chang S, Li Y, Yuan F, Qu M, Song Y, Zhang Z, Yang G Y, Wang Y: Monomeric CXCL12 outperforms its dimeric and wild type variants in the promotion of human endothelial progenitor cells' function. *Biochem Biophys Res Commun* 2017, 488:303-310.

75. Ziarek J J, Kleist A B, London N, Raveh B, Montpas N, Bonneterre J, St-onge G, Dicosmo-ponticello CJ, Koplinski C A, Roy I, et al.: Structural basis for chemokine recognition by a G protein—coupled receptor and implications for receptor activation. *Sci Signal* 2017, 5756.

76. Nady N, Min J, Kareta M S, Chedin F, Arrowsmith C H: Supplementary Materials: A SPOT on the chromatin landscape?Histone peptide arrays as a tool for epigenetic research. *Trends Biochem Sci* 2008, 33:305-313.

77. Veldkamp C T, Peterson F C, Pelzek A J, Volkman B F: The monomer—dimer equilibrium of stromal cell-derived factor-1 (CXCL12) is altered by pH, phosphate, sulfate, and heparin. *Protein Sci* 2005, 1:1071-1081.

78. Akira S: Toll-like Receptors and Innate Immunity. In Edited by Dixon FJBT-A in I. Academic Press; 2001:1-56.

79. Xu D, Young J, Song D, Esko J D: Heparan sulfate is essential for high mobility group protein 1 (HMGB1) signaling by the receptor for advanced glycation end products (RAGE). *J Biol Chem* 2011, 286:41736-41744.

80. Gurevich D B, Nguyen P D, Siegel A L, Ehrlich O V., Sonntag C, Phan J M N, Berger S, Ratnayake D, Hersey L, Berger J, et al.: Asymmetric division of clonal muscle stem cells coordinates muscle regeneration in vivo. *Science* 2016, 353.

81. Benjamin E J, Muntner P, Alonso A, Bittencourt M S, Callaway C W, Carson A P, Chamberlain A M, Chang A R, Cheng S, Das S R, et al.: *Heart Disease and Stroke Statistics-*2019 *Update: A Report From the American Heart Association.* 2019.

82. Limana F, Esposito G, D'Arcangelo D, Di Carlo A, Romani S, Melillo G, Mangoni A, Bertolami C, Pompilio G, Germani A, et al.: HMGB1 attenuates cardiac remodelling in the failing heart via enhanced cardiac regeneration and miR-206-mediated inhibition of TIMP-3. *PLoS One* 2011, 6:1-11.

83. Foglio E, Puddighinu G, Germani A, Russo M A, Limana F: HMGB1 Inhibits Apoptosis Following MI and Induces Autophagy via mTORC1 Inhibition. *J Cell Physiol* 2017, 232:1135-1143.

84. Bauzi M del R, Gimenez C S, Locatelli P, De Lorenzi A, Hnatiuk A, Capogrossi M C, Crottogini A, Cuniberti L, *Olea* FD: High-dose intramyocardial HMGB1 induces long-term cardioprotection in sheep with myocardial infarction. *Drug Deliv Transl Res* 2019, 9:935-944.

85. Chen X, Zaro J L, Shen W C: Fusion protein linkers: Property, design and functionality. *Adv Drug Deliv Rev* 2013, 65:1357-1369.

86. Savitsky P, Bray J, Cooper C D O, Marsden B D, Mahajan P, Burgess-Brown N A, Gileadi 0: High-throughput production of human proteins for crystallization: The SGC experience. *J Struct Biol* 2010, 172:3-13.

87. Yang 00, Swanberg S L, Lu Z, Dziejman M, McCoy J, Luster A D, Walker B D, Herrmann S H: Enhanced inhibition of human immunodeficiency virus type 1 by Met-stromal-derived factor 1 beta correlates with down-modulation of CXCR4. *J Virol* 1999, 73:4582-4589.

88. Crump M P, Gong J H, Loetscher P, Rajarathnam K, *Amara* A, Arenzana-Seisdedos F, Virelizier J L, Baggiolini M, Sykes B D, Clark-Lewis I: Solution structure and basis for functional activity of stromal cell-derived factor-1; dissociation of CXCR4 activation from binding and inhibition of HIV-1. *EMBO J* 1997, 16:6996-7007.

89. Turchetto J, Sequeira A F, Ramond L, Peysson F, Bris J L A, Saez N J, Duhoo Y, Blemont M, Guerreiro CIPD, Quinton L, et al.: High-throughput expression of animal venom toxins in *Escherichia coli* to generate a large library of oxidized disulphide-reticulated peptides for drug discovery. *Microb Cell Fact* 2017, 16:6.

90. Them M, Sauer G, Paramasivam N, Grin I, Linke D: Efficient subfractionation of gram-negative bacteria for proteomics studies. *J Proteome Res* 2010, 9:6135-6147.

91. Aida Y, Pabst M J: Removal of endotoxin from protein solutions by phase separation using triton X-114. *J Immunol Methods* 1990, 132:191-195.

92. Teodorowicz M, Perdijk O, Verhoek I, Govers C, Savelkoul H F J, Tang Y, Wichers H, Broersen K: Optimized Triton X-114 assisted lipopolysaccharide (LPS) removal method reveals the immunomodulatory effect of food proteins. *PLoS One* 2017, 12:e0173778.

93. Chalk R: Mass Spectrometric Analysis of Proteins. Humana Press, New York, NY; 2017:373-395.

94. Wu C, Li S S-C: CelluSpotsm: A Reproducible Means of Making Peptide Arrays for the Determination of SH2 Domain Binding Specificity BT—Peptide Microarrays: Methods and Protocols. In Edited by Cretich M, Chiari M. Humana Press; 2009:197-202.

95. Chalk R, Berridge G, Shrestha L, Strain-Damerell C, Mahajan P, Yue W, Gileadi 0, Burgess-Brown N: High-Throughput Mass Spectrometry Applied to Structural Genomics. *Chromatography* 2014, 1:159-175.

96. Kaltashow I A, Mohimen A: Electrospray ionization mass spectrometry can provide estimates of protein surface areas in solution. *Anal Chem* 2005, 77:5370-5379.

97. Testa L, Brocca S, Grandori R: Charge-surface correlation in electrospray ionization of folded and unfolded proteins. *Anal Chem* 2011, 83:6459-6463.

98. Yu G, Wang L G, Han Y, He Q Y: ClusterProfiler: An R package for comparing biological themes among gene clusters. Omi A *J Integr Biol* 2012, doi:10.1089/omi.2011.0118.

99. Carr C A, Stuckey D J, Tatton L, Tyler D J, Hale S J M, Sweeney D, Schneider J E, Martin-Rendon E, Radda G K, Harding S E, et al.: Bone marrow-derived stromal cells home to and remain in the infarcted rat heart but fail to improve function: An in vivo cine-MRI study. *Am J Physiol—Hear Circ Physiol* 2008, 295.

100. Lee S, Lee D K: Multiple Comparison Test and Its Imitations What is the proper way to apply the multiple comparison test? KJA. *Korean J Anesth* 2018, doi:10.4097/kja.d.18.00242.

101. E. J. Benjamin, P. Muntner, A. Alonso, M. S. Bittencourt, C. W. Callaway, A. P. Carson, A. M. Chamberlain, A. R. Chang, S. Cheng, S. R. Das, F. N. Delling, L. Djousse, M. S. V. Elkind, J. F. Ferguson, M. Fornage, L. C. Jordan, S. S. Khan, B. M. Kissela, K. L. Knutson, T. W. Kwan, D. T. Lackland, T. T. Lewis, J. H. Lichtman, C. T. Longenecker, M. S. Loop, P. L. Lutsey, S. S. Martin, K. Matsushita, A. E. Moran, M. E. Mussolino, M. O'Flaherty, A. Pandey, A. M. Perak, W. D. Rosamond, G. A. Roth, U. K. A. Sampson, G. M. Satou, E. B. Schroeder, S. H. Shah, N. L. Spartano, A. Stokes, D. L. Tirschwell, C. W. Tsao, M. P. Turakhia, L. B. VanWagner, J. T. Wilkins, S. S. Wong, S. S. Virani, E. American Heart Association Council on, C. Prevention Statistics, S. Stroke Statistics, Heart Disease and Stroke Statistics-2019 Update: A Report From the American Heart Association. *Circulation* 139, e56-e528 (2019).

102. G. B. D. DALYs, H. Collaborators, Global, regional, and national disability-adjusted life-years (DALYs) for 359 diseases and injuries and healthy life expectancy (HALE) for 195 countries and territories, 1990-2017: a systematic analysis for the Global Burden of Disease Study 2017. *Lancet* 392, 1859-1922 (2018).

103. BritishHeartFoundation, bhf.org.uk/what-we-do/our-research/heart-statistics/heart-statistics-publications/cardiovascular-disease-statistics-2019, (2020).

104. T. J. Cahill, R. K. Kharbanda, Heart failure after myocardial infarction in the era of primary percutaneous coronary intervention: Mechanisms, incidence and identification of patients at risk. *World J Cardiol* 9, 407-415 (2017).

105. L. Qian, Y. Huang, C. I. Spencer, A. Foley, V. Vedantham, L. Liu, S. J. Conway, J. D. Fu, D. Srivastava. In vivo reprogramming of murine cardiac fibroblasts into induced cardiomyocytes. *Nature* 485, 593-598 (2012).

106. M. Xin, Y. Kim, L. B. Sutherland, M. Murakami, X. Qi, J. McAnally, E. R. Porrello, A. I. Mahmoud, W. Tan, J. M. Shelton, J. A. Richardson, H. A. Sadek, R. Bassel-Duby, E. N. Olson, Hippo pathway effector Yap promotes cardiac regeneration. *Proc Natl Acad Sci USA* 110, 13839-13844 (2013).

107. J. P. Leach, T. Heallen, M. Zhang, M. Rahmani, Y. Morikawa, M. C. Hill, A. Segura, J. T. Willerson, J. F. Martin, Hippo pathway deficiency reverses systolic heart failure after infarction. *Nature* 550, 260-264 (2017).

108. T. M. A. Mohamed, Y. S. Ang, E. Radzinsky, P. Zhou, Y. Huang, A. Elfenbein, A. Foley, S. Magnitsky, D. Srivastava, Regulation of Cell Cycle to Stimulate Adult Cardiomyocyte Proliferation and Cardiac Regeneration. *Cell* 173, 104-116 el 12 (2018).

109. S. Hashmi, S. Al-Salam, Acute myocardial infarction and myocardial ischemia-reperfusion injury: a comparison. *Int J Clin Exp Pathol* 8, 8786-8796 (2015).

110. K. Stark, V. Philippi, S. Stockhausen, J. Busse, A. Antonelli, M. Miller, I. Schubert, P. Hoseinpour, S. Chandraratne, M. L. von Bruhl, F. Gaertner, M. Lorenz, A. Agresti, R. Coletti, D. J. Antoine, R. Heermann, K. Jung, S. Reese, I. Laitinen, M. Schwaiger, A. Walch, M. Sperandio, P. P. Nawroth, C. Reinhardt, S. Jackel, M. E. Bianchi, S. Massberg, Disulfide HMGB1 derived from platelets coordinates venous thrombosis in mice. *Blood* 128, 2435-2449 (2016).

111. S. Di Maggio, G. Milano, F. De Marchis, A. D'Ambrosio, M. Bertolotti, B. S. Palacios, I. Badi, E. Sommariva, G. Pompilio, M. C. Capogrossi, A. Raucci, Non-oxidizable HMGB1 induces cardiac fibroblasts migration via CXCR4 in a CXCL12-independent manner and worsens tissue remodeling after myocardial infarction. *Biochim Biophys Acta* 1863, 2693-2704 (2017).

112. J. Mersmann, F. Iskandar, K. Latsch, K. Habeck, V. Sprunck, R. Zimmermann, R. R. Schumann, K. Zacharowski, A. Koch, Attenuation of myocardial injury by HMGB1 blockade during ischemia/reperfusion is toll-like receptor 2-dependent. *Mediators Inflamm* 2013, 174168 (2013).

113. C. Monaco, S. M. Gregan, T. J. Navin, B. M. Foxwell, A. H. Davies, M. Feldmann, Toll-like receptor-2 mediates inflammation and matrix degradation in human atherosclerosis. *Circulation* 120, 2462-2469 (2009).

114. J. Oyama, C. Blais, Jr., X. Liu, M. Pu, L. Kobzik, R. A. Kelly, T. Bourcier, Reduced myocardial ischemia-reperfusion injury in toll-like receptor 4-deficient mice. Circulation 109, 784-789 (2004).

115. K. R. Chien, J. Frisen, R. Fritsche-Danielson, D. A. Melton, C. E. Murry, I. L. Weissman, Regenerating the field of cardiovascular cell therapy. *Nat Biotechnol* 37, 232-237 (2019).

116. R. J. Vagnozzi, M. Maillet, M. A. Sargent, H. Khalil, A. K. Z. Johansen, J. A. Schwanekamp, A. J. York, V. Huang, M. Nahrendorf, S. Sadayappan, J. D. Molkentin, An acute immune response underlies the benefit of cardiac stem cell therapy. *Nature* 577, 405-409 (2020).

117. C. E. Murry, W. R. MacLellan, Stem cells and the heart-the road ahead. *Science* 367, 854-855 (2020).

118. S. Bollini, N. Smart, P. R. Riley, Resident cardiac progenitor cells: at the heart of regeneration. *J Mol Cell Cardiol* 50, 296-303 (2011).

119. P. K. Nguyen, E. Neofytou, J. W. Rhee, J. C. Wu, Potential Strategies to Address the Major Clinical Barriers Facing Stem Cell Regenerative Therapy for Cardiovascular Disease: A Review. *JAMA Cardiol* 1, 953-962 (2016).

120. T. J. Cahill, R. P. Choudhury, P. R. Riley, Heart regeneration and repair after myocardial infarction: translational opportunities for novel therapeutics. *Nat Rev Drug Discov* 16, 699-717 (2017).

121. H. Sadek, E. N. Olson, Toward the Goal of Human Heart Regeneration. *Cell Stem Cell* 26, 7-16 (2020).

122. N. Smart, S. Bollini, K. N. Dube, J. M. Vieira, B. Zhou, S. Davidson, D. Yellon, J. Riegler, A. N. Price, M. F. Lythgoe, W. T. Pu, P. R. Riley, De novo cardiomyocytes from within the activated adult heart after injury. *Nature* 474, 640-644 (2011).

123. A. I. Mahmoud, F. Kocabas, S. A. Muralidhar, W. Kimura, A. S. Koura, S. Thet, E. R. Porrello, H. A. Sadek, Meis1 regulates postnatal cardiomyocyte cell cycle arrest. *Nature* 497, 249-253 (2013).

124. K. Bersell, S. Arab, B. Haring, B. Kuhn, Neuregulin1/ErbB4 signaling induces cardiomyocyte proliferation and repair of heart injury. *Cell* 138, 257-270 (2009).

125. S. Koudstaal, M. M. Bastings, D. A. Feyen, C. D. Waring, F. J. van Slochteren, P. Y. Dankers, D. Torella, J. P. Sluijter, B. Nadal-Ginard, P. A. Doevendans, G. M. Ellison, S. A. Chamuleau, Sustained delivery of insulin-like growth factor-1/hepatocyte growth factor stimulates endogenous cardiac repair in the chronic infarcted pig heart. *J Cardiovasc Transl Res* 7, 232-241 (2014).

126. K. Wei, V. Serpooshan, C. Hurtado, M. Diez-Cunado, M. Zhao, S. Maruyama, W. Zhu, G. Fajardo, M. Noseda, K. Nakamura, X. Tian, Q. Liu, A. Wang, Y. Matsuura, P. Bushway, W. Cai, A. Savchenko, M. Mahmoudi, M. D. Schneider, M. J. van den Hoff, M. J. Butte, P. C. Yang, K. Walsh, B. Zhou, D. Bernstein, M. Mercola, P. Ruiz-Lozano, Epicardial FSTL1 reconstitution regenerates the adult mammalian heart. *Nature* 525, 479-485 (2015).

127. K. Gabisonia, G. Prosdocimo, G. D. Aquaro, L. Carlucci, L. Zentilin, I. Secco, H. Ali, L. Braga, N. Gorgodze, F. Bernini, S. Burchielli, C. Collesi, L. Zandona, G. Sinagra, M. Piacenti, S. Zacchigna, R. Bussani, F. A. Recchia, M. Giacca, MicroRNA therapy stimulates uncontrolled cardiac repair after myocardial infarction in pigs. *Nature* 569, 418-422 (2019).

128. A. Vujic, N. Natarajan, R. T. Lee, Molecular mechanisms of heart regeneration. *Semin Cell Dev Biol*, (2019).

129. J. M. Vieira, S. Norman, C. Villa Del Campo, T. J. Cahill, D. N. Barnette, M. Gunadasa-Rohling, L. A. Johnson, D. R. Greaves, C. A. Carr, D. G. Jackson, P. R. Riley, The cardiac lymphatic system stimulates resolution of inflammation following myocardial infarction. *J Clin Invest* 128, 3402-3412 (2018).

130. L. R. Fiedler, K. Chapman, M. Xie, E. Maifoshie, M. Jenkins, P. A. Golforoush, M. Bellahcene, M. Noseda, D. Faust, A. Jarvis, G. Newton, M. A. Paiva, M. Harada, D. J. Stuckey, W. Song, J. Habib, P. Narasimhan, R. Agil, D. Sanmugalingam, R. Yan, L. Pavanello, M. Sano, S. C. Wang, R. D. Sampson, S. Kanayaganam, G. E. Taffet, L. H. Michael, M. L. Entman, T. H. Tan, S. E. Harding, C. M. R. Low, C. Tralau-Stewart, T. Perrior, M. D. Schneider, MAP4K4 Inhibition Promotes Survival of Human Stem Cell-Derived Cardiomyocytes and Reduces Infarct Size In Vivo. *Cell Stem Cell* 24, 579-591 e512 (2019).

131. H. Aghajanian, T. Kimura, J. G. Rurik, A. S. Hancock, M. S. Leibowitz, L. Li, J. Scholler, J. Monslow, A. Lo, W. Han, T. Wang, K. Bedi, M. P. Morley, R. A. Linares Saldana, N. A. Bolar, K. McDaid, C. A. Assenmacher, C. L. Smith, D. Wirth, C. H. June, K. B. Margulies, R. Jain, E. Pure, S. M. Albelda, J. A. Epstein, Targeting cardiac fibrosis with engineered T cells. *Nature* 573, 430-433 (2019).

132. N. Trainor, A. Pietak, T. Smith, Rethinking clinical delivery of adult stem cell therapies. *Nat Biotechnol* 32, 729-735 (2014).

133. M. J. Foglia, K. D. Poss, Building and re-building the heart by cardiomyocyte proliferation. *Development* 143, 729-740 (2016).

134. S. Oozawa, S. Mori, T. Kanke, H. Takahashi, K. Liu, Y. Tomono, M. Asanuma, I. Miyazaki, M. Nishibori, S. Sano, Effects of HMGB1 on ischemia-reperfusion injury in the rat heart. *Circ J* 72, 1178-1184 (2008).

135. T. Kitahara, Y. Takeishi, M. Harada, T. Niizeki, S. Suzuki, T. Sasaki, M. Ishino, O. Bilim, O. Nakajima, I. Kubota, High-mobility group box 1 restores cardiac function after myocardial infarction in transgenic mice. *Cardiovasc Res* 80, 40-46 (2008).

136. Y. Nakamura, S. Suzuki, T. Shimizu, M. Miyata, T. Shishido, K. Ikeda, S. Saitoh, I. Kubota, Y. Takeishi, High Mobility Group Box 1 Promotes Angiogenesis from Bone Marrow-derived Endothelial Progenitor Cells after Myocardial Infarction. *J Atheroscler Thromb* 22, 570-581 (2015).

137. F. Limana, G. Esposito, D. D'Arcangelo, A. Di Carlo, S. Romani, G. Melillo, A. Mangoni, C. Bertolami, G. Pompilio, A. Germani, M. C. Capogrossi, HMGB1 attenuates cardiac remodelling in the failing heart via enhanced cardiac regeneration and miR-206-mediated inhibition of TIMP-3. *PLoS One* 6, e19845 (2011).

138. E. Foglio, G. Puddighinu, A. Germani, M. A. Russo, F. Limana, HMGB1 Inhibits Apoptosis Following MI and Induces Autophagy via mTORC1 Inhibition. *J Cell Physiol* 232, 1135-1143 (2017).

139. M. D. R. Bauza, C. S. Gimenez, P. Locatelli, A. De Lorenzi, A. Hnatiuk, M. C. Capogrossi, A. Crottogini, L. Cuniberti, F. D. *Olea*, High-dose intramyocardial HMGB1 induces long-term cardioprotection in sheep with myocardial infarction. *Drug Deliv Transl Res* 9, 935-944 (2019).

140. M. E. Bianchi, Casalgrandi, M., Venereau, E. J., Brunelli, S., HMGB1 variants and uses thereof. European Patent Office —patentimages.storage.googleapis.com/cf/3c/6c/3b9d7ca70fl94a/EP2877248B1.pdf (2012).

141. M. Tirone, N. L. Tran, C. Ceriotti, A. Gorzanelli, M. Canepari, R. Bottinelli, A. Raucci, S. Di Maggio, C. Santiago, M. Mellado, M. Saclier, S. Francois, G. Careccia, M. He, F. De Marchis, V. Conti, S. Ben Larbi, S. Cuvellier, M. Casalgrandi, A. Preti, B. Chazaud, Y. Al-Abed, G. Messina, G. Sitia, S. Brunelli, M. E. Bianchi, E. Venereau, High mobility group box 1 orchestrates tissue regeneration via CXCR4. *J Exp Med* 215, 303-318 (2018).

142. G. Lee, A. I. Espirito Santo, S. Zwingenberger, L. Cai, T. Vogl, M. Feldmann, N. J. Horwood, J. K. Chan, J. Nanchahal, Fully reduced HMGB1 accelerates the regeneration of multiple tissues by transitioning stem cells to $G_{Alert}$. *Proc Natl Acad Sci USA* 115, E4463-E4472 (2018).

What is claimed is:

1. A polypeptide represented by the following formula:

H₂N-A-X-B-A-X-B-HOOC wherein each A represents consecutive amino acids, the sequence of which (1) is a sequence of four amino acids
  (a) identical to the sequence of amino acids 90-93 of wild type human HMGB1 (SEQ ID NO: 1), or
  (b) which differs from the sequence of (a) in respect to one or more amino acids; and
(2) has at its amino terminal end, between one and six consecutive amino acids, the sequence of which (a) is identical to the sequence of the corresponding one to six amino acids preceding amino acid 90 in wild type human HMGB1 (SEQ ID NO: 1), or
(b) differs from the sequence of (a) in respect to one or more amino acids;
and
(3) optionally has a methionine at the amino terminus, wherein each A may be the same or different;

wherein each X represents consecutive amino acids, the sequence of which is identical to the sequence of amino acids 94-162 of wild type human HMGB1 (SEQ ID NO: 1);

wherein each B represents consecutive amino acids, the sequence of which (1) is a sequence of five or six amino acids (a) identical to the sequence of amino acids 163-168 of wild type human HMGB1 (SEQ ID NO: 1), (b) identical to the sequence of amino acids 163-167 of wild type human HMGB1 (SEQ ID NO: 1), (c) the sequence of (a) in which any one of amino acids 163, 167, or 168 is changed to any other amino acid;

(d) the sequence of (b) in which any one of amino acids 163 or 167 is changed to any other amino acid;

(e) the sequence of (a) or (b) in which amino acid 164 is changed from lysine to arginine; or (f) the sequence of (a) or (b) in which amino acid 165 is changed from glycine to alanine, serine or threonine;

(g) the sequence of (a) or (b) in which amino acid 166 is changed from lysine to arginine; or (h) the sequence of (a) or (b) in combination with the changes in (e) and (f), (e) and (g), (f) and (g), or (e), (f) and (g);

(i) the sequence of (a), (b), or (c) in combination with the changes in one or more of (e), (f), and (g); or (j) the sequence of (d) in combination with the changes in one or more of (e), (f), and (g); and (2) has at its carboxy terminal end, between one and six consecutive amino acids, the sequence of which (a) is identical to the sequence of the corresponding one to six amino acids following amino acid 168 in wild type human HMGB1 (SEQ ID NO: 1), (b) is identical to the sequence of the corresponding one to six amino acids following amino acid 167 in wild type human HMGB1 (SEQ ID NO: 1), (c) differs at one or more positions from the sequence of the corresponding one to six amino acids following amino acid 168 in wild type human HMGB1 (SEQ ID NO: 1), or (d) differs at one or more positions from the sequence of the corresponding one to six amino acids following amino acid 167 in wild type human HMGB1 (SEQ ID NO: 1), and wherein each B may be the same or different; and wherein each - represents a peptide bond between each of A and X, X and B, B and A, A and X, and X and B; with the proviso that in the B-A between the two Xs, the number of amino acids must be at least 12; and with the additional proviso that in the B at the carboxy terminal end of the polypeptide, the one to six consecutive amino acids of (2) may be absent.

2. The polypeptide of claim 1, wherein each A represents consecutive amino acids, the sequence of which (1) is a sequence of four amino acids (a) identical to the sequence of amino acids 90-93 of wild type human HMGB1 (SEQ ID NO: 1);

(2) has at its amino terminal end, between one and six consecutive amino acids; and (3) optionally has a methionine at the amino terminus.

3. The polypeptide of claim 1, wherein each B represents consecutive amino acids, the sequence of which (1) is a sequence of six amino acids identical to the sequence of amino acids 163-168 of wild type human HMGB1 (SEQ ID NO: 1), and (2) has at its carboxy terminal end, between one and six consecutive amino acids.

4. The polypeptide of claim 1, wherein

A represents consecutive amino acids, the sequence of which (1) includes a sequence identical to the sequence of amino acids 90-93 of wild type HMGB1 (SEQ ID NO: 1), (2) has at its amino terminal end, between one and six consecutive amino acids, the sequence of which is identical to the sequence of the corresponding one to six amino acids preceding amino acid 90 in wild type HMGB1 (SEQ ID NO: 1), and optionally (3) has a methionine at the amino terminus; and B represents consecutive amino acids, the sequence of which (1) includes a sequence identical to the sequence of amino acids 163-168 of wild type HMGB1 (SEQ ID NO: 1) and (2) has at its carboxy terminal end, between one and six consecutive amino acids, the sequence of which is identical to the sequence of the corresponding one to six amino acids following amino acid 168 in wild type HMGB1 (SEQ ID NO: 1).

5. The polypeptide of claim 1, wherein a methionine is present at the amino terminus of the polypeptide.

6. The polypeptide of claim 1, wherein A has at its amino terminal end one amino acid corresponding to amino acid 89 of wild type human HMGB1 (SEQ ID NO: 1).

7. The polypeptide of claim 1, wherein B has at its carboxy terminal end six amino acids corresponding to amino acids 169-174 of wild type human HMGB1 (SEQ ID NO: 1).

8. The polypeptide of claim 1, wherein the number of amino acids in the B-A between the two Xs is between 12-22 inclusive.

9. The polypeptide of claim 1, wherein the sequence of (2) (c) or (2) (d) of either B or of both Bs differs at the one or more positions by the presence of a glycine, serine, proline, arginine, lysine, aspartic acid, glutamic acid, or histidine amino acid residue.

10. The polypeptide of claim 1, wherein either A or both As are five consecutive amino acids.

11. The polypeptide of claim 1, wherein the A between the Xs is five consecutive amino acids and the B between the Xs is at least seven consecutive amino acids.

12. The polypeptide of claim 1, wherein the B between the Xs is twelve consecutive amino acids and the A between the Xs is at least five consecutive amino acids.

13. The polypeptide of claim 1, wherein the one to six consecutive amino acids of the B at the carboxy terminal end of the polypeptide are absent.

14. The polypeptide of claim 1, wherein each A represents consecutive amino acids, the sequence of which is KDPNA.

15. The polypeptide of claim 1, wherein each B represents consecutive amino acids, the sequence of which is AKGKPDAAKKGV.

16. The polypeptide of claim 1, the sequence of which is SEQ ID NO: 2.

17. The polypeptide of claim 1, the sequence of which is a methionine followed by SEQ ID NO: 2.

18. A method of treating a subject suffering from, or at risk for developing, a condition which would be alleviated by promoting regeneration of a tissue or cells that rely upon CXCR4+ cells for repair which comprises administering to the subject the polypeptide of claim 16 in an amount effective to promote regeneration of the tissue or cells.

19. The method of claim 18, wherein the condition is a myocardial infarction.

20. The method of claim 19, wherein the polypeptide is administered within 5 hours following the myocardial infarction.

* * * * *